United States Patent [19]
Albright et al.

[11] Patent Number: 5,736,540
[45] Date of Patent: Apr. 7, 1998

[54] TRICYCLIC DIAZEPINE VASOPRESSIN ANTAGONISTS AND OXYTOCIN ANTAGONISTS

[75] Inventors: Jay Donald Albright, Nanuet; Marvin Fred Reich, Suffern; Fuk-Wah Sum, Pomona; Efren Guillermo Delos Santos, Nanuet, all of N.Y.

[73] Assignee: American Cyanamid Company, Madison, N.J.

[21] Appl. No.: 646,841

[22] Filed: May 8, 1996

Related U.S. Application Data

[60] Continuation-in-part of Ser. No. 468,737, Jun. 6, 1995, Pat. No. 5,624,923, which is a division of Ser. No. 254,822, Jun. 13, 1994, Pat. No. 5,516,774, which is a continuation-in-part of Ser. No. 100,004, Jul. 29, 1993, abandoned.

[51] Int. Cl.$^6$ .................... A61K 31/55; C07D 223/00; C07D 495/00
[52] U.S. Cl. .................... 514/220; 540/542; 540/560
[58] Field of Search ....................... 540/560, 542; 514/220

[56] References Cited

U.S. PATENT DOCUMENTS

| | | | |
|---|---|---|---|
| 5,521,173 | 5/1996 | Venkatesan et al. | 514/220 |
| 5,536,718 | 7/1996 | Albright et al. | 514/220 |

FOREIGN PATENT DOCUMENTS

| | | |
|---|---|---|
| 382185 | 8/1990 | European Pat. Off. |
| 470514 | 2/1992 | European Pat. Off. |
| 514667 | 11/1992 | European Pat. Off. |
| 533240 | 3/1993 | European Pat. Off. |
| 533242 | 3/1993 | European Pat. Off. |
| 533243 | 3/1993 | European Pat. Off. |
| 533244 | 3/1993 | European Pat. Off. |
| 9105549 | 5/1991 | WIPO |

OTHER PUBLICATIONS

Yamamura et al. Science, 252 pp. 572–574 (1991).
Yamamura et al., Br. J. Pharmacol., 105, pp. 787–791 (1992).

*Primary Examiner*—Mukund J. Shah
*Assistant Examiner*—Brenda Coleman
*Attorney, Agent, or Firm*—Steven R. Eck

[57] ABSTRACT

Tricyclic diazepines of the formula:

wherein A, B, D, E, F, Y and Z are defined in the specification which compounds have vasopressin and oxytocin antagonist activity.

64 Claims, No Drawings

TRICYCLIC DIAZEPINE VASOPRESSIN ANTAGONISTS AND OXYTOCIN ANTAGONISTS

This is a continuation-in-part of application Ser. No. 08/468,737, U.S. Pat. No. 5,624,925 filed Jun. 6, 1995, which is a Divisional of application Ser. No. 08/254,822, filed Jun. 13, 1994, U.S. Pat. No. 5,516,774 which is a continuation-in-part of application Ser. No. 08/100,004, filed Jul. 29, 1993 abandoned.

FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its actions through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induced increases in total peripheral resistance and altered local blood flow, $V_1$-antagonists may be therapeutic agents.

The blockade of $V_2$ receptors may be useful in treating diseases characterized by excess renal re-absorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephrotic syndrome, central nervous injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone. On the basis of the biochemical and pharmacological effects of the hormones antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephrotic syndrome, brain edema, cerebral ischemia, cerebral hemorrhage-stroke, thrombosis-bleeding, abnormal states of water retention.

The following prior art references describe peptide vasopressin antagonists; M. Manning et al., *J. Med. Chem.*, 35, 382(1992); M. Manning et al., *J. Med. Chem.*, 35, 3895 (1992); H. Gavras and B. Lammek, U.S. Pat. No. 5,070,187 (1991); M. Manning and W. H. Sawyer, U.S. Pat. No. 5,055,448(1991); F. E. Ali, U.S. Pat. No. 4,766,108(1988); R. R. Ruffolo et al., *Drug News and Perspective*, 4(4), 217, (May)(1991). P. D. Williams et al., have reported on potent hexapeptide oxytocin antagonists [*J. Med. Chem.*, 35, 3905 (1992)]which also exhibit weak vasopressin antagonist activity in binding to $V_1$ and $V_2$ receptors. Peptide vasopressin antagonists suffer from a lack or oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol.*, 105, 787(1992), Ogawa et al., (Otsuka Pharm Co., LTD.) EP 0514667-A1; JP 04154765-A; EPO 382185-A2; and WO9105549. Carbostyril derivatives and pharmaceutical compositions containing the same are disclosed by Ogawa et al., (Otsuka Pharm. Co.) in EP 470514A. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.*, 35, 3919(1992), *J. Med. Chem.*, 36, 3993 (1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonists activity of oxytocin receptors.

SUMMARY OF THE INVENTION

This invention relates to new compounds selected from those of the general formula I:

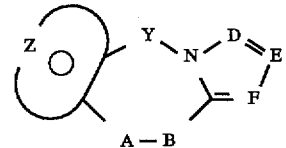

wherein Y is a moiety selected from; —$(CH_2)_n$— wherein n is an integer from 0 to 2,

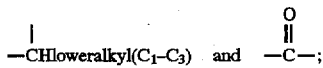

A-B is a moiety selected from

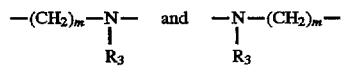

wherein m is an integer from 1 to 2 provided that when Y is —$(CH_3)_n$— and n is 2, m may also be zero and when n is zero, m may also be three, provided also that when Y is —$(CH_2)_n$— and n is 2, m may not be two; and the moiety:

represents: (1) fused phenyl or fused substituted phenyl optionally substituted by one or two substituents selected from ($C_1$–$C_3$)lower alkyl, halogen, amino, ($C_1$–$C_3$)lower alkoxy or ($C_1$–$C_3$)lower alkylamino; (2) a 5-membered aromatic (unsaturated) heterocyclic ring having one heteroatom selected from O, N or S; (3) a 6-membered aromatic (unsaturated) heterocyclic ring having one nitrogen atom; (4) a 5 or 6-membered aromatic (unsaturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by ($C_1$–$C_3$)lower alkyl, halogen or ($C_1$–$C_3$)lower alkoxy; the moiety:

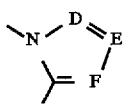

is a five membered aromatic(unsaturated) fused nitrogen containing heterocyclic ring wherein D, E and F are selected from carbon or nitrogen and wherein the carbon atoms may be optionally substituted by a substituent selected from halogen, ($C_1$–$C_3$)lower alkyl, hydroxy, —$COCl_3$, —$COCF_3$,

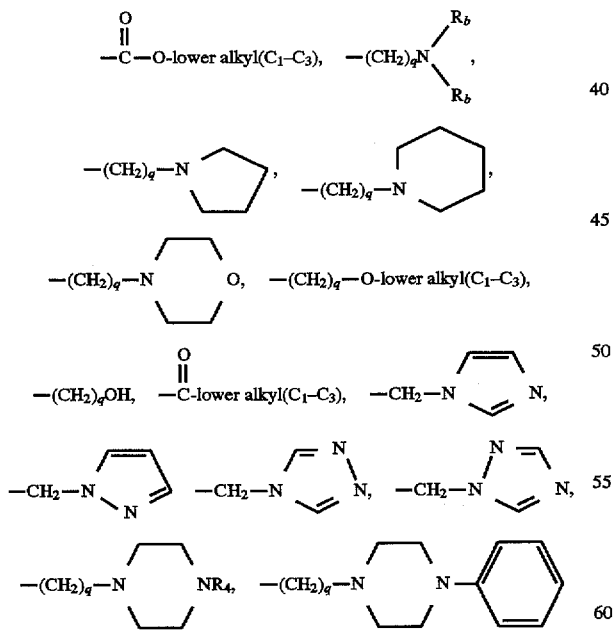

—CHO, amino, ($C_1$–$C_3$)lower alkoxy, ($C_1$–$C_3$)lower alkylamino, CONH-lower alkyl($C_1$–$C_3$), and —CON[lower alkyl($C_1$–$C_3$)]$_2$; q is one or two; $R_b$ is independently selected from hydrogen, —$CH_3$ or —$C_2H_5$;

$R_3$ is a moiety of the formula:

wherein Ar is a moiety selected from the group consisting of

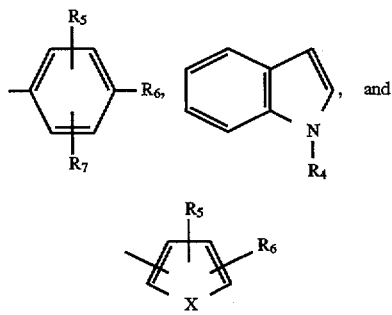

wherein X is selected from O, S, NH, $NCH_3$ and $NCOCH_3$;

$R_4$ is selected from hydrogen, lower alkyl($C_1$–$C_3$), -CO-lower alkyl($C_1$–$C_3$),

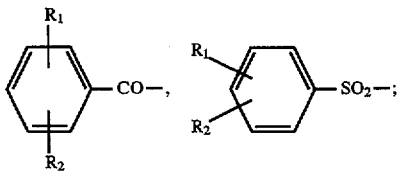

—$SO_2$lower alkyl($C_1$–$C_3$); $R_1$ and $R_2$ are selected from hydrogen, ($C_1$–$C_3$)lower alkyl, ($C_1$–$C_3$)lower alkoxy and halogen; $R_5$ is selected from hydrogen, ($C_1$–$C_3$)lower alkyl, ($C_1$–$C_3$)lower alkoxy and halogen;

$R_6$ is selected from (a) moieties of the formulae:

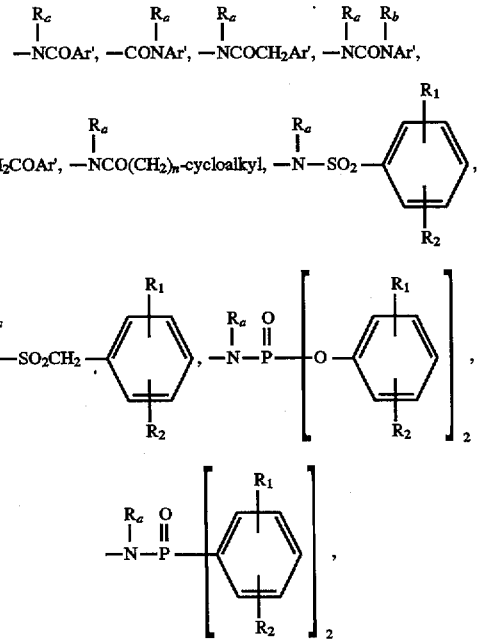

-continued

—NH—C(=O)—O-lower alkyl(C₁–C₈) straight or branched,

—NH—C(=O)-lower alkyl(C₁–C₈) straight or branched,

—NHSO₂-lower alkyl(C₁–C₈) straight or branched,

—NH—C(=O)—O-lower alkenyl(C₁–C₈) straight or branched,

—NH—C(=O)-lower alkenyl(C₁–C₈) straight or branched,

—NHSO₂-lower alkenyl(C₁–C₈) straight or branched, wherein cycloalkyl is defined as $C_3$–$C_6$ cycloalkyl, cyclohexenyl or cyclopentenyl; Ra is independently selected from hydrogen, —CH₃, —C₂H₅,

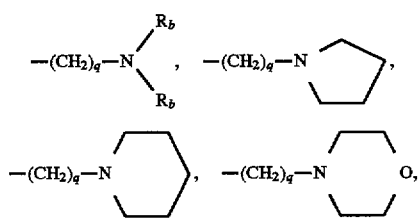

—(CH₂)$_q$—O-lower alkyl($C_1$–$C_3$) and —CH₂CH₂OH, q is one or two, and $R_1$, $R_2$ and $R_b$ are as hereinbefore defined;

(b) a moiety of the formula:

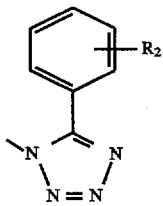

wherein $R_2$ is as hereinbefore defined;

(c) a moiety of the formula:

wherein J is $R_a$, lower alkyl($C_1$–$C_8$) branched or unbranched, lower alkenyl($C_1$–$C_8$) branched or unbranched, —O-lower alkyl($C_1$–$C_8$) branched or unbranched, —O-lower alkenyl($C_1$–$C_8$) branched or unbranched, tetrahydrofuran, tetrahydrothiophene, or —CH₂—K wherein K is ($C_1$–$C_3$) lower alkoxy, halogen, tetrahydrofuran, tetrahydrothiophene or the heterocyclic ring moiety:

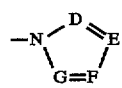

wherein D, E, F and G are selected from carbon or nitrogen and wherein the carbon atoms may be optionally substituted with halogen, ($C_1$–$C_3$)lower alkyl, hydroxy, —CO-lower alkyl($C_1$–$C_3$), CHO, ($C_1$–$C_3$)lower alkoxy, —CO₂-lower alkyl($C_1$–$C_3$), and $R_a$ and $R_b$ are as hereinbefore defined;

(d) a moiety of the formula:

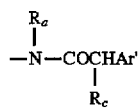

wherein $R_c$ is selected from halogen, ($C_1$–$C_3$) lower alkyl, —O-lower alkyl($C_1$–$C_3$), OH,

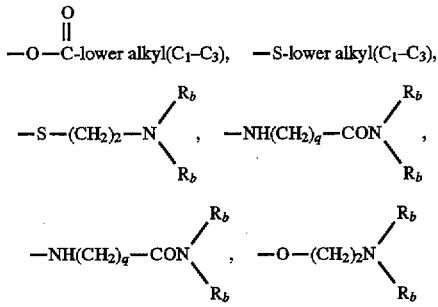

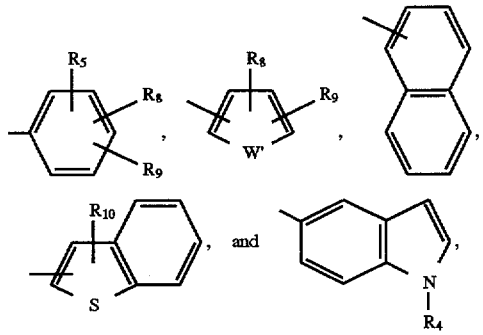

wherein $R_a$ and $R_b$ are as hereinbefore defined and Ar' is selected from moieties of the formula:

wherein W' is selected from O, S, NH, N-lower alkyl ($C_1$–$C_3$), NHCO-lower alkyl($C_1$–$C_3$), and NSO₂lower alkyl ($C_1$–$C_3$);

$R_7$ is selected from hydrogen, lower alkyl($C_1$–$C_3$), halogen, O-lower alkyl($C_1$–$C_3$) and CF₃;

$R_8$ and $R_9$ are independently selected from hydrogen, lower alkyl($C_1$–$C_3$), —S-lower alkyl($C_1$–$C_3$), halogen, —NH-lower alkyl($C_1$–$C_3$), —OCF₃, —OH, —CN, —S—CF₃, —NO₂, —NH₂, O-lower alkyl($C_1$–$C_3$),

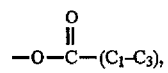

and CF₃ and;

$R_{10}$ is selected from hydrogen, halogen and lower alkyl ($C_1$–$C_3$), and the pharmaceutically acceptable salts thereof.

DETAILED DESCRIPTION OF THE INVENTION

Within the group of the compounds defined by Formula I, certain subgroups of compounds are broadly preferred. Broadly preferred are those compounds wherein $R_3$ is the moiety:

and Ar is selected from the moiety

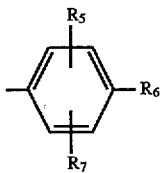

wherein $R_5$, $R_6$ and $R_7$ are as hereinbefore defined.

Especially preferred are compounds wherein $R_3$ is the moiety

and

Ar is selected from the moiety

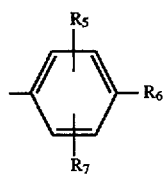

$R_6$ is

—NCOAr', —CONAr', —NCOCH$_2$Ar', —NCONAr',
(with $R_a$ on each N; $R_b$ on last N)

—CH$_2$COAr', —NCO—(CH$_2$)$_n$-cycloalkyl;

—NH—C(=O)—O-lower alkyl($C_1$–$C_8$) straight or branched,

—NH—C(=O)-lower alkyl($C_1$–$C_8$) straight or branched,

—NHSO$_2$-lower alkyl($C_1$–$C_8$) straight or branched,

—NH—C(=O)—O-lower alkenyl($C_1$–$C_8$) straight or branched,

—NH—C(=O)-lower alkenyl($C_1$–$C_8$) straight or branched,

—NHSO$_2$-lower alkenyl($C_1$–$C_8$) straight or branched, wherein cycloalkyl is defined as $C_3$–$C_6$ cycloalkyl, cyclohexenyl or cyclopentenyl;

$R_a$ and $R_b$ are as hereinbefore defined;

and Ar' is selected from the moieties:

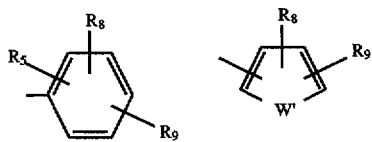

wherein $R_8$, $R_9$ and W' are as hereinbefore defined.

Also especially preferred are compounds wherein Y in Formula I is —(CH$_2$)$_n$— and n is zero or one; A-B is

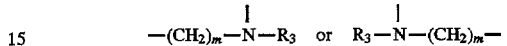

and $R_1$, $R_3$, $R_6$, $R_7$, $R_8$, $R_9$ and $R_{10}$ are as hereinbefore defined; and m is an integer from 1–2.

The most preferred of the compounds of Formula I are those wherein Y is —(CH$_2$)$_n$— and n is one; A-B is —CH$_2$—N($R_3$)— or —N($R_3$)—CH$_2$—

$R_3$ is the moiety

Ar is the moiety

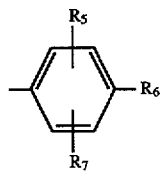

$R_6$ is

—NCOAr', —CONAr', —NCOCH$_2$Ar', —NCONAr',

—CH$_2$COAr', —NCO—(CH$_2$)$_n$-cycloalkyl;

—NH—C(=O)—O-lower alkyl ($C_1$–$C_8$) straight or branched,

—NH—C(=O)-lower alkyl ($C_1$–$C_8$) straight or branched,

—NHSO$_2$-lower alkyl ($C_1$–$C_8$) straight or branched,

—NH—C(=O)—O-lower alkenyl ($C_1$–$C_8$) straight or branched,

—NH—C(=O)-lower alkenyl ($C_1$–$C_8$) straight or branched,

—NHSO$_2$-lower alkenyl ($C_1$–$C_8$) straight or branched,

—(CH$_2$)$_n$—cycloalkyl wherein cycloalkyl is defined as $C_3$–$C_6$ cycloalkyl, cyclohexenyl or cyclopentenyl; $R_a$ and $R_b$ are as hereinbefore defined; and Ar' is

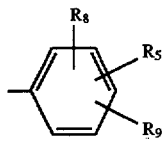

wherein $R_5$ $R_8$ and $R_9$ are as previously defined

The most highly broadly preferred of the compounds of Formula I are those wherein Y is —$(CH_2)_n$— and n is zero or one; wherein the moiety

is a fused phenyl, substituted phenyl, thiophene, furan, pyrrole or pyridine ring;

A—B is

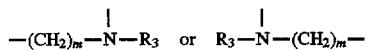

m is one when n is one and m is two when n is zero; D, E, F, $R_1$, $R_2$, $R_4$, $R_5$, $R_7$, $R_8$, $R_9$, $R_{10}$, are as previously defined;

$R_3$ is the moiety

wherein Ar is

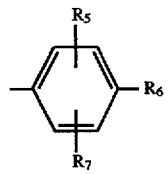

and $R_6$ is selected from the group

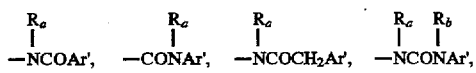

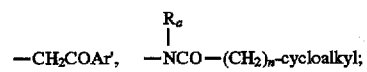

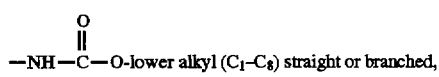

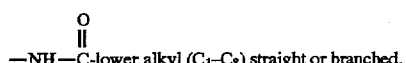

—$NHSO_2$-lower alkyl ($C_1$-$C_8$) straight or branched,

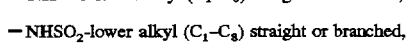

—$NHSO_2$-lower alkenyl ($C_1$-$C_8$) straight or branched, and W', $R_a$, $R_b$ and cycloalkyl are as previously described.

More particularly preferred are compounds of the formulae:

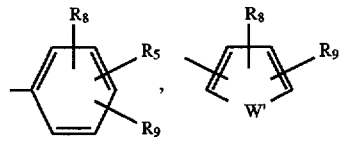

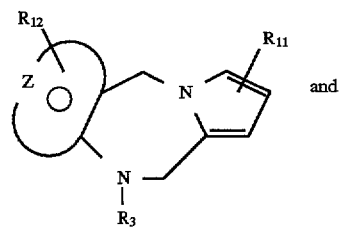

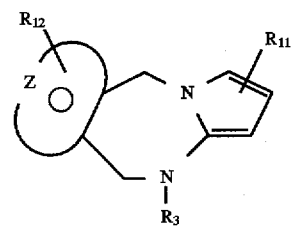

wherein the moiety:

is selected from a phenyl, thiophene, furan, pyrrole or pyridine ring;

$R_3$ is the moiety:

wherein Ar is the moiety:

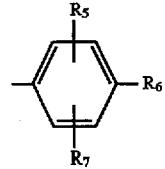

$R_6$ is

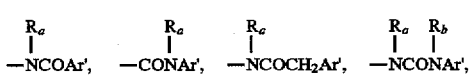

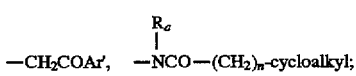

-continued

—NH—C(=O)-lower alkyl (C₁–C₈) straight or branched,

—NHSO₂-lower alkyl (C₁–C₈) straight or branched,

—NH—C(=O)—O-lower alkenyl (C₁–C₈) straight or branched,

—NH—C(=O)-lower alkenyl (C₁–C₈) straight or branched,

—NHSO₂-lower alkenyl (C₁–C₈) straight or branched, and Ar' is selected from the moieties:

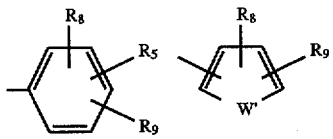

wherein $R_a$, $R_b$, $R_5$, $R_7$, $R_8$, $R_9$, cycloalkyl and W' are as hereinbefore described;

$R_{11}$ is selected from hydrogen, halogen, (C₁–C₃) lower alkyl, hydroxy,

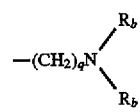

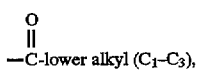

—CHO, and (C₁–C₃)lower alkoxy; and $R_{12}$ is selected from hydrogen, (C₁–C₃)lower alkyl, halogen and (C₁–C₃)lower alkoxy.

Also particularly preferred are compounds of the formulae:

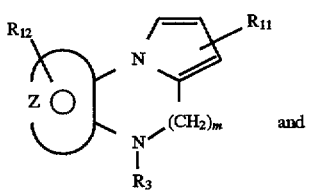

and

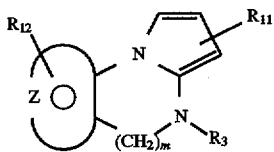

wherein m is one or two;

the moiety:

is selected from a phenyl, thiophene, furan, pyrrole or pyridine ring;

$R_3$ is the moiety:

wherein Ar is the moiety:

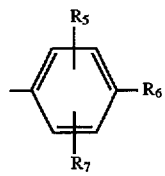

$R_6$ is

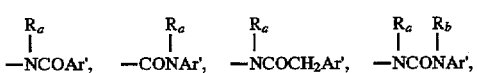

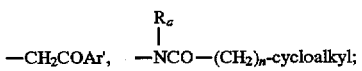

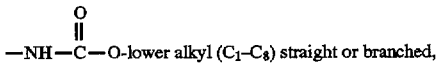

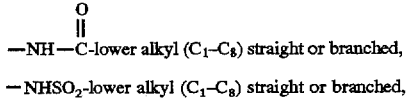

—NH—C(=O)—O-lower alkyl (C₁–C₈) straight or branched,

—NH—C(=O)-lower alkyl (C₁–C₈) straight or branched,

—NHSO₂-lower alkyl (C₁–C₈) straight or branched,

—NH—C(=O)—O-lower alkenyl (C₁–C₈) straight or branched,

—NH—C(=O)-lower alkenyl (C₁–C₈) straight or branched,

—NHSO₂-lower alkenyl (C₁–C₈) straight or branched, $(CH_2)_n$ cycloalkyl; Ar' is selected from the moieties:

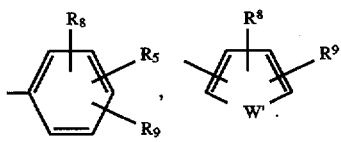

wherein $R_a$, $R_b$, $R_5$, $R_6$, $R_8$, $R_9$, cycloalkyl and W' are as hereinbefore defined;

$R_{11}$ is selected from hydrogen, halogen, (C₁–C₃) lower alkyl, hydroxy,

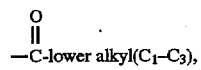

—CHO, and (C₁–C₃)lower alkoxy; and $R_{12}$ is selected from hydrogen, (C₁–C₃)lower alkyl, halogen and (C₁–C₃)lower alkoxy.

More particularly preferred are compounds of the formulae:

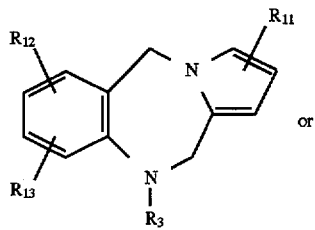

or

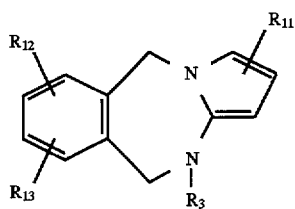

$R_3$ is the moiety:

wherein Ar is the moiety:

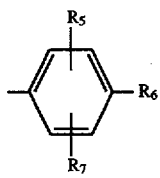

$R_6$ is

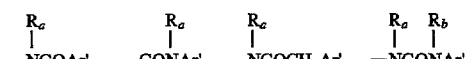

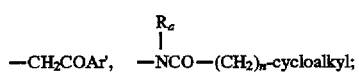

—NH—C(=O)—O-lower alkyl ($C_1$-$C_8$) straight or branched,

—NH—C(=O)-lower alkyl ($C_1$-$C_8$) straight or branched,

—$NHSO_2$-lower alkyl ($C_1$-$C_8$) straight or branched,

—NH—C(=O)—O-lower alkenyl ($C_1$-$C_8$) straight or branched,

—NH—C(=O)-lower alkenyl ($C_1$-$C_8$) straight or branched,

—$NHSO_2$-lower alkenyl ($C_1$-$C_8$) straight or branched, wherein cycloalkyl is defined as $C_3$-$C_6$ cycloalkyl, cyclohexenyl or cyclopentenyl; $R_b$ is hydrogen;

$R_a$ is independently selected from hydrogen, —$CH_3$, —$C_2H_5$ or —$(CH_2)_q N(CH_3)_2$; Ar' is selected from the moieties:

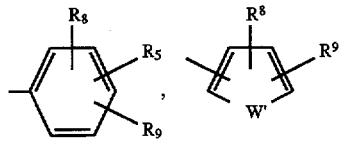

wherein q, $R_a$, $R_b$, $R_5$, $R_7$, $R_8$, $R_9$, $R_{11}$ and W' are as hereinbefore described;

$R_{12}$ and $R_{13}$ are independently selected from hydrogen, ($C_1$-$C_3$) lower alkyl, halogen, amino, ($C_1$-$C_3$) lower alkoxy or ($C_1$-$C_3$) lower alkylamino.

Also particularly preferred are compounds of the formulae:

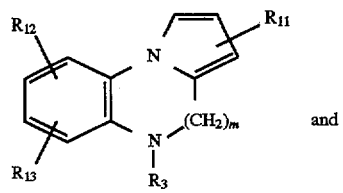 and

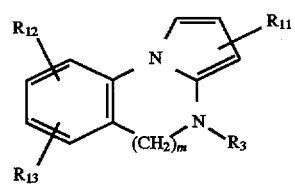

wherein m is one or two;

$R_3$ is the moiety:

wherein Ar is the moiety:

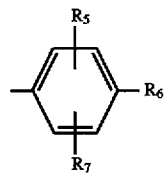

$R_6$ is

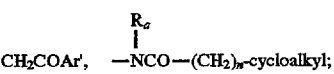

—NH—C(=O)—O-lower alkyl ($C_1$-$C_8$) straight or branched,

—NH—C(=O)-lower alkyl ($C_1$-$C_8$) straight or branched,

—$NHSO_2$-lower alkyl ($C_1$-$C_8$) straight or branched,

—NH—C(=O)—O-lower alkenyl ($C_1$-$C_8$) straight or branched,

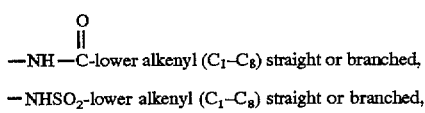
—NH—C-lower alkenyl ($C_1$–$C_8$) straight or branched,

—NHSO$_2$-lower alkenyl ($C_1$–$C_8$) straight or branched, wherein cycloalkyl is defined as $C_3$–$C_6$ cycloalkyl, cyclohexenyl or cyclopentenyl; $R_b$ is hydrogen;

$R_a$ is independently selected from hydroge, —CH$_3$, —C$_2$H$_5$ or —(CH$_2$)$_q$N(CH$_3$)$_2$; and Ar' is selected from the moieties:

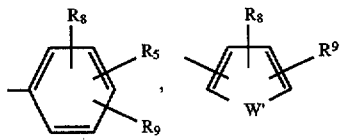

wherein q, $R_5$, $R_7$, $R_8$, $R_9$, $R_{11}$ and W' are as hereinbefore defined;

$R_{12}$ and $R_{13}$ are independently selected from hydrogen, ($C_1$–$C_3$) lower alkyl, halogen, amino, ($C_1$–$C_3$)lower alkoxy or ($C_1$–$C_3$)lower alkylamino.

Among the more preferred compounds of this invention are those selected from Formula I:

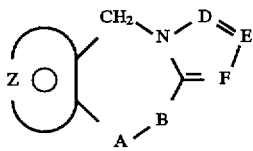

Formula I wherein;

A—B is

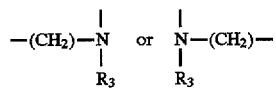

the moiety

represents a fused thiophene or fused substituted thiophene optionally substituted by one or two substituents selected from ($C_1$–$C_3$) lower alkyl, halogen, amino, ($C_1$–$C_3$) lower alkoxy, or ($C_1$–$C_3$) lower alkylamino;

the moiety:

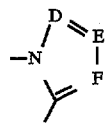

is a five-membered aromatic (unsaturated) fused nitrogen-containing heterocyclic ring wherein D is carbon or nitrogen, E, and F are carbon and wherein the carbon atoms may be optionally substituted by substituent selected from halogen, ($C_1$–$C_3$) lower alkyl, hydroxy, COCCl$_3$, COCF$_3$,

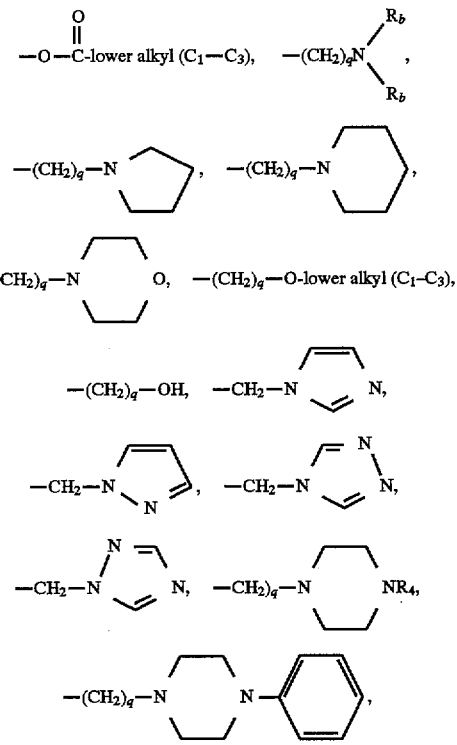

—CHO, amino, ($C_1$–$C_3$) lower alkoxy, ($C_1$–$C_3$) lower alkylamino , CONH ($C_1$–$C_3$) lower alkyl, or —CON[lower alkyl ($C_1$–$C_3$)]$_2$, $R_b$ is independently selected from H, —CH$_3$, or —C$_2$H$_5$;

q is 1 or 2;

$R_3$ is the moiety

—CAr wherein Ar is a moiety selected from the group

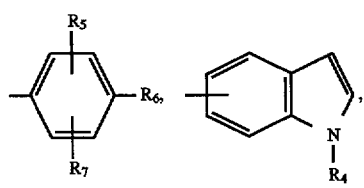

and X is selected from O, S, NH, —NCH$_3$, or —N—COCH$_3$;

$R_4$ is selected from H, lower alkyl ($C_1$–$C_3$), —CO-lower alkyl ($C_1$–$C_3$), SO$_2$ lower alkyl ($C_1$–$C_3$), or the moieties of the formulae:

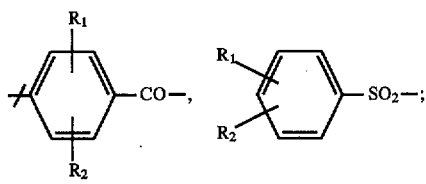

$R_1$ and $R_2$ are, independently, H, ($C_1$–$C_3$) lower alkyl, ($C_1$–$C_3$) lower alkoxy, or halogen;

$R_5$ is H, ($C_1$–$C_3$) lower alkyl, ($C_1$–$C_3$) lower alkoxy or halogen;

$R_6$ is selected from:
(a) moieties of the formula:

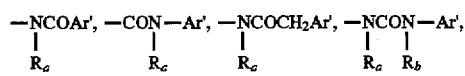

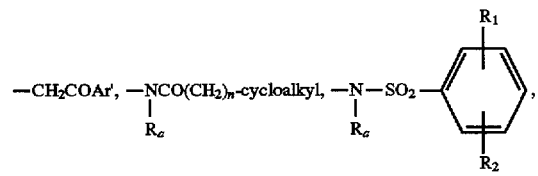

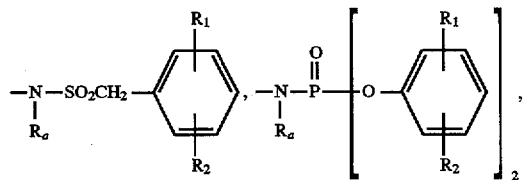

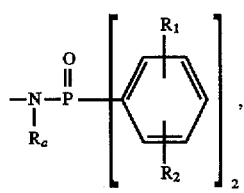

—NH—C(=O)—O-lower alkyl ($C_1$–$C_8$) straight or branched,

—NH—C(=O)-lower alkyl ($C_1$–$C_8$) straight or branched,

—NHSO$_2$-lower alkyl ($C_1$–$C_8$) straight or branched,

—NH—C(=O)—O-lower alkenyl ($C_1$–$C_8$) straight or branched,

—NH—C(=O)-lower alkenyl ($C_1$–$C_8$) straight or branched,

—NHSO$_2$-lower alkenyl ($C_1$–$C_8$) straight or branched, wherein cycloalkyl is defined as $C_3$ to $C_6$ cycloalkyl, cyclohexenyl or cyclopentenyl;

n is 0–2;

Ra is independently selected from H, —CH$_3$, —C$_2$H$_5$,

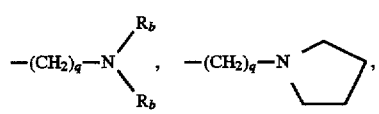

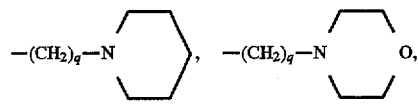

—(CH$_2$)$_q$Olower alkyl ($C_1$$C_3$), or —CH$_2$CH$_2$OH;

$R_b$ is as hereinbefore defined;

q is 1 or 2;

(b) a moiety of the formula:

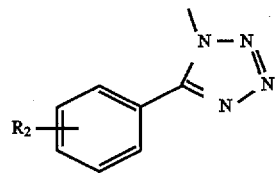

where $R_2$ is as hereinbefore defined;

(c) a moiety of the formula:

wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —CH$_2$—K wherein K is halogen, ($C_1$–$C_3$) lower alkoxy, tetrahydrofuran, tetrahydrothiophene or the heterocyclic ring moiety:

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$) lower alkoxy, or —CO$_2$-lower alkyl ($C_1$–$C_3$); and $R_a$ and $R_b$ are as hereinbefore defined;

(d) a moiety selected from those of the formulae:

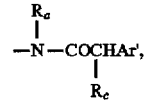

wherein $R_c$ is selected from halogen, ($C_1$–$C_3$)lower alkyl, —O-lower alkyl ($C_1$–$C_3$), OH

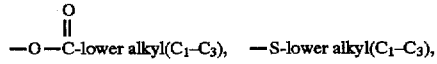

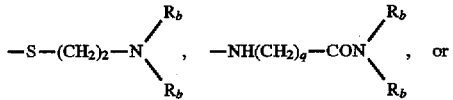

-continued

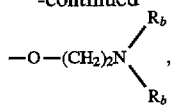

q is 1 or 2;

$R_a$ and $R_b$ are as hereinbefore defined; wherein Ar' is selected from the group:

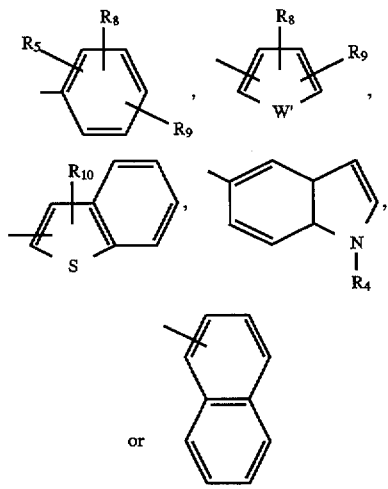

wherein

W' is selected from O, S, NH, N-lower alkyl ($C_1$–$C_3$), —NHCO-lower alkyl ($C_1$–$C_3$), or $NSO_2$-lower alkyl ($C_1$–$C_3$);

$R_7$ is selected from H, lower alkyl ($C_1$–$C_3$), halogen, —O-lower alkyl ($C_1$–$C_3$), or $CF_3$;

$R_8$ and $R_9$ are independently selected from hydrogen, lower alkyl ($C_1$–$C_3$), S-lower alkyl ($C_1$–$C_3$), halogen, —NH—lower alkyl ($C_1$–$C_3$), —$OCF_3$, —CN, —OH, —S—$CF_3$, —$NO_2$, $NH_2$, or —O-lower alkyl ($C_1$–$C_3$);

$R_{10}$ is H, halogen, or lower alkyl-($C_1$–$C_3$);

and the pharmaceutically acceptable salts, esters and pro-drug forms thereof.

Within the group above are the following preferred sub-groups 1 to 11 of compounds:

1. wherein $R_3$ is the moiety:

and Ar is the moiety

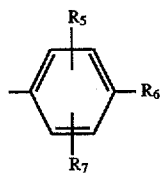

wherein $R_5$, $R_6$, and $R_7$ are as defined in the group above or a pharmaceutically acceptable salt, ester or pro-drug form thereof.

2. compounds of the formula:

and Ar is the moiety

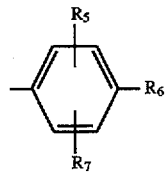

wherein $R_5$, $R_6$, and $R_7$ are as defined in the group above and Ar' is selected from the moieties

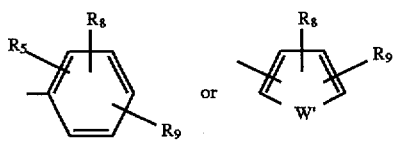

wherein $R_5$, $R_8$, $R_9$ and W' are as defined in the group above or a pharmaceutically acceptable salt, ester or pro-drug form thereof.

3. compounds of the formula:

and Ar is the moiety

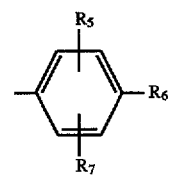

wherein $R_5$ and $R_7$ are as defined in the group above and $R_6$ is selected from:

(a) moieties of the formula:

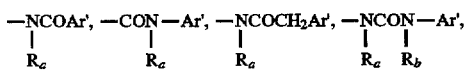

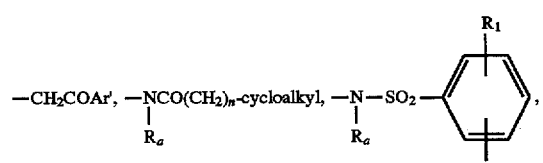

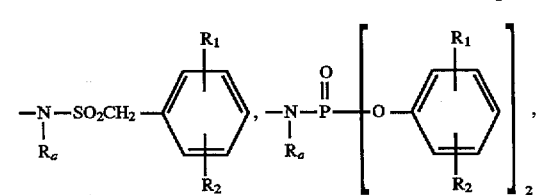

-continued

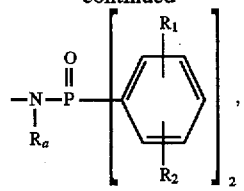

—NH—C(=O)—O-lower alkyl(C$_1$-C$_8$) straight or branched,

—NH—C(=O)-lower alkyl(C$_1$-C$_8$) straight or branched,

—NHSO$_2$-lower alkyl(C$_1$-C$_8$) straight or branched,

—NH—C(=O)—O-lower alkenyl(C$_1$-C$_8$) straight or branched,

—NH—C(=O)-lower alkenyl(C$_1$-C$_8$) straight or branched,

—NHSO$_2$-lower alkenyl(C$_1$-C$_8$) straight or branched, wherein cycloalkyl is defined as C$_3$ to C$_6$ cycloalkyl, cyclohexenyl or cyclopentenyl;

n is 0–2;

R$_a$ is independently selected from H, —CH$_3$, —C$_2$H$_5$,

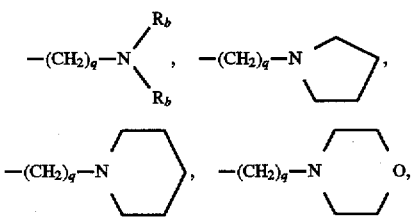

—(CH$_2$)$_q$ lower alkyl (C$_1$C$_3$), or —CH$_2$CH$_2$OH;

q is 1 or 2;

R$_b$ is selected from H, —CH$_3$, or C$_2$H$_5$; or (b) a moiety of the formula:

wherein J is R$_a$, lower alkyl (C$_1$-C$_8$) branched or unbranched, lower alkenyl (C$_2$-C$_8$) branched or unbranched, —O-lower alkyl (C$_1$-C$_8$) branched or unbranched, —O-lower alkenyl (C$_2$-C$_8$) branched or unbranched, tetrahydrofuran, tetrahydrothiophene, or —CH$_2$—K wherein K is halogen, (C$_1$-C$_3$) lower alkoxy, tetrahydrofuran, tetrahydrothiophene or the heterocyclic ring moiety:

wherein D, E, F and G are selected from carbon or nitrogen and wherein the carbon atoms may be optionally substituted with halogen, (C$_1$-C$_3$)lower alkyl, hydroxy, —CO-lower alkyl (C$_1$-C$_3$), CHO, (C$_1$-C$_3$)lower alkoxy, or —CO$_2$-lower alkyl (C$_1$-C$_3$); and R$_a$ and R$_b$ are as hereinbefore defined; or (c) a moiety selected from those of the formulae:

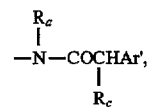

wherein R$_c$ is selected from halogen, (C$_1$-C$_3$)lower alkyl, —O-lower alkyl (C$_1$-C$_3$), OH,

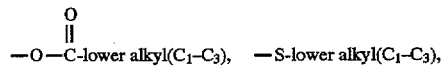

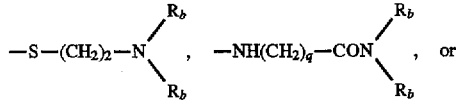

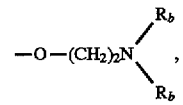

q is 1 or 2;

and R$_a$ and R$_b$ are as hereinbefore defined;

wherein Ar' is selected from the group:

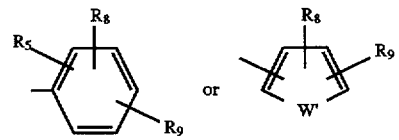

wherein R$_8$, R$_9$ and W' are as defined in the group above or a pharmaceutically acceptable salt, ester or pro-drug form thereof.

4. compounds of the formula:

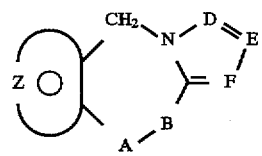   Formula I wherein;

A—B is

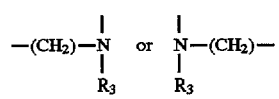

the moiety

represents a fused thiophene or fused substituted thiophene optionally substituted by one or two substituents selected from (C$_1$-C$_3$) lower alkyl, halogen, amino, (C$_1$-C$_3$) lower alkoxy, or (C$_1$-C$_3$) lower alkylamino;

the moiety:

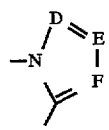

is a five-membered aromatic (unsaturated) fused nitrogen-containing heterocyclic ring wherein D, E, and F are carbon and wherein the carbon atoms may be optionally substituted by a substituent selected from halogen, $(C_1-C_3)$ lower alkyl, hydroxy, $COCCl_3$, $COCF_3$,

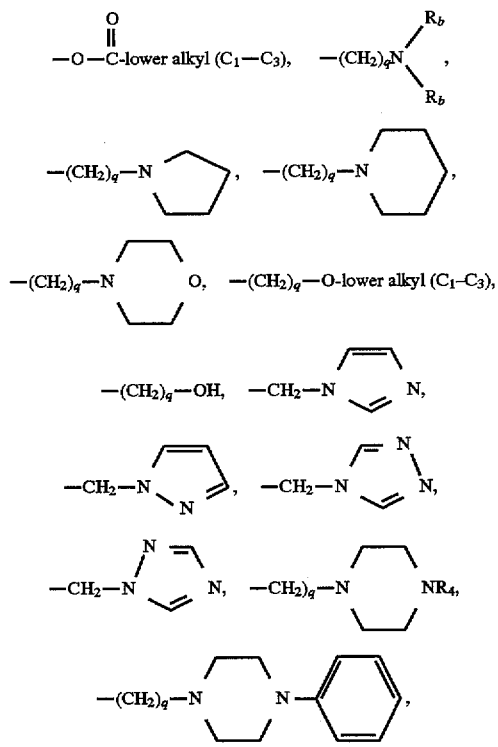

—CHO, amino, $(C_1-C_3)$ lower alkoxy, $(C_1-C_3)$ lower alkylamino, CONH $(C_1-C_3)$ lower alkyl, or —CON[lower alkyl $(C_1-C_3)$]$_2$, $R_b$ is independently selected from H, —$CH_3$, or —$C_2H_5$;

q is 1 or 2;

$R_3$ is the moiety

wherein Ar is a moiety selected from the group

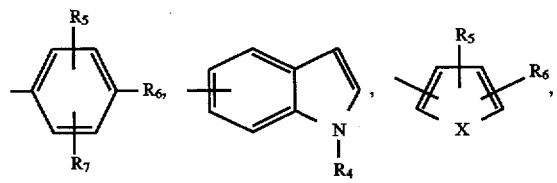

and X is selected from O, S, NH, —$NCH_3$, or —N—$COCH_3$;

$R_4$ is selected from H, lower alkyl $(C_1-C_3)$, —CO-lower alkyl $(C_1-C_3)$, $SO_2$ lower alkyl $(C_1-C_3)$, or the moieties of the formulae:

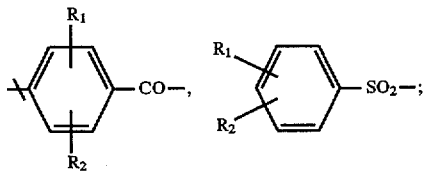

$R_1$ and $R_2$ are, independently, H, $(C_1-C_3)$ lower alkyl, $(C_1-C_3)$ lower alkoxy, or halogen;

$R_5$ is H, $(C_1-C_3)$ lower alkyl, $(C_1-C_3)$ lower alkoxy or halogen;

$R_6$ is selected from:

(a) moieties of the formula:

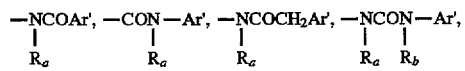

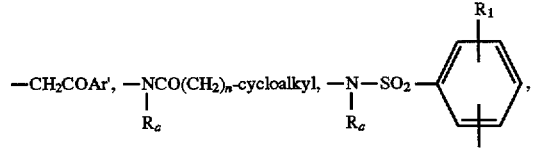

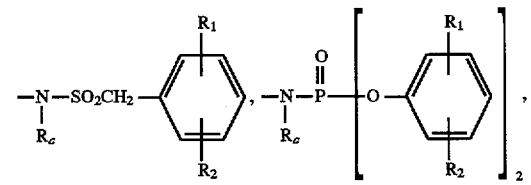

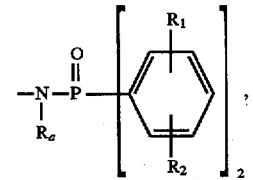

—NH—C(=O)—O-lower alkyl($C_1$–$C_8$) straight or branched,

—NH—C(=O)—lower alkyl($C_1$–$C_8$) straight or branched,

—$NHSO_2$-lower alkyl($C_1$–$C_8$) straight or branched,

—NH—C(=O)—O-lower alkenyl($C_1$–$C_8$) straight or branched,

—NH—C(=O)—lower alkenyl($C_1$–$C_8$) straight or branched,

—$NHSO_2$-lower alkenyl($C_1$–$C_8$) straight or branched, wherein cycloalkyl is defined as $C_3$ to $C_6$ cycloalkyl, cyclohexenyl or cyclopentenyl;

n is 0–2;

$R_a$ is independently selected from H, —$CH_3$, —$C_2H_5$,

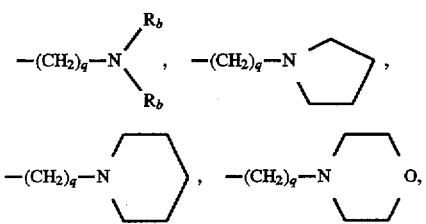

—$(CH_2)_q$Olower alkyl $(C_1C_3)$, or —$CH_2CH_2OH$;
$R_b$ is as hereinbefore defined;
q is 1 or 2;
(b) a moiety of the formula:

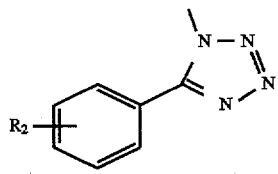

where $R_2$ is as hereinbefore defined;
(c) a moiety of the formula:

wherein J is $R_a$, lower alkyl $(C_1-C_8)$ branched or unbranched, lower alkenyl $(C_2-C_8)$ branched or unbranched, —O-lower alkyl $(C_1-C_8)$ branched or unbranched, —O-lower alkenyl $(C_2-C_8)$ branched or unbranched, tetrahydrofuran, tetrahydrothiophene, or —$CH_2$—K wherein K is halogen, $(C_1-C_3)$ lower alkoxy, tetrahydrofuran, tetrahydrothiophene or the heterocyclic ring moiety:

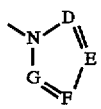

wherein D, E, F and G are selected from carbon or nitrogen and wherein the carbon atoms may be optionally substituted with halogen, $(C_1-C_3)$lower alkyl, hydroxy, —CO-lower alkyl $(C_1-C_3)$, CHO, $(C_1-C_3)$lower alkoxy, or —$CO_2$-lower alkyl $(C_1-C_3)$; and $R_a$ and $R_b$ are as hereinbefore defined;
(d) a moiety selected from those of the formulae:

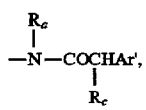

wherein $R_c$ is selected from halogen, $(C_1-C_3)$ lower alkyl, —O-lower alkyl $(C_1-C_3)$, OH

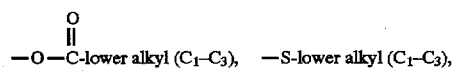

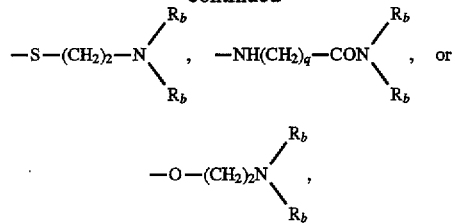

q is 1 or 2;
$R_a$ and $R_b$ are as hereinbefore defined; wherein Ar' is selected from the group:

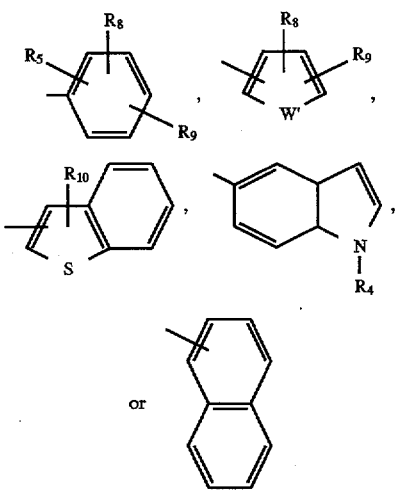

wherein
W' is selected from O, S, NH, N-lower alkyl $(C_1-C_3)$, —NHCO-lower alkyl $(C_1-C_3)$, or $NSO_2$-lower alkyl $(C_1-C_3)$;
$R_7$ is selected from H, lower alkyl $(C_1-C_3)$, halogen, —O-lower alkyl $(C_1-C_3)$, or $CF_3$;
$R_8$ and $R_9$ are independently selected from hydrogen, lower alkyl $(C_1-C_3)$, S-lower alkyl $(C_1-C_3)$, halogen, —N-lower alkyl $(C_1-C_3)$, —$OCF_3$, —CN, —OH, —S—$CF_3$, —$NO_2$, $NH_2$, or —O-lower alkyl $(C_1-C_3)$;
$R_{10}$ is H, halogen, or lower alkyl-$(C_1-C_3)$; and the pharmaceutically acceptable salts, esters and pro-drug forms thereof.

5. compounds of the formula:

and Ar is the moiety

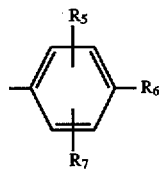

wherein $R_5$, $R_6$, and $R_7$ are as defined in the group above or a pharmaceutically acceptable salt, ester or pro-drug form thereof.

6. compounds of the formula:

$$-\overset{O}{\underset{\|}{C}}Ar$$

and Ar is the moiety

[benzene ring substituted with $R_5$, $R_6$, $R_7$]

wherein $R_5$, $R_6$, and $R_7$ are as defined in the group above and Ar' is selected from the moieties

[benzene ring substituted with $R_5$, $R_8$, $R_9$] or [five-membered ring with W', substituted with $R_8$, $R_9$]

wherein $R_5$, $R_8$, $R_9$ and W' are as defined in the group above, or a pharmaceutically acceptable salt, ester or pro-drug form thereof.

7. compounds of the formula:

$$-\overset{O}{\underset{\|}{C}}Ar$$

and Ar is the moiety

[benzene ring substituted with $R_5$, $R_6$, $R_7$]

wherein $R_5$ and $R_7$ are as defined in the group above and $R_6$ is selected from:

(a) moieties of the formula:

$$-\underset{R_a}{\overset{|}{N}}COAr', \quad -\underset{R_a}{\overset{|}{C}}ON-Ar', \quad -\underset{R_a}{\overset{|}{N}}COCH_2Ar', \quad -\underset{R_a}{\overset{|}{N}}\underset{R_b}{\overset{|}{C}}ON-Ar',$$

$$-CH_2COAr', \quad -\underset{R_a}{\overset{|}{N}}CO(CH_2)_n\text{-cycloalkyl}, \quad -\underset{R_a}{\overset{|}{N}}-SO_2-\text{[benzene with }R_1, R_2\text{]},$$

$$-\underset{R_a}{\overset{|}{N}}-SO_2CH_2-\text{[benzene with }R_1, R_2\text{]}, \quad -\underset{R_a}{\overset{|}{N}}-\overset{O}{\underset{\|}{P}}-O-\text{[benzene with }R_1, R_2\text{]},$$

$$\left[-\underset{R_a}{\overset{|}{N}}-\overset{O}{\underset{\|}{P}}-\text{[benzene with }R_1, R_2\text{]}\right]_2,$$

$$-NH-\overset{O}{\underset{\|}{C}}-O\text{-lower alkyl}(C_1-C_8) \text{ straight or branched},$$

$$-NH-\overset{O}{\underset{\|}{C}}\text{-lower alkyl}(C_1-C_8) \text{ straight or branched},$$

$-NHSO_2$-lower alkyl$(C_1-C_8)$ straight or branched, $$-NH-\overset{O}{\underset{\|}{C}}-O\text{-lower alkenyl}(C_1-C_8) \text{ straight or branched},$$

$$-NH-\overset{O}{\underset{\|}{C}}\text{-lower alkenyl}(C_1-C_8) \text{ straight or branched},$$

$-NHSO_2$-lower alkenyl$(C_1-C_8)$ straight or branched, wherein cycloalkyl is defined as $C_3$ to $C_6$ cycloalkyl, cyclohexenyl or cyclopentenyl;

n is 0–2;

$R_a$ is independently selected from H, $-CH_3$, $-C_2H_5$, $$-(CH_2)_q-N\underset{R_b}{\overset{R_b}{\diagup}}, \quad -(CH_2)_q-N\text{[pyrrolidine]},$$

$$-(CH_2)_q-N\text{[piperidine]}, \quad -(CH_2)_1-N\text{[morpholine]}O,$$

$-(CH_2)_q$ lower alkyl $(C_1C_3)$, or $-CH_2CH_2OH$;

q is 1 or 2;

$R_b$ is selected from H, $-CH_3$, or $C_2H_5$; or (b) a moiety of the formula:

$$-\underset{}{\overset{R_b}{\underset{|}{N}}}-COJ$$

wherein J is $R_a$, lower alkyl $(C_1-C_8)$ branched or unbranched, lower alkenyl $(C_2-C_8)$ branched or unbranched, $-O$-lower alkyl $(C_1-C_8)$ branched or unbranched, $-O$-lower alkenyl $(C_2-C_8)$ branched or unbranched, tetrahydrofuran, tetrahydrothiophene, or $-CH_2-K$ wherein K is halogen, $(C_1-C_3)$ lower alkoxy, tetrahydrofuran, tetrahydrothiophene or the heterocyclic ring moiety:

[five-membered ring with N, D, E, F, G]

wherein D, E, F and G are selected from carbon or nitrogen and wherein the carbon atoms may be optionally substituted with halogen, $(C_1-C_3)$lower alkyl, hydroxy, $-CO$-lower alkyl $(C_1-C_3)$, CHO, $(C_1-C_3)$lower alkoxy, or $-CO_2$-lower alkyl $(C_1-C_3)$; and $R_a$ and $R_b$ are as hereinbefore defined; or (c) a moiety selected from those of the formulae:

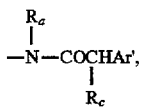

wherein $R_c$ is selected from halogen, $(C_1-C_3)$ lower alkyl, —O-lower alkyl $(C_1-C_3)$, OH,

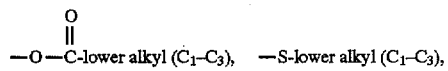

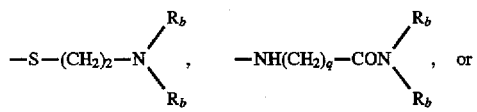

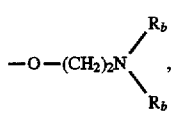

q is 1 or 2; and $R_a$ and $R_b$ are as hereinbefore defined; wherein Ar' is selected from the group:

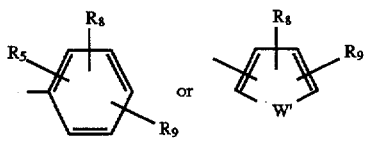

wherein $R_8$, $R_9$ and W' are as defined in the group above, or a pharmaceutically acceptable salt, ester or pro-drug form thereof.

8. compounds of the formula:

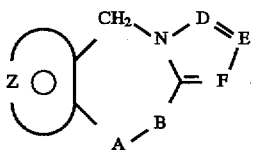
Formula I wherein;

A—B is

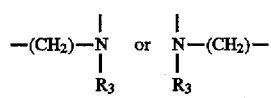

the moiety

represents a fused thiophene or fused substituted thiophene optionally substituted by one or two substituents selected from $(C_1-C_3)$ lower alkyl, halogen, amino, $(C_1-C_3)$ lower alkoxy, or $(C_1-C_3)$ lower alkylamino;

the moiety:

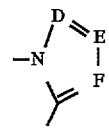

is a five-membered aromatic (unsaturated) fused nitrogen-containing heterocyclic ring wherein D is nitrogen and E, and F are carbon and wherein the carbon atoms may be optionally substituted by a substituent selected from halogen, $(C_1-C_3)$ lower alkyl, hydroxy, $COCCl_3$, $COCF_3$,

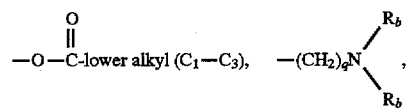

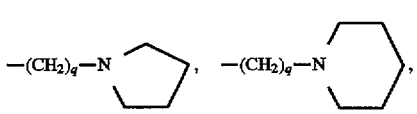

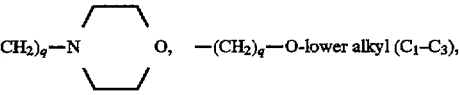

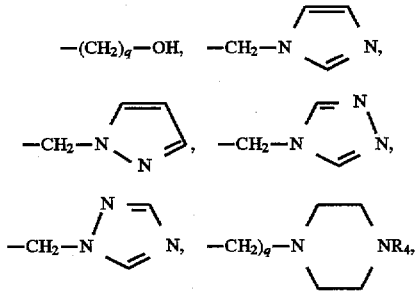

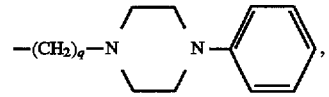

—CHO, amino, $(C_1-C_3)$ lower alkoxy, $(C_1-C_3)$ lower alkylamino , CONH $(C_1-C_3)$ lower alkyl, or —CON [lower alkyl $(C_1-C_3)$]$_2$, $R_b$ is independently selected from H, —$CH_3$, or —$C_2H_5$;

q is 1 or 2;

$R_3$ is the moiety

wherein Ar is a moiety selected from the group

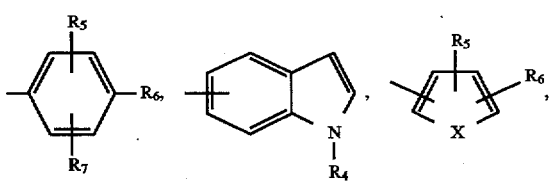

and X is selected from O, S, NH, —$NCH_3$, or —N—$COCH_3$;

$R_4$ is selected from H, lower alkyl ($C_1$-$C_3$), —CO-lower alkyl ($C_1$-$C_3$), $SO_2$ lower alkyl ($C_1$-$C_3$), or the moieties of the formulae:

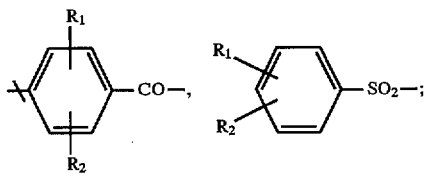

$R_1$ and $R_2$ are, independently, H, ($C_1$-$C_3$) lower alkyl, ($C_1$-$C_3$) lower alkoxy, or halogen;

$R_5$ is H, ($C_1$-$C_3$) lower alkyl, ($C_1$-$C_3$) lower alkoxy or halogen;

$R_6$ is selected from:
(a) moieties of the formula:

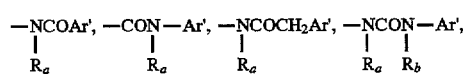

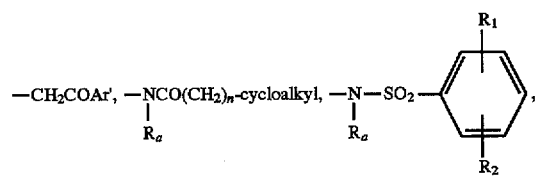

—NH—C(=O)—O-lower alkyl($C_1$-$C_8$) straight or branched,

—NH—C(=O)-lower alkyl($C_1$-$C_8$) straight or branched,

—NHSO$_2$-lower alkyl($C_1$-$C_8$) straight or branched,

—NH—C(=O)—O-lower alkenyl($C_1$-$C_8$) straight or branched,

—NH—C(=O)-lower alkenyl($C_1$-$C_8$) straight or branched,

—NHSO$_2$-lower alkenyl($C_1$-$C_8$) straight or branched, wherein cycloalkyl is defined as $C_3$ to $C_6$ cycloalkyl, cyclohexenyl or cyclopentenyl;

n is 0–2;

$R_a$ is independently selected from H, —CH$_3$, —C$_2$H$_5$,

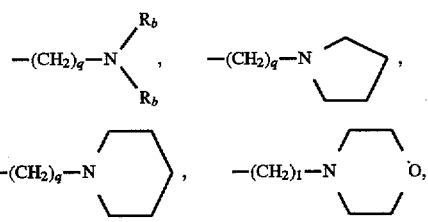

—(CH$_2$)$_q$Olower alkyl ($C_1$C$_3$), or —CH$_2$CH$_2$OH;

$R_b$ is as hereinbefore defined;

q is 1 or 2;

(b) a moiety of the formula:

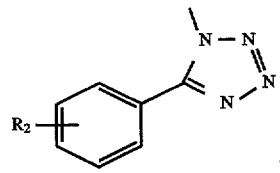

where $R_2$ is as hereinbefore defined;

(c) a moiety of the formula:

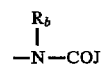

wherein J is $R_a$, lower alkyl ($C_1$-$C_8$) branched or unbranched, lower alkenyl ($C_2$-$C_8$) branched or unbranched, —O-lower alkyl ($C_1$-$C_8$) branched or unbranched, —O-lower alkenyl ($C_2$-$C_8$) branched or unbranched, tetrahydrofuran, tetrahydrothiophene, or —CH$_2$—K wherein K is halogen, ($C_1$-$C_3$) lower alkoxy, tetrahydrofuran, tetrahydrothiophene or the heterocyclic ring moiety:

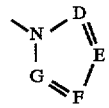

wherein D, E, F and G are selected from carbon or nitrogen and wherein the carbon atoms may be optionally substituted with halogen, ($C_1$-$C_3$)lower alkyl, hydroxy, —CO-lower alkyl ($C_1$-$C_3$), CHO, ($C_1$-$C_3$) lower alkoxy, or —CO$_2$-lower alkyl ($C_1$-$C_3$); and $R_a$ and $R_b$ are as hereinbefore defined;

(d) a moiety selected from those of the formulae:

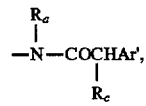

wherein $R_c$ is selected from halogen, ($C_1$-$C_3$) lower alkyl, —O-lower alkyl ($C_1$-$C_3$), OH

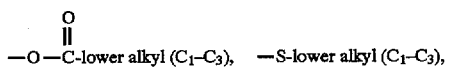

-continued

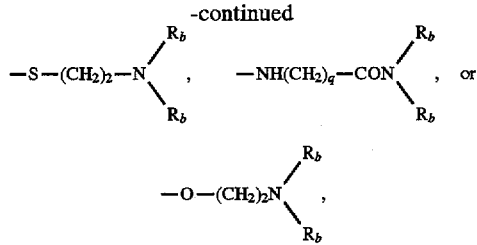

q is 1 or 2;

$R_a$ and $R_b$ are as hereinbefore defined;
wherein Ar' is selected from the group:

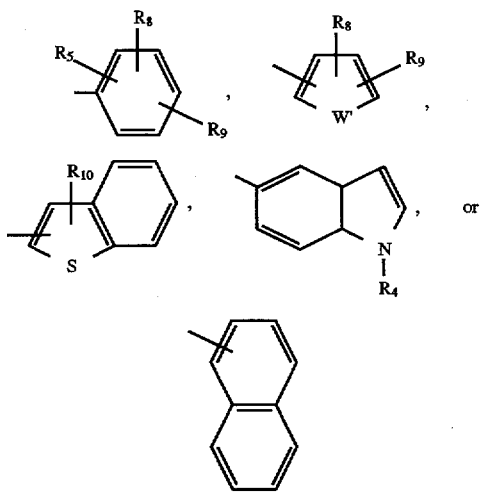

wherein
W' is selected from O, S, NH, N-lower alkyl ($C_1$–$C_3$), —NHCO-lower alkyl ($C_1$–$C_3$), or $NSO_2$-lower alkyl ($C_1$–$C_3$);

$R_7$ is selected from H, lower alkyl ($C_1$–$C_3$), halogen, —O-lower alkyl ($C_1$–$C_3$), or $CF_3$;

$R_8$ and $R_9$ are independently selected from hydrogen, lower alkyl ($C_1$–$C_3$), S-lower alkyl ($C_1$–$C_3$), halogen, —N-lower alkyl ($C_1$–$C_3$), —$OCF_3$, —CN, —OH, —S—$CF_3$, —$NO_2$, $NH_2$, or —O-lower alkyl ($C_1$–$C_3$);

$R_{10}$ is H, halogen, or lower alkyl-($C_1$–$C_3$); and the pharmaceutically acceptable salts, esters and pro-drug forms thereof.

9. compounds of the formula:

and Ar is the moiety

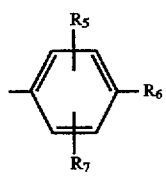

wherein $R_5$, $R_6$, and $R_7$ are as defined in the group above or a pharmaceutically acceptable salt, ester or pro-drug form thereof.

10. compounds of the formula:

and Ar is the moiety

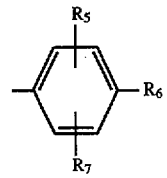

wherein $R_5$, $R_6$, and $R_7$ are as defined in the group above and Ar' is selected from the moieties

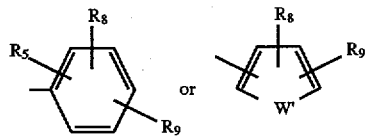

wherein $R_5$, $R_8$, $R_9$ and W' are as defined in the group above, or a pharmaceutically acceptable salt, ester or pro-drug form thereof.

11. compounds of the formula:

and Ar is the moiety

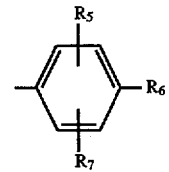

wherein $R_5$ and $R_7$ are as defined in the group above and $R_6$ is selected from:

(a) moieties of the formula:

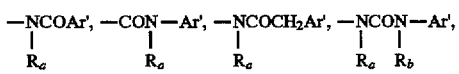
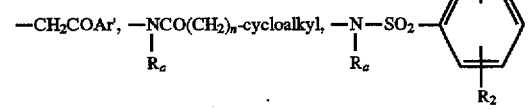
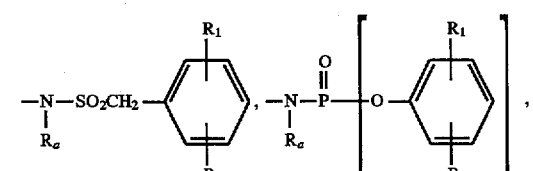

-continued

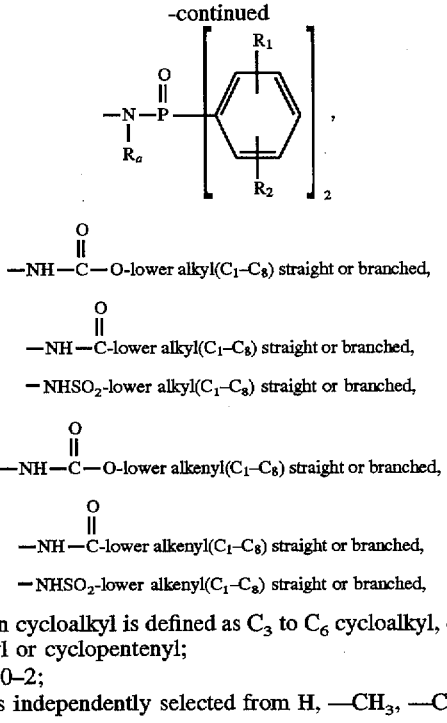

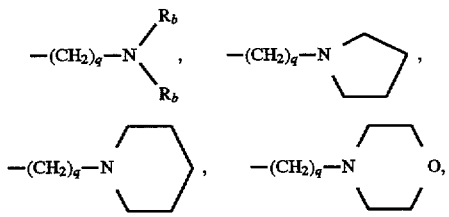

—NHSO₂-lower alkenyl(C₁–C₈) straight or branched, wherein cycloalkyl is defined as C₃ to C₆ cycloalkyl, cyclohexenyl or cyclopentenyl;

n is 0–2;

$R_a$ is independently selected from H, —CH₃, —C₂H₅,

—(CH₂)$_q$ lower alkyl (C₁C₃), or —CH₂CH₂OH;
q is 1 or 2;

$R_b$ is selected from H, —CH₃, or C₂H₅; or (b) a moiety of the formula:

$$\begin{array}{c} R_b \\ | \\ -N-COJ \end{array}$$

wherein J is $R_a$, lower alkyl (C₁–C₈) branched or unbranched, lower alkenyl (C₂–C₈) branched or unbranched, —O-lower alkyl (C₁–C₈) branched or unbranched, —O-lower alkenyl (C₂–C₈) branched or unbranched, tetrahydrofuran, tetrahydrothiophene, or —CH₂—K wherein K is halogen, (C₁–C₃) lower alkoxy, tetrahydrofuran, tetrahydrothiophene or the heterocyclic ring moiety:

wherein D, E, F and G are selected from carbon or nitrogen and wherein the carbon atoms may be optionally substituted with halogen, (C₁–C₃) lower alkyl, hydroxy, —CO-lower alkyl (C₁–C₃), CHO, (C₁–C₃) lower alkoxy, or —CO₂-lower alkyl (C₁–C₃); and $R_a$ and $R_b$ are as hereinbefore defined; or (c) a moiety selected from those of the formulae:

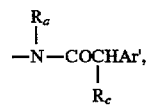

wherein $R_c$ is selected from halogen, (C₁–C₃) lower alkyl, —O-lower alkyl (C₁–C₃), OH,

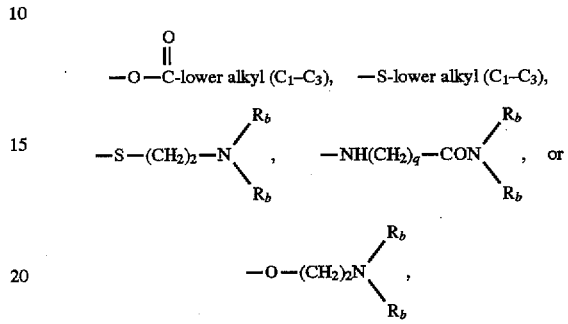

q is 1 or 2; and $R_a$ and $R_b$ are as hereinbefore defined; wherein Ar' is selected from the group:

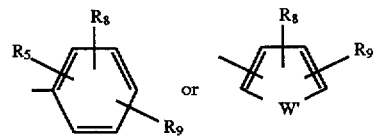

wherein $R_8$, $R_9$ and W' are as defined in the group above, or a pharmaceutically acceptable salt, ester or pro-drug form thereof.

Among the more preferred compounds of this invention are those selected from:

N-[4-(5H-pyrrolo[1,2-a]thieno[3,2-e][1,4]diazepin-4(10H)-ylcarbonyl)phenyl]-2,4-dichlorobenzamide.

N-[4-(5H-pyrrolo[1,2-a]thieno[3,2-e][1,4]diazepin-4(10H)-ylcarbonyl)-3-chlorophenyl]-5-fluoro-2-methylbenzamide.

N-[4-(5H-pyrrolo[1,2-a]thieno[3,2-e][1,4]diazepin-4(10H)-ylcarbonyl)-3-chlorophenyl]-3-fluoro-2-methylbenzamide.

N-[4-(5H-pyrrolo[1,2-a]thieno[3,2-e][1,4]diazepin-4(10H)-ylcarbonyl)-3-chlorophenyl]-2-chloro-4-fluorobenzamide.

N-[4-(5H-pyrrolo[1,2-a]thieno[3,2-e][1,4]diazepin-4(10H)-ylcarbonyl)-3-chlorophenyl]-2-chloro-5-fluorobenzamide.

N-[4-(5H-pyrrolo[1,2-a]thieno[3,2-e][1,4]diazepin-4(10H)-ylcarbonyl)-3-chlorophenyl]-2-methylbenzamide.

N-[4-(5H-pyrrolo[1,2-a]thieno[3,2-e][1,4]diazepin-4(10H)-ylcarbonyl)-3-chlorophenyl]-2,4-dichloro-benzamide.

N-[4-(5H-pyrrolo[1,2-a]thieno[3,2-e][1,4]diazepin-4(10H)-ylcarbonyl)-3-chlorophenyl]-2-chlorobenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-2-methylbenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-5-fluoro-2-methylbenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-3-fluoro-2-methylbenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-2,4-dichlorobenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-2-chlorobenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-2-chloro-4-fluorobenzamide.

N-[4-[[8-[(dimethylamino)methyl]-5H-pyrrolo[1,2-a]thieno[3,2-e][1,4]diazepin-4(10H)-yl]carbonyl]-3-chlorophenyl]-2-chloro-5-fluorobenzamide.

N-[4-(5H-pyrrolo[1,2-a]thieno[3,2-e][1,4]diazepin-4(10H)-ylcarbonyl)phenyl]-5-fluoro-2-methylbenzamide.

N-[4-(5H-pyrrolo[1,2-a]thieno[3,2-e][1,4]diazepin-4(10H)-ylcarbonyl)-3-methylphenyl]-5-fluoro-2-methylbenzamide.

N-[4-(5H-pyrrolo[1,2-a]thieno[3,2-e][1,4]diazepin-4(10H)-ylcarbonyl)-3-methylphenyl]-3-fluoro-2-methylbenzamide.

N-[4-(5H-pyrrolo[1,2-a]thieno[3,2-e][1,4]diazepin-4(10H)-ylcarbonyl)-3-methylphenyl]-2-chloro-4-fluorobenzamide.

N-[4-(5H-pyrrolo[1,2-a]thieno[3,2-e][1,4]diazepin-4(10H)-ylcarbonyl)-3-methylphenyl]-2-chloro-5-fluorobenzamide.

N-[4-(5H-pyrrolo[1,2-a]thieno[3,2-e][1,4]diazepin-4(10H)-ylcarbonyl)-3-methylphenyl]-2-methylbenzamide.

N-[4-(5H-pyrrolo[1,2-a]thieno[3,2-e][1,4]diazepin-4(10H)-ylcarbonyl)-3-methylphenyl]-2,4-dichlorobenzamide.

1N-[4-(5H-pyrrolo[1,2-a]thieno[3,2-e][1,4]diazepin-4(10H)-ylcarbonyl)-3-methylphenyl]-2-chlorobenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-2-methylbenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-5-fluoro-2-methylbenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-3-fluoro-2-methylbenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-2,4-dichlorobenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-2-chlorobenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-2-chloro-4-fluorobenzamide.

N-[4-[[8-[(dimethylamino)methyl]-5H-pyrrolo[1,2-a]thieno[3,2-e][1,4]diazepin-4(10H)-yl]carbonyl]-3-methylphenyl]-2-chloro-5-fluorobenzamide.

N-[4-(5H-pyrazolo[1,5-a]thieno[3,2-e][1,4]diazepin-4(10H)-ylcarbonyl)phenyl]-2-methylbenzamide.

N-[4-(5H-pyrazolo[1,5-a]thieno[3,2-e][1,4]diazepin-4(10H)-ylcarbonyl)-3-chlorophenyl]-2-methylbenzamide.

N-[4-(5H-pyrazolo[1,5-a]thieno[3,2-e][1,4]diazepin-4(10H)-ylcarbonyl)-3-chlorophenyl]-2-methyl-5-fluorobenzamide.

N-[4-(5H-pyrazolo[1,5-a]thieno[3,2-e][1,4]diazepin-4(10H)-ylcarbonyl)-3-chlorophenyl]-2-methyl-3-fluorobenzamide.

N-[4-(5H-pyrazolo[1,5-a]thieno[3,2-e][1,4]diazepin-4(10H)-ylcarbonyl)-3-chlorophenyl]-2-methyl-5-chlorobenzamide.

N-[4-(5H-pyrazolo[1,5-a]thieno[3,2-e][1,4]diazepin-4(10H)-ylcarbonyl)-3-chlorophenyl]-2,5-dimethylbenzamide.

N-[4-(5H-pyrazolo[1,5-a]thieno[3,2-e][1,4]diazepin-4(10H)-ylcarbonyl)phenyl]-2-chloro-5-fluorobenzamide.

N-[4-(5H-pyrazolo[1,5-a]thieno[3,2-e][1,4]diazepin-4(10H)-ylcarbonyl)-3-chlorophenyl]-2-(trifluoromethyl)benzamide.

N-[4-(5H-pyrazolo[1,5-a]thieno[3,2-e][1,4]diazepin-4(10H)-ylcarbonyl)-3-methylpheny]-2-methyl-5-fluorobenzamide.

N-[4-(5H-pyrazolo[1,5-a]thieno[3,2-e][1,4]diazepin-4(10H)-ylcarbonyl)-3-methylpheny]-2-methyl-3-fluorobenzamide.

N-[4-(5H-pyrazolo[1,5-a]thieno[3,2-e][1,4]diazepin-4(10H)-ylcarbonyl)-3-methylpheny]-2-chloro-5-fluorobenzamide.

N-[4-(5H-pyrazolo[1,5-a]thieno[3,2-e][1,4]diazepin-4(10H)-ylcarbonyl)-3,6-dimethylphenyl]-2-methyl-5-fluoro-benzamide.

N-[4-(5H-pyrazolo[1,5-a]thieno[3,2-e][1,4]diazepin-4(10H)-ylcarbonyl)phenyl]-2,5-dimethylbenzamide.

N-[4-(5H-pyrazolo[1,5-a]thieno[3,2-e][1,4]diazepin-4(10H)-ylcarbonyl)-3-chlorophenyl]-2,3-dimethylbenzamide.

N-[4-(5H-pyrazolo[1,5-a]thieno[3,2-e][1,4]diazepin-4(10H)-ylcarbonyl)-3-chlorophenyl]-3-methylthiophene-2-carboxamide.

N-[4-(5H-pyrazolo[1,5-a]thieno[3,2-e][1,4]diazepin-4(10H)-ylcarbonyl)-3-chlorophenyl]-2-methylthiophene-3-carboxamide.

N-[4-(5H-pyrazolo[1,5-a]thieno[3,2-e][1,4]diazepin-4(10H)-ylcarbonyl)-3-chlorophenyl]-2-(trifluoromethyl)benzamide.

N-[4-(5H-pyrazolo[1,5-a]thieno[3,2-e][1,4]diazepin-4(10H)-ylcarbonyl)-2-chloro-6-fluorobenzamide.

Compounds of this invention may be prepared as shown in Scheme I by reaction of tricyclic derivatives of Formula 3a and 3b with a substituted or unsubstituted 4-nitrobenzoyl chloride 4 to give the intermediates 5a and 5b. Reduction of the nitro group in intermediates 5a and 5b gives the 4-aminobenzoyl derivatives 6a and 6b. The reduction of the nitro group in intermediates 5a and 5b may be carried out under catalytic reduction conditions (hydrogen-Pd/C; Pd/C-hydrazine-ethanol) or under chemical reduction conditions ($SnCl_2$-ethanol; Zn-acetic acid; $TiCl_3$) and related reduction conditions known in the art for converting a nitro group to an amino group. The conditions for conversion of the nitro group to the amino group are chosen on the basis of compatability with the preservation of other functional groups in the molecule.

Reaction of compounds of Formula 6a and 6b with aroyl chloride or related activated arylcarboxylic acids in solvents such as chloroform, dichloromethane, dioxane, tetrahydrofuran, toluene and the like in the presence of a tertiary base such as triethylamine and diisopropylethylamine or pyridine and the like, affords the compounds 8a and 8b which are vasopressin antagonists.

Scheme 1
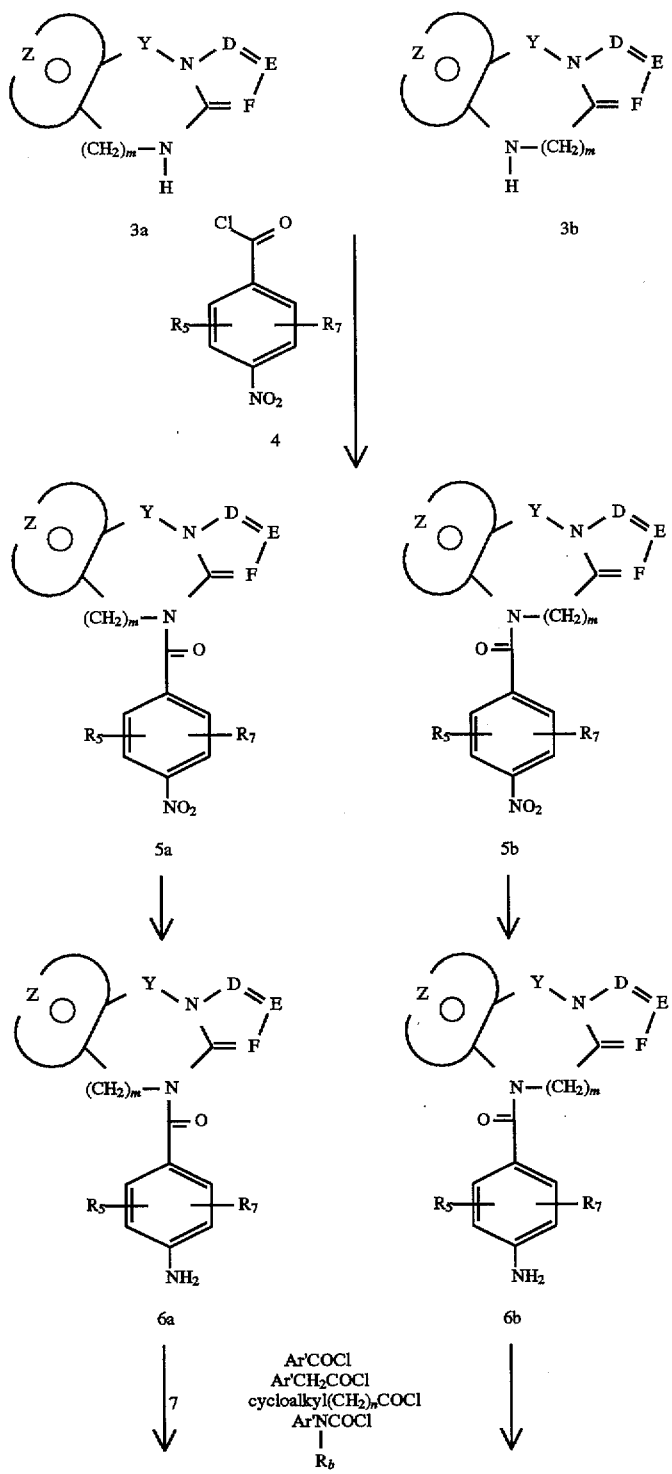

-continued
Scheme 1

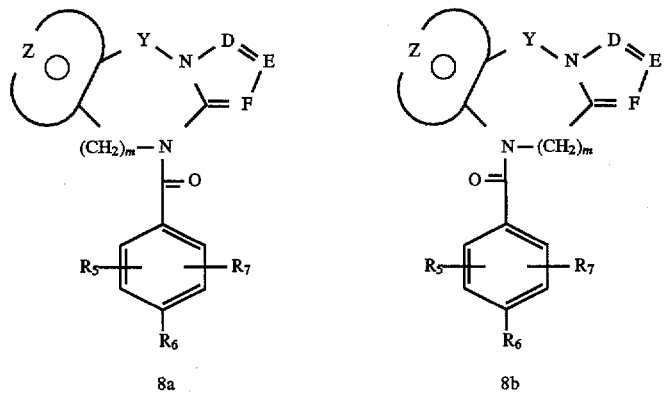

8a          8b $R_6$ = NHCOAr'; —NHCOCH$_2$Ar';
—NHCO(CH$_2$)$_n$cycloalkyl; —NHCON—Ar'
$\quad\quad\quad\quad\quad\quad\quad\quad\quad\quad\quad$ |
$\quad\quad\quad\quad\quad\quad\quad\quad\quad\quad\quad$ R$_b$ Reaction of tricyclic derivatives of Formula 6a and 6b with either a carbamoyl derivative 9 or a isocyanate derivative 10 gives compounds (Scheme 2) of Formula 11a and 11b which are vasopressin antagonists of Formula I wherein $R_6$ is

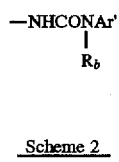

—NHCONAr'
$\quad\quad$ |
$\quad\quad$ R$_b$

Scheme 2

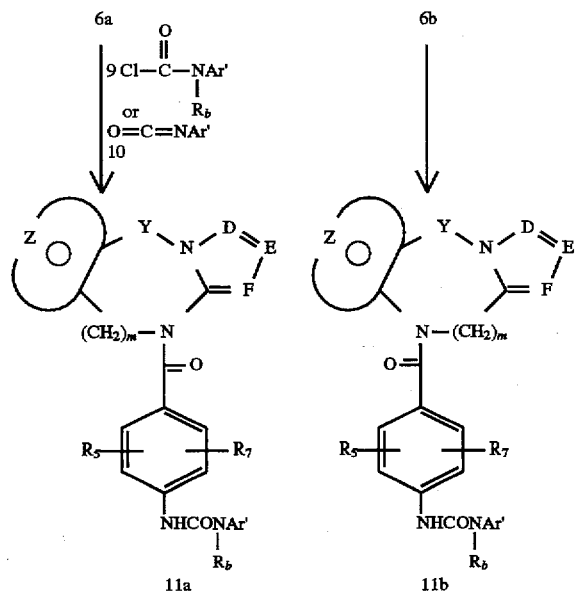

11a          11b

Reaction of tricyclic derivatives of Formula 6a and 6b with arylacetic acids, activated as the acid chlorides 12, anhydrides, mixed anhydrides or activated with known activating reagents, gives compounds 13a and 13b (Scheme 3).

Scheme 3

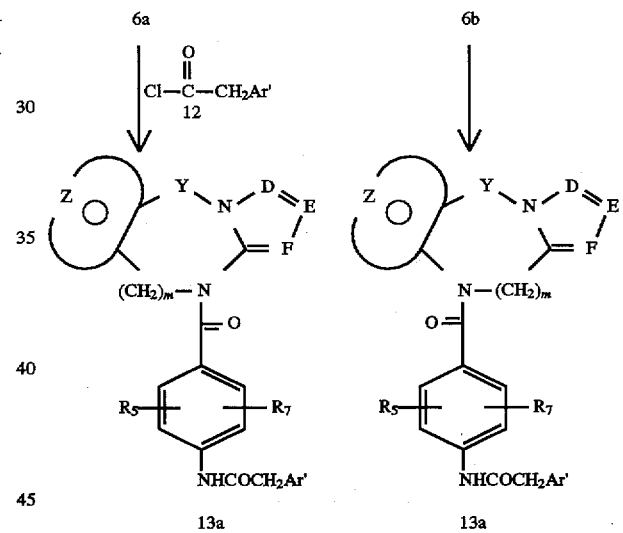

13a          13a

The compounds of Formula I wherein Y, A-B, Z, $R_1$, $R_2$ and $R_3$ are as defined and the Ar moiety of $R_3$ (—COAr) is

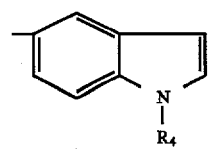

may be prepared, as shown in Scheme 4, by reacting an activated ester of the indole-5-carboxylic acids 14 with tricyclic derivatives 3a and 3b. The indole-5-carboxylic acids 14 may be activated by preparing the anhydride, a mixed anhydride or reacting with diethyl cyanophosphonate, N,N-carbonyldiimidazole or related peptide coupling reagents. As an example, the derivative 15 may be prepared by the acid 14 and N,N-carbonyldiimidazole in tetrahydrofuran; the solvent is removed and the derivative reacted with 3a or 3b at 100° C. to 120° C. without a solvent. Alternatively, 3a and 3b may be reacted with 15 in a solvent such as toluene or xylene at reflux temperatures. The activating reagent for the indole acids 14 is chosen on the basis of its compatibility with the $R_4$ group and its reactivity with the tricyclic derivatives 3a and 3b to give the vasopressin antagonists 163 and 16b.

Scheme 4

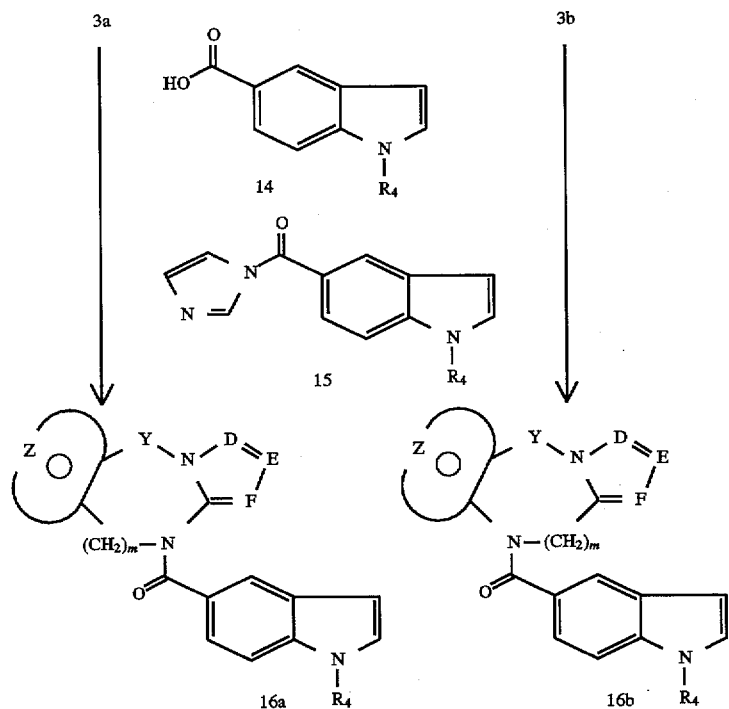

The compounds of Formula I wherein Y, A-B, Z, $R_1$ $R_2$ and $R_3$ are as defined and the Ar moiety of $R_3$ (—COAr) is

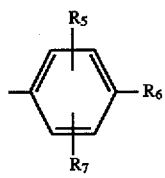

wherein $R_6$ is

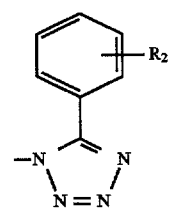

wherein may be prepared as shown in Scheme 5 by first converting derivatives 8a and 8b into the intermediates 17a and 17b and then reacting these intermediates with sodium or lithium azide to give the products 18a and 18b.

Scheme 5

-continued
Scheme 5

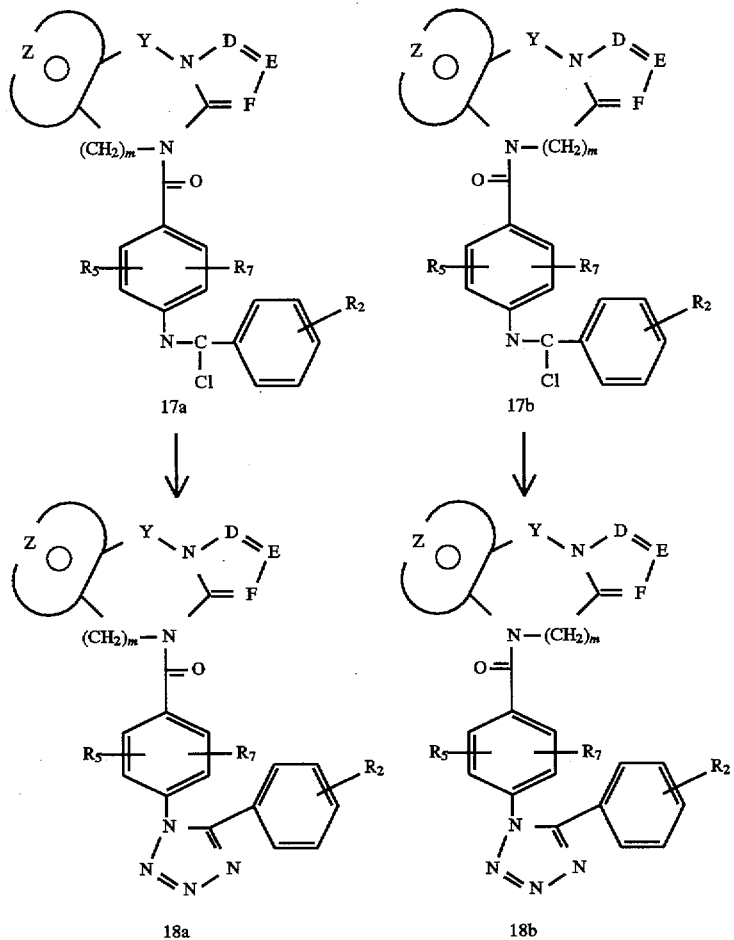

Alternatively, the products 18a and 18b may be prepared by coupling tetrazole derivatives of the Formula 19 with tricyclic derivatives 3a and 3b (Scheme 6). The tetrazole carboxylic acids are activated for coupling to the tricyclic compounds 3a and 3b by reaction with peptide coupling reagents, by conversion to the acid chlorides, anhydrides or mixed anhydrides.

Scheme 6

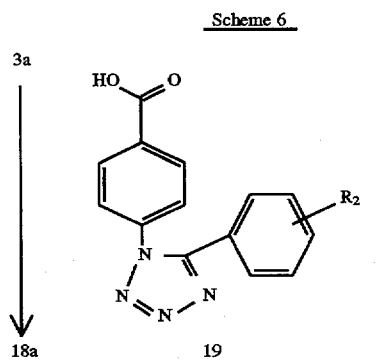

As an alternative method for synthesis of compounds of this invention as depicted in Formula I wherein Y, A-B, D, E, F and Z are as previously described and $R_3$ is $$\begin{matrix} O \\ \| \\ -CAr \end{matrix}$$

is the coupling of arylcarboxylic acids 20 with the tricyclic derivatives 3a and 3b to give 21a and 21b.

The arylcarboxylic acids are activated for coupling by conversion to an acid chloride, bromide or anhydride or by first reacting with an activating reagent such as N,N-dicyclocarbodiimide, diethyl cyanophosphonate and related "peptide type" activating reagents. The method of activating the acids 20 for coupling to the tricyclic derivatives 3a and 3b is chosen on the basis of compatibility with other substituent groups in the molecule. The method of choice is the conversion of the aryl carboxylic acids 20 to the corresponding aroyl chloride. The aryl acid chlorides 22 may be prepared by standard procedures known in the art, such as reaction with thionyl chloride, oxalyl chloride and the like. The coupling reaction is carried out in solvents such as halogenated hydrocarbons, toluene, xylene, tetrahydrofuran dioxane in the presence of pyridine or tertiary bases such as triethylamine and the like (Scheme 7). Alternatively, the aroyl chlorides 22, prepared from the aryl carboxylic acids 20, may be reacted with derivatives 3a and 3b in pyridine with or without 4-(dimethylamino)pyridine.

In general, when the arylcarboxylic acids 20 are activated with N,N-carbonyldiimidazole and other "peptide type"

activating reagents, higher temperatures are required than when the aroyl chlorides are used. The reaction may be carried out in a higher boiling solvent xylene or without a solvent (100° C. to 150° C.).
Scheme 7
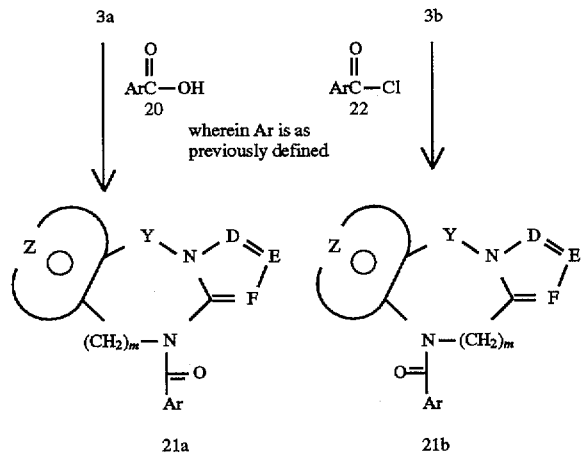
-continued
Scheme 7
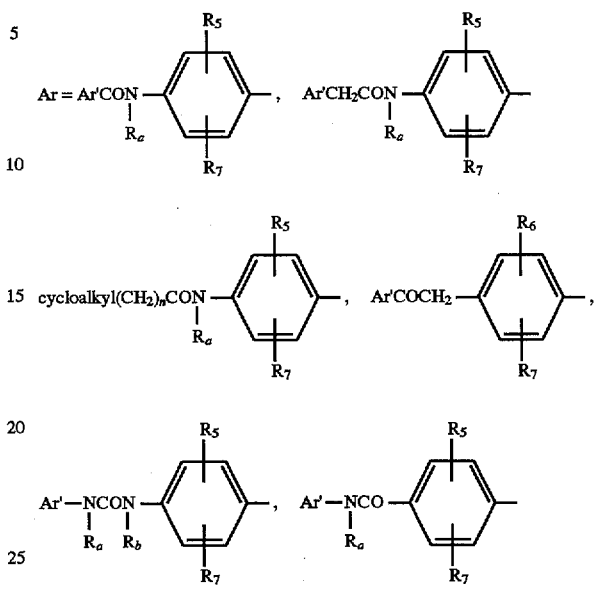
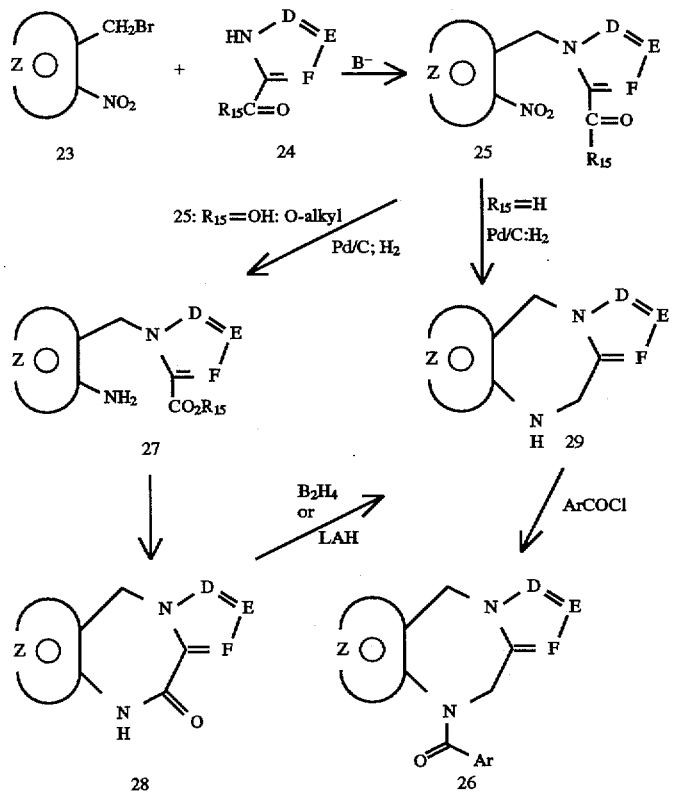

The starting materials 3a and 3b in the foregoing Schemes 1–7 may be prepared as follows. In accordance with Scheme 8, alkylation of heterocycles of structural type 24 with an alkylating moiety such as 23 gives intermediates 25. The heterocycle 24 may contain an α-carboxaldehyde function or an α-carboxylic and/or ester function as shown in Scheme 8. Where the intermediate 25 ($R_{15}$=H) contains an α-carboxaldehyde group, hydrogenation with palladium-on-carbon gives reduction and ring closure in one step to give 29.

In derivatives 25 where $R_{15}$ is an α-carboxylic and/or an α-carboxylic ester function, the intermediate amino acid derivative 27 is first isolated and then ring closed. The ring closure of derivatives 27 may be carried out by heating or by activation of the acid function (27:$R_{15}$=H) for ring closure. The cyclic lactams 28 are conveniently reduced with diborane or lithium aluminum hydride to give intermediates 29. Reaction of tricyclic derivatives 29 with aroyl chlorides (ArCOCl), where Ar is as hereinbefore defined, gives diazepines 26.

Tricyclic derivatives of structural type 36 may be prepared as shown in Scheme 9. Formylation of 32 under known conditions in the literature, such as Vilsmeier formylation, gives intermediates 35 which on reduction and ring closure affords tricyclics 37.

Where Z is a fused substituted or unsubstituted phenyl group, the procedure gives pyrrolo[1,2-a]quinoxalines 36. These derivatives 36 and 37 may be reacted with aroyl chlorides (ArCOCl) wherein Ar is as previously defined or with a substituted or unsubstituted 4-nitrobenzoyl chloride or with a nitrogen protecting group, such as benzyloxycarbonyl chloride to give compounds 38 and 39. The compounds 38 and 39 may be reacted with chlorine, bromine or halogenating reagents such as N-chlorosuccinimide, N-bromosuccinimide and the like to give compounds 40 and 41 wherein $R_{17}$ is a halogen atom. The derivatives 38 and 39 may be formylated and acetylated to give products 40 and 41 wherein $R_{17}$ is a CHO or a —COCH$_3$ group. Halogenation, formylation and acetylation of derivatives 36 gives 1-substituted pyrrolo[1,2-a]quinoxalines. The derivatives 38, 39, 40 and 41 wherein $R_{16}$ is a substituted or unsubstituted 4-nitrobenzoyl group are reduced to give the 4-aminobenzoyl derivatives 42d and 43d which are reacted with reagents Ar'COCl, Ar'CH$_2$COCl or Ar'—NCOCl;
|
$R_b$ wherein Ar' and $R_b$ are as previously hereinbefore defined, to give tricyclic diazepines 44 and 45.

Scheme 9

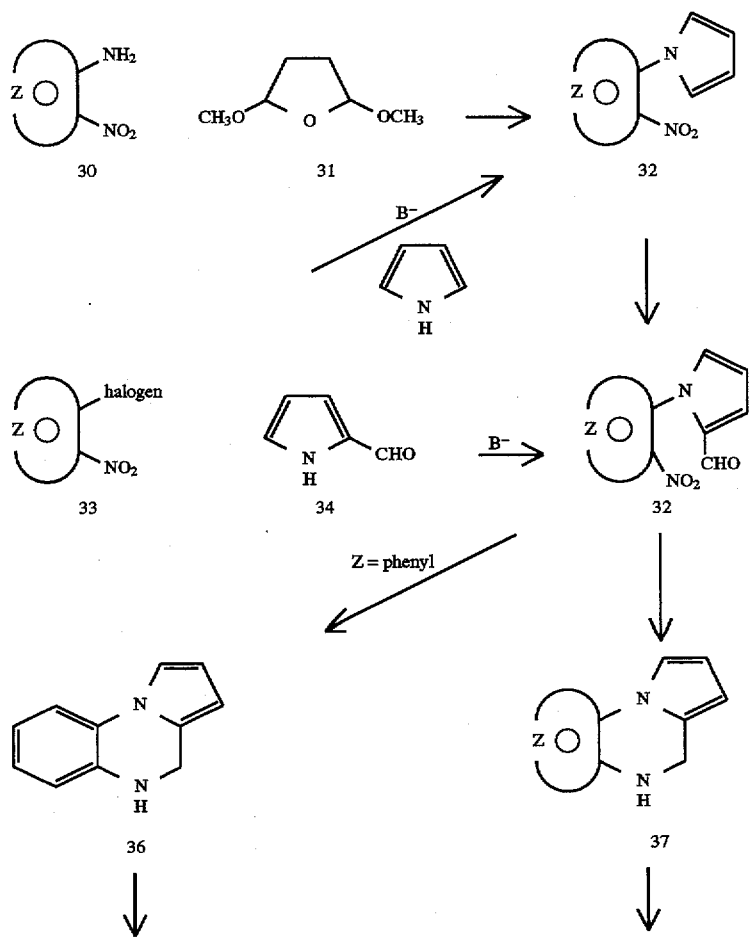

-continued
Scheme 9
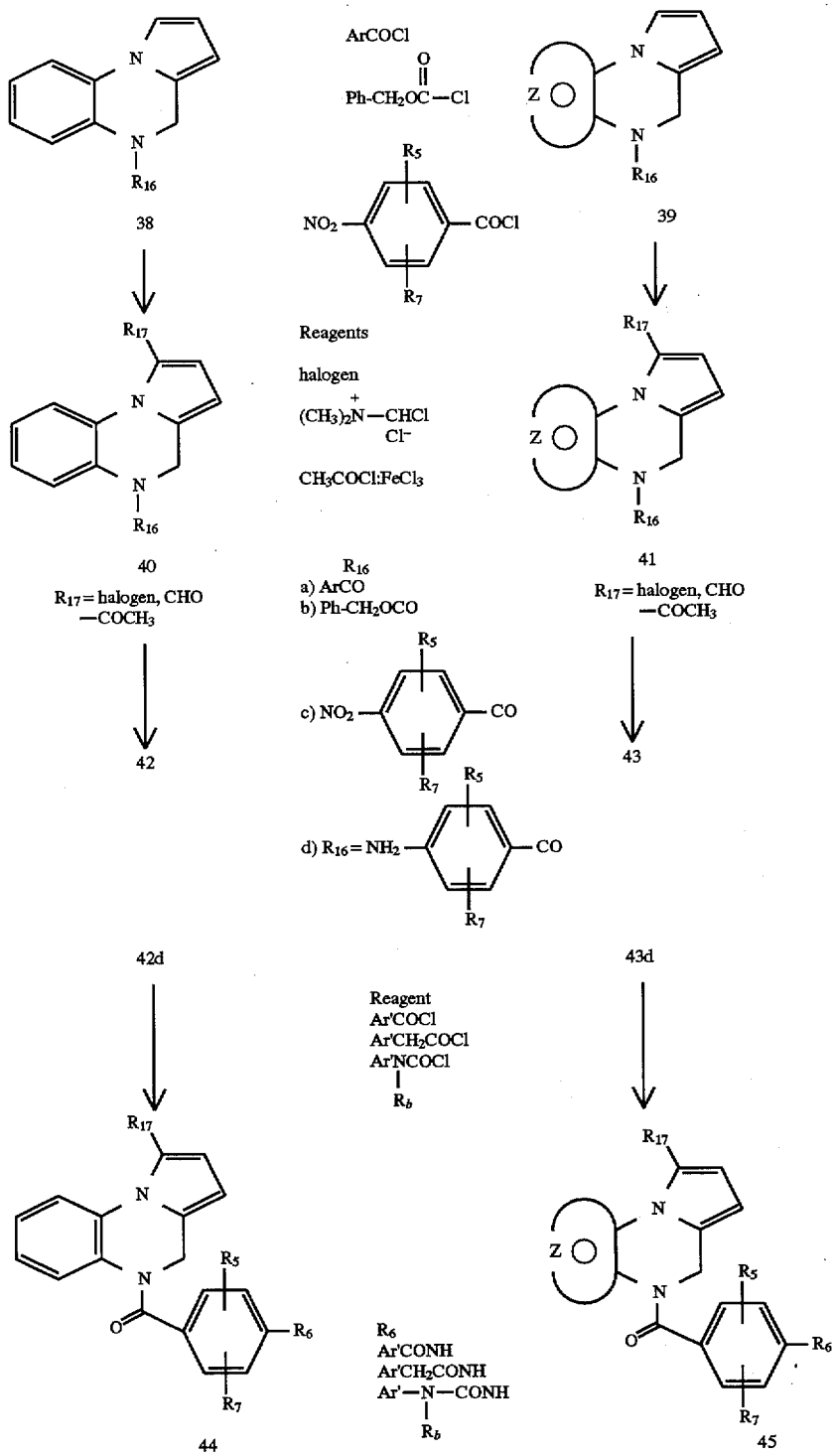

The compounds of this invention wherein $R_3$ is the moiety:

and the Ar group is the moiety:

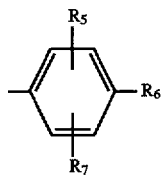

and $R_6$ is a

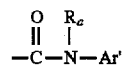

group, wherein $R_a$, $R_5$, $R_7$ and Ar' are as previously hereinbefore defined, are synthesized as shown in Scheme 10. The tricyclic derivatives 46 and 47 are reacted with the mono methyl terephthaloyl chloride 48 to give the aroylated methyl ester compounds 49 and 50. Hydrolysis of the methyl esters 49 and 50 gives the acids 51 and 52 which are activated for coupling by conversion to an activated ester or converted to the acid chlorides 53 and 54. Reaction of the acid chlorides 53 and 54 with the amines,

wherein $R_a$ and Ar' are as hereinbefore defined gives the derivatives 55 and 56.

Scheme 10

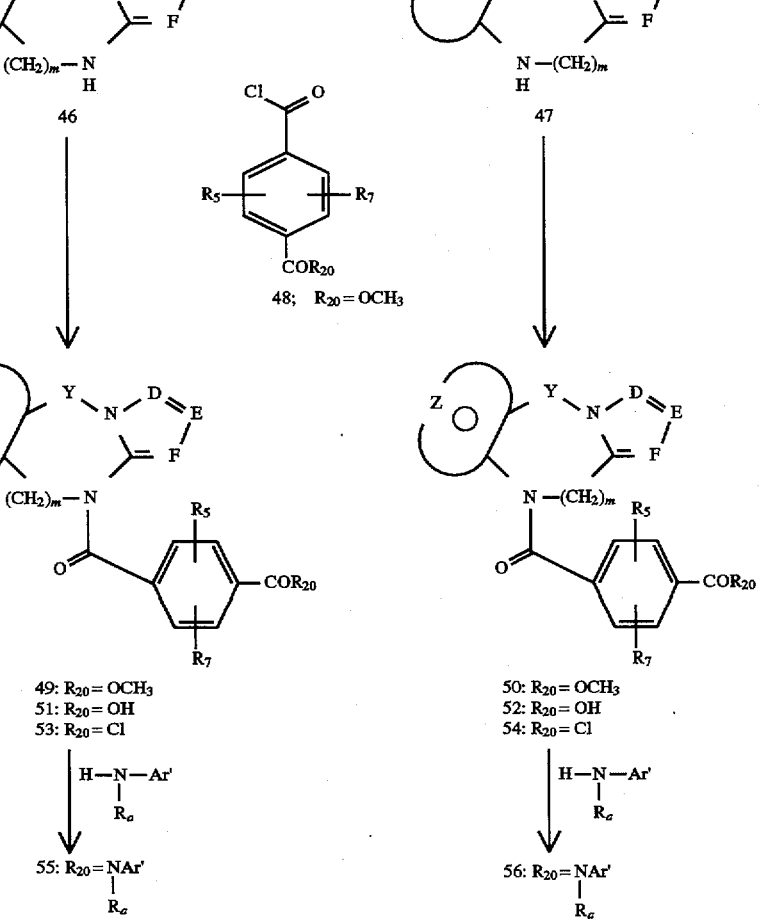

Preparation of some tricyclic diazepines useful for starting materials for the synthesis of compounds of this invention are shown in Schemes 8 and 9. Other tricyclic diazepines are prepared by literature procedures or by methods known in the art or by procedures reported for the synthesis of specific known tricyclic diazepines. These diazepine ring systems discussed below when subjected to reaction conditions shown in Schemes 1, 2, 3, 4, 5, 6, 7, 9 and 10 give the compounds of this invention.

The tricyclic diazepine ring system, 10,11-dihydro-5H-imidazo[2,1-c][1,4]benzodiazepine,

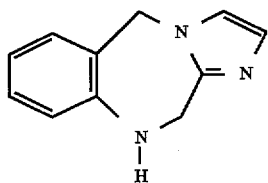

is reported by G. Stefancich, R. Silvestri and M. Artico, *J. Het. Chem.* 30, 529(1993); ring substitution on the same ring system is reported by G. Stefancich, M. Artico, F. Carelli, R. Silvestri, G. deFeo, G. Mazzanti, I. Durando, M. Palmery, *IL Farmaco, Ed. Sc.*, 40, 429(1985).

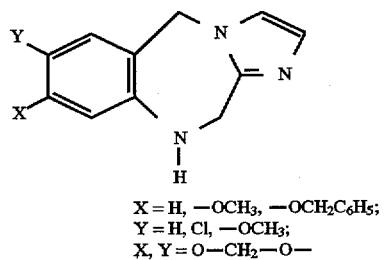

X = H, —OCH₃, —OCH₂C₆H₅;
Y = H, Cl, —OCH₃;
X, Y = O—CH₂—O—

The synthesis of 9,10-dihydro-4H-furo[2,3-e]-pyrrolo[1,2-a][1,4]diazepin-9-one

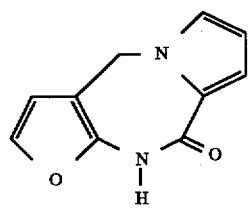

is reported by F. Povazunec, B. Decroix and J. Morel, *J. Het. Chem.* 29, 1507(1992) and is reduced to give the tricyclic heterocycle 9,10-dihydro-4H-furo[2,3-e]-pyrrolo[1,2-a][1,4]diazepine.

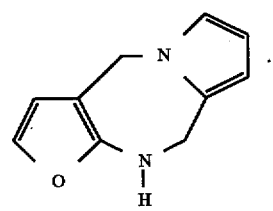

The tricyclic 5,10-dihydro-4H-pyrazolo[5,1-c][1,4]-benzodiazepine ring system is reported by L. Cecchi and G. Filacchioni, *J. Het. Chem.*, 20, 871(1983);

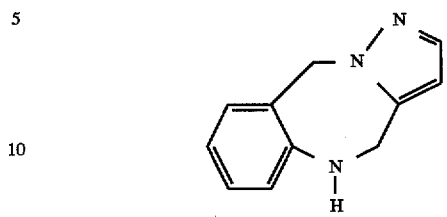

The synthesis of 9-oxo-9,10-dihydro-4H-pyrrolo[1,2-a]-thieno[2,3-e][1,4]diazepine is reported by A. Daich and B. Decroix, *Bull. Soc. Chim. Fr* 129, 360(1992);

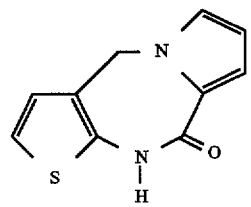

and is reduced with boron-dimethylsulfide to give 9,10-dihydro-4H-pyrrolo[1,2-a]thieno[2,3-e][1,4]diazepine.

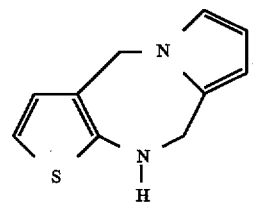

Also reported by A. Daich and B. Decroix is 5-oxo-4,5-dihydropyrrolo[1,2-a]thieno[3,2-e][1,4]diazepine

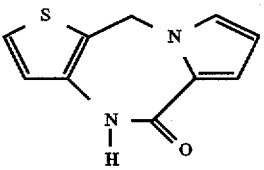

which is also reduced to give 4,10-dihydro-5H-pyrrolo[1,2-a]thieno[3,2-e][1,4]diazepine

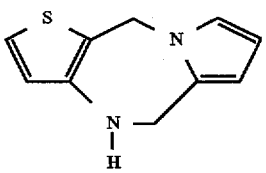

Reported by B. Decroix and J. Morel, *J. Het. Chem.*, 28, 81(1991) are pyrrolo[1,2-a]thieno[3,2-e][1,4]diazepine;

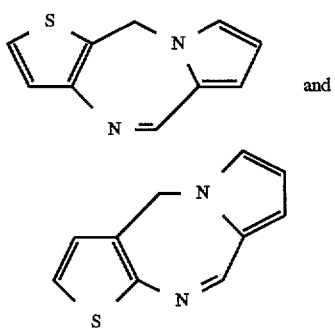

and pyrrolo[1,2-a]thieno[2,3-e][1,4]diazepine. Reduction by hydrogen-Pd/c or chemical reduction with reagents such as sodium cyanoborohydride and acetic acid gives the dihydro tricyclic heterocycles

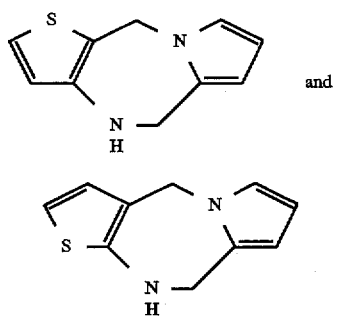

The synthesis of the tricyclic 1,5-benzodiazepine ring system, 6,7-dihydro-5H-pyrrolo[1,2-a][1,5]benzodiazepine, has been reported by F. Chimenti, S. Vomero, R. Giuliano and M. Artico, IL Farmaco, Ed. Sc., 32, 339(1977). Annelated 1,5-benzodiazepines containing five membered rings have been reviewed by A. Chimirri, R. Gitto, S. Grasso, A. M. Monforte, G. Romeo and M. Zappala, Heterocycles, 36, No. 3, 604(1993), and the ring system 6,7-dihydro-5H-pyrrolo[1,2-a][1,5]benzodiazepine is described.

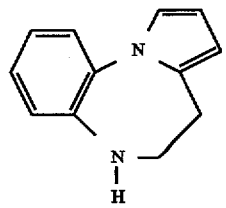

The preparation of 5,6-dihydro-4H-[1,2,4]-triazolo[4,3-a][1,5]benzodiazepin-5-ones from 1,2-dihydro-3H-4-dimethylamino-1,5-benzodiazepin-2-ones has been described by M. DiBroccio, G. Roma, G. Grossi, M. Ghia, and F. Mattioli Eur. J. Med. Chem; 26, 489(1991). Reduction of 5,6-dihydro-4H-[1,2,4]triazolo[4,3-a][1,5] benzodiazepin-5-ones with diborane or lithium hydride gives the tricyclic 5,6-dihydro derivatives.

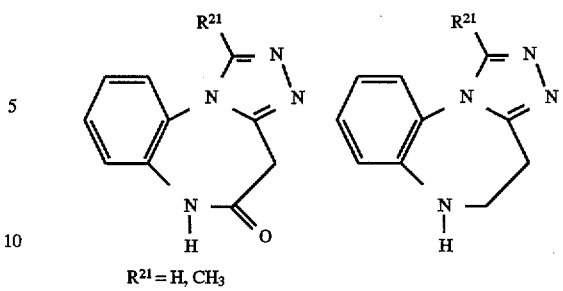

$R^{21}$ = H, $CH_3$

The compounds of this invention and their preparation can be understood further by the following examples, but should not constitute a limitation thereof.

EXAMPLE 1

N-[4-(5H-Pyrrolo[2,1-c][1,4]benzodiazepin-10(11H)-ylcarbonyl)phenyl]-2,3-difluorobenzamide To a stirred solution of 0.350 g of 2,3-difluorobenzoyl chloride in 5 ml of methylene chloride is added 0.346 ml of triethylamine. After stirring for 3 minutes, 0.500 g of 10,11-dihydro-10-(4-aminobenzoyl)-5H-pyrrolo[2,1-c][1,4]benzodiazepine is added and stirring continued for 72 hours. The reaction mixture is filtered and the solid washed with methylene chloride. The solid is saved. The combined filtrate is washed with water, 2N citric acid, 1M $NaHCO_3$, and brine. The reaction mixture is dried with $Na_2SO_4$, filtered and evaporated in vacuo to give 100 mg of a solid. The two solids are combined and dried to afford 790 mg of the desired product as a solid, m.p. 252°–258° C.

EXAMPLE 2

N-[4-(5H-Pyrrolo[2,1-c][1,4]benzodiazepin-10(11H)-ylcarbonyl)phenyl]-2-methoxybenzamide To a stirred solution of 0.362 g of 2-methoxybenzoyl chloride 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4]benzodiazepine is added and stirring continued for 18 hours at room temperature. The reaction mixture is diluted with 45 ml of methylene chloride and washed with water, 2N citric acid, 1M $NaHCO_3$, and brine. The reaction mixture is dried with $Na_2SO_4$, filtered through hydrous magnesium silicate and evaporated in vacuo to give a solid which is purified by crystallization from ethyl acetate to give 0.430 g of the desired product as a crystalline solid, m.p. 185°–188° C.

EXAMPLE 3

2-Methyl-N-[4-(5H-pyrrolo[2,1-c][1,4]-benzodiazepin-10(11H)-ylcarbonyl)phenyl] benzamide To a mixture of 1.93 g of 4-[(2-methylbenzoyl)amino] benzoyl chloride in 15 ml of methylene chloride, cooled to 0° C. is added 1.13 ml of triethylamine. After stirring for 3 minutes, a mixture of 1.0 g of 10,11-dihydro-5H-pyrrolo[2,1-c][1,4]benzodiazepine in 5 ml of methylene chloride is added. The cooling bath is removed and after about 30 minutes a complete solution is obtained. The reaction mixture is allowed to stir at room temperature for 48 hours and the volatiles are concentrated in vacuo to a residue. The residue is dissolved in 100 ml of ethyl acetate and washed with water, 2N citric acid, aqueous $NaHCO_3$ and brine. The solution is dried with Na$_2$SO$_4$ and the volatiles concentrated in vacuo to give 3.0 g of a residue. A 300 mg sample of the residue is purified by thick layer chromatography using 10% ethyl acetate-methylene chloride to give 160 mg of the desired product. The remainder of the crude material is purified by flash chromatography using 10% ethyl acetate in methylene chloride to give the desired product as a residue which is crystallized from ethyl acetate to give 800 mg of the desired product as white crystals, m.p. 212°–215° C.

EXAMPLE 4

N-[4-(5H-pyrrolo[2,1-c][1,4]benzodiazepin-10(11H)-ylcarbonyl)phenyl]-2,5-dichlorobenzamide To a solution of 414.5 mg of 2,5-dichlorobenzoyl chloride in 5 ml of methylene chloride is added 276 μl of triethylamine. After stirring at 0° C. for 3 minutes 400 mg of the 10,11-dihydro-10-(4-aminobenzoyl)-5H-pyrrolo[2,1-c][1,4]benzodiazepine is added. The bath is removed and the reaction mixture stirred at room temperature for 3 hours. The volatiles are concentrated in vacuo to give a residue which is dissolved in ethyl acetate and washed with water, 2N citric acid, 1M NaHCO$_3$ and brine. The organic layer is dried with Na$_2$SO$_4$ and concentrated in vacuo to a residue which is purified by thick layer chromatography by elution with 1:1 ethyl acetate-hexanes to give a residue. The residue is crystallized from ethyl acetate to give 220 mg of the desired product as white crystals, m.p. 218°–220° C.

EXAMPLE 5

N-[4-(5H-pyrrolo[2,1-c][1,4]benzodiazepin-10(11H)-ylcarbonyl)phenyl]-3-methyl-2-thiophenecarboxamide To a solution of 318 mg of 3-methyl-2-thiophenecarbonyl chloride in 5 ml of methylene chloride at 0° C. is added 346 μl of triethylamine. After stirring for 3 minutes, 500 mg of the 10,11-dihydro-10-(4-aminobenzoyl)-5H-pyrrolo[2,1-c][1,4]benzodiazepine is added. The bath is removed and the reaction mixture stirred at room temperature for 18 hours. The volatiles are concentrated in vacuo to give a residue which crystallizes from ethyl acetate to afford 800 mg of solid. The solid is dissolved in methylene chloride washed with water, 2N citric acid, 1M NaHCO$_3$ and brine. The organic layer is filtered through hydrous magnesium silicate, dried with Na$_2$SO$_4$ and concentrated in vacuo to give a residue which crystallizes from ethyl acetate to afford 400 mg of the desired product as a white solid, m.p. 232°–235° C.

EXAMPLE 6

N-[4-(5H-pyrrolo[2,1-c][1,4]benzodiazepin-10(11H)-ylcarbonyl)phenyl]-2,4-dichlorobenzamide To a solution of 415 mg of 2,4-dichlorobenzoyl chloride in 5 ml of methylene chloride at 0° C. is added 346 μl of triethylamine. After stirring for 3 minutes, 500 mg of 10,11-dihydro-10-(4-aminobenzoyl)-5H-pyrrolo[2,1-c][1,4]benzodiazepine is added. The bath is removed and the reaction mixture stirred at room temperature for 18 hours. The volatiles are concentrated in vacuo to give a residue which is dissolved in ethyl acetate, washed with water, 2N citric acid, 1M NaHCO$_3$ and brine. The organic layer is dried with Na$_2$SO$_4$, filtered and concentrated in vacuo to give a residue which is crystallized from ethyl acetate to give 420 mg of the desired product as a crystalline solid, m.p., 210°–212° C.

EXAMPLE 7

N-[4-(5H-pyrrolo[2,1-c][1,4]benzodiazepin-10(11H)-ylcarbonyl)phenyl]-2-chlorobenzamide To a solution of 347 mg of 2-chlorobenzoyl chloride in 5 ml of methylene chloride at 0° C. is added 346 μl of triethylamine. After stirring for 3 minutes, 500 mg of 10,11-dihydro-10-(4-aminobenzoyl)-5H-pyrrolo-[2,1-c][1,4]benzodiazepine is added. The bath is removed and the reaction mixture stirred at room temperature for 18 hours. The volatiles are concentrated in vacuo to give a residue which is dissolved in methylene chloride, washed with water, 2N citric acid, 1M NaHCO$_3$ and brine. The organic layer is dried with Na$_2$SO$_4$, filtered and concentrated in vacuo to give a residue which is crystallized from methylene chloride to give 525 mg of the desired product as a white crystalline solid, m.p. 228°–230° C.

EXAMPLE 8

N-[4-(5H-pyrrolo[2,1-c][1,4]benzodiazepin-10(11H)-ylcarbonyl)phenyl]-2-fluorobenzamide To a solution of 314 mg of 2-fluorobenzoyl chloride in 5 ml of methylene chloride at 0° C. is added 346 μl of triethylamine. After stirring for 3 minutes, 500 mg of 10,11-dihydro-10-(4-aminobenzoyl)-5H-pyrrolo[2,1-c][1,4]benzodiazepine is added. The bath is removed and the reaction mixture stirred at room temperature for 18 hours. The volatiles are concentrated in vacuo to give a residue which is dissolved in methylene chloride, washed with water, 2N citric acid, 1M NaHCO$_3$ and brine. The organic layer is dried with Na$_2$SO$_4$, filtered and concentrated in vacuo to give 620 mg of the desired product as a crystalline solid, m.p. 257°–260° C.

EXAMPLE 9

2-Chloro-N-[4-(5H-pyrrolo[2,1-c][1,4]-benzodiazepin-10(11H)-ylcarbonyl)phenyl]benzeneacetamide A mixture of 0.273 g of 2-chlorophenylacetic acid is stirred at room temperature for 2 hours. The volatiles are evaporated in vacuo to a residue which is distilled with toluene several times. The residue is dissolved in 10 ml of methylene chloride containing 0.26 ml of triethylamine and while stirring 0.485 g of 10,11-dihydro-10-(4-aminobenzoyl)-5H-pyrrolo[2,1-c][1,4]benzodiazepine added. The reaction mixture is stirred at room temperature for 18 hours. The volatiles are removed and the residue dissolved in ethyl acetate which is washed with water, 1N HCl, 1M NaHCO$_3$ and brine. The organic layer is dried and evaporated to a residue which is purified by flash chromatography using 1:1 ethyl acetate-hexane to give the desired product as a yellow solid, m.p. 99°–103° C.

EXAMPLE 10

1-(2-Nitrophenyl)-1H-pyrrole-2-carboxaldehyde

To a solution of 3.76 g of 1-(2-nitrophenyl)pyrrole in 20 ml of N,N-dimethylformamide at 0° C. is added dropwise with stirring 3 ml of phosphorus oxychloride. Stirring is continued for 30 minutes and the reaction mixture is heated at 90° C. for 1 hour. After cooling to room temperature the mixture is treated with crushed ice and the pH adjusted to 12 with 2N sodium hydroxide. The resulting suspension is filtered, washed with water and dried to give 5.81 g of the desired product as a light yellow solid m.p. 119°–122° C.

EXAMPLE 11

4,5-Dihydro-pyrrolo-[1,2-a]-quinoxaline

To a solution of 1.0 g of 1-(2-nitrophenyl)-1H-pyrrole-2-carboxaldehyde in 40 ml of ethyl alcohol and 40 ml of ethyl acetate, under argon, is added 40 mg of 10% Pd/C. The mixture is hydrogenated at 40 psi for 2 hours and filtered through diatomaceous earth. The filtrate is concentrated in vacuo to a residue which is dissolved in ether and treated with hexanes to give 0.35 g of the desired product as a beige solid m.p. 108°–110° C.

EXAMPLE 12

4-[(2-Methylbenzoyl)amino]benzoic acid

A mixture of 43.42 g of ethyl 4-aminobenzoate and 40.8 g of 2-methylbenzoyl chloride in 150 ml of dichloromethane is cooled in an ice bath and 26.56 g of triethylamine is added dropwise. After the addition, the solution is stirred at room temperature overnight. The mixture is poured into water and the organic layer separated. The organic layer is washed with water, 1N HCl, 1M NaHCO$_3$ and dried over Na$_2$SO$_4$. The solvent is removed and the solid slurried with ethyl acetate and filtered to give 57 g of ethyl 4-[(2-methylbenzoyl) amino]benzoate as crystals, m.p. 110°–115° C. A mixture of 50.7 g of the preceding compound in 280 ml of ethyl alcohol and 55 ml of 10N NaOH is refluxed for 5 minutes. The mixture is cooled to room temperature, diluted with 200 ml of water and acidified with concentrated hydrochloric acid (pH 1–2). The mixture is filtered and the solid washed with water and dried to give 51 g of the desired product as white crystals, m.p. 270°–275° C.

EXAMPLE 13

4-[(2-Methylbenzoyl)amino]benzoyl chloride

A mixture of 10.3 g of 4-[(2-methylbenzoyl)amino] benzoic acid and 32 ml of thionyl chloride is refluxed for 1.5 hours. The solution is concentrated in vacuo. Toluene is added and the solvent removed in vacuo. Toluene is added and the mixture chilled and filtered to give the desired product as a yellow solid, 135°–141° C.

EXAMPLE 14

2-Methyl-N-[4-(pyrrolo[1,2-a]quinoxalin-5(4H)-ylcarbonyl)phenyl]benzamide

A mixture of 0.51 g of 4-[(2-methylbenzoyl)amino] benzoyl chloride and 0.36 g of 1,1'-carbonyldiimidazole in 6 ml of tetrahydrofuran is stirred at room temperature for 1 hour. To the reaction mixture is added 0.17 g of 4,5-dihydropyrrolo-[1,2-a]-quinoxaline followed by heating at reflux for 60 hours. The volatiles are concentrated in vacuo to a residue which is dissolved in ethyl acetate. The organic layer is washed with 1N HCl, 1M NaHCO$_3$, brine, dried with Na$_2$SO$_4$ and filtered through hydrous magnesium silicate. The volatiles are concentrated in vacuo to a residue which is chromatographed by elution with 1:2 ethyl acetate-hexanes to give 0.14 g of the desired product as a white solid, m.p. 206°–207° C. ;

MASS SPEC (CI) 408(MH$^+$).

TABLE I

The following Examples are prepared using the conditions of Example 14 with the appropriately substituted aroyl chloride.

| Example No. | Compound |
|---|---|
| 15 | N-[4-(pyrrolo[1,2-a]quinoxalin-5(4H)-ylcarbonyl)phenyl]-2-chlorobenzamide |
| 16 | N-[4-(pyrrolo[1,2-a]quinoxalin-5(4H)-ylcarbonyl)phenyl]-2,5-dichloro-benzamide |
| 17 | N-[4-(pyrrolo[1,2-a]quinoxalin-5(4H)-ylcarbonyl)phenyl]-2,4-dichloro-benzamide, m.p. 200°–202° C. |
| 18 | N-[4-(pyrrolo[1,2-a]quinoxalin-5(4H)-ylcarbonyl)phenyl]-2-chloro-4-methyl-benzamide |
| 19 | N-[4-(pyrrolo[1,2-a]quinoxalin-5(4H)-ylcarbonyl)phenyl]-2-methyl-4-chloro-benzamide |
| 20 | N-[4-(pyrrolo[1,2-a]quinoxalin-5(4H)-ylcarbonyl)phenyl]-2,4-dimethyl-benzamide |
| 21 | N-[4-(pyrrolo[1,2-a]quinoxalin-5(4H)-ylcarbonyl)phenyl]-2,3-dimethyl-benzamide, m.p. 216°–220° C. |
| 22 | N-[4-(pyrrolo[1,2-a]quinoxalin-5(4H)-ylcarbonyl)phenyl]-2-methoxy-benzamide |
| 23 | N-[4-(pyrrolo[1,2-a]quinoxalin-5(4H)-ylcarbonyl)phenyl]-2-trifluoro-methoxybenzamide |
| 24 | N-[4-(pyrrolo[1,2-a]quinoxalin-5(4H)-ylcarbonyl)phenyl]-2,4-dimethoxy-benzamide |
| 25 | N-[4-(pyrrolo[1,2-a]quinoxalin-5(4H)-ylcarbonyl)phenyl]-2,6-dimethoxy-benzamide |
| 26 | N-[4-(pyrrolo[1,2-a]quinoxalin-5(4H)-ylcarbonyl)phenyl]-benzamide |
| 27 | N-[4-(pyrrolo[1,2-a]quinoxalin-5(4H)-ylcarbonyl)phenyl]-2,6-dichloro-benzamide |
| 28 | N-[4-(pyrrolo[1,2-a]quinoxalin-5(4H)-ylcarbonyl)phenyl]-2,6-dimethyl-benzamide |
| 29 | N-[4-(pyrrolo[1,2-a]quinoxalin-5(4H)-ylcarbonyl)phenyl]–2-(methylthio)-benzamide |
| 30 | N-[4-(pyrrolo[1,2-a]quinoxalin-5(4H)-ylcarbonyl)phenyl]-2-methyl-3-thiophenecarboxamide |
| 31 | N-[4-(pyrrolo[1,2-a]quinoxalin-5(4H)-ylcarbonyl)phenyl]-3-methyl-2-thiophenecarboxamide |
| 32 | N-[4-(pyrrolo[1,2-a]quinoxalin-5(4H)-ylcarbonyl)phenyl]-2-methyl-3-furanecarboxamide |
| 33 | N-[4-(pyrrolo[1,2-a]quinoxalin-5(4H)-ylcarbonyl)phenyl]-3-methyl-2-furanecarboxamide |
| 34 | N-[4-(pyrrolo[1,2-a]quinoxalin-5(4H)-ylcarbonyl)phenyl]-benzeneacetamide |
| 35 | N-[4-(pyrrolo[1,2-a]quinoxalin-5(4H)-ylcarbonyl)phenyl]-2-chlorobenzene-acetamide |
| 36 | N-[4-(pyrrolo[1,2-a]quinoxalin-5(4H)-ylcarbonyl)phenyl]–2-methylbenzene-acetamide (yellow foam); Anal. Calc'd for C$_{27}$H$_{23}$N$_3$O$_2$: C, 76.9; H, 5.5; N, 10.0; Found: C, 75.6; H, 6.0; N, 9.4 |
| 37 | N-[4-(pyrrolo[1,2-a]quinoxalin-5(4H)-ylcarbonyl)phenyl]-2-methyl-3-thiopheneacetamide |

EXAMPLE 38

N-(2-Nitrobenzoyl)pyrrole-2-carboxaldehyde

To an ice bath cooled solution of 5.6 g of 2-pyrrolecarboxaldehyde in 40 ml of tetrahydrofuran is added 2.4 g of 60% sodium hydride in mineral oil. The temperature elevates to 40° C. After stirring for 20 minutes a solution of 11.0 g of 2-nitrobenzoyl chloride in 20 ml of tetrahydrofuran is added dropwise over 20 minutes. After stirring in the cold for 45 minutes, the reaction mixture is poured into ice water and ether then filtered. The cake is washed with additional ether. The two phase filtrate is separate and the ether layer dried and concentrated in vacuo to give 10 g of a residue as a dark syrup which is scratched with ethanol to give crystals which are collected by filtration, washed with ether and then dried to afford 3.2 g of solid, m.p. 95°–99° C.

EXAMPLE 39

10,11-Dihydro-5H-pyrrolo[2,1-c][1,4] benzodiazepin-5-one

A mixture of 1.5 g of N-(2-nitrobenzoyl)pyrrole-2-carboxaldehyde in 50 ml of ethyl acetate, 2 drops of concentrated HCl and 0.3 g of 10% Pd/C is shaken in a Parr apparatus under hydrogen pressure for 1.75 hours. The mixture is filtered, 0.4 g of 10% Pd/C added and the mixture shaken in a Parr apparatus under hydrogen pressure for 2 hours. The reaction mixture is filtered through diatomaceous earth and the filtrate concentrated in vacuo to give 1.0 g of a yellow oil. The residue is purified on thick layer chromatography plates by elution with 4:1 ethyl acetate:hexane to give 107 mg of the desired product as an oily solid.

EXAMPLE 40

2-Methyl-N-[4-[(5-oxo-5H-pyrrolo[2,1-c]-[1,4] benzodiazepin-10(11H)-yl)carbonyl]phenyl] benzamide To a stirred solution of 107 mg of 10,11-dihydro-5H-pyrrolo[2,1-c][1,4]benzodiazepin-5-one in 3 ml of methylene chloride containing 0.084 ml of triethylamine is added 165 mg of 4-[(2-methylbenzoyl)amino]benzoyl chloride and stirring continued for 6 hours. The volatiles are removed in vacuo to a residue which is purified on thick layer chromatography plates with 7:3 hexane-ethyl acetate to afford the desired product as a foam.

EXAMPLE 41

N-[4-(3-Chloro-5H-pyrrolo[2,1-c][1,4] benzodiazepine-10(11H)ylcarbonyl)phenyl]-2-methylbenzamide To an ice-water cooled suspension of 211 mg of 2-methyl-N-[4-(5H-pyrrolo[2,1-c][1,4]-benzodiazepin-10(11H)-ylcarbonyl)-phenyl]benzamide in 5 ml of tetrahydrofuran is added 67 mg of N-chlorosuccinimide followed by continued stirring in the cold for 10 minutes. The bath is removed and stirring continued for 2.25 hours. The reaction mixture is added to ice-water and extracted with ether. The organic layer is dried and concentrated in vacuo to give a foam which is crystallized from ethyl acetate-hexane to give 157 mg of the desired product as an orange-pink solid, m.p. 185°–187° C.

EXAMPLE 42

2-Methyl-N-[4-(1-chloropyrrolo[1,2-a]quinoxalin-5 (4H)-ylcarbonyl)phenyl]benzamide To an ice-water cooled suspension of 5 mmol of 2-methyl-N-[4-(pyrrolo[1,2-a]quinoxalin-5(4H)-ylcarbonyl)-phenyl] benzamide in 5 ml of tetrahydrofuran is added 5.5 mmol of N-chlorosuccinimide followed by continued stirring in the cold for 10 minutes. The bath is removed and stirring continued for 2.25 hours. The reaction mixture is added to ice-water and extracted with ether. The organic layer is dried and concentrated in vacuo to give the desired product as a solid.

TABLE II

The following Examples are prepared using the conditions of Example 42.

| Example No. | Compound |
|---|---|
| 43 | 2-chloro-N-[4-(1-chloropyrrolo-[1,2-a]quinoxalin-5(4H)-ylcarbonyl)phenyl]-benzamide |
| 44 | 2,4-dichloro-N-[4-(1-chloro-pyrrolo-[1,2-a]quinoxalin-5(4H)-ylcarbonyl)phenyl]-benzamide |
| 45 | 2,5-dichloro-N-[4-(1-chloro-pyrrolo-[1,2-a]quinoxalin-5(4H)-ylcarbonyl)phenyl]-benzamide |
| 46 | 2,3-dimethyl-N-[4-(1-chloro-pyrrolo-[1,2-a]quinoxalin-5(4H)-ylcarbonyl)phenyl]-benzamide |
| 47 | 2,4-dimethyl-N-[4-(1-chloro-pyrrolo-[1,2-a]quinoxalin-5(4H)-ylcarbonyl)phenyl]-benzamide |
| 48 | 2,5-dimethyl-N-[4-(1-chloro-pyrrolo-[1,2-a]quinoxalin-5(4H)-ylcarbonyl)phenyl]-benzamide |

EXAMPLE 49

3-Chloro-10,11-dihydro-10-(4-nitrobenzoyl-5H-pyrrolo[2,1-c][1,4]-benzodiazepine To an ice-water cooled solution of 250 mg of 10,11-dihydro-10(4-nitrobenzoyl)-5H-pyrrolo[2,1-c][1,4] benzodiazepine in 6 ml of tetrahydrofuran is added mg of N-chlorosuccinimide. The reaction mixture is stirred in the cold for 30 minutes and at room temperature for 2 hours. The reaction mixture is poured into ice water, stirred for 5 minutes and extracted with ether. The organic layer is dried and concentrated in vacuo to give 0.2 g of a yellow foam. Trituration with ethyl alcohol gives 66 mg of the desired product as a yellow solid, m.p. 119°–125° C.

EXAMPLE 50

3-Chloro-10,11-dihydro-10-(4-aminobenzoyl-5H-pyrrolo[2,1-c][1,4]benzodiazepine A mixture of 1 mmol of 3-chloro-10,11-dihydro-10-(4-nitroaminobenzoyl)-5H-pyrrolo[2,1-c][1,4]benzodiazepine, 2.5 mmol of anhydrous hydrazine, 50 mg of palladium on carbon and 10 ml of ethyl alcohol is refluxed for 1.5 hours. The mixture is filtered through diatomaceous earth and the filtrate concentrated to dryness to give the desired product as a solid.

EXAMPLE 51

N-[4-(3-Chloro-5H-pyrrolo[2,1-c][1,4] benzodiazepin-10(11H)ylcarbonyl)phenyl]-2-methylbenzamide A mixture of 1 mmol of 3-chloro-10,11-dihydro-10-(4-aminobenzoyl)-5H-pyrrolo[2,1-c][1,4]benzodiazepine, 2 mmol of triethylamine, and 1.1 mmol of 2-methylbenzoylchloride in 8 ml of dichloromethane is stirred at room temperature overnight. The mixture is washed with water, and 1M NaHCO$_3$ and dried(Na$_2$SO$_4$). The solvent is removed in vacuo to give a solid which is recrystallized from dichloromethane-hexane to give crystals, 185°–187° C.

TABLE III

The following Examples are prepared using the conditions of Example 51 with the appropriately substituted aroyl chloride

| Example No. | Compound |
|---|---|
| 52 | N-[4-(3-Chloro-5H-pyrrolo[2,1-c]-[1,4]benzodiazepin-10(11H)yl-carbonyl)phenyl]-2-chlorobenzamide |
| 53 | N-[4-(3-Chloro-5H-pyrrolo[2,1-c]-[1,4]benzodiazepin-10(11H)yl-carbonyl)phenyl]-2,5-dichloro-benzamide |
| 54 | N-[4-(3-Chloro-5H-pyrrolo[2,1-c]-[1,4]benzodiazepin-10(11H)yl-carbonyl)phenyl]-2,4-dichloro-benzamide (solid foam), Anal. Calc'd for C$_{26}$H$_{18}$Cl$_3$N$_3$O$_2$: C, 61.1; H, 3.6; N, 8.2; Cl, 20.8; Found: C, 60.0; H, 3.5; N, 7.7; Cl, 20.3 |
| 55 | N-[4-(3-Chloro-5H-pyrrolo[2,1-c]-[1,4]benzodiazepin-10(11H)yl-carbonyl)phenyl]-2-fluoro-benzamide |
| 56 | N-[4-(3-Chloro-5H-pyrrolo[2,1-c]-[1,4]benzodiazepin-10(11H)yl-carbonyl)phenyl]-2-chloro-4-methylbenzamide |
| 57 | N-[4-(3-Chloro-5H-pyrrolo[2,1-c]-[1,4]benzodiazepin-10(11H)yl-carbonyl)phenyl]-2-methyl-4-chlorobenzamide |
| 58 | N-[4-(3-Chloro-5H-pyrrolo[2,1-c]-[1,4]benzodiazepin-10(11H)yl-carbonyl)phenyl]-2,4-dimethyl-benzamide |
| 59 | N-[4-(3-Chloro-5H-pyrrolo[2,1-c]-[1,4]benzodiazepin-10(11H)yl-carbonyl)phenyl]-2,3-dimethyl-benzamide |
| 60 | N-[4-(3-Chloro-5H-pyrrolo[2,1-c]-[1,4]benzodiazepin-10(11H)yl-carbonyl)phenyl]-2-methoxy-benzamide |
| 61 | N-[4-(3-Chloro-5H-pyrrolo[2,1-c]-[1,4]benzodiazepin-10(11H)yl-carbonyl)phenyl]-2-trifluoro-methoxybenzamide |
| 62 | N-[4-(3-Chloro-5H-pyrrolo[2,1-c]-[1,4]benzodiazepin-10(11H)yl-carbonyl)phenyl]-2,4-dimethoxy-benzamide |
| 63 | N-[4-(3-Chloro-5H-pyrrolo[2,1-c]-[1,4]benzodiazepin-10(11H)yl-carbonyl)phenyl]-2,6-dimethoxy-benzamide |
| 64 | N-[4-(3-Chloro-5H-pyrrolo[2,1-c]-[1,4]benzodiazepin-10(11H)yl-carbonyl)phenyl]-benzamide |
| 65 | N-[4-(3-Chloro-5H-pyrrolo[2,1-c]-[1,4]benzodiazepin-10(11H)yl-carbonyl)phenyl]-2,6-dichloro-benzamide |
| 66 | N-[4-(3-Chloro-5H-pyrrolo[2,1-c]-[1,4]benzodiazepin-10(11H)yl-carbonyl)phenyl]-2,6-dimethyl-benzamide |
| 67 | N-[4-(3-Chloro-5H-pyrrolo[2,1-c]-[1,4]benzodiazepin-10(11H)yl-carbonyl)phenyl]-2-methylthio-benzamide |
| 68 | N-[4-(3-Chloro-5H-pyrrolo[2,1-c]-[1,4]benzodiazepin-10(11H)yl-carbonyl)phenyl]-2-methyl-3-thiophenecarboxamide |
| 69 | N-[4-(3-Chloro-5H-pyrrolo[2,1-c]-[1,4]benzodiazepin-10(11H)yl-carbonyl)phenyl]-3-methyl-2-thiophenecarboxamide |
| 70 | N-[4-(3-Chloro-5H-pyrrolo[2,1-c]-[1,4]benzodiazepin-10(11H)yl-carbonyl)phenyl]-2-methyl-3-furanecarboxamide |
| 71 | N-[4-(3-Chloro-5H-pyrrolo[2,1-c]-[1,4]benzodiazepin-10(11H)yl-carbonyl)phenyl]-3-methyl-2-furanecarboxamide |
| 72 | N-[4-(3-Chloro-5H-pyrrolo[2,1-c]-[1,4]benzodiazepin-10(11H)yl-carbonyl)phenyl]-phenylacetamide |
| 73 | N-[4-(3-Chloro-5H-pyrrolo[2,1-c]-[1,4]benzodiazepin-10(11H)yl-carbonyl)phenyl]-2-chlorophenyl-acetamide |
| 74 | N-[4-(3-Chloro-5H-pyrrolo[2,1-c]-[1,4]benzodiazepin-10(11H)yl-carbonyl)phenyl]-2-methylbenzene-acetamide |
| 75 | N-[4-(3-Chloro-5H-pyrrolo[2,1-c]-[1,4]benzodiazepin-10(11H)yl-carbonyl)phenyl]-2-methyl-3-thiopheneacetamide |
| 76 | N-[4-(3-Chloro-5H-pyrrolo[2,1-c]-[1,4]benzodiazepin-10(11H)yl-carbonyl)phenyl]-2-methyl-3-furanacetamide |

EXAMPLE 77

1-(2-Nitrobenzyl)-2pyrrolecarboxaldehyde

To 5.56 g of 60% sodium hydride in mineral oil, washed three times with hexane, is added 300 ml of N,N-dimethylformamide under argon. The reaction mixture is cooled in an ice-bath and 13.2 g of pyrrole-2-carboxaldehyde is added slowly. The reaction mixture becomes a complete solution and is stirred for an additional 10 minutes. While stirring, 30.0 g of 2-nitrobenzyl bromide is added slowly. After complete addition, the reaction mixture is stirred for 30 minutes, the ice bath is removed and the reaction mixture stirred at room temperature for 24 hours. The N,N-dimethylformamide is concentrated in vacuo to give a residue which is stirred with ice water for 1 hour. The resulting solid is collected, air dried, then vacuum dried to give 30.64 g of the desired product as a tan solid, m.p. 128°–132° C.

EXAMPLE 78

10,11-dihydro-5H-pyrrolo[2,1-c][1,4]benzodiazepine

A mixture of 30.6 g of 1-(2-nitrobenzyl)-2-pyrrolecarboxaldehyde and 3.06 g of 10% Pd/C in 400 ml of ethyl acetate and 400 ml of ethyl alcohol is hydrogenated over 18 hours. The reaction mixture is filtered through diatomaceous earth and the filtrate is treated with activated carbon and filtered through diatomaceous earth. The filtrate is concentrated in vacuo to give a residue which is dissolved in methylene chloride containing ethyl alcohol. The solution is passed through a pad of silica gel and the pad washed with a 7:1 hexane-ethyl acetate solution to give 16.31 g of the desired product as solid, m.p. 145°–148° C.

EXAMPLE 79

10,11Dihydro-10(4-nitrobenzoyl)-5H-pyrrolo[2,1-c] [1,4]benzodiazepine

To a solution of 3.3 g of 10,11-dihydro-5H-pyrrolo[2,1-c][1,4]benzodiazepine in 50 ml of methylene chloride under argon is added 5.0 ml of triethylamine followed by ice bath cooling. A solution of 4.0 g of 4-nitrobenzoyl chloride in 20 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, 1N HCl, NaHCO$_3$, brine, dried with Na$_2$SO$_4$ and filtered. The filtrate is concentrated in vacuo to a solid which is dissolved in methylene chloride, passed through silica gel and the pad washed with ethyl acetate. The combined filtrate is concentrated in vacuo to give 5.3 g of the desired product as a yellow solid, m.p. 188°–190° C.

EXAMPLE 80

10,11-Dihydro-10-(4-aminobenzoyl)-5H-pyrrolo[2,1-c][1,4]benzodiazepine

A mixture of 2.00 g of 10,11-dihydro-10(4-itrobenzoyl)-5H-pyrrolo[2,1-c][1,4]benzodiazepine in 15 ml of ethyl alcohol and 15 ml of ethyl acetate containing 0.2 g of 10% Pd/C is hydrogenated for 5 hours. The reaction mixture is filtered through a pad of diatomaceous earth. The filtrate is concentrated in vacuo to a solid which is dissolved in methylene chloride, passed through silica gel and the pad washed with 3:1 ethyl acetate-hexane. The filtrate is concentrated in vacuo to give 1.5 g of the desired product as a yellow solid, m.p. 166°–168° C.

EXAMPLE 81

10,11-Dihydro-10-(4-aminobenzoyl)-5H-pyrrolo[2,1-c][1,4]benzodiazepine

To a solution of 21.58 g of 10,11-dihydro-10-(4-nitrobenzoyl)-5H-pyrrolo[2,1-c][1,4]benzodiazepine in 325 ml of ethyl alcohol is added 2.15 g of 10% Pd/C and 5.16 g of hydrazine followed by stirring and heating under reflux for 15 hours. The room temperature reaction mixture is filtered through diatomaceous earth. The filtrate is concentrated in vacuo to a solid which is dissolved in methylene chloride and passed through a pad of hydrous magnesium silicate. The filtrate is concentrated in vacuo to give 19.2 g of the desired product as a tan solid. The solid is purified by flash chromatography using 7:1 ethyl acetate-hexane to give 17.97 g of the desired product, m.p. 166°–168° C.

EXAMPLE 82

N-[4-(5H-Pyrrolo[2,1-c][1,4]benzodiazepin-10(11H) -ylcarbonyl)phenyl]-3-chlorobenzo[b]thiophene-2-carboxamide To a stirred solution of 0.440 g of 3-chlorobenzo[b] thiophen-2-carbonyl chloride in 10 ml of methylene chloride is added 0.33 ml of triethylamine. After stirring for 15 minutes, 0.485 g of 10,11-dihydro-10-(4-aminobenzoyl)-5H-pyrrolo[2,1-c][1,4]benzodiazepine is added and stirring continued for 18 hours. The reaction mixture is washed with water, 1N HCl, NaHCO$_3$, and brine. The reaction mixture is dried with Na$_2$SO$_4$, filtered and evaporated in vacuo to give a solid which is purified by flash chromatography using 1:1 ethyl acetate-hexane to give 0.49 g of solid, m.p. 220°–222° C.

EXAMPLE 83

N-[4-(5H-Pyrrolo[2,1-c][1,4]benzodiazepin-10(11H) -ylcarbonyl)phenyl]-2,3-dimethylbenzamide To a stirred solution of 0.320 g of 2,3-dimethylbenzoyl chloride in 10 ml of methylene chloride is added 0.33 ml of triethylamine. After stirring for 15 minutes, 0.485 g of 10,11-dihydro-10-(4-aminobenzoyl)-5H-pyrrolo[2,1-c][1,4] benzodiazepine is added and stirring continued for 5 hours. The reaction mixture is washed with water, 1N HCl, NaHCO$_3$, and brine. The reaction mixture is dried with Na$_2$SO$_4$, filtered and evaporated in vacuo to give a solid which is purified by flash chromatography using 1:1 ethyl acetate-hexane to give 0.39 g of solid, m.p. 168°–170° C.

EXAMPLE 84

N-[4-(5H-Pyrrolo[2,1-c][1,4]benzodiazepin-10(11H) -ylcarbonyl)phenyl]-2-ethoxybenzamide To a stirred solution of 0.362 g of 2-ethoxybenzoyl chloride 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4] benzodiazepine is added and stirring continued for 72 hours at room temperature. The reaction mixture is diluted with 45 ml of methylene chloride and washed with water, 2N citric acid, NaHCO$_3$, and brine. The reaction mixture is dried with Na$_2$SO$_4$, filtered and evaporated in vacuo to give a solid which is purified by flash chromatography using 1:1 ethyl acetate-hexane to give 0.890 g of solid which is crystallized from ethyl acetate to give 0.540 g of the desired product as a white solid, m.p. 160°–176° C.

EXAMPLE 85

N-[4-(5H-Pyrrolo[2,1-c][1,4]benzodiazepin-10(11H) -ylcarbonyl)phenyl]-2-(methylthio)benzamide To a stirred solution of 0.364 g of 2-(methylthio)benzoyl chloride 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4] benzodiazepine is added and stirring continued for 72 hours at room temperature. The reaction mixture is diluted with 45 ml of methylene chloride and washed with water, 2N citric acid, NaHCO$_3$, and brine. The reaction mixture is dried with Na$_2$SO$_4$, filtered and evaporated in vacuo to give a solid which is purified by flash chromatography using 1:1 ethyl acetate-hexane to give a solid which is crystallized from ethyl alcohol to give 0.480 g of the desired product as a white solid, m.p. 171°–174° C.

EXAMPLE 86

3-Methylbenzo[b]thiophene-2-acetyl chloride

A mixture of 2.0 g of 3-methylbenzo[b]thiophene-2-acetic acid and 19.4 ml of thionyl chloride is heated at reflux for 1 hour. The volatiles are evaporated in vacuo to give a residue which is concentrated from toluene three times and dried under vacuum to give 2.25 g of the desired product as a residue.

EXAMPLE 87

N-[4-(5H-Pyrrolo[2,1-c][1,4]benzodiazepin-10(11H)-ylcarbonyl)phenyl]-3-methylbenzo[b]thiophene-2-acetamide To a stirred solution of 0.445 g of 3-methylbenzo[b]thiophene-2-acetyl chloride in 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4]benzodiazepine is added and stirring continued for 72 hours at room temperature. An additional 0.445 g of 3-methylbenzo[b]thiophene-2-acetyl chloride, 0.346 g of triethylamine and 30 mg of dimethylaminopyridine is added and stirring continued for an additional 18 hours. The reaction mixture is diluted with 45 ml of methylene chloride and washed with water, 2N citric acid, 1M NaHCO$_3$, and brine. The reaction mixture is dried with Na$_2$SO$_4$, filtered and evaporated in vacuo to give a solid which is purified by flash chromatography using 1:1 ethyl acetate-hexane to give 0.320 g of the desired product as a yellow foam.

EXAMPLE 88

4-Chloro-2-methoxybenzoyl chloride

A solution of 2.0 g of 4-chloro-o-anisic acid in 22 ml of thionyl chloride is heated at reflux for 1 hour. The volatiles are evaporated in vacuo to give a residue which is is concentrated from toluene three times and dried under vacuum to give 2.0 g of the desired product as a residue.

EXAMPLE 89

N-[4-(5H-Pyrrolo[2,1-c][1,4]-benzodiazepin-10(11H)ylcarbonyl)phenyl]-4-chloro-2-methoxybenzamide To a stirred solution of 0.406 g of 4-chloro-2-methoxybenzoyl chloride in 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4]benzodiazepine is added and stirring continued for 18 hours at room temperature. An additional 0.406 g of 4-chloro-2-methoxybenzoyl chloride and 0.346 g of triethylamine is added and stirring is continued for 2 hours. The reaction mixture is diluted with 45 ml of methylene chloride and washed with water, 2N citric acid, 1M NaHCO$_3$, and brine. The reaction mixture is dried with Na$_2$SO$_4$, filtered and evaporated in vacuo to give a residue which is purified by flash chromatography using 1:1 ethyl acetate-hexane to give a solid which is crystallized from ethyl acetate to give 0.320 g of the desired product as a white crystals, m.p. 222°–224° C.

EXAMPLE 90

2-(Trifluoromethyl)benzoyl chloride

A solution of 2.0 g of o-trifluoromethylbenzoic acid in 21 ml of thionyl chloride is heated at reflux for 1 hour. The volatiles are evaporated in vacuo to give a residue which is concentrated from toluene three times and dried under vacuum to give 2.1 g of the desired product as a residue.

EXAMPLE 91

N-[4-([5H-Pyrrolo[2,1-c][1,4]benzodiazepin-10(11H)ylcarbonyl)phenyl]-2-(trifluoromethyl)benzamide To a stirred solution of 0.413 g of 2-trifluoromethylbenzoyl chloride in 5 ml of methylene chloride is added 0.346 g of triethylamine at 0° C. After stirring for 3 minutes, 0.500 g of 10,11-dihydro-10-((4-aminobenzoyl)-5H-pyrrolo[2,1-c][1,4]benzodiazepine is added and stirring continued for 18 hours at room temperature. The reaction mixture is diluted with 50 ml of ethyl acetate and washed with water, 2N citric acid, NaHCO$_3$, and brine. The reaction mixture is dried with Na$_2$SO$_4$, filtered and evaporated in vacuo to give a solid which is crystallized from ethyl acetate to afford 0.5 g of a solid which is dissolved in methylene chloride and passed through a pad of hydrous magnesium silicate. The filtrate is evaporated in vacuo to give a solid which is crystallized from ethyl acetate to afford 0.210 g of the desired product as a white crystals, m.p. 226°–228° C.

EXAMPLE 92

2-Methylphenylacetyl chloride

A solution of 2.0 g of o-tolylacetic acid in 27 ml of thionyl chloride is heated at reflux for 1 hour. The volatiles are evaporated in vacuo to give a residue which is concentrated from toluene three times and dried under vacuum to give 2.1 g of the desired product as a light brown oil.

EXAMPLE 93

N-[4(5H-Pyrrolo[2,1-c][1,4]benzodiazepin-10(11H)-ylcarbonyl)phenyl]-2-methylbenzeneacetamide To a stirred solution of 0.334 g of 2-methylphenylacetyl chloride 5 ml of methylene chloride is added 0.346 g of triethylamine at 0° C. After stirring for 3 minutes, 0.500 g of 10,11-dihydro-10-(4-aminobenzoyl)-5H-pyrrolo[2,1-c][1,4]benzodiazepine is added and stirring continued for 72 hours at room temperature. The reaction mixture is diluted with 45 ml of methylene chloride and washed with water, 2N citric acid, NaHCO$_3$, and brine. The reaction mixture is dried with Na$_2$SO$_4$, filtered through a pad of hydrous magnesium silicate and evaporated in vacuo to give a solid which is purified by flash chromatography using 1:1 ethyl acetate-hexane to give a solid which is crystallized from ethyl acetate to give 0.385 g of the desired product as white crystals, m.p. 198°–200° C.

EXAMPLE 94

10,11-Dihydro-10-(3-methyl-4-nitro-benzoyl)-5H-pyrrolo[2,1-c][1,4]benzodiazepine A mixture of 1.81 g of 3-methyl-4-nitrobenzoic acid and 1.25 g of thionyl chloride in 75 ml of chloroform is heated at reflux under argon for 48 hours. The volatiles are removed in vacuo to a residue which is evaporated with toluene several times in vacuo. The residue is partially dissolved in methylene chloride and filtered free of solids and the filtrate evaporated in vacuo to give 1.47 g of the desired acid chloride. A 1.36 g sample of the acid chloride, 0.90 g of N,N-diisopropylethylamine and 1.25 g of 10,11-dihydro-5H-pyrrolo[2,1-c][1,4]benzodiazepine in 25 ml of methylene chloride is allowed to stand at room temperature for 8 hours. Water is added to the reaction mixture, the organic layer is separated and dried over Na₂SO₄, filtered and hexane added to the filtrate at the boil to give 1.4 g of the desired product as crystals, m.p. 246°–248° C.

EXAMPLE 95

10,11-Dihydro-10-(4-amino-3-methylbenzoyl)-5H-pyrrolo[2,1-c][1,4]benzodiazepine

A mixture of 1.22 g 10,11-dihydro-10-(3-methyl-4-nitrobenzoyl)-5H-pyrrolo[2,1-c][1,4]benzodiazepine, 0.2 g of 10% Pd/C and 0.35 g of anhydrous hydrazine in 50 ml of absolute ethyl alcohol is heated on a steam bath for 1 hour. The reaction mixture is filtered hot through diatomaceous earth and evaporated in vacuo to a residue. The residue is crystallized from methylene chloride-hexane to give 0.95 g of the desired product as crystals, m.p. 232°–234° C.

EXAMPLE 96

N-[4-(5H-Pyrrolo[2,1-c][1,4]benzodiazepin-10(11H) ylcarbonyl)-2-methylphenyl]-2-methylbenzamide A solution of 0.83 g of 10,11-dihydro-10-(4-amino-3-methylbenzoyl)-5H-pyrrolo[2,1-c][1,4]benzodiazepine, 0.5 g of N,N-diisopropylethylamine and 0.6 g of 2-methylbenzoyl chloride in 50 ml of methylene chloride is stirred at room temperature for 18 hours. The reaction mixture is washed with water, the organic layer dried with Na₂SO₄ and passed through a pad of hydrous magnesium silicate. Hexane is added at the boil to give 0.75 g of a solid which is crystallized from methylene chloride-hexane to give 0.61 g of the desired product, m.p. 125°–130° C.

TABLE IV

The following Examples are prepared using the conditions of Example 96 with the appropriately substituted aroyl chloride

| Example No. | Compound |
|---|---|
| 97 | N-[4-(5H-pyrrolo[2,1-c][1,4]-benzodiazepin-10(11H)-yl-carbonyl-2-methylphenyl]-2-chlorobenzamide |
| 98 | N-[4-(5H-pyrrolo[2,1-c][1,4]-benzodiazepin-10(11H)-yl-carbonyl-2-methylphenyl]-2,-5-dichlorobenzamide |
| 99 | N-[4-(5H-pyrrolo[2,1-c][1,4]-benzodiazepin-10(11H)-yl-carbonyl-2-methylphenyl]-2,4-dichlorobenzamide, m.p. 213°–215° C. |
| 100 | N-[4-(5H-pyrrolo[2,1-c][1,4]-benzodiazepin-10(11H)-yl-carbonyl-2-methylphenyl]-2-chloro-4-methylbenzamide |
| 101 | N-[4-(5H-pyrrolo[2,1-c][1,4]-benzodiazepin-10(11H)-yl-carbonyl-2-methylphenyl]-2-methyl-4-chlorobenzamide |
| 102 | N-[4-(5H-pyrrolo[2,1-c][1,4]-benzodiazepin-10(11H)-yl-carbonyl-2-methylphenyl]-2,3-dimethylbenzamide |
| 103 | N-[4-(5H-pyrrolo[2,1-c][1,4]-benzodiazepin-10(11H)-yl-carbonyl-2-methylphenyl]-2-methoxybenzamide |
| 104 | N-[4-(5H-pyrrolo[2,1-c][1,4]-benzodiazepin-10(11H)-yl-carbonyl-2-methylphenyl]-2-trifluoromethoxybenzamide |
| 105 | N-[4-(5H-pyrrolo[2,1-c][1,4]-benzodiazepin-10(11H)-yl-carbonyl-2-methylphenyl]-2,-4-dimethoxybenzamide |
| 106 | N-[4-(5H-pyrrolo[2,1-c][1,4]-benzodiazepin-10(11H)-yl-carbonyl-2-methylphenyl]-benzamide |
| 107 | N-[4-(5H-pyrrolo[2,1-c][1,4]-benzodiazepin-10(11H)-yl-carbonyl-2-methylphenyl]-2-methylthiobenzamide |
| 108 | N-[4-(5H-pyrrolo[2,1-c][1,4]-benzodiazepin-10(11H)-yl-carbonyl-2-methylphenyl]-2,6-dichlorobenzamide |
| 109 | N-[4-(5H-pyrrolo[2,1-c][1,4]-benzodiazepin-10(11H)-yl-carbonyl-2-methylphenyl]-2-methyl-3-thiophenecarboxamide |
| 110 | N-[4-(5H-pyrrolo[2,1-c][1,4]-benzodiazepin-10(11H)-yl-carbonyl-2-methylphenyl]-2-methyl-3-thiophenecarboxamide |
| 111 | N-[4-(5H-pyrrolo[2,1-c][1,4]-benzodiazepin-10(11H)-yl-carbonyl-2-methylphenyl]-2-methyl-3-furancarboxamide |
| 112 | N-[4-(5H-pyrrolo[2,1-c][1,4]-benzodiazepin-10(11H)-yl-carbonyl-2-methylphenyl]-3-methyl-2-furancarboxamide |
| 113 | N-[4-(5H-pyrrolo[2,1-c][1,4]-benzodiazepin-10(11H)-yl-carbonyl-2-methylphenyl]-phenylacetamide |
| 114 | N-[4-(5H-pyrrolo[2,1-c][1,4]-benzodiazepin-10(11H)-yl-carbonyl-2-methylphenyl]-2-chlorophenylacetamide |
| 115 | N-[4-(5H-pyrrolo[2,1-c][1,4]-benzodiazepin-10(11H)-yl-carbonyl-2-methylphenyl]-2-methylphenylacetamide |

EXAMPLE 116

10,11-Dihydro-10-[4-[[[(2-methylphenyl]amino] carbonyl]amino]benzoyl]-5H-pyrrolo[2,1-c][1,4] benzodiazepine A mixture of 0.93 g 10,11-dihydro-10-(4-amino-3-methylbenzoyl)-5H-pyrrolo[2,1-c][1,4]benzodiazepine and 0.37 g of o-tolyl isocyanate in 50 ml of tetrahydrofuran is heated at reflux under argon for 24 hours. The volatiles are evaporated in vacuo to a residue which is dissolved in methylene chloride and passed through a pad of hydrous magnesium silicate. Hexane is added to the filtrate at the boil to give 0.68 g of the desired product as crystals, m.p. 155°–158° C.

EXAMPLE 117

N-[4-(5H-pyrrolo[2,1-c][1,4]benzodiazepin-10(11H) -ylcarbonyl)phenyl]-1H-indole-5-carboxamide To a solution of 319 mg of indole-5-carboxylic acid in 5 ml of tetrahydrofuran is added 418.4 mg of 1,1'- carbonyldiimidazole under argon with ice-bath cooling. The cooling bath is removed and the reaction mixture stirred at room temperature for 2 hours. The volatiles are evaporated in vacuo to a residue which is dissolved in 3 ml of xylene followed by 500 mg of 10,11-dihydro-10-(4-aminobenzoyl)-5H-pyrrolo[2,1-c][1,4]benzodiazepine and heating at 120° C. for 18 hours. The volatiles are evaporated in vacuo to a residue which is partitioned between 40 ml of ethyl acetate and water. The organic layer is dried over $Na_2SO_4$ and the volatiles evaporated in vacuo to a residue which is purified by chromatography on preparative plates by elution with 1:1 ethyl acetate-hexane to give 140 mg of the desired product as an orange solid, m.p. 130°–170° C.

EXAMPLE 118

1-(o-Nitrobenzyl)-imidazole-2-carboxaldehyde

A 2.0 g portion of sodium hydride (60% in oil) is washed with pentane two times. To the residue is added 110 ml of N,N-dimethylformamide under argon. With stirring and external cooling, 4.80 g of 2-imidazolecarboxaldehyde is added and the cooling bath removed. Slight external heating results in a yellow solution. The reaction mixture is chilled in ice and 10.8 g of 2-nitrobenzyl bromide is added. The reaction mixture is stirred at 0° C. for 18 hours. The volatiles are removed in vacuo to a residue which is stirred with ice water, filtered and the cake washed well with water and suction dried to give 10.9 g of the desired product as a solid, m.p. 141°–144° C. MH+232.

EXAMPLE 119

10,11-Dihydro-5H-imidazo[2,1-c][1,4]benzodiazepine

A 5.0 g sample of 1-(o-nitrobenzyl)-imidazole-2-carboxaldehyde is dissolved in 150 ml of hot ethyl alcohol, cooled to room temperature and filtered. To the filtrate is added 0.5 g of 10% Pd/C and the mixture hydrogenated at 48 psi for 4 hours. An additional 0.5 g of 10% Pd/C is added and hydrogenation continued for 25 hours at 65 psi. The mixture is filtered through diatomaceous earth and the cake washed with ethyl acetate. The filtrate is evaporated in vacuo to a residue which is dissolved in methylene chloride, treated with activated carbon, filtered through diatomaceous earth and hexanes added to the filtrate at the boil to give 1.86 g of the desired product as a crystalline solid, m.p. 164°–170° C.

EXAMPLE 120

10,11-Dihydro-5H-imidazo[2,1-c][1,4]benzodiazepine

To a suspension of 4 mmol of lithium aluminum hydride in 20 ml of anhydrous tetrahydrofuran is added a 1 mmol solution of 10,11-dihydro-11-oxo-5H-imidazo[2,1-c][1,4]benzodiazepine and the mixture is refluxed for 24 hours and cooled at 0° C. To the mixture is added dropwise 0.12 ml of water and 6 ml of 1N sodium hydroxide. The mixture is extracted with ethyl acetate and the solvent removed to give the desired product as a solid. Recrystallization from methylene chloride-hexane gives crystals, m.p. 164°–170° C.

EXAMPLE 121

N-[4-(5H-imidazo[2,1-c][1,4]benzodiazepin-10(11H)-ylcarbonyl)phenyl]-2-methylbenzamide To a mixture of 1.37 g (5 mmol) of 4-[(2-methylbenzoyl)amino]benzoyl chloride in 15 ml of methylene chloride, cooled to 0° C. is added 1.5 ml of triethylamine. After stirring for 3 minutes, 5 mmol of 10, 1-dihydro-5H-imidazo[2,1-c][1,4]benzodiazepine in 5 ml of methylene chloride is added. The cooling bath is removed and after about 30 minutes a complete solution is obtained. The reaction mixture is allowed to stir at room temperature for 1 hour and the volatiles are concentrated in vacuo. The residue is dissolved in 100 ml of ethyl acetate and washed with water, 2N citric acid, and brine. The solution is dried with $Na_2SO_4$ and the volatiles concentrated in vacuo to give the desired product as a solid.

EXAMPLE 122

10,11,Dihydro-10-(4-nitrobenzoyl)-5H-imidazo[2,1-c][1,4]benzodiazepine

To a solution of 10 mmol of 10,11-dihydro-5H-imidazo[2,1-c][1,4]benzodiazepine in 50 ml of methylene chloride under argon is added 15 mmol of triethylamine followed by ice bath cooling. A solution of 10 mmol of 4-nitrobenzoyl chloride in 10 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, and brine. The organic layer is dried with $Na_2SO_4$, filtered and evaporated in vacuo to give a solid which is purified by flash chromatography to give desired product as a solid.

EXAMPLE 123

10,11-Dihydro-10-(4-aminobenzoyl)-5H-imidazo[2,1-c][1,4]benzodiazepine

A mixture of 5 mmol of 10,11-dihydro-10-(4-nitrobenzoyl)-5H-imidazo[2,1-c][1,4]benzodiazepine in 10 ml of ethyl alcohol and 10 ml of ethyl acetate containing 0.2 g of 10% Pd/C is hydrogenated for 5 hours in a Parr hydrogenator at 35 psi of hydrogen. The reaction mixture is filtered through a pad of diatomaceous earth. The filtrate is concentrated in vacuo to a solid which is purified by flash chromatography to give the desired product.

EXAMPLE 124

10,11-Dihydro-10-(4-aminobenzoyl)-5H-imidazo[2,1-c][1,4]benzodiazepine

To a solution of 5 mmol of 10,11-dihydro-10-(4-nitrobenzoyl)-5H-imidazo[2,1-c][1,4]benzodiazepine in 100 ml of ethyl alcohol is added 0.5 g of 10% Pd/C and 10 mmol of hydrazine followed by stirring and heating under reflux for 3 hours. The reaction mixture is filtered through diatomaceous earth. The filtrate is concentrated in vacuo to a residue which is dissolved in methylene chloride and passed through a pad of hydrous magnesium silicate. The filtrate is concentrated in vacuo to give the desired product which is purified by flash chromatography to give the desired product as a solid.

EXAMPLE 125

N-[4-(5H-Imidazo[2,1-c][1,4]benzodiazepin-10(11H)-ylcarbonyl)phenyl]-2-methylbenzamide To a stirred solution of 1 mmol of 2-methylbenzoyl chloride in 10 ml of methylene chloride is added 1.5 mmol of triethylamine. After stirring for 15 minutes, 1 mmol of 10,11-dihydro-10-(4-aminobenzoyl)-5H-imidazo[2,1-c][1,4]benzodiazepine is added and the mixture stirred for 5 hours. The reaction mixture is washed with water, and brine. The reaction mixture is dried with $Na_2SO_4$, filtered and evaporated in vacuo to give a solid which is purified by flash chromatography to give the desired product as a solid.

TABLE V

The following Examples are prepared using the conditions of Example 125 with the appropriately substituted aroyl chloride

| Example No. | Compound |
|---|---|
| 126 | N-[4-(5H-imidazo[2,1-c][1,4]-benzodiazepin-10(11H)-ylcarbonyl)phenyl]-2-chlorobenzamide |
| 127 | N-[4-(5H-imidazo[2,1-c][1,4]-benzodiazepin-10(11H)-ylcarbonyl)phenyl]-2,5-dichlorobenzamide |
| 128 | N-[4-(5H-imidazo[2,1-c][1,4]-benzodiazepin-10(11H)-ylcarbonyl)phenyl]-2,4-dichlorobenzamide |
| 129 | N-[4-(5H-imidazo[2,1-c][1,4]-benzodiazepin-10(11H)-ylcarbonyl)phenyl]-2-fluorobenzamide |
| 130 | N-[4-(5H-imidazo[2,1-c][1,4]-benzodiazepin-10(11H)-ylcarbonyl)phenyl]-2-chloro-4-methylbenzamide |
| 131 | N-[4-(5H-imidazo[2,1-c][1,4]-benzodiazepin-10(11H)-ylcarbonyl)phenyl]-2-methyl-4-chlorobenzamide |
| 132 | N-[4-(5H-imidazo[2,1-c][1,4]-benzodiazepin-10(11H)-ylcarbonyl)phenyl]-2,4-dimethylbenzamide |
| 133 | N-[4-(5H-imidazo[2,1-c][1,4]-benzodiazepin-10(11H)-ylcarbonyl)phenyl]-2,3-dimethylbenzamide |
| 134 | N-[4-(5H-imidazo[2,1-c][1,4]-benzodiazepin-10(11H)-ylcarbonyl)phenyl]-2-methoxybenzamide |
| 135 | N-[4-(5H-imidazo[2,1-c][1,4]-benzodiazepin-10(11H)-ylcarbonyl)phenyl]-2-trifluoromethoxybenzamide |
| 136 | N-[4-(5H-imidazo[2,1-c][1,4]-benzodiazepin-10(11H)-ylcarbonyl)phenyl]-2,-4-dimethoxybenzamide |
| 137 | N-[4-(5H-imidazo[2,1-c][1,4]-benzodiazepin-10(11H)-ylcarbonyl)phenyl]-2,-6-dimethoxybenzamide |
| 138 | N-[4-(5H-imidazo[2,1-c][1,4]-benzodiazepin-10(11H)-ylcarbonyl)phenyl]-benzamide |
| 139 | N-[4-(5H-imidazo[2,1-c][1,4]-benzodiazepin-10(11H)-ylcarbonyl)phenyl]-2,-6-dichlorobenzamide |
| 140 | N-[4-(5H-imidazo[2,1-c][1,4]-benzodiazepin-10(11H)-ylcarbonyl)phenyl]-2,-6-dimethylbenzamide |
| 141 | N-[4-(5H-imidazo[2,1-c][1,4]-benzodiazepin-10(11H)-ylcarbonyl)phenyl]-2,-methylthiobenzamide |

TABLE V-continued

The following Examples are prepared using the conditions of Example 125 with the appropriately substituted aroyl chloride

| Example No. | Compound |
|---|---|
| 142 | N-[4-(5H-imidazo[2,1-c][1,4]-benzodiazepin-10(11H)-ylcarbonyl)phenyl]-2,-methyl-3-thiophenecarboxamide |
| 143 | N-[4-(5H-imidazo[2,1-c][1,4]-benzodiazepin-10(11H)-ylcarbonyl)phenyl]-3,-methyl-2-thiophenecarboxamide |
| 144 | N-[4-(5H-imidazo[2,1-c][1,4]-benzodiazepin-10(11H)-ylcarbonyl)phenyl]-2,-methyl-3-furanecarboxamide |
| 145 | N-[4-(5H-imidazo[2,1-c][1,4]-benzodiazepin-10(11H)-ylcarbonyl)phenyl]-3,-methyl-2-furanecarboxamide |
| 146 | N-[4-(5H-imidazo[2,1-c][1,4]-benzodiazepin-10(11H)-ylcarbonyl)phenyl]-phenylacetamide |
| 147 | N-[4-(5H-imidazo[2,1-c][1,4]-benzodiazepin-10(11H)-ylcarbonyl)phenyl]-2-chlorophenylacetamide |
| 148 | N-[4-(5H-imidazo[2,1-c][1,4]-benzodiazepin-10(11H)-ylcarbonyl)phenyl]-2-methylphenylacetamide |
| 149 | N-[4-(5H-imidazo[2,1-c][1,4]-benzodiazepin-10(11H)-ylcarbonyl)phenyl]-2-methyl-3-thiopheneacetamide |
| 150 | N-[4-(5H-imidazo[2,1-c][1,4]-benzodiazepin-10(11H)-ylcarbonyl)phenyl]-2-methyl-3-furanacetamide |

EXAMPLE 151

N-[4-(7-Chloro-5H-imidazo[2,1-c][1,4]benzodiazepin-10(11H)-ylcarbonyl]phenyl]-2-methylbenzamide As described for Example 125 a mixture of 1 mmol of 7-chloro-10,11-dihydro-5H-imidazo[2,1-c][1,4]benzodiazepine, 1.1 mmol of 4-[(2-methylbenzoyl)amino]benzoyl chloride and 1.5 mmol of triethylamine in 10 ml of dichloromethane is stirred at room temperature for 3 hours and worked up to give the desired product as a solid.

EXAMPLE 152

N-[4-(7-Methoxy-5H-imidazo[2,1-c][1,4]benzodiazepin-10(11H)-ylcarbonyl]phenyl]-2-methylbenzamide As described for Example 125 a mixture of 1.0 mmol of 7-methoxy-10,11-dihydro-5H-imidazo[2,1-c][1,4]benzodiazepine, 1.1 mmol of 4-[(2-methylbenzoyl)amino]benzoyl chloride and 1.5 mmol of triethylamine in 10 ml of dichloromethane is stirred for 3 hours at room temperature and worked up to give the product as a solid.

EXAMPLE 153

N-[4-(7,8-Methylenedioxy-5H-imidazo[2,1-c][1,4]benzodiazepin-10(11H)-ylcarbonyl]phenyl]-2-methylbenzamide As described for Example 125 a mixture of mmol of 7,8-methylenedioxy-10,11-dihydro-5H-imidazo[2, 1-c][1,4]

benzodiazepine, 1.1 mmol of 4-[(2-methylbenzoyl)amino]
benzoyl chloride and 1.5 mmol of triethylamine in 10 ml of
dichloromethane is stirred at room temperature for 3 hours
and worked up to give the desired product as a solid.

EXAMPLE 154

4,5-Dihydro-5-(4-nitrobenzoyl)pyrrolo[1,2-a]
quinoxaline

To a solution of 5 mmol of 4,5-dihydropyrrolo-[1,2-a]
quinoxaline in 50 ml of methylene chloride under argon is
added 10 mmol of triethylamine followed by ice bath
cooling. A solution of 5 mmol of 4-nitrobenzoyl chloride in
10 ml of methylene chloride is added dropwise. Following
complete addition, the ice bath is removed and the reaction
mixture stirred at room temperature for 2 hours. The volatiles are removed in vacuo to give a residue which is
dissolved in ethyl acetate. The solution is washed with
water, 1N HCl, NaHCO₃, and brine. The reaction mixture is
dried with Na₂SO₄, filtered and evaporated in vacuo to give
a solid which is purified by flash chromatography to give the
desired product (from ethyl acetate) as a solid, m.p.
174°–178° C.

EXAMPLE 155

4,5-Dihydro-5(4-aminobenzoyl)pyrrolo[1,2-a]
quinoxaline

A mixture of 1 mmol of 4,5-dihydro-5-(4-nitrobenzoyl)
pyrrolo[1,2-a]quinoxaline in 10 ml of ethyl alcohol and 10
ml of ethyl acetate containing 0.2 g of 10% Pd/C is hydrogenated for 5 hours. The reaction mixture is filtered through
a pad of diatomaceous earth. The filtrate is concentrated in
vacuo to a solid which is purified by flash chromatography
to give the desired product, m.p. 225°–228° C.

EXAMPLE 156

4,5-Dihydro-5(4-aminobenzoyl)pyrrolo[1,2-a]
quinoxaline

To a solution of 1 mmol of 4,5-dihydro-5-(4-nitrobenzoyl)pyrrolo[1,2-a]quinoxaline in 20 ml of ethyl
alcohol is added 0.2 g of 10% Pd/C and 2.5 mmol of
hydrazine followed by stirring and heating under reflux for
2 hours. The hot reaction mixture is filtered through diatomaceous earth and the filter cake washed with hot chloroform and the filtrate concentrated in vacuo. The residue is
triturated with ethyl acetate and the mixture filtered to give
the desired product as crystals, m.p. 225°–228° C.

EXAMPLE 157

N-[4-(pyrrolo[1,2-a]quinoxalin-5(4H)-yl-carbonyl)
phenyl]-2-methylbenzamide

To a stirred solution of 1.5 mmol of 2-methylbenzoyl
chloride in 10 ml of methylene chloride is added 3 mmol of
triethylamine. After stirring for 15 minutes, 1.5 mmol of
4,5-dihydro-5-(4-aminobenzoyl)pyrrolo[1,2-a]quinoxaline
is added and the mixture stirred for 5 hours. The reaction
mixture is washed with water, 1N HCl, NaHCO₃, and brine.
The reaction mixture is dried with Na₂SO₄, filtered and
evaporated in vacuo to give a solid which is purified by flash
chromatography to give the desired product as a solid, m.p.
206°–207° C.

TABLE VI

The following Examples are prepared using
the conditions of Example 157 with the
appropriately substituted aroyl chloride

| Example No. | Compound |
| --- | --- |
| 158 | N-[4-(pyrrolo[1,2-a]quinoxalin-5(4H)ylcarbonyl)phenyl]-2-chlorobenzamide |
| 159 | N-[4-(pyrrolo[1,2-a]quinoxalin-5(4H)-ylcarbonyl)phenyl]-2,5-dichloro-benzamide |
| 160 | N-[4-(pyrrolo[1,2-a]quinoxalin-5(4H)-ylcarbonyl)phenyl]-2,4-dichloro-benzamide, m.p. 200°–202° C. |
| 161 | N-[4-(pyrrolo[1,2-a]quinoxalin-5(4H)-ylcarbonyl)phenyl]-2-chloro-4-methyl-benzamide |
| 162 | N-[4-(pyrrolo[1,2-a]quinoxalin-5(4H)-ylcarbonyl)phenyl]-2-methyl-4-chloro-benzamide |
| 163 | N-[4-(pyrrolo[1,2-a]quinoxalin-5(4H)-ylcarbonyl)phenyl]-2,4-dimethyl-benzamide |
| 164 | N-[4-(pyrrolo[1,2-a]quinoxalin-5(4H)-ylcarbonyl)phenyl]-2,3-dimethyl-benzamide, m.p. 216°–220° C. |
| 165 | N-[4-(pyrrolo[1,2-a]quinoxalin-5(4H)-ylcarbonyl)phenyl]-2-methoxy-benzamide |
| 166 | N-[4-(pyrrolo[1,2-a]quinoxalin-5(4H)-ylcarbonyl)phenyl]-2-trifluoro-methoxybenzamide |
| 167 | N-[4-(pyrrolo[1,2-a]quinoxalin-5(4H)-ylcarbonyl)phenyl]-2,4-dimethoxy-benzamide |
| 168 | N-[4-(pyrrolo[1,2-a]quinoxalin-5(4H)-ylcarbonyl)phenyl]-2,6-dimethoxy-benzamide |
| 169 | N-[4-(pyrrolo[1,2-a]quinoxalin-5(4H)-ylcarbonyl)phenyl]benzamide |
| 170 | N-[4-(pyrrolo[1,2-a]quinoxalin-5(4H)-ylcarbonyl)phenyl]-2,6-dichloro-benzamide |
| 171 | N-[4-(pyrrolo[1,2-a]quinoxalin-5(4H)-ylcarbonyl)phenyl]-2,6-dimethyl-benzamide |
| 172 | N-[4-(pyrrolo[1,2-a]quinoxalin-5(4H)-ylcarbonyl)phenyl]-2-(methylthio)-benzamide |
| 173 | N-[4-(pyrrolo[1,2-a]quinoxalin-5(4H)-ylcarbonyl)phenyl]-2-methyl-3-thiphenecarboxamide |
| 174 | N-[4-(pyrrolo[1,2-a]quinoxalin-5(4H)-ylcarbonyl)phenyl]-3-methyl-2-thiophenecarboxamide |
| 175 | N-[4-(pyrrolo[1,2-a]quinoxalin-5(4H)-ylcarbonyl)phenyl]-2-methyl-3-furanecarboxamide |
| 176 | N-[4-(pyrrolo[1,2-a]quinoxalin-5(4H)-ylcarbonyl)phenyl]-3-methyl-2-furanecarboxamide |
| 177 | N-[4-(pyrrolo[1,2-a]quinoxalin-5(4H)-ylcarbonyl)phenyl]benzeneacetamide |
| 178 | N-[4-(pyrrolo[1,2-a]quinoxalin-5(4H)-ylcarbonyl)phenyl]-2-chlorobenzene acetamide |
| 179 | N-[4-(pyrrolo[1,2-a]quinoxalin-5(4H)-ylcarbonyl)phenyl]-2-methylbenzene acetamide, yellow foam |
| 180 | N-[4-(pyrrolo[1,2-a]quinoxalin-5(4H)-ylcarbonyl)phenyl]-2-methyl-3-thiopheneacetamide |

EXAMPLE 181

9,10-Dihydro-4H-furo 2,3-e]pyrrolo[1,2-a][1,4-diazepine

To a suspension of 4 mmol of lithium aluminum hydride in 25 ml of anhydrous tetrahydrofuran is added 1 mmol of 9,10-dihydro-4H-furo[2,3-e]pyrrolo[1,2-a]-[1,4]diazepin-9-one. The mixture is refluxed for 12 hours and allowed to stand overnight. To the mixture is added dropwise 0.12 ml of water and then 6 ml of 1N sodium hydroxide. The mixture is extracted with ethyl acetate and the extract dried ($Na_2SO_4$). The volatiles are removed in vacuo to give the desired product as a solid.

EXAMPLE 182

9,10-Dihydro-4H-furo 2,3-e]pyrrolo 1,2][1,4]diazepine

A solution of 1 mmol of 4H-furo[2,3-e]pyrrolo[1,2-a][1,4]diazepine and 0.2 g of 10% Pd/C in ml of 10 ml of ethanol is hydrogenated for 18 hours. The reaction mixture is filtered through diatomaceous earth and the filtrate is evaporated in vacuo to give the desired product as a solid.

EXAMPLE 183

N-[4H-Furo[2,3-e]pyrrolo 1,2-a][1,4]diazepin-10-(9H)-ylcarbonyl)phenyl]-2-methylbenzamide To a mixture of 1.1 mmol of 4-[(2-methylbenzoyl)amino] benzoyl chloride in 10 ml of methylene chloride, cooled to 0° C. is added 1.5 mmol of triethylamine. To the mixture is added 1 mmol of 9,10-dihydro-4H-furo[2,3-e]pyrrolo[1,2-a][1,4]diazepine and the mixture stirred at room temperature for 2 hours. The reaction mixture is concentrated in vacuo and the residue is dissolved in 100 ml of ethyl acetate and washed with water, 2N citric acid, aqueous $NaHCO_3$ and brine. The solution is dried with $Na_2SO_4$ and the volatiles concentrated in vacuo to give a solid which is purified by flash chromatography to give the desired product.

EXAMPLE 184

9,10-Dihydro-10-(4-nitrobenzoyl)-4H-furo[2,3-e] pyrrolo[1,2-a][1,4]diazepine

To a solution of 1.0 mmol of 9,10-dihydro-4H-furo[2,3-e]pyrrolo[1,2-a][1,4]diazepine in 10 ml of methylene chloride under argon is added 1.5 mmol of triethylamine followed by ice bath cooling. A solution of 1.1 mmol of 4-nitrobenzoyl chloride in 5 ml of methylene chloride is added dropwise. Following complete addition, the ice bath is removed and the reaction mixture is stirred at room temperature for 2 hours. The volatiles are removed in vacuo to give a residue which is dissolved in ethyl acetate. The solution is washed with water, 1N HCl, $NaHCO_3$, and brine. The reaction mixture is dried with $Na_2SO_4$, filtered and evaporated in vacuo to give a solid which is purified by flash chromatography on silica gel to give desired product as a solid.

EXAMPLE 185

9,10-Dihydro-10-(4-aminobenzoyl)-4H-furo[2,3-e] pyrrolo[1,2-a][1,4]diazepine

A mixture of 1 mmol of 9,10-dihydro-10-(4-nitrobenzoyl) -4H-furo[2,3-e]pyrrolo[1,2-a][1,4]diazepine in 10 ml of ethyl alcohol and 10 ml of ethyl acetate containing 0.2 g of 10% Pd/C is hydrogenated for 5 hours. The reaction mixture is filtered through a pad of diatomaceous earth. The filtrate is concentrated in vacuo to a solid which is purified by flash chromatography on silica gel to give the desired product.

EXAMPLE 186

9,10-Dihydro-10-(4-aminobenzoyl)-4H-furo[2,3-e] pyrrolo[1,2-a][1,4]diazepine

To a solution of 1 mmol of 9,10-dihydro-10-(4-nitrobenzoyl)-4H-furo[2,3-e]pyrrolo[1,2-a][1,4]diazepine in 20 ml of ethyl alcohol is added 0.2 g of 10% Pd/C and 2.5 mmol of hydrazine followed by stirring and heating under reflux for 3 hours. The room temperature reaction mixture is filtered through diatomaceous earth and the filtrate concentrated in vacuo. The residue is dissolved in methylene chloride and passed through a thin pad of hydrous magnesium silicate. The filtrate is concentrated in vacuo to give the desired product which is purified by flash chromatography on silica gel to give the desired product as a solid.

EXAMPLE 187

N-[4-(4H-Furo[2,3-e]pyrrolo[1,2-a][1,4]diazepin-10 (9H)-ylcarbonyl)phenyl]-2-methyl benzamide To a stirred solution of 1.1 mmol of 2-methylbenzoyl chloride in 10 ml of methylene chloride is added 1.5 mmol of triethylamine. To the mixture is added 1.1 mmol of 9,10-dihydro-10-(4-aminobenzoyl)-4H-furo-[2,3-e]pyrrolo [1,2-a][1,4]diazepine and the mixture is stirred for 5 hours. The reaction mixture is washed with water, 1N citric acid, $NaHCO_3$, and brine. The reaction mixture is dried with $Na_2SO_4$, filtered and evaporated in vacuo to give a solid which is purified by flash chromatography on silica gel with ethyl acetate-hexane as solvent to give the desired product as a solid.

TABLE VII

The following Examples are prepared using the conditions of Example 187 with the appropriately substituted aroyl chloride

| Example No. | Compound |
|---|---|
| 188 | N-[4-(4H-Furo[2,3-e]pyrrolo[1,2-a]-[1,4]diazepin-10(9H)-ylcarbonyl)-phenyl]-2-chlorobenzamide |
| 189 | N-[4-(4H-Furo[2,3-e]pyrrolo[1,2-a]-[1,4]diazepin-10(9H)-ylcarbonyl)-phenyl]-2,5-dichlorobenzamide |
| 190 | N-[4-(4H-Furo[2,3-e]pyrrolo[1,2-a]-[1,4]diazepin-10(9H)-ylcarbonyl)-phenyl]-2,4-dichlorobenzamide |
| 191 | N-[4-(4H-Furo[2,3-e]pyrrolo[1,2-a]-[1,4]diazepin-10(9H)-ylcarbonyl)-phenyl]-2-chloro-4-methylbenzamide |
| 192 | N-[4-(4H-Furo[2,3-e]pyrrolo[1,2-a]-[1,4]diazepin-10(9H)-ylcarbonyl)-phenyl]-2-methyl-4-chlorobenzamide |
| 193 | N-[4-(4H-Furo[2,3-e]pyrrolo[1,2-a]-[1,4]diazepin-10(9H)-ylcarbonyl)-phenyl]-2,4-dimethylbenzamide |
| 194 | N-[4-(4H-Furo[2,3-e]pyrrolo[1,2-a]-[1,4]diazepin-10(9H)-ylcarbonyl)-phenyl]-2,3-dimethylbenzamide |
| 195 | N-[4-(4H-Furo[2,3-e]pyrrolo[1,2-a]-[1,4]diazepin-10(9H)-ylcarbonyl)-phenyl]-2-methoxybenzamide |

TABLE VII-continued

The following Examples are prepared using the conditions of Example 187 with the appropriately substituted aroyl chloride

| Example No. | Compound |
|---|---|
| 196 | N-[4-(4H-Furo[2,3-e]pyrrolo[1,2-a]-[1,4]diazepin-10(9H)-ylcarbonyl)-phenyl]-2-trifluoromethoxybenzamide |
| 197 | N-[4-(4H-Furo[2,3-e]pyrrolo[1,2-a]-[1,4]diazepin-10(9H)-ylcarbonyl)-phenyl]-2,4-dimethoxybenzamide |
| 198 | N-[4-(4H-Furo[2,3-e]pyrrolo[1,2-a]-[1,4]diazepin-10(9H)-ylcarbonyl)-phenyl]-2-methoxy-4-chlorobenzamide |
| 199 | N-[4-(4H-Furo[2,3-e]pyrrolo[1,2-a]-[1,4]diazepin-10(9H)-ylcarbonyl)-phenyl]-2,6-dichlorobenzamide |
| 200 | N-[4-(4H-Furo[2,3-e]pyrrolo[1,2-a]-[1,4]diazepin-10(9H)-ylcarbonyl)-phenyl]-2-methylthiobenzamide |
| 201 | N-[4-(4H-Furo[2,3-e]pyrrolo[1,2-a]-[1,4]diazepin-10(9H)-ylcarbonyl)-phenyl]-2-methyl-3-thiphene-carboxamide |
| 202 | N-[4-(4H-Furo[2,3-e]pyrrolo[1,2-a]-[1,4]diazepin-10(9H)-ylcarbonyl)-phenyl]-3-methyl-2-thiophene-carboxamide |
| 203 | N-[4-(4H-Furo[2,3-e]pyrrolo[1,2-a]-[1,4]diazepin-10(9H)-ylcarbonyl)-phenyl]-2-methyl-3-furane-carboxamide |
| 204 | N-[4-(4H-Furo[2,3-e]pyrrolo[1,2-a]-[1,4]diazepin-10(9H)-ylcarbonyl)-phenyl]-3-methyl-2-furane-carboxamide |
| 205 | N-[4-(4H-Furo[2,3-e]pyrrolo[1,2-a]-[1,4]diazepin-10(9H)-ylcarbonyl)-phenyl]-2-chlorobenzeneacetamide |
| 206 | N-[4-(4H-Furo[2,3-e]pyrrolo[1,2-a]-[1,4]diazepin-10(9H)-ylcarbonyl)-phenyl]-2-methylbenzeneacetamide |
| 207 | N-[4-(4H-Furo[2,3-e]pyrrolo[1,2-a]-[1,4]diazepin-10(9H)-ylcarbonyl)-phenyl]-2-methyl-3-thiophene-acetamide |
| 208 | N-[4-(4H-Furo[2,3-e]pyrrolo[1,2-a]-[1,4]diazepin-10(9H)-ylcarbonyl)-phenyl]-cyclohexanecarboxamide |
| 209 | N-[4-(4H-Furo[2,3-e]pyrrolo[1,2-a]-[1,4]diazepin-10(9H)-ylcarbonyl)-phenyl]-cyclohexylacetamide |

EXAMPLE 210

N-[4-(4H-Pyrazolo[5,1-c][1,4]benzodiazepin-5(10H)-ylcarbonyl)phenyl]-2-methylbenzamide To a mixture of 1.37 g of 4-[(2-methylbenzoyl)amino] benzoyl chloride in 15 ml of methylene chloride, cooled to 0° C. is added 1.5 ml of triethylamine. To the mixture is added 5 mmol of 5,10-dihydro-4H-pyrazolo[5,1-c][1,4] benzodiazepine. The reaction mixture is allowed to stir at room temperature for 48 hours and the volatiles are removed in vacuo to give a residue. The residue is dissolved in 100 ml of ethyl acetate and washed with water, 2N citric acid, aqueous NaHCO₃ and brine. The solution is dried with Na₂SO₄ and the solvent removed in vacuo. The residue is purified by flash chromatography on silica gel with ethyl acetate-hexane to give the desired product, m.p. 142°–146° C.

EXAMPLE 211

5,10-Dihydro-5-(4-nitrobenzoyl)-4H-pyrazolo-[5,1-c][1,4]benzodiazepine

To a solution of 10 mmol of 5,10-dihydro-4H-pyrazolo [5,1-c][1,4]benzodiazepine in 50 ml of methylene chloride under argon is added 15 mmol of triethylamine followed by ice bath cooling. A solution of 11 mmol of 4-nitrobenzoyl chloride in 10 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, NaHCO₃, and brine. The reaction mixture is dried with Na₂SO₄, filtered and evaporated in vacuo to give a solid which is purified by flash chromatography on silica gel to give desired product as a solid, m.p. 227°–229° C.

EXAMPLE 212

5,10-Dihydro-5-(4-aminobenzoyl)-4H-pyrazolo-[5,1-c][1,4]benzodiazepine

A mixture of 5 mmol of 5,10-dihydro-5-(4-nitrobenzoyl)-4H-pyrazolo-[5,1-c][1,4]benzodiazepine in 25 ml of ethyl alcohol and 10 ml of ethyl acetate containing 0.2 g of 10% Pd/C is hydrogenated for 5 hours. The reaction mixture is filtered through a pad of diatomaceous earth. The filtrate is concentrated in vacuo to a solid which is purified by flash chromatography on silica gel to give the desired product as a tan solid.

EXAMPLE.213

5,10-Dihydro-5-(4-aminobenzoyl)-4H-pyrazolo-[5,1-c][1,4]benzodiazepine

To a solution of 5 mmol of 5,10-dihydro-5-(4-nitrobenzoyl)-4H-pyrazolo-[5,1-c][1,4]benzodiazepine in 25 ml of ethyl alcohol is added 0.3 g of 10% Pd/C and 15 mmol of hydrazine. The mixture is heated under reflux for 3 hours, and the mixture is filtered through diatomaceous earth. The filtrate is concentrated in vacuo to a residue which is dissolved in methylene chloride and passed through a thin pad of hydrous magnesium silicate. The filtrate is concentrated in vacuo to give the desired product which is purified by flash chromatography on silica gel to give the desired product as a solid, exact mass by mass spectrometry: 305.1402(M+H).

EXAMPLE 214

N-[4-([4H-Pyrazolo[5,1-c][1,4]benzodiazepin-5(10H)-ylcarbonyl)phenyl]-2-methylbenzamide To a stirred solution of 3 mmol of 2-methylbenzoyl chloride in 10 ml of methylene chloride is added 5 mmol of triethylamine and 3 mmol of 5,10-dihydro-5-(4-aminobenzoyl)-4H-pyrazolo-[5,1-c][1,4]benzodiazepine. The mixture is stirred at room temperature for 5 hours and is then washed with water, NaHCO₃, and brine. The organic layer is dried with Na₂SO₄, filtered and evaporated in vacuo to give a solid which is purified by flash chromatography on silica gel to give the desired product as a solid, m.p. 142°–146° C.

TABLE VIII

The following Examples are prepared using the conditions of Example 214 with the appropriately substituted aroyl chloride.

| Example No. | Compound |
|---|---|
| 215 | N-[4-(4H-Pyrazolo[5,1-c][1,4]benzodiazepin-5(10H)-ylcarbonyl)phenyl]-2-methoxybenzeneacetamide, m.p. 185°–188° C. |
| 216 | N-[4-(4H-Pyrazolo[5,1-c][1,4]benzodiazepin-5(10H)-ylcarbonyl)phenyl]-2,5-dichlorobenzamide |
| 217 | N-[4-(4H-Pyrazolo[5,1-c][1,4]benzodiazepin-5(10H)-ylcarbonyl)phenyl]-2,4-dichlorobenzamide, colorless foam; exact mass by mass spectrometry: 479.0896 (M+H) |
| 218 | N-[4-(4H-Pyrazolo[5,1-c][1,4]benzodiazepin-5(10H)-ylcarbonyl)phenyl]-2-chloro-4-methylbenzamide |
| 219 | N-[4-(4H-Pyrazolo[5,1-c][1,4]benzodiazepin-5(10H)-ylcarbonyl)phenyl]-2-methyl-4-chlorobenzamide |
| 220 | N-[4-(4H-Pyrazolo[5,1-c][1,4]benzodiazepin-5(10H)-ylcarbonyl)phenyl]-2,4-dimethylbenzamide |
| 221 | N-[4-(4H-Pyrazolo[5,1-c][1,4]benzodiazepin-5(10H)-ylcarbonyl)phenyl]-2,3-dimethylbenzamide |
| 222 | N-[4-(4H-Pyrazolo[5,1-c][1,4]benzodiazepin-5(10H)-ylcarbonyl)phenyl]-2-methoxybenzamide |
| 223 | N-[4-(4H-Pyrazolo[5,1-c][1,4]benzodiazepin-5(10H)-ylcarbonyl)phenyl]-2-trifluoromethoxybenzamide |
| 224 | N-[4-(4H-Pyrazolo[5,1-c][1,4]benzodiazepin-5(10H)-ylcarbonyl)phenyl]-2,4-dimethoxybenzamide |
| 225 | N-[4-(4H-Pyrazolo[5,1-c][1,4]benzodiazepin-5(10H)-ylcarbonyl)phenyl]-2,6-dimethoxybenzamide |
| 226 | N-[4-(4H-Pyrazolo[5,1-c][1,4]benzodiazepin-5(10H)-ylcarbonyl)phenyl]-benzamide |
| 227 | N-[4-(4H-Pyrazolo[5,1-c][1,4]benzodiazepin-5(10H)-ylcarbonyl)phenyl]-2,6-dichlorobenzamide |
| 228 | N-[4-(4H-Pyrazolo[5,1-c][1,4]benzodiazepin-5(10H)-ylcarbonyl)phenyl]-2,6-dimethylbenzamide |
| 229 | N-[4-(4H-Pyrazolo[5,1-c][1,4]benzodiazepin-5(10H)-ylcarbonyl)phenyl]-2-methylthiobenzamide |
| 230 | N-[4-(4H-Pyrazolo[5,1-c][1,4]benzodiazepin-5(10H)-ylcarbonyl)phenyl]-2-methyl-3-thiophenecarboxamide |
| 231 | N-[4-(4H-Pyrazolo[5,1-c][1,4]benzodiazepin-5(10H)-ylcarbonyl)phenyl]-3-methyl-2-thiophenecarboxamide |
| 232 | N-[4-(4H-Pyrazolo[5,1-c][1,4]benzodiazepin-5(10H)-ylcarbonyl)phenyl]-2-methyl-3-furanecarboxamide |
| 233 | N-[4-(4H-Pyrazolo[5,1-c][1,4]benzodiazepin-5(10H)-ylcarbonyl)phenyl]-3-methyl-2-furanecarboxamide |
| 234 | N-[4-(4H-Pyrazolo[5,1-c][1,4]benzodiazepin-5(10H)-ylcarbonyl)phenyl]-3-cyclohexenecarboxamide |
| 235 | N-[4-(4H-Pyrazolo[5,1-c][1,4]benzodiazepin-5(10H)-ylcarbonyl)phenyl]-2-chlorobenzeneacetamide |
| 236 | N-[4-(4H-Pyrazolo[5,1-c][1,4]benzodiazepin-5(10H)-ylcarbonyl)phenyl]-2-methylbenzeneacetamide |
| 237 | N-[4-(4H-Pyrazolo[5,1-c][1,4]benzodiazepin-5(10H)-ylcarbonyl)phenyl]-2-methyl-3-thipheneacetamide |

EXAMPLE 238

9,10-Dihydro-4H-pyrrolo[1,2-a]thieno[2,3-e][1,4]diazepine

To a mixture of 7.0 g of 9-oxo-9,10-dihydro-4H-pyrrolo[1,2-a]thieno[2,3-e][1,4]diazepin in 25 ml of anhydrous tetrahydrofuran is added 9 ml of 10 molar boron-dimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried (Na$_2$SO$_4$). The solvent is removed in vacuo to give the desired product as a solid.

EXAMPLE 239

N-[4-(4H-Pyrazolo[1,2-a]thieno-2,3-a][1,4]diazepin-10(9H)-ylcarbonyl)phenyl]-2-methylbenzamide To a mixture of 1.37 g (5 mmol) of 4-[(2-methylbenzoyl)amino]benzoyl chloride in 15 ml of methylene chloride, cooled to 0° C. is added 1.5 ml of triethylamine. To the mixture is added 5 mmol of 9,10-dihydro-4H-pyrazolo[1,2-a]thieno[2,3-e][1,4]diazepine. The cooling bath is removed and the reaction mixture is allowed to stir at room temperature for 48 hours. The volatiles are removed in vacuo to give a residue. The residue is dissolved in 100 ml of ethyl acetate and washed with water, 2N citric acid, aqueous NaHCO$_3$ and brine. The solution is dried with Na$_2$SO$_4$ and the solvent removed in vacuo to give a solid. The solid is purified by flash chromatography on silica gel to give the desired product.

EXAMPLE 240

9,10-Dihydro-10-(4-nitrobenzoyl)-4H-pyrrolo[1,2-a]thieno[2,3-e][1,4]diazepine

To a solution of 10 mmol of 9,10-dihydro-4H-pyrrolo[1,2-a]thieno[2,3-e][1,4]diazepine in 50 ml of methylene chloride under argon is added 15 mmol of triethylamine followed by ice bath cooling. A solution of 11 mmol of 4-nitrobenzoyl chloride in 10 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, 1N HCl, NaHCO$_3$, and brine. The organic layer is dried with Na$_2$SO$_4$, filtered and evaporated in vacuo to give a solid which is purified by flash chromatography on silica gel to give desired product as a solid.

EXAMPLE 241

9,10-Dihydro-10-(4-aminobenzoyl)-4H-pyrrolo[1,2-a]thieno[2,3-e][1,4]diazepine

A mixture of 2 g of 9,10-dihydro-10-(4-nitrobenzoyl)-4H-pyrrolo-[1,2-a]thieno[2,3-e][1,4]diazepine in 20 ml of ethyl alcohol and 20 ml of ethyl acetate containing 0.2 g of 10% Pd/C is hydrogenated for 5 hours. The reaction mixture is filtered through a pad of diatomaceous earth. The filtrate is concentrated in vacuo to a solid which is purified by flash chromatography to give the desired product.

EXAMPLE 242

9,10-Dihydro-10-(4-aminobenzoyl)-4H-pyrrolo[1,2-a]thieno[2,3-e][1,4]diazepine

To a solution of 5 mmol of 9,10-dihydro-10-(4-nitrobenzoyl)-4H-pyrrolo-[1,2-a]thieno[2,3-e][1,4]diazepine in 25 ml of ethyl alcohol is added 0.13 g of 10% Pd/C and 15 mmol of hydrazine followed by stirring and heating under reflux for 3 hours. The cooled reaction mixture is filtered through diatomaceous earth. The filtrate is concentrated in vacuo to a residue which is dissolved in methylene chloride and passed through a pad of hydrous magnesium silicate. The filtrate is concentrated in vacuo to give the desired product which is purified by flash chromatography on silica gel to give the desired product as a solid.

EXAMPLE 243

N-[4-(4H-Pyrrolo[1,2-a]thieno[2,3-e][1,4]diazepin-10(9H)-ylcarbonyl)phenyl]-2-methylbenzamide To a stirred solution of 5 mmol of 2-methylbenzoyl chloride in 10 ml of methylene chloride is added 7 mmol of triethylamine and 5 mmol of 9,10-dihydro-10-(4-aminobenzoyl)-4H-pyrrolo-[1,2-a]thieno[2,3-e][1,4]diazepine and the mixture stirred for 5 hours. The reaction mixture is washed with water, 2N citric acid, NaHCO$_3$, and brine. The organic layer is dried with Na$_2$SO$_4$, filtered and evaporated in vacuo to give a solid which is purified by flash chromatography on silica gel to give the desired product as a solid.

TABLE IX

The following Examples are prepared using the conditions of Example 243 with the appropriately substituted aroyl chloride.

| Example No. | Compound |
| --- | --- |
| 244 | N-[4-(4H-pyrrolo[1,2-a]thieno-[2,3-e][1,4]diazepin-10(9H)-yl carbonyl)phenyl]-2-chlorobenzamide |
| 245 | N-[4-(4H-pyrrolo[1,2-a]thieno-[2,3-e][1,4]diazepin-10(9H)-yl carbonyl)phenyl]-2,5-dichlorobenzamide |
| 246 | N-[4-(4H-pyrrolo[1,2-a]thieno-[2,3-e][1,4]diazepin-10(9H)-yl carbonyl)phenyl]-2,4-dichlorobenzamide |
| 247 | N-[4-(4H-pyrrolo[1,2-a]thieno-[2,3-e][1,4]diazepin-10(9H)-yl carbonyl)phenyl]-2-chloro-4-methylbenzamide |
| 248 | N-[4-(4H-pyrrolo[1,2-a]thieno-[2,3-e][1,4]diazepin-10(9H)-yl carbonyl)phenyl]-2-methyl-4-chlorobenzamide |
| 249 | N-[4-(4H-pyrrolo[1,2-a]thieno-[2,3-e][1,4]diazepin-10(9H)-yl carbonyl)phenyl]-2,4-dimethylbenzamide |
| 250 | N-[4-(4H-pyrrolo[1,2-a]thieno-[2,3-e][1,4]diazepin-10(9H)-yl carbonyl)phenyl]-2,3-dimethylbenzamide |
| 251 | N-[4-(4H-pyrrolo[1,2-a]thieno-[2,3-e][1,4]diazepin-10(9H)-yl carbonyl)phenyl]-2-methoxybenzamide |
| 252 | N-[4-(4H-pyrrolo[1,2-a]thieno-[2,3-e][1,4]diazepin-10(9H)-yl carbonyl)phenyl]-2-trifluoromethoxybenzamide |
| 253 | N-[4-(4H-pyrrolo[1,2-a]thieno-[2,3-e][1,4]diazepin-10(9H)-yl carbonyl)phenyl]-2,4-dimethoxybenzamide |
| 254 | N-[4-(4H-pyrrolo[1,2-a]thieno-[2,3-e][1,4]diazepin-10(9H)-yl carbonyl)phenyl]-2,6-dimethoxybenzamide |
| 255 | N-[4-(4H-pyrrolo[1,2-a]thieno-[2,3-e][1,4]diazepin-10(9H)-yl carbonyl)phenyl]-2,6-dichlorobenzamide |
| 256 | N-[4-(4H-pyrrolo[1,2-a]thieno-[2,3-e][1,4]diazepin-10(9H)-yl carbonyl)phenyl]-2,6-dimethylbenzamide |
| 257 | N-[4-(4H-pyrrolo[1,2-a]thieno-[2,3-e][1,4]diazepin-10(9H)-yl carbonyl)phenyl]-2-methoxy-4-chlorobenzamide |
| 258 | N-[4-(4H-pyrrolo[1,2-a]thieno-[2,3-e][1,4]diazepin-10(9H)-yl carbonyl)phenyl]-2-methoxybenzeneacetamide |
| 259 | N-[4-(4H-pyrrolo[1,2-a]thieno-[2,3-e][1,4]diazepin-10(9H)-yl carbonyl)phenyl]-2-(methylthio)-benzamide |
| 260 | N-[4-(4H-pyrrolo[1,2-a]thieno-[2,3-e][1,4]diazepin-10(9H)-yl carbonyl)phenyl]-2-methyl-3-thiophenecarboxamide |
| 261 | N-[4-(4H-pyrrolo[1,2-a]thieno-[2,3-e][1,4]diazepin-10(9H)-yl carbonyl)phenyl]-3-methyl-2-thiophenecarboxamide |
| 262 | N-[4-(4H-pyrrolo[1,2-a]thieno-[2,3-e][1,4]diazepin-10(9H)-yl carbonyl)phenyl]-3-methyl-2-furancarboxamide |
| 263 | N-[4-(4H-pyrrolo[1,2-a]thieno-[2,3-e][1,4]diazepin-10(9H)-yl carbonyl)phenyl]-3-chlorophenylacetamide |
| 264 | N-[4-(4H-pyrrolo[1,2-a]thieno-[2,3-e][1,4]diazepin-10(9H)-yl carbonyl)phenyl]-2-methylbenzeneacetamide |
| 265 | N-[4-(4H-pyrrolo[1,2-a]thieno-[2,3-e][1,4]diazepin-10(9H)-yl carbonyl)phenyl]-2-methyl-3-thiopheneacetamide |

EXAMPLE 266

4,10-Dihydro-5H-pyrrolo[1,2-a]thieno[3,2-e][1,4]diazepine

To a suspension of 7.0 g of 5-oxo-4,5-dihydropyrrolo[1,2-a]thieno[3,2-e][1,4]diazepine in 25 ml of anhydrous tetrahydrofuran is added 9 ml of 10M borane-dimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried ($Na_2SO_4$). The solvent is removed to give a solid.

EXAMPLE 267

N-[4-(5H-Pyrazolo[1,2-a]thieno[3,2-e][1,4]diazepin-4(10H)-ylcarbonyl)phenyl]-2-methylbenzamide To a mixture of 5.5 mmol of 4-[(2-methylbenzoyl)amino] benzoyl chloride in 20 ml of methylene chloride, cooled to 0° C. is added 7.5 mmol of triethylamine and 5 mmol of 4,10-dihydro-5H-pyrazolo[1,2-a]thieno[3,2-e][1,4] diazepine. The cooling bath is removed and the reaction mixture is allowed to stir at room temperature for 48 hours. The volatiles are removed in vacuo to give a residue. The residue is dissolved in 100 ml of ethyl acetate and the solution washed with water, 2N citric acid, aqueous $NaHCO_3$ and brine. The solution is dried with $Na_2SO_4$ and the solvent concentrated in vacuo to give a solid. The solid is purified by flash chromatography on silica gel to give the desired product as a solid and foam, m.p. 162°–188° C., Anal. Calc'd for $C_{25}H_{21}N_3O_2S$: C,70.2; H,5.0 N,9.8; S,7.5 Found: C,69.5, H,5.2 N,9.6; S,7.0.

EXAMPLE 268

4,10-Dihydro-4-(4-nitrobenzoyl)-5H-pyrrolo1,2-a]thieno[3,2-e][1,4]diazepine

To a solution of 3 mmol of 4,10-dihydro-5H-pyrrolo[1,2-a]thieno[3,2-e][1,4]diazepine in 10 ml of methylene chloride under argon is added 5 mmol of triethylamine followed by ice bath cooling. A solution of 3.3 mmol of 4-nitrobenzoyl chloride in 3 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, 2N citric acid, $NaHCO_3$, and brine. The reaction mixture is dried with $Na_2SO_4$, filtered and evaporated in vacuo to give a solid which is purified by flash chromatography on silica gel to give desired product as a solid.

EXAMPLE 269

4,10-Dihydro-4-(4-aminobenzoyl)-5H-pyrrolo[1,2-a]thieno[3,2-e][1,4]diazepine

A mixture of 5 mmol of 4,10-dihydro-4-(4-nitrobenzoyl)-5H-pyrrolo-[1,2-a]thieno[3,2-e][1,4]diazepine in 25 ml of ethyl alcohol and 25 ml of ethyl acetate containing 0.2 g of 10% Pd/C is hydrogenated for 5 hours. The reaction mixture is filtered through a pad of diatomaceous earth. The filtrate is concentrated in vacuo to a solid which is purified by flash chromatography on silica gel to give the desired product.

EXAMPLE 270

4,10-Dihydro-4-(4-aminobenzoyl)-5H-pyrrolo-[1,2-a]thieno[3,2-e][1,4]diazepine

To a mixture of 5 mmol of 4,10-dihydro-4-(4-nitrobenzoyl)-5H-pyrrolo-[1,2-a]thieno[3,2-e][1,4] diazepine in 25 ml of ethyl alcohol is added 0.3 g of 10% Pd/C and 15 mmol of hydrazine followed by stirring and heating under reflux for 3 hours. The cooled reaction mixture is filtered through diatomaceous earth. The filtrate is concentrated in vacuo to a residue which is dissolved in methylene chloride and passed through a pad of hydrous magnesium silicate. The filtrate is concentrated in vacuo to give the desired product which is purified by flash chromatography on silica gel to give the desired product as a solid.

EXAMPLE 271

N-[4-(5H-Pyrrolo[1,2-a]thieno[3,2-e][1,4]diazepin-4(10H)-ylcarbonyl)phenyl]-2-methylbenzamide To a stirred solution of 3 mmol of 2-methylbenzoyl chloride in 10 ml of methylene chloride is added 5 mmol of triethylamine and 3 mmol of 4,10-dihydro-4-(4-aminobenzoyl)-5H-pyrrolo-[1,2-a]thieno[3,2-e][1,4] diazepine. The mixture is stirred for 5 hours. The reaction mixture is washed with water, 2N citric acid, $NaHCO_3$, and brine. The reaction mixture is dried with $Na_2SO_4$, filtered and evaporated in vacuo to give a solid which is purified by flash chromatography on silica gel to give the desired product as a solid, m.p. 162°–188° C. (amorphous)

TABLE X

The following Examples are prepared using the conditions of Example 271 with the appropriately substituted aroyl chloride.

| Example No. | Compound |
|---|---|
| 272 | N-[4-(5H-pyrrolo[1,2-a]thieno-[3,2-e][1,4]diazepin-4(10H)-yl carbonyl)phenyl]-2-chloro-benzamide |
| 273 | N-[4-(5H-pyrrolo[1,2-a]thieno-[3,2-e][1,4]diazepin-4(10H)-yl carbonyl)phenyl]-2,5-dichloro-benzamide |
| 274 | N-[4-(5H-pyrrolo[1,2-a]thieno-[3,2-e][1,4]diazepin-4(10H)-yl carbonyl)phenyl]-2,4-dichloro-benzamide (solid foam), m.p. 105–190° C.; Anal Calc'd for $C_{24}H_{17}N_3Cl_2O_2S$: C, 59.8; H, 3.6; N, 8.7; S, 6.6, Cl, 14.7 Found: C, 59.6; H, 3.8; N, 8.1; S, 5.5; Cl, 14.0 |
| 275 | N-[4-(5H-pyrrolo[1,2-a]thieno-[3,2-e][1,4]diazepin-4(10H)-yl carbonyl)phenyl]-2-chloro-4-methylbenzamide |
| 276 | N-[4-(5H-pyrrolo[1,2-a]thieno-[3,2-e][1,4]diazepin-4(10H)-yl carbonyl)phenyl]-2-methyl-4-chlorobenzamide |
| 277 | N-[4-(5H-pyrrolo[1,2-a]thieno-[3,2-e][1,4]diazepin-4(10H)-yl carbonyl)phenyl]-2,4-dimethyl-benzamide |
| 278 | N-[4-(5H-pyrrolo[1,2-a]thieno-[3,2-e][1,4]diazepin-4(10H)-yl carbonyl)phenyl]-2,3-dimethyl-benzamide |
| 279 | N-[4-(5H-pyrrolo[1,2-a]thieno-[3,2-e][1,4]diazepin-4(10H)-yl carbonyl)phenyl]-2-methoxy-benzamide |
| 280 | N-[4-(5H-pyrrolo[1,2-a]thieno-[3,2-e][1,4]diazepin-4(10H)-yl carbonyl)phenyl]-2-trifluoro-methoxybenzamide |
| 281 | N-[4-(5H-pyrrolo[1,2-a]thieno- |

TABLE X-continued

The following Examples are prepared using the conditions of Example 271 with the appropriately substituted aroyl chloride.

| Example No. | Compound |
|---|---|
| | [3,2-e][1,4]diazepin-4(10H)-yl carbonyl)phenyl]-2,4-dimethoxybenzamide |
| 282 | N-[4-(5H-pyrrolo[1,2-a]thieno-[3,2-e][1,4]diazepin-4(10H)-yl carbonyl)phenyl]-2,6-dimethoxybenzamide |
| 283 | N-[4-(5H-pyrrolo[1,2-a]thieno-[3,2-e][1,4]diazepin-4(10H)-yl carbonyl)phenyl]-2,6-dichlorobenzamide |
| 284 | N-[4-(5H-pyrrolo[1,2-a]thieno-[3,2-e][1,4]diazepin-4(10H)-yl carbonyl)phenyl]-2,6-dimethylbenzamide |
| 285 | N-[4-(5H-pyrrolo[1,2-a]thieno-[3,2-e][1,4]diazepin-4(10H)-yl carbonyl)phenyl]-2-methylthiobenzamide |
| 286 | N-[4-(5H-pyrrolo[1,2-a]thieno-[3,2-e][1,4]diazepin-4(10H)-yl carbonyl)phenyl]-2-methyl-3-thiophenecarboxamide |
| 287 | N-[4-(5H-pyrrolo[1,2-a]thieno-[3,2-e][1,4]diazepin-4(10H)-yl carbonyl)phenyl-3-methyl-2-thiophenecarboxamide |
| 288 | N-[4-(5H-pyrrolo[1,2-a]thieno-[3,2-e][1,4]diazepin-4(10H)-yl carbonyl)phenyl-3-methyl-2-furancarboxamide |
| 289 | N-[4-(5H-pyrrolo[1,2-a]thieno-[3,2-e][1,4]diazepin-4(10H)-yl carbonyl)phenyl-3-chlorobenzeneacetamide |
| 290 | N-[4-(5H-pyrrolo[1,2-a]thieno-[3,2-e][1,4]diazepin-4(10H)-yl carbonyl)phenyl]-2-methoxybenzeneacetamide |
| 291 | N-[4-(5H-pyrrolo[1,2-a]thieno-[3,2-e][1,4]diazepin-4(10H)-yl carbonyl)phenyl]-2-methoxy-4-chlorobenzamide |
| 292 | N-[4-(5H-pyrrolo[1,2-a]thieno-[3,2-e][1,4]diazepin-4(10H)-yl carbonyl)phenyl]-2-methylbenzeneacetamide |
| 293 | N-[4-(5H-pyrrolo[1,2-a]thieno-[3,2-e][1,4]diazepin-4(10H)-yl carbonyl)phenyl]-2-methyl-3-thiopheneacetamide |

EXAMPLE 294

6,7-Dihydro-5-(4-nitrobenzoyl)-5H-pyrrolo[1,2-a][1,5]benzodiazepine

To a solution of 10 mmol of 6,7-dihydro-5H-pyrrolo[1,2-a][1,5]benzodiazepine in 30 ml of methylene chloride under argon is added 15 mmol of triethylamine followed by ice bath cooling. A solution of 11 mmol of 4-nitrobenzoyl chloride in 10 ml of methylene chloride is added dropwise. Following complete addition, the ice bath is removed and the reaction mixture stirred at room temperature for 2 hours. The volatiles are removed in vacuo to give a residue which is dissolved in ethyl acetate. The solution is washed with water, 2N citric acid, NaHCO$_3$, and brine. The reaction mixture is dried with Na$_2$SO$_4$, filtered and evaporated in vacuo to give a solid which is purified by flash chromatography on silica gel to give the desired product as a solid.

EXAMPLE 295

6,7-Dihydro-5-(4-aminobenzoyl)-5H-pyrrolo[1,2-a][1,5]benzodiazepine

A mixture of 2.0 g of 6,7-dihydro-5-(4-nitrobenzoyl)-5H-pyrrolo[1,2-a][1,5]benzodiazepine, 20 ml of ethyl alcohol and 20 ml of ethyl acetate containing 0.2 g of 10% Pd/C is hydrogenated for 5 hours. The reaction mixture is filtered through a pad of diatomaceous earth. The filtrate is concentrated in vacuo to a solid which is purified by flash chromatography on silica gel to give the desired product.

EXAMPLE 296

6,7-Dihydro-5-(4-aminobenzoyl)-5H-pyrrolo[1,2-a][1,5]benzodiazepine

To a solution of 5 mmol of 6,7-dihydro-5-(4-nitrobenzoyl)-5H-pyrrolo[1,2-a][1,5]benzodiazepine in 25 ml of ethyl alcohol is added 0.3 g of 10% Pd/C and 15 mmol of hydrazine followed by stirring and heating under reflux for 3 hours. The reaction mixture is filtered through diatomaceous earth. The filtrate is concentrated in vacuo to a residue which is dissolved in methylene chloride and passed through a pad of hydrous magnesium silicate. The filtrate is concentrated in vacuo to give the desired product which is purified by flash chromatography on silica gel to give the desired product as a solid.

EXAMPLE 297

N-[4-6,7-Dihydro-5H-pyrrolo[1,2-a][1,5]benzodiazepin-5-yl)carbonyl]phenyl]-2-methylbenzamide To a mixture of 1.37 g (5 mmol) of 4-[(2-methylbenzoyl)amino]benzoyl chloride in 10 ml of methylene chloride, cooled to 0° C. is added 7 mmol of triethylamine and 5 mmol of 6,7-dihydro-5H-pyrrolo[1,2-a][1,5]benzodiazepine. The cooling bath is removed and the reaction mixture is allowed to stir at room temperature for 48 hours. The volatiles are removed in vacuo to give a residue. The residue is dissolved in 100 ml of ethyl acetate and washed with water, 2N citric acid, aqueous NaHCO$_3$ and brine. The solution is dried with Na$_2$SO$_4$ and the solvent removed in vacuo to give a solid. The solid is triturated with ether-hexane to give the desired product, mass spectrum (CI):422(M+H).

EXAMPLE 298

N-4-6,7-Dihydro-5H-pyrrolo[1,2-a][1,5[benzodiazepin-5-yl)carbonyl)phenyl]-2-methylbenzamide To a stirred solution of 5 mmol of 2-methylbenzoyl chloride in 10 ml of methylene chloride is added 7 mmol of triethylamine and 5 mmol of 6,7-dihydro-5-(4-aminobenzoyl)-5H-pyrrolo[1,2-a][1,5]benzodiazepine. The reaction mixture is washed with water, 2M citric acid, NaHCO$_3$, and brine. The organic layer is dried with Na$_2$SO$_4$, filtered and evaporated in vacuo to give a solid which is purified by flash chromatography on silica gel to give the desired product as a solid; mass spectrum (CI) :422(M+H).

TABLE XI

The following Examples are prepared using the conditions of Example 298 with the appropriately substituted aroyl chloride.

| Example No. | Compound |
|---|---|
| 299 | N-[4-[(6,7-dihydro-5H-pyrrolo[1,2-a][1,5]benzodiazepin-5-yl)carbonyl]phenyl]-2-chlorobenzamide |
| 300 | N-[4-[(6,7-dihydro-5H-pyrrolo[1,2-a][1,5]benzodiazepin-5-yl)carbonyl]phenyl]-2,5-dichlorobenzamide |
| 301 | N-[4-[(6,7-dihydro-5H-pyrrolo[1,2-a][1,5]benzodiazepin-5-yl)carbonyl]phenyl]-2,4-dichlorobenzamide |
| 302 | N-[4-[(6,7-dihydro-5H-pyrrolo[1,2-a][1,5]benzodiazepin-5-yl)carbonyl]phenyl]-2-chloro-4-methylbenzamide |
| 303 | N-[4-[(6,7-dihydro-5H-pyrrolo[1,2-a][1,5]benzodiazepin-5-yl)carbonyl]phenyl]-2-methyl-4-chlorobenzamide |
| 304 | N-[4-[(6,7-dihydro-5H-pyrrolo[1,2-a][1,5]benzodiazepin-5-yl)carbonyl]phenyl]-2,4-dimethylbenzamide |
| 305 | N-[4-[(6,7-dihydro-5H-pyrrolo[1,2-a][1,5]benzodiazepin-5-yl)carbonyl]phenyl]-2,3-dimethylbenzamide |
| 306 | N-[4-[(6,7-dihydro-5H-pyrrolo[1,2-a][1,5]benzodiazepin-5-yl)carbonyl]phenyl]-2-methoxybenzamide |
| 307 | N-[4-[(6,7-dihydro-5H-pyrrolo[1,2-a][1,5]benzodiazepin-5-yl)carbonyl]phenyl]-2-trifluoromethoxybenzamide |
| 308 | N-[4-[(6,7-dihydro-5H-pyrrolo[1,2-a][1,5]benzodiazepin-5-yl)carbonyl]phenyl]-2,4-dimethoxybenzamide |
| 309 | N-[4-[(6,7-dihydro-5H-pyrrolo[1,2-a][1,5]benzodiazepin-5-yl)carbonyl]phenyl]-2,6-dimethoxybenzamide |
| 310 | N-[4-[(6,7-dihydro-5H-pyrrolo[1,2-a][1,5]benzodiazepin-5-yl)carbonyl]phenyl]-2,6-dichlorobenzamide |
| 311 | N-[4-[(6,7-dihydro-5H-pyrrolo[1,2-a][1,5]benzodiazepin-5-yl)carbonyl]phenyl]-2,6-dimethylbenzamide |
| 312 | N-[4-[(6,7-dihydro-5H-pyrrolo[1,2-a][1,5]benzodiazepin-5-yl)carbonyl]phenyl]-2-methylthiobenzamide |
| 313 | N-[4-[(6,7-dihydro-5H-pyrrolo[1,2-a][1,5]benzodiazepin-5-yl)carbonyl]phenyl]-2-methyl-3-thiophenecarboxamide |
| 314 | N-[4-[(6,7-dihydro-5H-pyrrolo[1,2-a][1,5]benzodiazepin-5-yl)carbonyl]phenyl]-3-methyl-2-thiophenecarboxamide |
| 315 | N-[4-[(6,7-dihydro-5H-pyrrolo[1,2-a][1,5]benzodiazepin-5-yl)carbonyl]phenyl]-2-methyl-3-furanecarboxamide |
| 316 | N-[4-[(6,7-dihydro-5H-pyrrolo[1,2-a][1,5]benzodiazepin-5-yl)carbonyl]phenyl]-3-methyl-2-furanecarboxamide |
| 317 | N-[4-[(6,7-dihydro-5H-pyrrolo[1,2-a][1,5]benzodiazepin-5-yl)carbonyl]phenyl]benzeneacetamide |
| 318 | N-[4-[(6,7-dihydro-5H-pyrrolo[1,2-a][1,5]benzodiazepin-5-yl)carbonyl]phenyl]-2-chlorobenzeneacetamide |
| 319 | N-[4-[(6,7-dihydro-5H-pyrrolo[1,2-a][1,5]benzodiazepin-5-yl)carbonyl]phenyl]-2-methylbenzeneacetamide |
| 320 | N-[4-[(6,7-dihydro-5H-pyrrolo[1,2-a][1,5]benzodiazepin-5-yl)carbonyl]phenyl]-2-methyl-3-thiopheneacetamide |

EXAMPLE 321

5,6-Dihydro-4H-[1,2,4]triazolo[4,3-a][1,5]benzodiazepine

A mixture of 7.0 g of 5,6-dihydro-4H-[1,2,4]-triazolo-[4,3-a][1,5]benzodiazepin-5-one in 25 ml of tetrahydrofuran is added 9 ml of 10M borane-dimethylsulfide in tetrahydrofuran. The mixture is refluxed for 6 hours, cooled to room temperature and ml of methanol added dropwise. The volatiles are removed under vacuum and to the residue is added 100 ml of 2N sodium hydroxide. The mixture is refluxed for 5 hours, chilled and extracted with dichloromethane. The extract is washed with 2N citric acid, water and dried ($Na_2SO_4$). The solvent is removed under vacuum to give a solid. The solid is purified by chromatography on silica gel to give the desired product.

EXAMPLE 322

N-[4-(4H-1,2,4]triazolo 4,3-a][1,5]benzodiazepin-6-(5H)-ylcarbonyl)phenyl]-2-methyl benzamide To a mixture of 5 mmol of 5,6-dihydro-4H-[1,2,4]triazolo[4,3-a][1,5]benzodiazepine in 20 ml of dichloromethane is added 5.5 mmol of 4-[(2-methylbenzoyl)amino]benzoyl chloride and then 7.5 mmol of triethylamine. The mixture is stirred at room temperature for 8 hours and then washed with water, aqueous $NaHCO_3$ and brine. The solution is dried ($Na_2SO_4$) and the solvent removed in vacuo to give a solid. The solid is purified by chromatography on silica gel with ethyl acetate-hexane as solvent to give the desired product as a glass.

EXAMPLE 323

5,6-Dihydro-6-(4-nitrobenzoyl)-4H-[1,2,4]triazolo[4,3-a][1,5]benzodiazepine

To a mixture of 3 mmol of 5,6-dihydro-4H-[1,2,4]-triazolo[4,3-a][1,5]benzodiazepine in 10 ml of dichloromethane under argon is added 5 mmol of triethylamine. To the mixture is added dropwise 3.3 mmol of 4-nitrobenzoyl chloride in 3 ml of dichloromethane. The mixture is stirred at room temperature 3 hours and then washed with water, aqueous $NaHCO_3$ and brine. The organic layer is dried

EXAMPLE 324

5,6-Dihydro-6-(aminobenzoyl)-4H-[1,2,4]triazolo[4,3-a][1,4benzodiazepine

To a mixture of 5 mmol of 5,6-dihydro-6-(4-nitrobenzoyl)-4H-[1,2,4]triazolo[4,3-a][1,4]benzodiazepine in 25 ml of ethanol is added 0.3 g of 10% Pd/C and 15 mmol of hydrazine. The mixture is refluxed for 3 hours, cooled and filtered through diatomaceous earth. The filtrate is concentrated in vacuo and the residue purified by chromatography on silica gel to give the desired product as a solid.

TABLE XII

The following Examples are prepared using the conditions of Example 322 with the appropriately substituted aroyl chloride.

| Example No. | Compound |
|---|---|
| 325 | N-[4-(4H-[1,2,4]triazolo[4,3-a][1,5]benzodiazepin-6(5H)-ylcarbonyl)phenyl] 2-chlorobenzamide |
| 326 | N-[4-(4H-[1,2,4]triazolo[4,3-a][1,5]benzodiazepin-6(5H)-ylcarbonyl)phenyl] 2,5-dichlorobenzamide |
| 327 | N-[4-(4H-[1,2,4]triazolo[4,3-a][1,5]benzodiazepin-6(5H)-ylcarbonyl)phenyl] 2,4-dichlorobenzamide |
| 328 | N-[4-(4H-[1,2,4]triazolo[4,3-a][1,5]benzodiazepin-6(5H)-ylcarbonyl)phenyl] 2,3-difluorobenzamide |
| 329 | N-[4-(4H-[1,2,4]triazolo[4,3-a][1,5]benzodiazepin-6(5H)-ylcarbonyl)phenyl] 2-chloro-4-methylbenzamide |
| 330 | N-[4-(4H-[1,2,4]triazolo[4,3-a][1,5]benzodiazepin-6(5H)-ylcarbonyl)phenyl] 2-methyl-4-chlorobenzamide |
| 331 | N-[4-(4H-[1,2,4]triazolo[4,3-a][1,5]benzodiazepin-6(5H)-ylcarbonyl)phenyl] 2,4-dimethylbenzamide |
| 332 | N-[4-(4H-[1,2,4]triazolo[4,3-a][1,5]benzodiazepin-6(5H)-ylcarbonyl)phenyl] 2,3-dimethylbenzamide |
| 333 | N-[4-(4H-[1,2,4]triazolo[4,3-a][1,5]benzodiazepin-6(5H)-ylcarbonyl)phenyl] 2-methoxybenzamide |
| 334 | N-[4-(4H-[1,2,4]triazolo[4,3-a][1,5]benzodiazepin-6(5H)-ylcarbonyl)phenyl] 2-trifluoromethoxybenzamide |
| 335 | N-[4-(4H-[1,2,4]triazolo[4,3-a][1,5]benzodiazepin-6(5H)-ylcarbonyl)phenyl] 2,3-dichlorobenzamide |
| 336 | N-[4-(4H-[1,2,4]triazolo[4,3-a][1,5]benzodiazepin-6(5H)-ylcarbonyl)phenyl] 2,4-dimethoxybenzamide |
| 337 | N-[4-(4H-[1,2,4]triazolo[4,3-a][1,5]benzodiazepin-6(5H)-ylcarbonyl)phenyl] 2,6-dimethoxybenzamide |
| 338 | N-[4-(4H-[1,2,4]triazolo[4,3-a][1,5]benzodiazepin-6(5H)-ylcarbonyl)phenyl] 2-methoxy-4-chlorobenzamide |
| 339 | N-[4-(4H-[1,2,4]triazolo[4,3-a][1,5]benzodiazepin-6(5H)-ylcarbonyl)phenyl] 2-trifluoromethylbenzamide |
| 340 | N-[4-(4H-[1,2,4]triazolo[4,3-a][1,5]benzodiazepin-6(5H)-ylcarbonyl)phenyl] 2,6-dichlorobenzamide |
| 341 | N-[4-(4H-[1,2,4]triazolo[4,3-a][1,5]benzodiazepin-6(5H)-ylcarbonyl)phenyl] 2,6-dimethylbenzamide |
| 342 | N-[4-(4H-[1,2,4]triazolo[4,3-a][1,5]benzodiazepin-6(5H)-ylcarbonyl)phenyl] 2-methylthiobenzamide |
| 343 | N-[4-(4H-[1,2,4]triazolo[4,3-a][1,5]benzodiazepin-6(5H)-ylcarbonyl)phenyl] 2-methyl-3-thiophenecarboxamide |
| 344 | N-[4-(4H-[1,2,4]triazolo[4,3-a][1,5]benzodiazepin-6(5H)-ylcarbonyl)phenyl] 3-methyl-2-thiophenecarboxamide |
| 345 | N-[4-(4H-[1,2,4]triazolo[4,3-a][1,5]benzodiazepin-6(5H)-ylcarbonyl)phenyl] 2-methyl-3-furanecarboxamide |
| 346 | N-[4-(4H-[1,2,4]triazolo[4,3-a][1,5]benzodiazepin-6(5H)-ylcarbonyl)phenyl] 2-methyl-3-furanecarboxamide |
| 347 | N-[4-(4H-[1,2,4]triazolo[4,3-a][1,5]benzodiazepin-6(5H)-ylcarbonyl)phenyl] 3-methyl-2-furanecarboxamide |
| 348 | N-[4-(4H-[1,2,4]triazolo[4,3-a][1,5]benzodiazepin-6(5H)-ylcarbonyl)phenyl] 2-methoxybenzeneacetamide |
| 349 | N-[4-(4H-[1,2,4]triazolo[4,3-a][1,5]benzodiazepin-6(5H)-ylcarbonyl)phenyl] 2-methylbenzeneacetamide |
| 350 | N-[4-(4H-[1,2,4]triazolo[4,3-a][1,5]benzodiazepin-6(5H)-ylcarbonyl)phenyl] 2-chlorobenzeneacetamide |
| 351 | N-[4-(4H-[1,2,4]triazolo[4,3-a][1,5]benzodiazepin-6(5H)-ylcarbonyl)phenyl] 2-methyl-3-thiopheneacetamide |

EXAMPLE 352

N-[4-(1-Methyl-4H-1,2,4]triazolo[4,3-a][benzodiazepin-6(5H)-ylcarbonyl)phenyl]-2benzamide To a mixture of 5 mmol of 5,6-dihydro-1-methyl-4H-[1,2,4]triazolo[4,3-a][1,5]benzodiazepine in 20 ml of dichloromethane is added 5.5 mmol of 4-[(2-methylbenzoyl)amino]benzoyl chloride and 7.5 mmol of triethylamine. The mixture is stirred at room temperature for 8 hours and then washed with water, aqueous NaHCO₃ and brine. The organic layer is dried (Na₂SO₄) and the solvent removed in vacuo to give a solid. The solid is purified by chromatography on silica gel with ethyl acetate-hexane as solvent to give the desired product.

EXAMPLE 353

N-[4-(1-Methyl-4H-[1,2,4]triazolo[4,3-a][1,5]benzodiazepin-6(5H)-ylcarbonyl)phenyl]-2,4dichlorobenzamide To a mixture of 5 mmol of 5,6-dihydro-1-methyl-4H-[1,2,4]triazolo[4,3-a][1,5]benzodiazepine in 20 ml of dichloromethane is added 5.5 mmol of 4-[(2,4-dichlorobenzoyl)amino]benzoyl chloride and 7.5 mmol of triethylamine. The mixture is stirred at room temperature for 8 hours and then washed with water, aqueous NaHCO₃ and brine. The organic layer is dried (Na₂SO₄) and the solvent removed in vacuo to give a solid. The solid is purified by chromatography on silica gel to give the desired product as a solid.

EXAMPLE 354

N-[4-(5H-Pyrrolo[2,1-c][1,4]benzodiazepin-10(11)ylcarbonyl)phenyl]-3-cyclohexenecarboxamide A mixture of 0.50 g of 10,11-dihydro-10(4-aminobenzoyl-5H-pyrrolo[2,1-c][1,4]benzodiazepine, 0.286 g of 3-cyclohexenecarbonyl chloride and 346 µl of triethylamine in 5 ml of dichloromethane is stirred at room temperature 16 hours. The mixture is diluted with 50 ml of dichloromethane and the solution washed with 20 ml of water, 2N citric acid, 1N NaHCO$_3$, brine and dried (Na$_2$SO$_4$). The solution is filtered through a thin pad of hydrous magnesium silicate and the filtrate evaporated in vacuo. The residue is chromatographed on thick layer silica gel plates to give a solid which is crystallized from ethyl acetate to give 0.34 g of crystals, m.p. 216°–218° C.

EXAMPLE 355

N-[4-(5H-Pyrrolo[2,1-c][1,4]benzodiazepin-10(11) ylcarbonyl)phenyl]-5-methyl-2-thiophenecarboxamide To a solution of 0.318 g of 5-methyl-2-thiophenecarbonyl chloride in 5 ml of dichloromethane cooled to 0° C. is added 0.50 g of 10,11-dihydro-10-(4-aminobenzoyl-5H-pyrrolo[2,1-c][1,4]benzodiazepine and 346 µl of triethylamine. The mixture is stirred at room temperature 16 hours and diluted with 50 ml of dichloromethane. The solution is washed with 20 ml each of water, 2N citric acid. 1M NaHCO$_3$, brine and dried (Na$_2$SO$_4$). The solution is filtered through a thin pad of hydrous magnesium silicate and the filtrate evaporated in vacuo to give a solid. The solid is crystallized from ethyl acetate to give 0.53 g of crystals, m.p. 235°–238° C.

EXAMPLE 356

N-[4-Pyrrolo[2,1-c][1,4]benzodiazepin-10(11) ylcarbonyl)phenyl]-cyclohexylacetamide To a solution of 0.318 g of cyclohexylacetyl chloride in 5 ml of dichloromethane cooled to 0° C. is added 0.50 g of 10,11-dihydro-10-(4-aminobenzoyl-5H-pyrrolo[2,1-c][1,4] benzodiazepine and 346 µl of triethylamine. The mixture is stirred at room temperature 16 hours and diluted with 50 ml of dichloromethane. The solution is washed with 20 ml each of water, 2N citric acid. 1M NaHCO$_3$, brine and dried (Na$_2$SO$_4$). The solution is filtered through a thin pad of hydrous magnesium silicate and the filtrate evaporated in vacuo to give a solid. The solid is crystallized from ethyl acetate to give 0.52 g of crystals, m.p. 231°–234° C.

EXAMPLE 357

N-[4-(5H-Pyrrolo[2,1-c][1,4]benzodiazepin-10(11) ylcarbonyl)phenyl]-2-fluorobenzeneacetamide To a solution of 0.342 g of 2-fluorophenylacetyl chloride in 5 ml of dichloromethane cooled to 0° C. is added 0.50 g of 10,11-dihydro-10-(4-aminobenzoyl-5H-pyrrolo[2,1-c][1,4]benzodiazepine and 346 µl of triethylamine. The mixture is stirred at room temperature 16 hours and diluted with 50 ml of dichloromethane. The solution is washed with 20 ml each of water, 2N citric acid. 1M NaHCO$_3$, brine and dried (Na$_2$SO$_4$). The solution is filtered through a thin pad of hydrous magnesium silicate and the filtrate evaporated in vacuo to give a solid. The solid is crystallized from ethyl acetate to give 0.43 g of crystals, m.p. 204°–207° C.

EXAMPLE 358

N-[4-(5H-Pyrrolo[2,1-c][1,4]benzodiazepin-10(11) ylcarbonyl)phenyl]-cyclohexanecarboxamide To a solution of 0.342 g of cyclohexanecarbonyl chloride in 5 ml of dichloromethane cooled to 0° C. is added 0.50 g of 10,11-dihydro-10-(4-aminobenzoyl-5H-pyrrolo[2,1-c][1,4]benzodiazepine and 346 µl of triethylamine. The mixture is stirred at room temperature 16 hours and diluted with 50 ml of dichloromethane. The solution is washed with 20 ml each of water, 2N citric acid. 1M NaHCO$_3$, brine and dried (Na$_2$SO$_4$). The solution is filtered through a thin pad of hydrous magnesium silicate and the filtrate evaporated in vacuo to give a solid. The solid is crystallized from ethyl acetate to give 0.54 g of crystals, m.p. 202°–204° C.

EXAMPLE 359

4-[N-Methyl-N-(2-methylbenzoylamino]benzoyl chloride

A solution of 6.72 g of 4-[N-methyl-N-(2-methylbenzoyl) amino]benzoic acid in 20 ml of thionyl chloride is refluxed for one hour. The volatiles are removed in vacuo. Toluene is added to the residue and then the toluene removed in vacuo (repeated several times) to give the 7.3 g of product as a brown oil.

EXAMPLE 360

4-[N-Methyl -N-(2-methylbenzoyl)amino]benzoic acid

A sample of 1.51 g of sodium hydride (60% in oil) is washed with hexane under argon to remove the oil. To the washed sodium hydride is added 5 ml of N,N-dimethylformamide. To this mixture is added dropwise a solution of 8.69 g of ethyl 4-[(2-methylbenzoyl)amino] benzoate in 20 ml of N,N-dimethylformamide. The mixture is stirred at room temperature for 0.5 hour and then 5.23 g of methyl iodide is added. The mixture is stirred at room temperature for 16 hours. The mixture is diluted with water and extracted with dichloromethane. The extract is dried (Na$_2$SO$_4$), concentrated to reduce the volume and the solution filtered through a thin pad of hydrous magnesium silicate. The filtrate is concentrated in vacuo to give 11 g of an oil (1:1 mixture of product and N,N-dimethylformamide). The preceding product, ethyl 4-[N-methyl-N-(2-methylbenzoyl)amino]benzoate, (11 g) is dissolved in 30 ml of methanol and 25 ml of 2N NaOH added. The mixture is refluxed for 2 hours and the solvent removed. The residue is extracted with ether (discard) and the remaining residue dissolved in 50 ml of water. The basic solution is acidified with 2N citric acid and the solid filtered off and washed with water. The product is air dried to give 6.72 g of crystals, m.p. 187°–190° C.

As described for Example 360 but substituting the appropriate ethyl 4-[(N-aroyl)amino]benzoate, the following compounds are prepared.

EXAMPLE 361

4-[N-Methyl-N-(2-chlorobenzoyl)amino]benzoic acid

EXAMPLE 362

4-[N-Methyl-N-[2,5-dichlorobenzoyl)amino]benzoic acid

EXAMPLE 363

4-[N-Methyl-N-(2,4-dichlorobenzoyl)amino]benzoic acid

EXAMPLE 364

4-[N-Methyl-N-(2-chloro-4-methylbenzoyl)amino]
benzoic acid

EXAMPLE 365

4-[N-Methyl-N-(2-methyl-4-chlorobenzoyl)amino]
benzoic acid

EXAMPLE 366

4-[N-Methyl-N-(2,4-dimethylbenzoyl)amino]
benzoic acid

EXAMPLE 367

4-[N-Methyl-N-(2,3-dimethylbenzoyl)amino]
benzoic acid

EXAMPLE 368

4-[N-Methyl-N-(2-methoxybenzoyl)amino]benzoic
acid

EXAMPLE 369

4-[N-Methyl-N-(2-trifluoromethoxybenzoyl)amino]
benzoic acid

EXAMPLE 370

4-[N-Methyl-N-(2,4-dimethoxybenzoyl)amino]
benzoic acid

EXAMPLE 371

4-[N-Methyl-N-(2-methoxy-4-chlorobenzoyl)amino]
benzoic acid

EXAMPLE 372

4-[N-Methyl-N-(2-methylthiobenzoyl)amino]
benzoic acid

EXAMPLE 373

4-[N-Methyl-N-(2-methylthiophen-3-ylcarbonyl)
amino]benzoic acid

EXAMPLE 374

4-[N-Methyl-N-(3-methylthiophene-2-ylcarbonyl)
amino]benzoic acid

EXAMPLE 375

4-[N-Methyl-N-(2-methylfuran-3-ylcarbonyl)
amino]benzoic acid

EXAMPLE 376

4-[N-Methyl-N-(3-methylfuran-2-ylcarbonyl)
amino]benzoic acid

EXAMPLE 377

4-[-N-Methyl-N-(phenylacetyl)amino]benzoic acid

EXAMPLE 378

4-[N-Methyl-N-(2-chlorophenylacetyl)amino]
benzoic acid

EXAMPLE 379

4-[N-Methyl-N-(2-methoxyphenylacetyl)amino]
benzoic acid

EXAMPLE 380

4-[N-Methyl-N-(2-methylphenylacetyl)amino]
benzoic acid

EXAMPLE 381

4-[N-Methyl-N-(cyclohexylcarbonyl)amino]
benzoic acid

EXAMPLE 382

4-[N-Methyl-N-(3-cyclohexenecarbonyl)amino]
benzoic acid

EXAMPLE 383

4-[N-Methyl-N-(cyclohexylacetyl)amino]
benzoic acid

EXAMPLE 384

N-[4-(5H-Pyrrolo[2,1-c][1,4]benzodiazepin-10(11H)
ylcarbonyl)phenyl]-N-methyl-2-methylbenzamide A mixture of 0.27 g of 10,11-dihydro-5H-pyrrolo[2,1-c]
[1,4]benzodiazepine, 0.518 g of 4-[N-methyl-N-(2-methylbenzoyl)amino]benzoyl chloride, 0.182 g of triethylamine and 7 ml of tetrahydrofuran is stirred at room temperature for 3 hours. To the mixture is added 0.29 g of 4-[N-methyl-N-(2-methylbenzoyl) amino]benzoyl chloride and 0.10 g of triethylamine in 2 ml of dichloromethane and the mixture stirred for 2 days. The mixture is poured into water and extracted with dichloromethane. The extract is washed with water, 1N HCl, 1N NaHCO$_3$, brine and dried (Na$_2$SO$_4$). The solution is filtered through a thin pad of hydrous magnesium silicate. The filtrate is evaporated in vacuo and the residue crystallized from dichloromethane-hexane to give 0.38 g of crystals, m.p. 168°–170° C.

As described for Example 384, but substituting the appropriate aroyl chloride, the following compounds are prepared.

EXAMPLE 385

N-[4-(5H-Pyrrolo[2,1-c][1,4]benzodiazepin-
10(11H)ylcarbonyl)phenyl]-N-methyl-2-
chlorobenzamide

EXAMPLE 386

N-[4-(5H-Pyrrolo[2,1-c][1,4]benzodiazepin-
10(11H)ylcarbonyl)phenyl]-N-methyl-2,5-
dichlorobenzamide

EXAMPLE 387

N-[4-(5H-Pyrrolo[2,1-c][1,4]benzodiazepin-
10(11H)ylcarbonyl)phenyl]-N-methyl-2-chloro-4-
methylbenzamide

EXAMPLE 388

N-[4-(5H-Pyrrolo[2,1-c][1,4]benzodiazepin-
10(11H)ylcarbonyl)phenyl]-N-methyl-2-methyl-4-
chlorobenzamide

EXAMPLE 389

N-[4-(5H-Pyrrolo[2,1-c][1,4]benzodiazepin-10(11H)ylcarbonyl)phenyl]-N-methyl-2,4-dimethylbenzamide

EXAMPLE 390

N-[4-(5H-Pyrrolo[2,1-c][1,4]benzodiazepin-10(11H)ylcarbonyl)phenyl]-N-methyl-2,3-dimethylbenzamide

EXAMPLE 391

N-[4-(5H-Pyrrolo[2,1-c][1,4]benzodiazepin-10(11H)ylcarbonyl)phenyl]-N-methyl-2-methoxybenzamide

EXAMPLE 392

N-[4-(5H-Pyrrolo[2,1-c][1,4]benzodiazepin-10(11H)ylcarbonyl)phenyl]-N-methyl-2-trifluoromethoxybenzamide

EXAMPLE 393

N-[4-(5H-Pyrrolo[2,1-c][1,4]benzodiazepin-10(11H)ylcarbonyl)phenyl]-N-methyl-2,4-dimethoxybenzamide

EXAMPLE 394

N-[4-(5H-Pyrrolo[2,1-c][1,4]benzodiazepin-10(11H)ylcarbonyl)phenyl]-N-methyl-2-methoxy-4-chlorobenzamide

EXAMPLE 395

N-[4-(5H-Pyrrolo[2,1-c][1,4]benzodiazepin-10(11H)ylcarbonyl)phenyl]-N-methyl-2-methylthiobenzamide

EXAMPLE 396

N-[4-(5H-Pyrrolo[2,1-c][1,4]benzodiazepin-10(11H)ylcarbonyl)phenyl]-N-methyl-2-methyl-3-thiophenecarboxamide

EXAMPLE 397

N-[4-(5H-Pyrrolo[2,1-c][1,4]benzodiazepin-10(11H)ylcarbonyl)phenyl]-N-methyl-3-methyl-2-thiophenecarboxamide

EXAMPLE 398

N-[4-(5H-Pyrrolo[2,1-c][1,4]benzodiazepin-10(11H)ylcarbonyl)phenyl]-N-methyl-2-methyl-3-furanecarboxamide

EXAMPLE 399

N-[4-(5H-Pyrrolo[2,1-c][1,4]benzodiazepin-10(11H)ylcarbonyl)phenyl]-N-methylbenzeneacetamide

EXAMPLE 400

N-[4-(5H-Pyrrolo[2,1-c][1,4]benzodiazepin-10(11H)ylcarbonyl)phenyl]-N-methyl-2-chlorobenzeneacetamide

EXAMPLE 401

N-[4-(5H-Pyrrolo[2,1-c][1,4]benzodiazepin-10(11H)ylcarbonyl)phenyl]-N-methyl-2-methoxybenzeneacetamide

EXAMPLE 402

N-[4-(5H-Pyrrolo[2,1-c][1,4]benzodiazepin-10(11H)ylcarbonyl)phenyl]-N-methyl-2-methylbenzeneacetamide

EXAMPLE 403

N-[4-(5H-Pyrrolo[2,1-c][1,4]benzodiazepin-10(11H)ylcarbonyl)phenyl]-N-methyl-2-methyl-3-thiopheneacetamide

EXAMPLE 404

N-[4-(5H-Pyrrolo[2,1-c][1,4]benzodiazepin-10(11H)ylcarbonyl)phenyl]-N-methylcyclohexanecarboxamide

EXAMPLE 405

N-[4-(5H-Pyrrolo[2,1-c][1,4]benzodiazepin-10(11Hylcarbonyl)phenyl]-N-methylcyclohexylacetamide

EXAMPLE 406

N-[4-(5H-Pyrrolo[2,1-c][1,4]benzodiazepin-10(11H)ylcarbonyl)phenyl]-N-methyl-3-cyclohexenecarboxamide

EXAMPLE 407

N-[4-(5H-Pyrrolo[2,1-c][1,4 ]benzodiazepin-10(11H)ylcarbonyl)-2-methylphenyl]-2,4-dichlorobenzamide A mixture of 0.40 g of 10,11-dihydro-10-(3-methyl-4-aminobenzoyl)-5H-pyrrolo[2,1-c][1,4]benzodiazepine, 0.40 g of 2,4-dichlorobenzoyl chloride and 0.75 g of diisopropylethylamine in 50 ml of dichloromethane is stirred at room temperature for 16 hours. The mixture is washed with water, dried (MgSO$_4$) and the solution passed through a thin pad of hydrous magnesium silicate. The filtrate is concentrated and hexane added to give crystals. Recrystallization from dichloromethane-hexane gives 0.52 g of crystals, m.p. 213°–215° C.

EXAMPLE 408

1-(2-Nitrophenyl)-1H-pyrrole-2-carboxaldehyde

A sample of 4.7 g of sodium hydride (60% in oil) is washed with hexane (under argon). To the sodium hydride is added 200 ml of dry N,N-dimethylformamide and the mixture is chilled to 0° C. To the mixture is added 10.11 g of pyrrole-2-carboxaldehyde in small portions. The mixture is stirred 10 minutes and 15.0 g of 1-fluoro-2-nitrobenzene added dropwise. After the addition, the mixture is stirred at room temperature 16 hours and the mixture concentrated (65° C.) under high vacuum. To the residue is added 400 ml of dichloromethane and the mixture washed with 150 ml each of H$_2$O, brine and dried (Na$_2$SO$_4$). The solvent is removed in vacuo to give a yellow solid. Crystallization from ethyl acetate-hexane (9:1) gives 17.0 g of light yellow crystals, m.p. 119°–122° C.

EXAMPLE 409

4,10-Dihydro-5H-pyrrolo[1,2-a]thieno[3,2-e][1,4]diazepine

To an ice cooled mixture of 2.1 g of pyrrole-2-carboxylic acid and 3.2 g of methyl 3-aminothiophene-2-carboxylate in 40 ml of dry dichloromethane is added 4 g of N,N-dicyclohexylcarbodiimide. The mixture is stirred at room temperature for 3 hours and filtered. The filter cake is washed with dichloromethane and then extracted twice with 60 ml of acetone. The acetone extract is concentrated to dryness to give 0.8 g of solid, m.p. 214°–218° C. To a suspension of the preceding compound (1.19 g) in 20 ml of dry tetrahydrofuran is added 0.2 g of sodium hydride (60% in oil). After the hydrogen evolution, the mixture is stirred and refluxed for 4.5 hours, cooled and poured into ice-water. The precipitated solid is filtered and the solid triturated with petroleum ether (bp 30°–60° C.) to give 0.75 g of 4,10-dihydro-4,10-dioxo-5H-pyrrolo[1,2-a]thieno[3,2-e][1,4]diazepine as a solid, m.p. 280°–290° C. The preceding compound (0.362 g) is added to an ice-water cooled solution of 1M diborane in tetrahydrofuran. The mixture is stirred at room temperature for 65 hours. The solution is concentrated to dryness and ice-water added to the residue. The mixture is acidified with dilute HCl, stirred and then basified with solid $NaHCO_3$. The mixture is filtered to give 0.223 g of a solid (foam) m.p. 80°–85° C.

EXAMPLE 410

10,11-Dihydro-5H-1,2,4-triazolo[3,4-c][1,4]benzodiazepine

A mixture of 2.2 g of 2-cyanoaniline, 2.0 g of methyl bromoacetate and 1.3 g of potassium carbonate in 12 ml of dry N,N-dimethylformamide is heated at 150°–155° C. for 40 minutes. The cooled mixture is poured into ice-water and the mixture filtered to give 2 g of methyl [N-(2-cyanophenyl)amino]acetate as a yellow solid, m.p. 70°–78° C. The preceding compound (2.0 g) is added to a solution of 0.5 g of sodium methoxide in 50 ml of methanol. The mixture is shaken under an atmosphere of hydrogen with the catalyst Raney-Ni for 19 hours. The mixture is filtered through diatomaceous earth and the filtrate evaporated. Water is added to the residue and the mixture filtered to give 2,3,4,5-tetrahydro-1H-1,4-benzodiazepin-3-one as a yellow solid, m.p. 167°–170° C.

A mixture of the preceding compound (1.6 g) and 0.84 g of phosphorus pentasulfide in 10 ml of dry (dried over KOH) pyridine is stirred and heated at 80°–85° C. for 15 minutes. The mixture is poured into water and stirred for 30 minutes. Filtration gives 1.0 g of 1,2,4,5-tetrahydro-3H-1,4-benzodiazepin-3-thione as yellow solid, m.p. 150°–153° C.

The preceding compound (0.5 g) and 0.5 g of N-formylhydrazine in 6 ml of dry n-butanol is refluxed for 16 hours and the solvent removed. The gummy residue is triturated with cold water and the mixture filtered. The solid is triturated with acetone to give 0.19 g of yellow solid, m.p. 232°–237° C.

EXAMPLE 411

4,5-Dihydro-6H-[1,2,4]triazolo[4,3-a][1,5]-benzodiazepine

A mixture of 2,3,4,5-tetrahydro-1H-1,5-benzodiazepin-2-thione (0.8 g) and 0.80 g of N-formylhydrazine in 8 ml of n-butanol is stirred and refluxed for 18 hours and the solvent removed under vacuum. Ice water is added to the residual solid and the mixture filtered to give 0.312 g of a gray solid, m.p. 162°–165° C.

EXAMPLE 412

4,5-Dihydro-6H-imidazo[1,2-a][1,5]benzodiazepine

A mixture of 30 g of acrylic acid, 33 g of o-phenylenediamine is heated on a steam bath for 1.5 hours and the cooled black mixture triturated with ice-water. The aqueous phase is decanted and ice and aqueous ammonium hydroxide added to the residue. The mixture is extracted with dichloromethane and the extract concentrated to dryness. The residue is triturated with carbon tetrachloride and filtered. The oily solid is triturated with a small amount of ethanol to give 9.7 g of a solid. Trituration of the solid with ethyl acetate gives 2,3,4,5-tetrahydro-1H-1,5-benzodiazepin-2-one as an impure solid, m.p. 75°–107° C.

A mixture of the preceding compound (11.3 g) and 5.9 g of phosphorus pentasulfide in 70 ml of dry pyridine is stirred and heated at approximately 80° C. for 20 minutes. The mixture is poured into water and the mixture stirred for 30 minutes. Filtration gives 8.6 g of 2,3,4,5-tetrahydro-1H-1,5-benzodiazepin-2-thione as a solid, m.p. 154°–157° C.

A mixture of the preceding compound (0.70 g), 1.0 g of aminoacetaldehyde dimethyl acetal and 15 mg of 4-methylbenzenesulfonic acid monohydrate in 6 ml of dry n-butanol is refluxed for 4 hours and the solvent removed under vacuum. The residue is heated (refluxed) with 10 ml of 3N hydrochloric acid for 55 minutes. Ice is added to the cooled mixture and the mixture made basic with solid $NaHCO_3$. The mixture is extracted with dichloromethane and the extract dried ($Na_2SO_4$). The solvent is removed to give an orange syrup which solidified on standing. The oily solid is triturated with acetone to give a light yellow solid (0.185 g) m.p. 119°–122° C.

EXAMPLE 413

1-(2-Nitrophenyl)-2-pyrroleacetic acid, ethyl ester

To a stirred mixture of 1.88 g of 1-(2-nitrophenyl)pyrrole, 4.80 g of ethyl iodoacetate and 2.22 g of $FeSO_4.7H_2O$ in 40 ml of dimethyl sulfoxide is added dropwise 10 ml of 30% hydrogen peroxide while keeping the reaction mixture at room temperature with a cold water bath. The mixture is stirred at room temperature for one day. An additional 2.4 g of ethyl iodoacetate, 1.1 g of $FeSO_4.7H_2O$ and 5 ml of 30% hydrogen peroxide is added and the mixture stirred at room temperature for 1 day. The mixture is diluted with water and extracted with diethyl ether. The organic extract is washed with water, brine and dried ($Na_2SO_4$). The solvent is removed and the residue (2.12 g) chromatographed on silica gel with ethyl acetate-hexane (1:4) as solvent to give 0.30 g of product as a brown gum.

EXAMPLE 414

6,7-Dihydro-5H-pyrrolo[1,2-a][1,5]benzodiazepin-6-one

To a solution of 0.8 mmol of 1-(2-nitrophenyl)-2-pyrroleacetic acid, ethyl ester in 3 ml of ethanol is added stannus chloride dihydrate ($SnCl_2.2H_2O$) in 2 ml of concentrated hydrochloric acid (with cooling in water bath). The mixture is stirred at room temperature for 5 hours and chilled in an ice bath. To the mixture is added slowly saturated sodium carbonate solution. The solid which precipitates is filtered and the solid washed with water and then extracted with ethyl acetate. The ethyl acetate extract is dried (Na$_2$SO$_4$) and the solvent removed to give 0.16 g of solid which is triturated with ether to give 0.11 g of product as an off-white solid.

EXAMPLE 415

6,7-Dihydro-5H-pyrrolo[1,2-a][1,5]benzodiazepine

To a solution of 0.070 g of 6,7-dihydro-5H-pyrrolo[1,2-a][1,5]benzodiazepin-6-one in 2 ml of tetrahydrofuran is added 0.45 ml of a 2.0M solution of diborane-dimethylsulfide in tetrahydrofuran. The mixture is refluxed for 3 hours, poured into water and make basic with 2N NaOH. The tetrahydrofuran is removed under vacuum and the residual aqueous mixture extracted with diethyl ether. The extract is washed with brine, dried (Na$_2$SO$_4$) and the solvent removed to give 0.065 g of a colorless oil; one spot by thin layer chromatography (silica gel) with ethyl acetate-hexane (1:2) as solvent (Rf 0.81).

EXAMPLE 416

10,11-Dihydro-10-(2-chloro-4-aminobenzoyl)-5H-pyrrolo[2,1-c][1,4]benzodiazepine

A mixture of 5.0 g of 10,11-dihydro-10-(2-chloronitrobenzoyl)-5H-pyrrolo[2,1-c][1,4]benzodiazepine, 15.4 g of stannus chloride and 170 ml of ethanol is heated at 70°–80° C. for 1 hour. The mixture is chilled (ice bath) and made basic with 1M NaHCO$_3$ solution (350 ml) and then stirred at room temperature for 1 hour. The mixture is brought to pH 5 with acetic acid and extracted with 500 ml of ethyl acetate and with 300 ml of ethyl acetate. The combined extract is washed with 250 ml of brine and dried (Na$_2$SO$_4$). The solution is filtered through a thin pad of hydrous magnesium silicate and the filter pad washed with ethyl acetate. The filtrate is concentrated to dryness and the residue dissolved in 200 ml of hot chloroform-methanol (1:1) and the solution filtered through a thin pad of hydrous magnesium silicate. The filtrate is concentrated under vacuum to give 4.36 g (after drying under vacuum at 60° C. overnight) of product as a white solid. A sample is recrystallized from chloroform-methanol to give white crystals, m.p. 210°–212° C.

EXAMPLE 417

4-[(5-Fluoro-2-methylbenzoyl)amino]benzoic acid

A mixture of 0.60 g of ethyl 4-[(5-fluoro-2-methylbenzoyl)amino]benzoate 0.60 ml of 10N NaOH, 25 ml of water and 50 ml of absolute ethyl alcohol is heated on a steam bath for 1 hour, cooled and acidified with acetic acid. The resulting solid is filtered and dried in vacuo at 60°–80° C. to give 0.47 g of the desired product as a solid, m.p. 272°–275° C.

The following Examples are prepared using the conditions of Example 417.

| Example No. | Compound |
| --- | --- |
| 418 | 4-[(3-fluoro-2-methylbenzoyl)amino]benzoic acid, m.p. 309–311° C. |
| 419 | 4-[(5-fluoro-2-methylbenzoyl)amino]-2-chlorobenzoic acid, m.p. 247–249° C. |
| 420 | 4-[3-fluoro-2-methylbenzoyl)amino]-2-chlorobenzoic acid, m.p. 260–263° C. |
| 421 | 4-[[4-fluoro-3-(trifluoromethyl)]benzoyl]amino]-2-chlorobenzoic acid |
| 422 | 4-[[2-fluoro-3-(trifluoromethyl)]benzoyl]amino]-2-chlorobenzoic acid |
| 423 | 4-[(2,5-difluorobenzoyl)amino]-2-chlorobenzoic acid |
| 424 | 4-[(2,5-dichlorobenzoyl)amino]-2-chlorobenzoic acid |
| 425 | 4-[(2,3-dimethylbenzoyl)amino]-2-chlorobenzoic acid |
| 426 | 4-[(2,3-dichlorobenzoyl)amino]-2-chlorobenzoic acid |
| 427 | 4-[(2,5-dimethylbenzoyl)amino]-2-chlorobenzoic acid |
| 428 | 4-[2,3-difluorobenzoyl)amino]-2-chlorobenzoic acid |

EXAMPLE 429

4-[(2,4-Dichlorobenzoyl)amino]-2-chlorobenzoic acid

To a stirred mixture of 5.19 g of 2-chloro-4-aminobenzoic acid in 150 ml of methylene chloride is added 7.86 g of N,N-diisopropylethylamine and 12.67 g of 2,4-dichlorobenzylchloride and stirring continued for 18 hours. Water is added to the filtrate and the organic layer dried with Na$_2$SO$_4$ and concentrated in vacuo to give 13.68 g of the desired product, m.p. 171°–175° C.

The following Examples are prepared using the conditions of Example 429.

| Example No. | Compound |
| --- | --- |
| 430 | 4-[(2-methylbenzoyl)amino]-2-chlorobenzoic acid, m.p. 196–199° C. |
| 431 | 4-[(2-methylbenzoyl)amino]-3,5-dimethylbenzoic acid, m.p. 286–289° C. |
| 432 | 4-[(2,4-dichlorobenzoyl)amino]-3,5-dimethylbenzoic acid, m.p. 209–212° C. |
| 433 | 4-[(2-methylbenzoyl)amino]-3-chlorobenzoic acid, m.p. 199–202° C. |
| 434 | 4-[(2,5-dichlorobenzoyl)amino]-2-chlorobenzoic acid |
| 435 | 4-[(3-fluoro-2-methylbenzoyl)amino]-3-chlorobenzoic acid, m.p. 225–227° C. |
| 436 | 4-[(5-fluoro-2-methylbenzoyl)amino]-3-chlorobenzoic acid, m.p. 182–185° C. |
| 437 | 4-[(2,3-dimethylbenzoyl)amino]-3-chlorobenzoic acid |
| 438 | 4-[2,3-dichlorolbenzoyl)amino]-3-chlorobenzoic acid |
| 439 | 4-[(2,3-dimethylbenzoyl)amino]-3-chlorobenzoic acid |
| 440 | 4-[[4-fluoro-2-(trifluoromethyl)benzoyl]amino]-3-chlorobenzoic acid |
| 441 | 4-[[3-fluorobenzoyl]amino]-2-chlorobenzoic acid, m.p. 249–252° C. |
| 442 | 4-[[2-(trifluoromethyl)benzoyl]amino]-3-chlorobenzoic acid |

EXAMPLE 443

Ethyl 10,11-dihydro-10-(2-chloro-4-nitrobenzoyl)-5H-pyrrolo[2,1-c][1,4]benzodiazepine-3-carboxylate To 25 ml of absolute ethanol is added 0.12 g of sodium metal with stirring followed by 0.68 g of 10,11-dihydro-10-(2-chloro-4-nitrobenzoyl)-[3-(trichloroacetyl)]-5H-pyrrolo[2,1-c][1,4]benzodiazepine.

Stirring is continued for 18 hours. The volatiles are removed in vacuo to a residue which is partitioned between methylene chloride and water. The organic layer is separated, dried with $Na_2SO_4$ and filtrate heated on a steam bath while hexane is added to give 0.45 g of the desired product as a solid, m.p. 165°–166° C.

The following Examples are prepared using the conditions of Example 443.

| Example No. | Compound |
| --- | --- |
| 444 | ethyl 10,11-dihydro-10-(3-methyl-4-nitrobenzoyl)-5H-pyrrolo[2,1-c][1,4]-benzodiazepine-3-carboxylate, m.p. 200–202° C. |
| 445 | ethyl 10,11-dihydro-10-(2-methyl-4-nitrobenzoyl)-5H-pyrrolo[2,1-c][1,4]-benzodiazepine-3-carboxylate |
| 446 | ethyl 10,11-dihydro-10-(2-chloro-4-nitrobenzoyl)-5H-pyrrolo[2,1-c][1,4]-benzodiazepine-3-carboxylate |
| 447 | ethyl 10,11-dihydro-10-(3-chloro-4-nitrobenzoyl)-5H-pyrrolo[2,1-c][1,4]-benzodiazepine-3-carboxylate |

EXAMPLE 448

10,11-Dihydro-10-([3-methyl-4-nitrobenzoyl)-[3-trichloroacetyl)]-5H-pyrrolo[2,1-c][1,4] benzodiazepine To a stirred solution of 3.47 g of 10,11-dihydro-10(4-nitro-3-methylbenzoyl)-5H-pyrrolo[2,1-c]-[1,4] benzodiazepine in 50 ml of methylene chloride is added 3.40 g of trichloroacetic anhydride and stirring continued for 18 hours. Water is added and the separated organic layer washed with saturated sodium bicarbonate, dried with $Na_2SO_4$ and passed through a short pad of hydrous magnesium silicate. Hexane is added to the filtrate at the boil to give 4.07 g of the desired product as a solid. MASS SPEC (CI) 491(MH$^+$).

The following Examples are prepared using the conditions of Example 448.

| Example No. | Compound |
| --- | --- |
| 449 | 10,11-dihydro-10-(4-nitrobenzoyl)-[3-(trichloroacetyl)]-5H-pyrazolo[2,1-c]-[1,4]benzodiazepine, m.p. 122–123° C. |
| 450 | 10,11-dihydro-10-(2-chloro-4-nitrobenzoyl)-[3-(trichloroacetyl)]-5H-pyrrolo[2,1-c][1,4]benzodiazepine, m.p. 149–151° C. |

EXAMPLE 451

10,11-Dihydro-10-(4-nitrobenzoyl)-[3-(trifluoroacetyl)]-5H-pyrrolo[2,1-c][1,4] benzodiazepine A mixture of 0.50 g of 10,11-dihydro-10(4-nitrobenzoyl)-5H-pyrrolo[2,1-c][1,4]benzodiazepine in 10 ml of methylene chloride is cooled in an ice bath and 2.0 g of trifluoroacetic anhydride added. The bath is removed and the reactants stirred for 18 hrs, partitioned with saturated sodium bicarbonate and the separated organic layer dried with $Na_2SO_4$ then passed through a short pad of hydrous magnesium silicate. The filtrate is heated at the boil while hexane is added to give 0.40 g of the desired product, m.p. 169°–170° C.

The following Examples are prepared using the conditions of Example 451.

| Example No. | Compound |
| --- | --- |
| 452 | 10,11-dihydro-10-(2-chloro-4-nitrobenzoyl)[3-(trifluoroacetyl)]-5H-pyrrolo[2,1-c][1,4]benzodiazepine, m.p. 151–153° C. |
| 453 | 10,11-dihydro-10-(3-chloro-4-nitrobenzoyl)[3-(trifluoroacetyl)]-5H-pyrrolo[2,1-c][1,4]benzodiazepine |
| 454 | 10,11-dihydro-10-(2-methyl-4-nitrobenzoyl)[3-(trifluoroacetyl)]-5H-pyrrolo[2,1-c][1,4]benzodiazepine |

EXAMPLE 455

10,11-Dihydro-10-(3-methoxy-4-nitrobenzoyl)-5H-pyrrolo[2,1-c][1,4]benzodiazepine A mixture of 5.0 g of 3-methoxy-4-nitrobenzoic acid and 5.0 g of thionyl chloride is heated under argon for 1 hour. The volatiles are removed in vacuo to give 2.85 g of a 3-methoxy-4-nitrobenzoyl chloride as a residue which is dissolved in 50 ml of methylene chloride. To the preceding solution is added with stirring 1.75 g of N,N-diisopropylethylamine followed by 1.84 g of 10,11-dihydro-5H-pyrrolo[2,1-c][1,4]benzodiazepine. The reaction mixture is stirred under argon for 18 hours and diluted with saturated sodium bicarbonate. The organic layer is dried with $Na_2SO_4$ and passed through a short pad of hydrous magnesium silicate. While boiling, hexane is added to the filtrate to give, upon cooling, 3.39 g of the desired product as a solid, m.p. 191°–192° C.

The following Examples are prepared using the conditions of Example 455.

| Example No. | Compound |
| --- | --- |
| 456 | 10,11-dihydro-10-(2-methoxy-4-nitrobenzoyl)-5H-pyrrolo[2,1-c][1,4]benzodiazepine |
| 457 | 10,11-dihydro-10-(2-methyl-4-nitrobenzoyl)-5H-pyrrolo[2,1-c][1,4]-benzodiazepine |
| 458 | 10,11-dihydro-10-(3-methoxy-6-chloro-4-nitrobenzoyl)-5H-pyrrolo[2,1-c][1,4]-benzodiazepine |
| 459 | 10,11-dihydro-10-(3-methoxy-6-methyl-4-nitrobenzoyl)-5H-pyrrolo[2,1-c][1,4]-benzodiazepine |

EXAMPLE 460

10,11-Dihydro-10-(4-amino-3-methoxybenzoyl)-5H-pyrrolo[2,1-c][1,4]benzodiazepine A mixture of 3.24 g of 10,11-dihydro-10-(4-nitro-3-methoxybenzoyl)-5H-pyrrolo[2,1-c][1,4]benzodiazepine, 0.35 g of 10% Pd/c and 0.60 g of anhydrous hydrazine in 100 ml of absolute ethyl alcohol and heated on a steam bath for 1 hour. The hot reaction mixture is filtered through diatomaceous earth and the filtrate evaporated in vacuo to a residue which is partitioned between methylene chloride and water. The organic layer is dried with $Na_2SO_4$ and passed through a short pad of hydrous magnesium silicate. Hexane is added to the filtrate while heating on a steam bath to give 2 g of crystals, m.p. 184°–185° C.

The following Examples are prepared using the conditions of Example 460.

| Example No. | Compound |
|---|---|
| 461 | 10,11-dihydro-10-(4-amino-2-chlorobenzoyl)-5H-pyrrolo[2,1-c][1,4]benzodiazepine, m.p. 197–199° C. |
| 462 | 10,11-dihydro-10-(4-aminobenzoyl)[3-(trifluoroacetyl)]-5H-pyrrolo[2,1-c]-[1,4]benzodiazepine, m.p. 200–206° C. |
| 463 | ethyl 10,11-dihydro-10-(4-amino-3-methylbenzoyl)-5H-pyrrolo[2,1-c]-[1,4]benzodiazepine-3-carboxylate, m.p. 210–211° C. |
| 464 | ethyl 10,11-dihydro-10-(4-aminobenzoyl)-5H-pyrrolo[2,1-c][1,4]benzodiazepine-3-carboxylate, m.p. 174–175° C. |

EXAMPLE 465

N-[4-(5H-Pyrrolo[2,1-c][1,4]benzodiazepin-10(11H)-ylcarbonyl)phenyl]-5-fluoro-2-methylbenzamide To a stirred solution of 500 mg of 10,11-dihydro-10-(4-aminobenzoyl)-5H-pyrrolo[2,1-c][1,4-]benzodiazepine in 3 ml of methylene chloride, cooled to 0° C., under argon, is added 346 µl of triethylamine followed by the addition of 340 mg of 2-methyl-5-fluorobenzoyl chloride in 2 ml of methylene chloride. The cooling bath is removed and stirring continued for 18 hours. After cooling to 0° C., an additional 342 mg of 2-methyl-5-fluorobenzoyl chloride in 2 ml of methylene chloride is added. The cooling bath is removed and stirring continued for 18 hours. The volatiles are removed in vacuo to a residue which is dissolved in 50 ml of methylene chloride and washed with 20 ml each of water, 2N citric acid, 1M sodium bicarbonate and brine. The organic layer is dried over $Na_2SO_4$ and passed through a pad of hydrous magnesium silicate. The filtrate is evaporated in vacuo to a residue which is crystallized from ethyl acetate-hexane to give 295 mg of the desired product as a white solid, m.p. 170°–180° C.

The following Examples are prepared using the conditions of Example 465 with the appropriately substituted aroyl chloride.

| Example No. | Compound |
|---|---|
| 466 | N-[4-(5H-pyrrolo[2,1-c][1,4]benzodiazepin-10(11H)-ylcarbonyl)phenyl]-3-fluoro-2-methylbenzamide, m.p. 194–208° C. |
| 467 | N-[4-(5H-pyrrolo[2,1-c][1,4]benzodiazepin-10(11H)-ylcarbonyl)phenyl]-2,3-dimethylbenzamide, m.p. 168–170° C. |
| 468 | N-[4-(5H-pyrrolo[2,1-c][1,4]benzodiazepin-10(11H)-ylcarbonyl)phenyl]-2,3-dichlorobenamide, m.p. 219–222° C. |
| 469 | N-[4-(5H-pyrrolo[2,1-c][1,4]benzodiazepin-10(11H)-ylcarbonyl)phenyl]-2,6-dichlorobenzamide, m.p. 174–182° C. |
| 470 | N-[4-(5H-pyrrolo[2,1-c][1,4]benzodiazepin-10(11H)-ylcarbonyl-3-chlorophenyl]-2-methylbenzamide, m.p. 190–195° C. |
| 471 | N-[4-(5H-pyrrolo[2,1-c][1,4]benzodiazepin-10(11H)-ylcarbonyl-3-chlorophenyl]-2,4-dichlorobenzamide, m.p. 144–160° C. |
| 472 | N-[4-(5H-pyrrolo[2,1-c][1,4]benzodiazepin-10(11H)-ylcarbonyl-2,6-dimethyl phenyl]-2-methylbenzamide, amorphous solid |
| 473 | N-[4-(5H-pyrrolo[2,1-c][1,4]benzodiazepin-10(11H)-ylcarbonyl-2,6-dimethyl phenyl]-2,4-dichlorobenzamide, amorphous solid |
| 474 | N-[4-(5H-pyrrolo[2,1-c][1,4]benzodiazepin-10(11H)-ylcarbonyl)phenyl]-3-(trifluoromethyl)benzamide, amorphous solid |
| 475 | N-[4-(5H-pyrrolo[2,1-c][1,4]benzodiazepin-10(11H)-ylcarbonyl)-2-chlorophenyl]-3-methylthiophene-2-carboxamide |
| 476 | N-[4-(5H-pyrrolo[2,1-c][1,4]benzodiazepin-10(11H)-ylcarbonyl)phenyl]-3-chlorothiophene-2-carboxamide, solid; MASS SPEC (CI): 448 (M+H) |
| 477 | N-[4-(5H-pyrrolo[2,1-c][1,4]benzodiazepin-10(11H)-ylcarbonyl)-2-methoxyphenyl]-2-methylbenzamide, m.p. 184–186° C. |
| 478 | N-[4-(5H-pyrrolo[2,1-c][1,4]benzodiazepin-10(11H)-ylcarbonyl)-2-methoxyphenyl]-2,4-dichlorobenzamide, m.p. 192–194° C. |
| 479 | N-[4-(5H-pyrrolo[2,1-c][1,4]benzodiazepin-10(11H)-ylcarbonyl)-2-methoxyphenyl]-3-fluoro-2-methylbenzamide m.p. 203–204° C. |
| 480 | N-[4-(5H-pyrrolo[2,1-c][1,4]benzodiazepin-10(11H)-ylcarbonyl)phenyl]-2-chloro-5-nitrobenzamide, m.p. 110–160° C. (amorphous solid) |
| 267 | N-(5H-pyrrolo[1,2-a]thieno[3,2-e][1,4]-diazepin-4(10H)-ylcarbonyl)phenyl]-2-methylbenzamide, m.p. 162–188° C. (amorphous solid) |
| 274 | N-[4-(5H-pyrrolo[1,2-a]thieno[3,2-e]-[1,4]-diazepin-4(10H)-ylcarbonyl)-phenyl]-2,4-dichlorobenzamide, m.p. 105–190° C. |

EXAMPLE 481

N-[4-(5H-pyrrolo[2,1-c][1,4]benzodiazepin-10(11H)-ylcarbonyl)-3-chlorophenyl]-3-fluoro-2-methylbenzamide To a solution of 1.50 g of 10,11-dihydro-5H-pyrrolo[2,1-c][1,4]benzodiazepine in 25 ml of methylene chloride is added 1.23 g of N,N-diisopropylethylamine. While cooling in an ice bath, a solution of 3.08 g of [4-(2-methyl-5-fluorobenzoyl)amino]-2-chlorobenzoyl chloride in 50 ml of methylene chloride is added. The reaction mixture becomes homogeneous and is stirred at room temperature for 18 hours. Water is added and the separated organic layer washed with saturated sodium bicarbonate, dried with $Na_2SO_4$ and passed through a short pad of hydrous magnesium silicate two times. The methylene chloride is removed in vacuo to give 3.81 g of a glass. A sample is crystallized from ethyl acetate to give crystalline solid, m.p. 200°–205° C.

EXAMPLE 482

N-[4-(5H-pyrrolo[2,1-c][1,4]benzodiazepin-10(11H) ylcarbonyl)-3-chlorophenyl]-5-fluoro-2-methylbenzamide To a solution of 1.84 g of 10,11-dihydro-5H-pyrrolo[2,1-c][1,4]benzodiazepine in 25 ml of methylene chloride is added 1.30 g of N,N-diisopropylethylamine. While cooling in an ice bath, a solution of 3.45 g of [4-[(2-methyl-5-fluorobenzoyl)amino]-2-chlorobenzoyl chloride in 50 ml of methylene chloride is added. The reaction mixture becomes homogeneous after 5 minutes and is stirred at room temperature for 18 hours. Water is added and the separated organic layer washed with saturated sodium bicarbonate, dried with $Na_2SO_4$ and passed through a short pad of hydrous magnesium silicate. The methylene chloride is removed in vacuo to give 4.60 g of the desired product as a glass. A sample is crystallized from ethyl acetate to give crystalline solid, m.p. 191°–195° C.

EXAMPLE 483

4-(5H-Pyrrolo[2,1-c][1,4]benzodiazepin-10(11H) ylcarbonyl)benzoic acid

A solution of 0.92 g of 10,11-dihydro-5H-pyrrolo[2,1-c][1,4]benzodiazepine, 1.19 g of monomethyl terephthaloyl chloride in 20 ml of pyridine is refluxed for 2 hours. The mixture is chilled and 1N HCl added until the pH is 5. The mixture is filtered and washed with water to give 1.53 g of solid. Recrystallization from dichloromethane-hexane gives crystals, m.p. 186°–188° C. of methyl 4-(5H-pyrrolo[2,1-c][1,4]benzodiazepin-10(11H)-yl-carbonyl)benzoate.

A mixture of 1.83 g of the preceding compound, 8 ml of 2N NaOH and 14 ml of methanol is refluxed for 0.5 hour and then concentrated under vacuum. The residue is extracted with ether and the aqueous layer acidified with 2N citric acid. The mixture is filtered and the solid washed with water and dried (60° C. under vacuum) to give 1.61 g of crystals, m.p. 210°–214° C.

EXAMPLE 484

N-(2-Methylphenyl)-4-(5H-pyrrolo[2,1-c][1,4]-benzodiazepin-10(11H)-ylcarbonyl)benzamide A mixture of 0.332 g of 4-(5H-pyrrolo[2,1-c]-[1,4]benzodiazepin-10(11H)-ylcarbonyl)benzoic acid, 0.111 g of triethylamine, 0.107 g of o-toluidine, and 0.15 ml of diethylphosphoryl cyanide in 20 ml of dichloromethane is heated on a steam bath overnight. The mixture is washed with water, 1M $NaHCO_3$, 1N HCl, brine and dried ($Na_2SO_4$). The dichloromethane solution is filtered through a thin pad of hydrous magnesium silicate and the filtrate concentrated to dryness. The residue is crystallized from dichloromethane-hexane to give 0.23 g of white crystals, m.p. 228°–231° C.

EXAMPLE 485

N-(2,3-Dimethylphenyl)-4-(5H-pyrrolo[2,1-c][1,4]-benzodiazepin-10(11H)-ylcarbonyl)benzamide A mixture of 0.332 g of 4-(5H-pyrrolo[2,1-c][1,4]benzodiazepin-10(11H)-ylcarbonyl)benzoic acid, 0.222 g of triethylamine, 0.157 g of 2,3-dimethylaniline hydrochloride, 0.15 ml of diethylphosphoryl cyanide in 20 ml of dichloromethane is heated on a steam bath for 3 hours. The mixture is washed with $H_2O$, 1M $NaHCO_3$, $H_2O$, 1N HCl, brine and dried ($Na_2SO_4$). The solution is filtered through a thin pad of hydrous magnesium silicate and the filter cake washed with dichloromethane. The filtrate is concentrated to dryness under vacuum and the residue crystallized from dichloromethane-hexane to give 0.11 g of crystals, m.p. 239°–240° C.

EXAMPLE 486

N-[4-[(4,5-Dihydro-6H-[1,2,4]triazolo[4,3-a][1,5]-benzodiazepin-6-yl)carbonyl)phenyl]-2-methylbenzoate A mixture of 0.246 g of [4-(2-methylbenzoyl)amino]benzoyl chloride, 0.14 g of 4,5-dihydro-6H-[1,2,4]triazolo[4,3-a][1,5]benzodiazepine and 2 ml of pyridine is heated on a steam bath for 4.5 hours and heated (oil bath) at 110° C. overnight. The mixture is chilled and poured into water. The mixture is neutralized with 1N HCl and filtered. The solid is washed with dichloromethane and the dichloromethane filtrate evaporated under vacuum to give 0.151 g of product, MASS SPEC (FAB) 424.2(M+H).

EXAMPLE 487

N-[4-(Pyrrolo[1,2-a]quinoxalin-5(4H)-ylcarbonyl) phenyl]-2,3-dichlorobenzamide

As described for Example 157, 0.47 g of 4,5-dihydro-5-(4-aminobenzoyl)pyrrolo[1,2-a]quinoxaline, 346 µl of triethylamine and 5 ml of dichloromethane are chilled (ice bath) and 0.415 g of 2,3-dichlorobenzoyl chloride in 2 ml of dichloromethane added. After stirring overnight, an additional 346 µl of triethylamine is added and an additional 0.415 g of 2,3-dichlorobenzoyl chloride added. The mixture is stirred for 2 hours, diluted with 50 ml of dichloromethane and the solution washed with 20 ml each of $H_2O$, 2N citric acid, 1M $NaHCO_3$ and brine. The organic layer is dried ($Na_2SO_4$) and filtered through a thin pad of hydrous magnesium silicate and the filtrate concentrated to dryness. The residue is chromatographed on thick layer silica gel plates with ethyl acetate-hexane (1:1) as solvent to give 0.100 g of white solid, m.p. 230°–240° C.

EXAMPLE 488

10-[4-[[(2-Chlorophenyl)sulfonyl]amino]benzoyl]-10,11-dihydro-5H-pyrrolo[2,1-c][1,4]benzodiazepine To a solution of 0.418 g of 2-chlorobenzene-sulfonyl chloride in 5 ml of dichloromethane, cooled to 0° C. is added 0.50 g of 10,11-dihydro-10-(4-amino-benzoyl)-5H-pyrrolo[2,1-c][1,4]benzodiazepine and 0.346 µl of triethylamine. The mixture is stirred at room temperature overnight and diluted with 50 ml of dichloromethane. The mixture is washed with 20 ml each of $H_2O$, 2N citric acid, 1M $NaHCO_3$, brine and dried ($Na_2SO_4$). The solution is filtered through a thin pad of hydrous magnesium silicate and the filtrate concentrated to dryness. The residue is chromatographed on thick layer silica gel plates (4) with the solvent ethyl acetate-hexane (1:1) to give a solid. Crystallization from ethyl acetate gives 0.165 g of white crystals, m.p. 206°–210° C.

EXAMPLE 489

Methyl 4-(5H-pyrrolo[2,1-c][1,4]benzodiazepin-10 (11H)ylcarbonyl)benzoate

To a cooled solution of 0.50 g of 10,11-dihydro-10-(4-aminobenzoyl)-5H-pyrrolo[2,1-c][1,4]benzodiazepine and 346 µl of triethylamine in 5 ml of dichloromethane is added 0.394 g of mono methyl terephthaloyl chloride. The mixture is stirred overnight under argon and diluted with 50 ml of dichloromethane. The mixture is washed with 20 ml each of $H_2O$, 2N citric acid, 1M $NaHCO_3$, brine and dried ($Na_2SO_4$). The solution is filtered through a thin pad of hydrous magnesium silicate and the filter cake washed with dichloromethane. The filtrate is concentrated to dryness and the residue crystallized from ethyl acetate to give 0.50 g of white crystals, m.p. 224°–228° C.

EXAMPLE 490

N-[(Dimethylamino)methyl]-N-[4-(5H-pyrrolo[2,1-c][1,4]benzodiazepin-10(11H)-ylcarbonyl)phenyl]-2,4-dichlorobenzamide To a suspension under argon of 0.072 g of sodium hydride (60% in oil) in 10 ml of tetrahydrofuran is added 0.71 g of N-[4-(5H-pyrrolo[2,1-c][1,4]benzo-diazepin-10(11H)-ylcarbonyl)phenyl]-2,4-dichlorobenzamide and the mixture stirred at room temperature for 1 hour. To the mixture is added N,N-dimethylmethylene-ammonium iodide and the mixture stirred 20 hours. The mixture is diluted with diethyl ether (30 ml), filtered and the filtrate concentrated under vacuum. The residue is triturated with hexane to give 0.76 g of white solid, m.p. 126°–129° C.

EXAMPLE 491

10-[4-[(Diphenylphosphinyl)amino]benzoyl]-10,11-dihydro-5H-pyrrolo-[2,1-c][1,4]benzodiazepine A mixture of 0.10 g of 10,11-dihydro-10-(4-aminobenzoyl)-5H-pyrrolo[2,1-c][1,4]benzodiazepine 0.060 g of triethylamine and 0.12 g of diphenylphosphinyl chloride in 2 ml of dichloromethane is stirred at room temperature for 2 hours and then 1N NaOH is added. The mixture is extracted with ethyl acetate and the extract washed with brine and dried (Na$_2$SO$_4$). The solvent is removed and the residue triturated with ether-hexane to give 0.16 g of a white solid.

EXAMPLE 492

10-[4-[Diphenoxyphosphinyl)amino]benzoyl]-10,11-dihydro-5H-pyrrolo[2,1-c][1,4]benzodiazepine To a solution of 0.10 g of 10,11-dihydro-10-(4-aminobenzoyl)-5H-pyrrolo[2,1-c][1,4]benzodiazepine and 0.060 g of triethylamine in 2 ml of dichloromethane is added 0.14 g of diphenoxyphosphinyl chloride. The mixture is stirred at room temperature for 2 hours and 1N NaOH added. The mixture is extracted with ethyl acetate and the extract washed with brine and dried (Na$_2$SO$_4$). The solvent is removed to give a solid. Trituration with ether-hexane gives 0.20 g of product as a white solid.

EXAMPLE 493

10-[4-[[(2,5-Dichlorophenyl)sulfonyl]amino]benzoyl]-10,11-dihydro-5H-pyrrolo[2,1-c][1,4]benzodiazepine A mixture of 0.10 g of 10,11-dihydro-10-(4-aminobenzoyl)-5H-pyrrolo[2,1-c][1,4]benzodiazepine, 0.050 g of triethylamine and 0.083 g of 2,5-dichlorobenzenesulfonyl chloride in 2 ml of dichloromethane is stirred at room temperature for 1 hour and then 4 mg of 4-(N,N-dimethylamino)pyridine is added. After another hour, 93 mg of 2,5-dichlorobenzenesulfonyl chloride is added along with 50 mg of triethylamine. The mixture is stirred at room temperature for 2 days and 1N NaOH added. The mixture is extracted with ethyl acetate and the extract washed with 50% ammonium chloride solution, brine and dried (Na$_2$SO$_4$). The solvent is removed to give 0.30 g of solid. Trituration with ether-hexane gives 0.26 g of solid. This solid is dissolved in a mixture of 5 ml of tetrahydrofuran, 1 ml of methanol, 1 ml of 1N NaOH and the mixture stirred for 18 hours at room temperature. The organic solvents are removed and the mixture extracted with ether acetate. The extract is washed with NaHCO$_3$, brine and dried (Na$_2$SO$_4$). The solvent is removed and the residue (0.16 g) triturated with ether to give 0.14 g of yellow solid.

EXAMPLE 494

10-[4-[[(Phenylmethyl)sulfonyl]amino]benzoyl]-10,11-dihydro-5H-pyrrolo[2,1-c][1,4]benzodiazepine To a solution of 0.10 g of 10,11-dihydro-10-(4-aminobenzoyl)-5H-pyrrolo[2,1-c][1,4]benzodiazepine and 0.060 g of triethylamine in 2 ml of dichloromethane is added 0.10 g of α-toluenesulfonyl chloride. The mixture is stirred at room temperature for 2 hours and 1N NaOH is added. The mixture is extracted with ethyl acetate and the extract washed with brine and dried (Na$_2$SO$_4$). The solvent is removed and the residue (0.20 g) is chromatographed on silica gel with the solvent ethyl acetate-hexane (3:2) to give 0.080 g of product as a white solid and 0.080 g of 10-[4-[[bis(phenylmethyl)sulfonyl]amino]benzoyl]10,11-dihydro-5H-pyrrolo[2,1-c][1,4]benzodiazepine as a white solid. The preceding compound in methanol, 2N NaOH is heated on a steam bath, the solvent removed and the basic aqueous residue extracted with ethyl acetate to give an additional amount of the product.

EXAMPLE 495

Ethyl 4-[(2-methylbenzoyl)amino]-3-chlorobenzoate

A mixture of 8.26 g of ethyl 4-aminobenzoate, 8.26 g of N-chlorosuccinimide in 50 ml of dichloromethane is refluxed overnight. The mixture is washed with saturated NaHCO$_3$ solution and dried (Na$_2$SO$_4$). The solution is passed through a thin pad of hydrous magnesium silicate and the filter cake washed with dichloromethane. The filtrate is concentrated and hexane added. Chilling gives 7.38 g of ethyl 3-chloro-4-aminobenzoate, m.p. 82°–83° C.

To the preceding compound (3.66 g), 3.0 g of diisopropylethylamine in 50 ml of dichloromethane is added 3.55 g of 2-methylbenzoyl chloride in 10 ml of dichloromethane. The mixture is stirred at room temperature overnight, washed with H$_2$O, NaHCO$_3$ and dried (Na$_2$SO$_4$). The solution is passed through a thin pad of hydrous magnesium silicate and the filter cake washed with dichloromethane. The filtrate is concentrated and diluted with hexane. Chilling gives 4.71 g of the product as crystals, 129°–130° C.

The following Examples are prepared using the conditions of Example 495.

| Example No. | Compound |
| --- | --- |
| 496 | Ethyl 4-[(2-chlorobenzoyl)amino]-3-chlorobenzoate |
| 497 | Ethyl 4-[(2,5-dichlorobenzoyl)amino]-3-chlorobenzoate |
| 498 | Ethyl 4-[(2,4-dichlorobenzoyl)amino]-3-chlorobenzoate |
| 499 | Ethyl 4-[(3,5-dichlorobenzoyl)amino]-3-chlorobenzoate |
| 500 | Ethyl 4-[(2-methyl-4-chlorobenzoyl)amino]-3-chlorobenzoate |
| 501 | Ethyl 4-[(2,3-dimethylbenzoyl)amino]-3-chlorobenzoate |
| 502 | Ethyl 4-[(2-methoxybenzoyl)amino]-3-chlorobenzoate |
| 503 | Ethyl 4-[(2-(trifluoromethxoy)benzoyl]amino]-3-chlorobenzoate |
| 504 | Ethyl 4-[(2-methoxy-4-chlorobenzoyl)amino]-3-chlorobenzoate |
| 505 | Ethyl 4-[[2-(methylthio)benzoyl]amino]-3-chlorobenzoate |
| 506 | Ethyl 4-[(2-methylbenzeneacetyl]amino]-3-chlorobenzoate |
| 507 | Ethyl 4-[[4-fluoro-2-(trifluoromethyl)-benzoyl]amino]-3-chlorobenzoate |
| 508 | Ethyl 4-[[4-fluoro-3-(trifluoromethyl)-benzoyl]amino]-3-chlorobenzoate |
| 509 | Ethyl 4-[[2-fluoro-3-(trifluoromethyl)-benzoyl]amino]-3-chlorobenzoate |
| 510 | Ethyl 4-[(3-fluoro-2-methylbenzoyl)-amino]-3-chlorobenzoate |

| Example No. | Compound |
|---|---|
| 511 | Ethyl 4-[(2,3-dichlorobenzoyl)amino]-3-chlorobenzoate |
| 512 | Ethyl 4-[(4-fluoro-2-methylbenzoyl)amino]-3-chlorobenzoate |
| 513 | Ethyl 4-[(5-fluoro-2-methylbenzoyl)amino]-3-chlorobenzoate |
| 514 | Ethyl 4-[[2-fluoro-5-(trifluoromethyl)benzoyl]amino]-3-chlorobenzoate |
| 515 | Ethyl 4-[[2-(trifluoromethyl)benzoyl]amino]-3-chlorobenzoate |
| 516 | Ethyl 4-[[3-(trifluoromethyl)benzoyl]amino-3-chlorobenzoate |

EXAMPLE 517

N-[4-(4H-Pyrazolo[5,1-c][1,4]benzodiazepin-5(10H)ylcarbonyl)phenyl]-3-fluoro-2-methylbenzamide A solution of 2.87 g of 3-fluoro-2-methylbenzoic acid in 25 ml of thionyl chloride is refluxed for 1.75 hour and the excess thionyl chloride removed under vacuum. To the residue is added toluene (several times) and the toluene removed under vacuum after each addition to give 3-fluoro-2-methylbenzoyl chloride.

To a solution of 0.25 g of 5,10-dihydro-5-(4-aminobenzoyl)-4H-pyrazolo[5,1-c][1,4]benzodiazepine and 0.0914 g of triethylamine in 6 ml of dichloromethane under argon is added a solution of 0.156 g of 3-fluoro-2-methylbenzoyl chloride in 1.5 ml of dichloromethane. The mixture is stirred overnight at room temperature and is washed with H$_2$O and saturated NaHCO$_3$. The organic layer is treated with activated carbon and filtered through magnesium sulfate. The filtrate is evaporated, ethyl acetate added and the solvent removed to give 0.38 g of white crystals, m.p. 245°–250° C.: Exact mass by mass spectrometry–441.1720(M+H).

EXAMPLE 518

N-[4-(4H-Pyrazolo[5,1-c][1,4]benzodiazepin-5(10H)ylcarbonyl)-3-chlorophenyl]-5-fluoro-2-methylbenzamide A mixture of 0.185 g of 5,10-dihydro-4H-pyrazolo[5,1-c][1,4]benzodiazepine, 0.391 g of 4-[(5-fluoro-2-methylbenzoyl)amino]-2-chlorobenzoyl chloride and 0.158 g of diisopropylethylamine in 10 ml of dichloromethane is stirred at room temperature overnight. The mixture is washed with H$_2$O, 1N HCl, H$_2$O, 1M NaHCO$_3$, brine and dried (Na$_2$SO$_4$). The solution is passed through a thin pad of hydrous magnesium silicate and the filter cake washed with dichloromethane. The filtrate is again passed through a thin pad of hydrous magnesium silicate. The filtrate is concentrated and the solid crystallized from ethyl acetate to give crystals, m.p. 137°–140° C.

EXAMPLE 519

N-[4-(4H-pyrazolo[5,1-c][1,4]benzodiazepin-5(10H)-ylcarbonyl)-3-chlorophenyl]-2-methylbenzamide As described for Example 518, a mixture of 0.185 g of 5,10-dihydro-4H-pyrazolo[5,1-c][1,4]benzodiazepine, 0.369 g of 4-[(2-methylbenzoyl)amino]-2-chlorobenzoyl chloride and 0.158 g of diisopropylethylamine in 10 ml of dichloromethane is stirred at room temperature to give crystals (from ethyl acetate) m.p. 241°–244° C.

EXAMPLE 520

N-[4-(4H-Pyrazolo[5,1-c][1,4]benzodiazepin-5(10H)-ylcarbonyl)-3-chlorophenyl]-2,4-dichlorobenzamide As described for Example 518, a mixture of 0.185 g of 5,10-dihydro-4H-pyrazolo[5,1-c][1,4]benzodiazepine, 0.472 g of 4-[(2,4-dichlorobenzoyl)amino]-benzoyl chloride and 0.158 g of diisopropylethylamine in 10 ml of dichloromethane is stirred at room temperature overnight to give the product (0.27 g) as a pale yellow glass; anal. calc'd: C, 58.7; H, 3.4; N, 11.0; Cl, 20.8 Found C, 57.3; H, 3.3; N, 9.5; Cl, 21.3.

EXAMPLE 521

5,10-Dihydro-5-(4-nitro-2-chlorobenzoyl)-4H)pyrazolo[5,1-c][1,4]benzodiazepine

To a solution of 1.85 g of 5,10-dihydro-4H-pyrazolo[5,1-c][1,4]benzodiazepine and 1.60 g of diisopropylethylamine in 50 ml of dichloromethane, cooled in an ice bath, is added dropwise a solution of 2.64 g of 4-nitro-2-chlorobenzoyl chloride in 25 ml of dichloromethane. The mixture is stirred at room temperature overnight and poured into water. The organic layer is separated and washed with H$_2$O, saturated NaHCO$_3$, H$_2$O and dried (Na$_2$SO$_4$). The solution is passed through a thin pad of hydrous magnesium silicate and the filtrate evaporated. The residue is crystallized from dichloromethane-hexane to give 3.0 g of crystals, m.p. 197°–199° C.

EXAMPLE 522

5,10-Dihydro-5-(4-amino-2-chlorobenzoyl)-4H-pyrazolo-[5,1-c][1,4]benzodiazepine

A mixture of 0.553 g of 5,10-dihydro-5-(4-nitro-2-chlorobenzoyl)-4H-pyrazolo[5,1-c][1,4]benzodiazepine, 1.70 g of stannous chloride dihydrate in 20 ml of ethanol is heated at 70°–80° C. for 1 hour. The mixture is chilled, made basic with 1M NaHCO$_3$ and then stirred at room temperature for 0.5 hour. The mixture is brought to pH 5 with acetic acid and extracted (several times) with ethyl acetate. The combined extracts are dried (Na$_2$SO$_4$) and passed through a pad of hydrous magnesium silicate. The filtrate is evaporated and the residue dissolved in dichloromethane and the solution passed through a thin pad of hydrous magnesium silicate. The filtrate is evaporated in vacuo to give 0.40 g of a glass, m.p. 98°–117° C.; Anal. Calc'd: C, 62.9; H, 4.7; N, 16.3; Cl, 11.6. Found: C, 62.4; H, 4.3; N, 15.6; Cl, 11.7.

The following examples are prepared using the conditions of Example 465.

| Example No. | Compound |
|---|---|
| 523 | N-[4-(5H-pyrrolo[2,1-c][1,4]benzodiazepin-10(11H)-ylcarbonyl)-3-chlorophenyl]-2-fluorobenzamide, m.p. 223–226° C. |
| 524 | N-[4-(5H-pyrrolo[2,1-c][1,4]benzodiazepin-10(11H)-ylcarbonyl)-3-chlorophenyl]-2-(thiomethylbenzamide), white foam |
| 525 | N-[4-(5H-pyrrolo[2,1-c][1,4]benzodiazepin-10(11H)-ylcarbonyl)-3-chlorophenyl]-2,3-dimethylbenzamide, m.p. 189–192° C. |
| 526 | N-[4-(5H-pyrrolo[2,1-c][1,4]benzodiazepin-10(11H)-ylcarbonyl)-3-chlorophenyl]-2-chlorobenzamide, m.p. 198–203° C. |
| 527 | N-[4-(5H-pyrrolo[2,1-c][1,4]benzodiaze- |

| Example No. | Compound |
|---|---|
|  | pin-10(11H)-ylcarbonyl)-3-chlorophenyl]-4-fluoro-2-chlorobenzamide, m.p. 139–141° C. |
| 528 | N-[4-(5H-pyrrolo[2,1-c][1,4]benzodiazepin-10(11H)-ylcarbonyl)-3-chlorophenyl]-2-(trifluoromethyl)benzamide, white foam |
| 529 | N-[4-(5H-pyrrolo[2,1-c][1,4]benzodiazepin-10(11H)-ylcarbonyl)-3-chlorophenyl]-2,6-dichlorobenzamide, m.p. 246–248° C. |

EXAMPLE 530

N-[4-(5H-Pyrrolo[2,1-c][1,4]benzodiazepin-10(11H)ylcarbonyl-2-chlorophenyl-2-methylbenzamide To a mixture of 1.38 g of 10,11-dihydro-5H-pyrrolo[2,1-c][1,4]benzodiazepine, 1.11 g of N,N-diisopropylethylamine in 50 ml of dichloromethane is added 2.61 g of 4-[(2-methylbenzoyl)amino]-3-chlorobenzoyl chloride in 25 ml of dichloromethane. The mixture is stirred at room temperature overnight and then washed with $H_2O$ and saturated $NaHCO_3$. The organic layer is dried ($Na_2SO_4$) and passed through a pad of hydrous magnesium silicate. The filtrate is concentrated, the residue (4.0 g) dissolved in dichloromethane and again filtered through a pad of hydrous magnesium silicate. The filtrate is evaporated to give the product as a glass (3.62 g). A 1.8 g sample of the glass is crystallized from ethyl acetate to give 1.4 g of crystals, m.p. 176°–178° C.

The following Examples are prepared using the conditions of Example 530.

| Example No. | Compound |
|---|---|
| 531 | N-[4-(5H-pyrrolo[2,1-c][1,4]benzodiazepin-10(11H)-ylcarbonyl)-2-chlorophenyl]-2,3-dimethylbenzamide |
| 532 | N-[4-(5H-pyrrolo[2,1-c][1,4]benzodiazepin-10(11H)-ylcarbonyl)-2-chlorophenyl]-2,5-dimethylbenzamide |
| 533 | N-[4-(5H-pyrrolo[2,1-c][1,4]benzodiazepin-10(11H)-ylcarbonyl)-2-chlorophenyl]-2,6-dimethylbenzamide |
| 534 | N-[4-(5H-pyrrolo[2,1-c][1,4]benzodiazepin-10(11H)-ylcarbonyl)-2-chlorophenyl]-2-chlorobenzamide |
| 535 | N-[4-(5H-pyrrolo[2,1-c][1,4]benzodiazepin-10(11H)-ylcarbonyl)-2-chlorophenyl]-2,4-dichlorobenzamide |
| 536 | N-[4-(5H-pyrrolo[2,1-c][1,4]benzodiazepin-10(11H)-ylcarbonyl)-2-chlorophenyl]-2,5-dichlorobenzamide |
| 537 | N-[4-(5H-pyrrolo[2,1-c][1,4]benzodiazepin-10(11H)-ylcarbonyl)-2-chlorophenyl]-3,5-dichlorobenzamide |
| 538 | N-[4-(5H-pyrrolo[2,1-c][1,4]benzodiazepin-10(11H)-ylcarbonyl)-3-chlorophenyl]-3-fluorobenzamide, amorphous solid |
| 539 | N-[4-(5H-pyrrolo[2,1-c][1,4]benzodiazepin-10(11H)-ylcarbonyl)-2-chlorophenyl]-2-chloro-4-fluorobenzamide |
| 540 | N-[4-(5H-pyrrolo[2,1-c][1,4]benzodiazepin-10(11H)-ylcarbonyl)-2-chlorophenyl]-2-methyl-4-chlorobenzamide |
| 541 | N-[4-(5H-pyrrolo[2,1-c][1,4]benzodiazepin-10(11H)-ylcarbonyl)-2-chlorophenyl]-2-(methylthio)benzamide |
| 542 | N-[4-(5H-pyrrolo[2,1-c][1,4]benzodiazepin-10(11H)-ylcarbonyl)-2-chlorophenyl]-2-chlorobenzeneacetamide |
| 543 | N-[4-(5H-pyrrolo[2,1-c][1,4]benzodiazepin-10(11H)-ylcarbonyl)-2-chlorophenyl]-2-methylbenzeneacetamide |
| 544 | N-[4-(5H-pyrrolo[2,1-c][1,4]benzodiazepin-10(11H)-ylcarbonyl)-2-chlorophenyl]-2-methylthiophene-3-carboxyamide |
| 545 | N-[4-(5H-pyrrolo[2,1-c][1,4]benzodiazepin-10(11H)-ylcarbonyl)-2-chlorophenyl]-3-methylthiophene-2-carboxamide |
| 546 | N-[4-(5H-pyrrolo[2,1-c][1,4]benzodiazepin-10(11H)-ylcarbonyl)-2-chlorophenyl]-3-fluoro-2-methylbenzamide, m.p. 230–231° C. |
| 547 | N-[4-(5H-pyrrolo[2,1-c][1,4]benzodiazepin-10(11H)-ylcarbonyl)-2-chlorophenyl]-5-fluoro-2-methylbenzamide, m.p. 178–180° C. |
| 548 | N-[4-(5H-pyrrolo[2,1-c][1,4]benzodiazepin-10(11H)-ylcarbonyl)-2-chlorophenyl]-2,3-dichlorobenzamide |
| 549 | N-[4-(5H-pyrrolo[2,1-c][1,4]benzodiazepin-10(11H)-ylcarbonyl)-2-chlorophenyl]-2,3-difluorobenzamide |
| 550 | N-[4-(5H-pyrrolo[2,1-c][1,4]benzodiazepin-10(11H)-ylcarbonyl)-2-chlorophenyl]-4-fluoro-2-methylbenzamide |
| 551 | N-[4-(5H-pyrrolo[2,1-c][1,4]benzodiazepin-10(11H)-ylcarbonyl)-2-chlorophenyl]-2-methoxybenzamide |
| 552 | N-[4-(5H-pyrrolo[2,1-c][1,4]benzodiazepin-10(11H)-ylcarbonyl)-2-chlorophenyl]-2-(trifluoromethoxy)benzamide |
| 553 | N-[4-(5H-pyrrolo[2,1-c][1,4]benzodiazepin-10(11H)-ylcarbonyl)-2-chlorophenyl]-2-methoxy-4-chlorobenzamide |
| 554 | N-[4-(5H-pyrrolo[2,1-c][1,4]benzodiazepin-10(11H)-ylcarbonyl)-2-chlorophenyl]-2-(trifluoromethyl)benzamide |
| 555 | N-[4-(5H-pyrrolo[2,1-c][1,4]benzodiazepin-10(11H)-ylcarbonyl)-2-chlorophenyl]-3-(trifluoromethyl)benzamide |
| 556 | N-[4-(5H-pyrrolo[2,1-c][1,4]benzodiazepin-10(11H)-ylcarbonyl)-2-chlorophenyl]-2,6-dichlorobenzamide |
| 557 | N-[4-(5H-pyrrolo[2,1-c][1,4]benzodiazepin-10(11H)-ylcarbonyl)-2-chlorophenyl]-2,3,5-trichlorobenzamide |
| 558 | N-[4-(5H-pyrrolo[2,1-c][1,4]benzodiazepin-10(11H)-ylcarbonyl)-2-chlorophenyl]-2-fluoro-5-(trifluoromethyl)benzamide |
| 559 | N-[4-(5H-pyrrolo[2,1-c][1,4]benzodiazepin-10(11H)-ylcarbonyl)-2-chlorophenyl]-4-fluoro-2-(trifluoromethyl)benzamide |
| 560 | N-[4-(5H-pyrrolo[2,1-c][1,4]benzodiazepin-10(11H)-ylcarbonyl)-2-chlorophenyl]-2-fluoro-3-(trifluoromethyl)benzamide |
| 561 | N-[4-(5H-pyrrolo[2,1-c][1,4]benzodiazepin-10(11H)-ylcarbonyl)-2-chlorophenyl]-2,5-difluorobenzamide |
| 562 | N-[4-(5H-pyrrolo[2,1-c][1,4]benzodiazepin-10(11H)-ylcarbonyl)-2,3-dichlorophenyl]-5-fluoro-2-methylbenzamide |
| 563 | N-[4-(5H-pyrrolo[2,1-c][1,4]benzodiazepin-10(11H)-ylcarbonyl)-2,3-dichlorophenyl]-2,3-dimethylbenzamide |
| 564 | N-[4-(5H-pyrrolo[2,1-c][1,4]benzodiazepin-10(11H)-ylcarbonyl)-2,3-dichlorophenyl]-3-fluoro-2-methylbenzamide |
| 565 | N-[4-(5H-pyrrolo[2,1-c][1,4]benzodiazepin-10(11H)-ylcarbonyl)-2,3-dichlorophenyl]-2,4-dichlorobenzamide |
| 566 | N-[4-(5H-pyrrolo[2,1-c][1,4]benzodiazepin-10(11H)-ylcarbonyl)-2,3-dichlorophenyl]-2,3-dichlorobenzamide |
| 567 | N-[4-(5H-pyrrolo[2,1-c][1,4]benzodiazepin-10(11H)-ylcarbonyl)-2,3-dichlorophenyl]-2-methylbenzamide |
| 568 | N-[4-(5H-pyrrolo[2,1-c][1,4]benzodiaze- |

-continued

| Example No. | Compound |
|---|---|
| | pin-10(11H)-ylcarbonyl)-2,5-dichlorophenyl]-5-fluoro-2-methylbenzamide |
| 569 | N-[4-(5H-pyrrolo[2,1-c][1,4]benzodiazepin-10(11H)-ylcarbonyl)-2,5-dichlorophenyl]-2,3-dimethylbenzamide |
| 570 | N-[4-(5H-pyrrolo[2,1-c][1,4]benzodiazepin-10(11H)-ylcarbonyl)-2,5-dichlorophenyl]-3-fluoro-2-methylbenzamide |
| 571 | N-[4-(5H-pyrrolo[2,1-c][1,4]benzodiazepin-10(11H)-ylcarbonyl)-2,5-dichlorophenyl]-2,4-dichlorobenzamide |
| 572 | N-[4-(5H-pyrrolo[2,1-c][1,4]benzodiazepin-10(11H)-ylcarbonyl)-2,5-dichlorophenyl]-2,3-dichlorobenzamide |
| 573 | N-[4-(5H-pyrrolo[2,1-c][1,4]benzodiazepin-10(11H)-ylcarbonyl)-2,5-dichlorophenyl]-2-methylbenzamide |
| 574 | N-[4-(5H-pyrrolo[2,1-c][1,4]benzodiazepin-10(11H)-ylcarbonyl)-2,5-dichlorophenyl]-2,3-dichlorobenzamide |
| 575 | N-[4-(5H-pyrrolo[2,1-c][1,4]benzodiazepin-10(11H)-ylcarbonyl)-2,5-dichlorophenyl]-2,5-dichlorobenzamide |
| 576 | N-[4-(5H-pyrrolo[2,1-c][1,4]benzodiazepin-10(11H)-ylcarbonyl)-2,5-dichlorophenyl]-2-(methylthio)benzamide |
| 577 | N-[4-(5H-pyrrolo[2,1-c][1,4]benzodiazepin-10(11H)-ylcarbonyl)-2,5-dichlorophenyl]-2-chlorobenzamide |
| 578 | N-[4-(5H-pyrrolo[2,1-c][1,4]benzodiazepin-10(11H)-ylcarbonyl)-2,5-dichlorophenyl]-2-(trifluoromethyl)benzamide |
| 579 | N-[4-(5H-pyrrolo[2,1-c][1,4]benzodiazepin-10(11H)-ylcarbonyl)-2,5-dichlorophenyl]-2-(trifluoromethoxy)benzamide |

EXAMPLE 580

2,4-Dichloro-N-[4-[(3-formyl-5H-pyrrolo[2,1-c][1,4]benzodiazepin-10(11H)-yl)carbonyl]phenyl]benzamide To a solution of 0.48 g of 2,4-dichloro-N-[4-(5H-pyrrolo[2,1-c][1,4]benzodiazepin-10(11H)-yl)carbonyl)phenyl]benzamide in 2 ml of N,N-dimethylformamide at 0° C. is slowly added 0.3 ml of POCl$_3$. The mixture is stirred at 0° C. for 30 minutes and at room temperature for 1 hour. The final mixture is quenched with ice and made alkaline with 2N NaOH to pH 12. The resulting precipitate is collected, washed with water and dried in vacuo to give 0.55 g of solid. Further washing with 1:2 ether-isopropanol gives 0.50 g of white solid. MS(CI) calculated 503.0774; found 503.0789.

EXAMPLE 581

2,4-Dichloro-N-[4-[[3-(hydroxymethyl)-5H-pyrrolo[2,1-c][1,4]benzodiazepin-10(11H)-yl]carbonyl]phenyl]benzamide To a suspension of 39 mg of NaBH$_4$ in 1 ml of tetrahydrofuran is added 0.42 g of 2,4-dichloro-N-[4-[(3-formyl-5H-pyrrolo[2,1-a][1,4]benzodiazepin-10 (11H)-yl)carbonyl]phenyl]benzamide and the reaction mixture stirred at room temperature for 18 hours and then quenched with water. The tetrahydrofuran is evaporated in vacuo and the aqueous residue treated with 5 ml of 1N NaOH and extracted with 50 ml of ethyl acetate. The organic extract is washed with brine, dried over Na$_2$SO$_4$ and evaporated to give 0.47 g of a foam. Preparative thick layer chromatography by elution with 2:1 ethyl acetate-hexane gives 0.24 g of white solid. MS(FAB): 488(MH$^+$—OH).

EXAMPLE 582

2,4-Dichloro-N-[4-[[3-(1H-imidazol-1-ylmethyl)-5H-pyrrolo[2,1-c][1,4]benzodiazepin-10(11H)-yl]carbonyl]phenyl]benzamide To a suspension of 0.28 g of N,N-dimethyl-glycine hydrochloride in 5 ml of tetrahydrofuran is added 0.21 g of triethylamine and 0.35 g of carbonyldiimidazole. After stirring at room temperature for 30 minutes and then heating at reflux for 18 hours, the tetrahydrofuran is evaporated in vacuo to a residue which is dissolved in ethyl acetate and washed with water, saturated NaHCO$_3$ and brine and dried over Na$_2$SO$_4$, filtered and evaporated in vacuo to a residue. The residue is washed with ether-hexanes (1:1) to give 0.17 g of white solid. MS(FAB): 556(M+H)

EXAMPLE 583

α-Chloro-N-[4-(5H-pyrrolo[2,1-c][1,4]benzodiazepin-10(11H)-ylcarbonyl)phenyl]benzeneacetamide To a solution of 0.61 g of 10,11-dihydro-10-(4-aminobenzoyl)-5H-pyrrolo[2,1-c][1,4]benzodiazepine in 8 ml of methylene chloride is added 0.30 g of triethylamine followed by 0.47 g of (±)-2-chloro-2-phenylacetyl chloride in 2 ml of methylene chloride. The mixture is stirred at room temperature for 1 hour and then diluted with 10 ml of 50% NaHCO$_3$. The methylene chloride is evaporated and the residue is extracted with ethyl acetate. The separated organic layer is washed with saturated NaHCO$_3$ and brine and then dried with Na$_2$SO$_4$ followed by filtering through a pad of hydrous magnesium silicate. The filtrate is evaporated to a residue which is stirred with ether-hexane to give 0.98 g of pink solid. MS(CI): 456(M+H).

EXAMPLE 584

α-[[2-(Dimethylamino)ethyl]thio]-N-[4-(5H-pyrrolo[2,1-c][1,4]benzodiazepin-10(11H)-ylcarbonyl)phenyl]benzeneacetamide A mixture of 0.14 g of α-chloro-N-[4-(5H-pyrrolo[2,1-c][1,4]benzodiazepin-10(11H)-ylcarbonyl)phenyl]benzeneacetamide, 0.47 g of 2-dimethylaminoethanethiol hydrochloride in 2 ml of methyl alcohol, 0.30 g of triethylamine and 3 ml of 1,3-dimethyl-3,4,5,6-tetrahydro-2(1H)-pyrimidinone is heated at 60° C. for 48 hours. The methyl alcohol is evaporated and the residue diluted with water. The resulting suspension is filtered and the precipitate washed with water. The solid is dissolved in ethyl acetate and washed with saturated NaHCO$_3$, brine and dried with Na$_2$SO$_4$. The mixture is filtered and the filtrate evaporated in vacuo to a residue which is stirred with ether-hexane to give 0.15 g of beige solid. MS(CI): 525(M+H).

EXAMPLE 585

α-[N-(Acetamido)amino]-N-[4-(5H-pyrrolo[2,1-c][1,4]-benzodiazepin-10(11H)-ylcarbonyl)phenyl]benzeneacetamide A mixture of 0.14 g of α-chloro-N-[4-(5H-pyrrolo[2,1-c][1,4]benzodiazepin-10(11H)-ylcarbonyl)phenyl]benzeneacetamide, 0.17 g of glycinamide HCl, 0.15 g of triethylamine, 3 ml of 1,3-dimethyl-3,4,5,6-tetrahydro-2(1M)-pyrimidinone and 1 ml of methyl alcohol is heated at 75° C. for 2 days. The methyl alcohol is evaporated and the residue diluted with water. The resulting suspension is filtered and the precipitate washed with water. The solid is dissolved in ethyl acetate and washed with saturated NaHCO₃, brine and dried with Na₂SO₄. The mixture is filtered and the filtrate evaporated in vacuo to a residue which is stirred with ether-hexanes to give 0.13 g of tan solid. MS(CI): 494(M+H).

EXAMPLE 586

α-(Dimethylamino)-N-[4-(5H-pyrrolo[2,1-c][1,4]
benzodiazepin-10(11H)-ylcarbonyl)phenyl]
benzeneacetamide A partial solution of 0.14 g of α-chloro-N-[4-(5H-pyrrolo [2,1-c][1,4]benzodiazepin-10(11H)-ylcarbonyl)phenyl] benzeneacetamide in 1 ml of methanol is treated with 0.5 ml of dimethylamine and 1 ml of 1,3-dimethyl-3,4,5,6-tetrahydro-2(1H)-pyrimidinone and stirring continued for 20 hours. The methanol is evaporated and the residue diluted with water. The resulting solid is washed with water, dissolved in ethyl acetate and the organic layer washed with saturated NaHCO₃, brine and dried with Na₂SO₄. The mixture is filtered and the filtrate evaporated in vacuo to give a residue which is stirred with ethyl acetate-hexane to give 0.15 g of a beige solid. MS (CI): 465(M+H).

EXAMPLE 587

α-(Acetyloxy)-N-[4-(5H-pyrrolo[2,1-c][1,4]
benzodiazepin-10(11H)-ylcarbonyl)phenyl]
benzeneacetamide To a solution of 0.30 g of 10,11-dihydro-10-(4-aminobenzoyl)-5H-pyrrolo[2,1-c][1,4]benzodiazepine in 5 ml of methylene chloride is added 0.15 g of triethylamine followed by 0.27 g of O-acetylmandelic acid chloride. The mixture is stirred at room temperature for 1 hour and then diluted with 50% NaHCO₃. The methylene chloride is evaporated and the residue is extracted with ethyl acetate. The separated organic layer is washed with saturated NaHCO₃ and brine and then dried with Na₂SO₄ followed by filtering through a pad of hydrous magnesium silicate. The filtrate is evaporated to a residue which is stirred with ether-hexane to give 0.54 g of beige solid. MS(CI): 480(M+H).

EXAMPLE 588

(±)α-Hydroxy-N-[4-(5H-pyrrolo[2,1-c][1,4]
benzodiazepin-10(11H)-ylcarbonyl)phenyl]
benzeneacetamide A solution of 0.34 g of α-(acetyloxy)-N-[4-(5H-pyrrolo [2,1-c][1,4]benzodiazepin-10(11H)-ylcarbonyl)phenyl] benzeneacetamide in 2 ml of 1N NaOH and 4 ml of methyl alcohol is stirred at room temperature for 30 minutes, diluted with 2 ml of water and evaporated in vacuo. The aqueous suspension is extracted with 30 ml of ethyl acetate and the extract washed with brine, dried with Na₂SO₄ and filtered through a pad of hydrous magnesium silicate and evaporated in vacuo to a residue. The residue is stirred with ether-hexanes to give 0.26 g of cream colored solid. MS(CI): 438(M+H).

EXAMPLE 589

2-Chloro-N-[4-(5H-pyrrolo[2,1-c][1,4]
benzodiazepin-10(11H)-ylcarbonyl)phenyl]
acetamide To a stirred solution of 0.91 g of 10,11-dihydro-10-(4-aminobenzoyl)-5H-pyrrolo[2,1-c][1,4]benzodiazepine in 10 ml of methylene chloride is added 0.46 g of triethylamine and 36 mg of dimethylaminopyridine followed by the slow addition of 0.42 g of chloroacetyl chloride in 5 ml of methylene chloride. The resulting mixture is stirred at room temperature for 3 hours then partitioned with 10 ml of 50% NaHCO₃ and the methylene chloride evaporated in vacuo. The remaining suspension is filtered, washed with 50% NaHCO₃, H₂O, EtOAc (2×2 ml), ether (2×5 ml) and dried in vacuo to give 1.14 g of beige solid. MS(CI): 380(M+H).

EXAMPLE 590

N-[4-(5H-pyrrolo[2,1-c][1,4]benzodiazepin-10(11H)
ylcarbonyl]phenyl]-4-morpholineacetamide A stirred suspension of 0.19 g of 2-chloro-N-[4-(5H-pyrrolo[2,1-c][1,4]benzodiazepin-10(11H)ylcarbonyl) phenyl]acetamide in 1 ml of methylene chloride is added 0.44 g of morpholine followed by 1 ml of 1,3-di- methyl-3,4,5,6-tetrahydro-2(1H)-pyrimidinone and stirring continued for 20 hours. The methylene chloride is evaporated and the residue diluted with water. The resulting suspension is filtered and the precipitate washed with water. The brown solid is dissolved in 15 ml of ethyl acetate and washed with saturated NaHCO₃, brine and dried with Na₂SO₄. The mixture is filtered and the filtrate evaporated in vacuo to give 0.23 g of a colorless gum which is stirred with ethyl acetate-hexanes to give 0.21 g of white solid. MS(CI): 431(M+H).

EXAMPLE 591

N-[(2-Chlorophenyl)methyl]-N-[4-(5H-pyrrolo[2,1-
c][1,4]benzodiazepin-10(11H)-ylcarbonyl)phenyl]-4-
morpholineacetamide A mixture of 0.11 g of N-[4-(5H-pyrrolo[-2,1-c][1,4] benzodiazepin-10(11H)-ylcarbonyl)phenyl]-4-morpholineacetamide, 56 mg of 0-chlorobenzyl bromide and 0.41 g of K₂CO₃ in 5 ml of acetonitrile is heated at reflux for 18 hours. An additional 30 mg of O-chlorobenzyl bromide and 0.4 mmol of sodium hydride is added followed by heating for 24 hours. The reaction mixture is diluted with water and extracted with ethyl acetate. The organic layer is dried with Na₂SO₄ and evaporated to give 0.18 g of a residue which is purified by chromatography on silica gel with 1:1 ethyl acetate-methylene chloride to give 80 mg of off white solid. MS(CI): 555(M+H).

EXAMPLE 592

Ethyl 10-[4-[(2,4-dichlorobenzoyl)amino]-3-
methylbenzoyl]-10,11-dihydro-5H-pyrrolo[2,1-c][1,
4]-benzodiazepine-3-carboxylate To a solution of 0.30 g of ethyl 10,11-dihydro-10-(4-amino-3-methylbenzoyl)-5H-pyrrolo[2,1-c][1,4] benzodiazepine-3-carboxylate in 20 ml of methylene chloride is added 0.15 g of N,N-diisopropylethylamine and 0.24 g of 2,4-dichlorobenzoyl chloride. The reaction mixture is stirred at room temperature for 18 hours and washed with water, saturated NaHCO₃ and dried with Na₂SO₄. The organic layer is passed through a pad of hydrous magnesium silicate. Hexane is added to the filtrate at the boil to give 0.24 g of solid, m.p. 174°–184° C.

EXAMPLE 593

Methyl 10-4-2,4-dichlorobenzoylamino]benzoyl]-
10,11-dihydro-5H-pyrrolo[2,1-c][1,4]
benzodiazepine-3-carboxylate To 50 ml of absolute methyl alcohol is added 0.15 g of sodium metal. After complete solution, 1.0 g of N-[4-[[3-

(trichloroacetyl)-5H-pyrrolo[2,1-c][1,4]benzodiazepin-10 (11H)-yl)]carbonyl]phenyl]-2,4-dichlorobenzamide is added and the reaction mixture stirred overnight at room temperature. Methylene chloride is added followed by Na$_2$SO$_4$. The organic layer is filtered through hydrous magnesium silicate. Hexane is added at the boil to the filtrate to give 0.29 g of solid.

EXAMPLE 594

N-[4-[[3-(trifluoroacetyl)-5H-pyrrolo[2,1-c][1,4] benzodiazepin-10(11H)-yl)]carbonyl]phenyl]-2-trifluoromethyl)benzamide To a solution of 1.0 g of N-[4-(5H-pyrrolo[2,1-c][1,4] benzodiazepin-10(11H)-ylcarbonyl)phenyl]-2-(trifluoromethyl)benzamide in 10 ml of methylene chloride is added 1.0 ml of trifluoroacetic anhydride followed by stirring for 18 hours at room temperature. The reaction mixture is washed with saturated NaHCO$_3$, dried with Na$_2$SO$_4$, filtered and hexane added at the boil to give a solid which is crystallized from methylene chloride-hexane to give 0.89 g of solid, m.p. 248°–250° C.

EXAMPLE 595

N-[4-[[3-(Trifluoroacetyl)-5H-pyrrolo[2,1-c][1,4] benzodiazepin-10(11H)-yl]carbonyl]-3-chlorophenyl]-2-methylbenzamide To a solution of 0.30 g of N-[4-(5H-pyrrolo[2,1-c][1,4] benzodiazepin-10(11H)-ylcarbonyl)-3-chlorophenyl]-2-methylbenzamide in 25 ml of methylene chloride is added 0.5 ml of trifluoroacetic anhydride followed by stirring at room temperature for 18 hours. The reaction mixture is washed with saturated NaHCO$_3$, dried with Na$_2$SO$_4$, filtered through hydrous magnesium silicate and hexane added to the filtrate at the boil to give 0.22 g of colorless solid. MS: M+551.

EXAMPLE 596

Ethyl 10-[4-[2,4-dichlorobenzoyl)amino]benzoyl]-10,11-dihydro-5H-pyrrolo[2,1-c][1,4]benzodiazepine-3-carboxylate To 50 ml of absolute ethyl alcohol is added 0.30 g of sodium metal, followed by the addition of 2.0 g of N-[4-[[3-(trichloroacetyl)-5H-pyrrolo[2,1-c][1,4]benzodiazepin-10(11H)yl]carbonyl]phenyl]-2,4-dichlorobenzamide and the mixture is stirred for 18 hours at room temperature. The volatiles are evaporated in vacuo to a residue which is dissolved in methylene chloride and washed with H$_2$O. The organic layer is dried with Na$_2$SO$_4$ and filtered through hydrous magnesium silicate. Hexane is added to the filtrate at the boil to give a solid which is crystallized from methylene chloride-hexane to give 0.57 g of a solid. MS(M$^+$):548.2

EXAMPLE 597

N-[4-[[3-(Trichloroacetyl)-5H-pyrrolo[2,1-c][1,4] benzodiazepin-10(11H)-yl]carbonyl]phenyl]-2-(trifluoromethyl)benzamide To a stirred solution of 0.48 g of N-[4-(5H-pyrrolo[2,1-c][1,4]benzodiazepin-10(11H)-ylcarbonyl)phenyl]-2-(trifluoromethyl)benzamide in 20 ml of methylene chloride is added 0.40 g of trichloroacetic anhydride followed by stirring at room temperature for 18 hours. The reaction mixture is washed with water and saturated NaHCO$_3$, dried over Na$_2$SO$_4$ and passed through a pad of hydrous magnesium silicate. Hexane is added at the boil to give 0.37 g of solid, m.p. 219°–221° C.

EXAMPLE 598

N-[4-[[3-(Trichloroacetyl)-5H-pyrrolo[2,1-c][1,4] benzodiazepin-10(11H)-yl]carbonyl]phenyl]-2,4-dichlorobenzamide To a stirred solution of 4.76 g of N-[4-(5H-pyrrolo[2,1-c][1,4]benzodiazepin-10(11H)-ylcarbonyl)phenyl]-2,4-dichlorobenzamide in 150 ml of methylene chloride is added 3.75 g of trichloroacetic anhydride followed by stirring for 18 hours. The reaction mixture is washed with water and saturated NaHCO$_3$, dried over Na$_2$SO$_4$ and passed through a pad of hydrous magnesium silicate. The filtrate is evaporated in vacuo to give 2.91 g of solid.

EXAMPLE 599

N-[4-(5H-Pyrrolo[2,1-c][1,4]benzodiazepin-10(11H) ylcarbonyl)phenyl]-2,3,5-trichlorobenzamide As described for Example 8, 0.50 g of 10,11-dihydro-10-(4-aminobenzoyl)-5H-pyrrolo[2,1-c][1,4]benzodiazepine is reacted with 0.483 g of 2,3,5-trichlorobenzoyl chloride to give a glass which is crystallized from ethyl acetate to give 0.686 g of crystals, m.p. 231°–234° C.

EXAMPLE 600

N-[4-(5H-Pyrrolo[2,1-c][1,4]benzodiazepin-10(11H) ylcarbonyl)phenyl]tetrahydrofurane-2-carboxamide As described for Example 8, 0.500 g of 10,11-dihydro-10-(4-aminobenzoyl)-5H-pyrrolo[2,1-c][1,4]benzodiazepine is reacted with 0.267 g of tetrahydrofurane-2-carbonyl chloride to give a glass which is crystallized from ethyl acetate to give 0.22 g of crystals, m.p. 208°–214° C.

The following Examples are prepared using conditions of Example 297 with the appropriately substituted aroyl chloride.

| Example No. | Compound |
| --- | --- |
| 601 | N-[4-[(6,7-Dihydro-5H-pyrrolo[1,2-a]-[1,5]benzodiazepin-5-yl)carbonyl]-2,5-dichlorophenyl]-2,3-dimethylbenzamide |
| 602 | N-[4-[(6,7-Dihydro-5H-pyrrolo[1,2-a]-[1,5]benzodiazepin-5-yl)carbonyl]-2,5-dichlorophenyl]-2-chlorobenzamide |
| 603 | N-[4-[(6,7-Dihydro-5H-pyrrolo[1,2-a]-[1,5]benzodiazepin-5-yl)carbonyl]-2,5-dichlorophenyl]-2,4-dichlorobenzamide |
| 604 | N-[4-[(6,7-Dihydro-5H-pyrrolo[1,2-a]-[1,5]benzodiazepin-5-yl)carbonyl]-2,5-dichlorophenyl]-3,5-dichlorobenzamide |
| 605 | N-[4-[(6,7-Dihydro-5H-pyrrolo[1,2-a]-[1,5]benzodiazepin-5-yl)carbonyl]-2,5-dichlorophenyl]-2-methyl-4-chlorobenzamide |
| 606 | N-[4-[(6,7-Dihydro-5H-pyrrolo[1,2-a]-[1,5]benzodiazepin-5-yl)carbonyl]-3-chlorophenyl]-2-methoxybenzamide |
| 607 | N-[4-[(6,7-Dihydro-5H-pyrrolo[1,2-a]-[1,5]benzodiazepin-5-yl)carbonyl]-3-chlorophenyl]-2-(trifluoromethoxy)benzamide |

| Example No. | Compound |
|---|---|
| 608 | N-[4-[(6,7-Dihydro-5H-pyrrolo[1,2-a]-[1,5]benzodiazepin-5-yl)carbonyl]-3-chlorophenyl]-2-(trifluoromethyl)benzamide |
| 609 | N-[4-[(6,7-Dihydro-5H-pyrrolo[1,2-a]-[1,5]benzodiazepin-5-yl)carbonyl]-3-chlorophenyl]-2,4-dichlorobenzamide, amorphous white solid, m.p. 134–137° C. |
| 610 | N-[4-[(6,7-Dihydro-5H-pyrrolo[1,2-a]-[1,5]benzodiazepin-5-yl)carbonyl]-3-chlorophenyl]-2-(methylthio)benzamide |
| 611 | N-[4-[(6,7-Dihydro-5H-pyrrolo[1,2-a]-[1,5]benzodiazepin-5-yl)carbonyl]-3-chlorophenyl]-3-fluoro-2-methylbenzamide, amorphous white solid, m.p. 136–138° C. |
| 612 | N-[4-[(6,7-Dihydro-5H-pyrrolo[1,2-a]-[1,5]benzodiazepin-5-yl)carbonyl]-3-chlorophenyl]-5-fluoro-2-methylbenzamide, amorphous solid, m.p. 132–135° C. |
| 613 | N-[4-[(6,7-Dihydro-5H-pyrrolo[1,2-a]-[1,5]benzodiazepin-5-yl)carbonyl]-3-chlorophenyl]-4-fluoro-2-methylbenzamide |
| 614 | N-[4-[(6,7-Dihydro-5H-pyrrolo[1,2-a]-[1,5]benzodiazepin-5-yl)carbonyl]-3-chlorophenyl]-4-fluoro-2-(trifluoromethyl)benzamide |
| 615 | N-[4-[(6,7-Dihydro-5H-pyrrolo[1,2-a]-[1,5]benzodiazepin-5-yl)carbonyl]-3-chlorophenyl]-2,3-dichlorobenzamide |
| 616 | N-[4-[(6,7-Dihydro-5H-pyrrolo[1,2-a]-[1,5]benzodiazepin-5-yl)carbonyl]-3-chlorophenyl]-2,3-difluorobenzamide |
| 617 | N-[4-[(6,7-Dihydro-5H-pyrrolo[1,2-a]-[1,5]benzodiazepin-5-yl)carbonyl]-3-chlorophenyl]-2-fluoro-5-(trifluoromethyl)benzamide |
| 618 | N-[4-[(6,7-Dihydro-5H-pyrrolo[1,2-a]-[1,5]benzodiazepin-5-yl)carbonyl]-3-chlorophenyl]-2-fluoro-3-(trifluoromethyl)benzamide |
| 619 | N-[4-[(6,7-Dihydro-5H-pyrrolo[1,2-a]-[1,5]benzodiazepin-5-yl)carbonyl]-3-chlorophenyl]-4-fluoro-2-(trifluoromethyl)benzamide |
| 620 | N-[4-[(6,7-Dihydro-5H-pyrrolo[1,2-a]-[1,5]benzodiazepin-5-yl)carbonyl]-3-chlorophenyl]-2,5-difluorobenzamide |
| 621 | N-[4-[(6,7-Dihydro-5H-pyrrolo[1,2-a]-[1,5]benzodiazepin-5-yl)carbonyl]-3-chlorophenyl]-2,3-difluorobenzamide |
| 622 | N-[4-[(6,7-Dihydro-5H-pyrrolo[1,2-a]-[1,5]benzodiazepin-5-yl)carbonyl]-3-chlorophenyl]-2,5-dimethylbenzamide |
| 623 | N-[4-[(6,7-Dihydro-5H-pyrrolo[1,2-a]-[1,5]benzodiazepin-5-yl)carbonyl]-3-chlorophenyl]-3-methyl-2-thiophenecarboxamide |
| 624 | N-[4-[(6,7-Dihydro-5H-pyrrolo[1,2-a]-[1,5]benzodiazepin-5-yl)carbonyl]-3-chlorophenyl]-2-methyl-3-thiophenecarboxamide |
| 625 | N-[4-[(6,7-Dihydro-5H-pyrrolo[1,2-a]-[1,5]benzodiazepin-5-yl)carbonyl]-3-chlorophenyl]-2-methyl-3-furanecarboxamide |
| 626 | N-[4-[(6,7-Dihydro-5H-pyrrolo[1,2-a]-[1,5]benzodiazepin-5-yl)carbonyl]-3-chlorophenyl]-3-methyl-2-furanecarboxamide |
| 627 | N-[4-[(6,7-Dihydro-5H-pyrrolo[1,2-a]-[1,5]benzodiazepin-5-yl)carbonyl]-3-chlorophenyl]-2-chlorobenzeneacetamide |
| 628 | N-[4-[(6,7-Dihydro-5H-pyrrolo[1,2-a]-[1,5]benzodiazepin-5-yl)carbonyl]-3-chlorophenyl]-2-methylbenzeneacetamide |
| 629 | N-[4-[(6,7-Dihydro-5H-pyrrolo[1,2-a]-[1,5]benzodiazepin-5-yl)carbonyl]-3-chlorophenyl]-4-fluoro-3-(trifluoromethyl)benzamide |
| 630 | N-[4-[(6,7-Dihydro-5H-pyrrolo[1,2-a]-[1,5]benzodiazepin-5-yl)carbonyl]-2-chlorophenyl]-3-fluoro-2-methylbenzamide |
| 631 | N-[4-[(6,7-Dihydro-5H-pyrrolo[1,2-a]-[1,5]benzodiazepin-5-yl)carbonyl]-2-chlorophenyl]-2,3-dichlorobenzamide |
| 632 | N-[4-[(6,7-Dihydro-5H-pyrrolo[1,2-a]-[1,5]benzodiazepin-5-yl)carbonyl]-2-chlorophenyl]-2,3-difluorobenzamide |
| 633 | N-[4-[(6,7-Dihydro-5H-pyrrolo[1,2-a]-[1,5]benzodiazepin-5-yl)carbonyl]-2-chlorophenyl]-4-fluoro-2-methylbenzamide |
| 634 | N-[4-[(6,7-Dihydro-5H-pyrrolo[1,2-a]-[1,5]benzodiazepin-5-yl)carbonyl]-2-chlorophenyl]-5-fluoro-2-methylbenzamide |
| 635 | N-[4-[(6,7-Dihydro-5H-pyrrolo[1,2-a]-[1,5]benzodiazepin-5-yl)carbonyl]-2-chlorophenyl]-2-fluoro-5-(trifluoromethyl)benzamide |
| 636 | N-[4-[(6,7-Dihydro-5H-pyrrolo[1,2-a]-[1,5]benzodiazepin-5-yl)carbonyl]-2-chlorophenyl]-2-methylbenzamide |
| 637 | N-[4-[(6,7-Dihydro-5H-pyrrolo[1,2-a]-[1,5]benzodiazepin-5-yl)carbonyl]-2-chlorophenyl]-2-chlorobenzamide |
| 638 | N-[4-[(6,7-Dihydro-5H-pyrrolo[1,2-a]-[1,5]benzodiazepin-5-yl)carbonyl]-2-chlorophenyl]-2,3-dimethylbenzamide |
| 639 | N-[4-[(6,7-Dihydro-5H-pyrrolo[1,2-a]-[1,5]benzodiazepin-5-yl)carbonyl]-2-chlorophenyl]-2,5-dimethylbenzamide |
| 640 | N-[4-[(6,7-Dihydro-5H-pyrrolo[1,2-a]-[1,5]benzodiazepin-5-yl)carbonyl]-2-chlorophenyl]-2-methoxybenzamide |
| 641 | N-[4-[(6,7-Dihydro-5H-pyrrolo[1,2-a]-[1,5]benzodiazepin-5-yl)carbonyl]-2-chlorophenyl]-2-(trifluoromethoxy)benzamide |
| 642 | N-[4-[(6,7-Dihydro-5H-pyrrolo[1,2-a]-[1,5]benzodiazepin-5-yl)carbonyl]-2-chlorophenyl]-2-methoxy-4-chlorobenzamide |
| 643 | N-[4-[(6,7-Dihydro-5H-pyrrolo[1,2-a]-[1,5]benzodiazepin-5-yl)carbonyl]-2-chlorophenyl]-2,6-dichlorobenzamide |
| 644 | N-[4-[(6,7-Dihydro-5H-pyrrolo[1,2-a]-[1,5]benzodiazepin-5-yl)carbonyl]-2-chlorophenyl]-2-(methylthio)benzamide |
| 645 | N-[4-[(6,7-Dihydro-5H-pyrrolo[1,2-a]-[1,5]benzodiazepin-5-yl)carbonyl]-2-chlorophenyl]-2-(trifluoromethyl)benzamide |
| 646 | N-[4-[(6,7-Dihydro-5H-pyrrolo[1,2-a]-[1,5]benzodiazepin-5-yl)carbonyl]-2-chlorophenyl]-3-(trifluoromethyl)benzamide |
| 647 | N-[4-[(6,7-Dihydro-5H-pyrrolo[1,2-a]-[1,5]benzodiazepin-5-yl)carbonyl]-2-chlorophenyl]-2,3,5-trichlorobenzamide |
| 648 | N-[4-[(6,7-Dihydro-5H-pyrrolo[1,2-a]-[1,5]benzodiazepin-5-yl)carbonyl]-3-methoxyphenyl]-3-fluoro-2-methylbenzamide |
| 649 | N-[4-[(6,7-Dihydro-5H-pyrrolo[1,2-a]-[1,5]benzodiazepin-5-yl)carbonyl]-3-methoxyphenyl]-5-fluoro-2-methylbenzamide |
| 650 | N-[4-[(6,7-Dihydro-5H-pyrrolo[1,2-a]-[1,5]benzodiazepin-5-yl)carbonyl]-3-methoxyphenyl]-4-fluoro-2-methylbenzamide |

-continued

| Example No. | Compound |
|---|---|
| 651 | N-[4-[(6,7-Dihydro-5H-pyrrolo[1,2-a]-[1,5]benzodiazepin-5-yl)carbonyl]-3-methoxyphenyl]-2,4-dichlorobenzamide |
| 652 | N-[4-[(6,7-Dihydro-5H-pyrrolo[1,2-a]-[1,5]benzodiazepin-5-yl)carbonyl]-3-methoxyphenyl]-2,3-dimethylbenzamide |
| 653 | N-[4-[(6,7-Dihydro-5H-pyrrolo[1,2-a]-[1,5]benzodiazepin-5-yl)carbonyl]-3-methoxyphenyl]-3-fluoro-5-(trifluoromethyl)benzamide |
| 654 | N-[4-[(6,7-Dihydro-5H-pyrrolo[1,2-a]-[1,5]benzodiazepin-5-yl)carbonyl]-2-methoxyphenyl]-3-fluoro-2-methylbenzamide |
| 655 | N-[4-[(6,7-Dihydro-5H-pyrrolo[1,2-a]-[1,5]benzodiazepin-5-yl)carbonyl]-2-methoxyphenyl]-5-fluoro-2-methylbenzamide |
| 656 | N-[4-[(6,7-Dihydro-5H-pyrrolo[1,2-a]-[1,5]benzodiazepin-5-yl)carbonyl]-2-methoxyphenyl]-4-fluoro-2-methylbenzamide |
| 657 | N-[4-[(6,7-Dihydro-5H-pyrrolo[1,2-a]-[1,5]benzodiazepin-5-yl)carbonyl]-2-methoxyphenyl]-2,4-dichlorobenzamide |
| 658 | N-[4-[(6,7-Dihydro-5H-pyrrolo[1,2-a]-[1,5]benzodiazepin-5-yl)carbonyl]-2-methoxyphenyl]-2,3-dimethylbenzamide |
| 659 | N-[4-[(6,7-Dihydro-5H-pyrrolo[1,2-a]-[1,5]benzodiazepin-5-yl)carbonyl]-2-methoxyphenyl]-3-fluoro-5-(trifluoromethyl)benzamide |

EXAMPLE 660

N-[4-[[3-[-[(Dimethylamino)methyl]-5H-pyrrolo[2,1-c][1,4]benzodiazepin-10(11H)-yl]carbonyl]phenyl]-2-methylbenzamide To a stirred solution of 0.842 g of 2-methyl-N-[4-(5H-pyrrolo[2,1-c][1,4]benzodiazepin-10(11H)-ylcarbonyl)phenyl]benzamide in 25 ml of 1:1 methanol:tetrahydrofuran is added 10 ml of 35% formaldehyde and 10 ml of 30% N,N-dimethylamine at 0° C. After 2 drops of acetic acid is added, the reaction mixture is stirred at room temperature for 16 hours. The reaction mixture is concentrated in vacuo to a residue which is dissolved in chloroform and washed with water. The organic layer is dried with $Na_2SO_4$ and evaporated in vacuo to a residue. The residue is chromatographed on silica gel with 10:1 ethyl acetate-methanol as eluent to give 0.800 g of the desired product, M+H:479.

The following products are prepared by using the condition of Example 660 and by using the appropriately substituted benzamide.

| Example No. | Compound |
|---|---|
| 661 | N-[4-[[3-(1-piperidinylmethyl)-5H-pyrrolo[2,1-c][1,4]benzodiazepin-10(11H)-yl]carbonyl]phenyl]-2-methylbenzamide, solid; mass spectrum (M⁺H) 518 |
| 662 | N-[4-[[3-(1-piperidinylmethyl)-5H-pyrrolo[2,1-c][1,4]benzodiazepin-10(11H)-yl]carbonyl]phenyl]-2-methylbenzamide, solid; mass spectrum (M⁺H) 521 |
| 663 | N-[4-[[3-[[4-(phenylmethyl)-1-piperazinyl]methyl]-5H-pyrrolo[2,1-c][1,4]-benzodiazepin-10(11H)-yl]carbonyl]phenyl]-2-methylbenzamide, solid; mass spectrum (M⁺H) 610 |
| 664 | N-[4-[[3-[(dimethylaminomethyl]-5H-pyrrolo[2,1-c][1,4]benzodiazepin-10(11H)-yl]carbonyl]phenyl]-2,4-dichlorobenzamide, solid; mass spectrum (M⁺H) 535 |
| 665 | N-[4-[[3-(1-pyrrolidinylmethyl)-5H-pyrrolo[2,1-c][1,4]benzodiazepin-10(11H)-yl]carbonyl]phenyl]-2,4-dichlorobenzamide, solid; mass spectrum (M⁺H) 561 |
| 666 | N-[4-[[3-(4-morpholinomethyl)-5H-pyrrolo[2,1-c][1,4]benzodiazepin-10(11H)-yl]carbonyl]phenyl]-2,4-dichlorobenzamide, solid; mass spectrum (M⁺H) 576 |
| 667 | N-[4-[[3-[(diethylamino)methyl]-5H-pyrrolo[2,1-c][1,4]benzodiazepin-10(11H)-yl]carbonyl]phenyl]-2,4-dichlorobenzamide, solid; mass spectrum (M⁺H) 562 |
| 668 | N-[4-[[3-[(dimethylamino)methyl]-5H-pyrrolo[2,1-c][1,4]benzodiazepin-10(11H)-yl]carbonyl]phenyl]-3-chlorophenyl]-5-fluoro-2-methylbenzamide, solid; mass spectrum (M⁺H) 531 |
| 669 | N-[4-[[3-[(dimethylamino)methyl]-5H-pyrrolo[2,1-c][1,4]benzodiazepin-10(11H)-yl]carbonyl]-3-chlorophenyl]-2-methylbenzamide, solid; mass spectrum (M⁺H) 513 |

EXAMPLE 670

N-[4-[(3-Acetyl-5H-pyrrolo[2,1-c][1,4]benzodiazepin-10(11H)-yl]carbonyl]phenyl]-2,4-dichlorobenzamide A stirred solution of 0.954 g of N-[4-(5H-pyrrolo[2,1-c][1,4]benzodiazepin-10(11H)-ylcarbonyl)phenyl]-2,4-dichlorobenzamide in 25 ml of methylene chloride and 5 ml of acetic anhydride is heated at reflux for 24 hours. The volatiles are evaporated in vacuo to a residue which is purified by column chromatography on silica gel by elution with ethyl acetate:hexane (7:3) to give 0.800 g of a white solid; mass spectrum (M⁺H)519.

EXAMPLE 671

1-[2-Nitro-5-(ethoxycarbonyl)benzyl]-pyrrole-2-carboxaldehyde

To a stirred slurry of 2.2 g of sodium hydride (60% in oil, washed with hexane) in tetrahydrofuran is added at 0° C. a solution of 4.5 g of pyrrole-2-carboxaldehyde in 25 ml of tetrahydrofuran. After the addition is complete, a solution of 15 g of ethyl 4-nitro-3-bromomethylbenzoate in 30 ml of dry tetrahydrofuran is slowly added under nitrogen. The reaction mixture is stirred at 20° C. for 8 hours and carefully quenched with water. The reaction mixture is extracted with chloroform which is washed with water, dried with $Na_2SO_4$ and concentrated in vacuo to give 12 g of the desired product as a solid; mass spectrum (M⁺H) 349.

EXAMPLE 672

1-[2-Nitro-4-(ethoxycarbonyl)benzyl]-pyrrole-2-carboxaldehyde

The conditions of Example 671 are used with ethyl 3-nitro-4-bromomethylbenzoate to give 13.0 g of the desired product as a solid; mass spectrum (M⁺H)349.

EXAMPLE 673

Ethyl 10,11-Dihydro-5H-pyrrolo[2,1-c][1,4] benzodiazepine-7-carboxylate

A solution of 10.0 g of 1-[2-nitro-5-(ethoxycarbonyl) benzyl]-pyrrole-2-carboxaldehyde in 150 ml of absolute ethanol containing 1.0 g of 10% Pd/c is hydrogenated in a Parr apparatus for 16 hours under 40 psi of hydrogen. The reaction mixture is filtered through a pad of diatomaceous earth and the filtrate concentrated in vacuo to a residue of 5.5 g of the desired product as a solid; mass spectrum (M$^+$H) 255.

EXAMPLE 674

Ethyl 10,11-Dihydro-5H-pyrrolo[2,1-c][1,4] benzodiazepine-8-carboxylate

The hydrogenation conditions of Example 673 are used with 1-[2-nitro-4-(ethoxycarbonyl)benzyl]pyrrole-2-carboxaldehyde to give 5.0 g of the desired product as a solid; mass spectrum (M$^+$H)255.

EXAMPLE 675

Ethyl 10,11-Dihydro-10-[4-[(2-methylbenzoyl) amino]benzoyl]-5H-pyrrolo[2,1-c][1,4] benzodiazepine-7-carboxylate A solution of 1.2 g of ethyl 10,11-dihydro-5H-pyrrolo[2, 1-c][1,4]benzodiazepine-7-carboxylate in ml of methylene chloride is cooled to 0° C. and 10 ml of triethylamine added followed by 1.5 g of 4-[(2-methylbenzoyl)amino)benzoyl chloride. The reaction mixture is stirred at room temperature for 18 hours and concentrated in vacuo to a residue which is partitioned between water and chloroform. The organic layer is dried over Na$_2$SO$_4$ and concentrated in vacuo to a residue. The residue is purified by column chromatography on silica gel by elution with 40% ethyl acetatehexane to give 1.0 g of the desired product as a solid; mass spectrum (M$^+$H)494.

EXAMPLE 676

Ethyl 10,11-Dihydro-10-[4-[(2-methylbenzoyl) amino]benzoyl]-5H-pyrrolo[2,1-c][1,4] benzodiazepin-8-carboxylate The conditions of Example 675 are used with ethyl 10,11-dihydro-5H-pyrrolo[2,1-c][1,4]benzodiazepine-8-carboxylate to give 1.2 g of the desired product as a solid; mass spectrum (M$^+$H)494.

The subject compounds of the present invention are tested for biological activity as follows:

EXAMPLE 677

10,11-Dihydro-10-(4-nitrobenzoyl)-5H-imidazo[2,1-c][1,4]benzodiazepine

A 292 mg sample of sodium hydride in oil is washed, under argon, with pentane. The residue is diluted with 17 ml of dioxane and then 1.35 g of 10,11-dihydro-5H-imidazo[2, 1-c][1,4]benzodiazepine is added. The reaction mixture is warmed slightly until the hydrogen evolution ceases. To the cooled reaction mixture is added a solution of 1.36 g of p-nitrobenzoyl chloride in 45 ml of dioxane and the mixture is stirred at room temperature for 18 hours. The solvent is evaporated in vacuo and the residue is heated with CHCl$_3$, filtered hot and the filter cake washed with hot CHCl$_3$. The combined CHCl$_3$ layers are washed with water, saturated NaHCO$_3$, treated with activated charcoal, filtered through a pad of MgSO$_4$ and the filtrate evaporated in vacuo to give 1.82 g of brown solid residue. The residue is purified by flash chromatography by elution with CHCl$_3$—MeOH to give 630 mg of the desired product as a solid. HR FABMS: (M+H)=335.3433.

EXAMPLE 678

10,11-Dihydro-10-(4-aminobenzoyl)-5H-imidazo[2, 1-c][1,4]benzodiazepine

A mixture of 0.550 g of 10,11-dihydro-10-(4-nitrobenzoyl)-5H-imidazo[2,1-c][1,4]benzodiazepine and 1.86 g of SnCl$_2$.2H$_2$O in 22 ml of ethyl alcohol is refluxed for 1 hour under argon. The mixture is diluted with water and then a solution of 10% NaHCO$_3$ is added until the reaction mixture is basic. Additional ethyl alcohol is added and reaction mixture evaporated in vacuo to give a residue which is triturated with 1:1 CHCl$_3$—CH$_3$OH several times and filtered. The filtrates are combined, treated with activated carbon and filtered through diatomaceous earth. The filtrate is evaporated in vacuo to give 680 mg of tan crystalline solid. The solid is stirred in ethanol, water and 10% NaHCO$_3$ to pH=8, for 5 hours and extracted with CHCl$_3$ three times. The combined extracts are treated with activated carbon, filtered through MgSO$_4$ and evaporated in vacuo to give 370 mg of tan crystalline solid. CIMS(CH$_4$) :MH$^+$=305.

EXAMPLE 679

N-[4-(5H-Imidazo[2,1-c][1,4]benzodiazepin-10 (11H)ylcarbonyl)phenyl]-2 4-dichlorobenzamide A slurry of 0.330 g of 10,11-dihydro-10-(4-aminobenzoyl)-5H-imidazo[2,1-c][1,4]benzodiazepine in 15 ml of dioxane is stirred and warmed slightly to obtain a nearly complete solution. The reaction mixture is cooled to room temperature and 43 mg of sodium hydride in oil added. The mixture is warmed slightly. Gas evolution stops in a few minutes. The reaction mixture is cooled to room temperature and 153 μl of 2,4-dichlorobenzoyl chloride in 2.5 ml of dioxane added. An additional 3.5 ml of dioxane is added and the reaction mixture stirred at room temperature for 2 days. The volatiles are evaporated in vacuo to a residue which is partitioned between water and chloroform. The organic layer is separated and the aqueous phase extracted with chloroform two more times. The combined organic layers are treated with activated carbon and filtered through MgSO$_4$. The filtrate is evaporated in vacuo to a tan foam which is purified by flash chromatography on silica gel by elution with CHCl$_3$ and 3–7% CH$_3$OH in chloroform to give 310 mg of tan foam.

EXAMPLE 680

6,7-Dihydro-5-(2-chloro-4-nitrobenzoyl)-5H-pyrrolo [1,2-a][1,5]benzodiazepine

To a solution of 0.28 g of 6,7-dihydro-5H-pyrrolo[1,2-a] [1,5]benzodiazepine in 6 ml of methylene chloride is added 0.30 g of triethylamine followed by 0.50 g of 2-chloro-4-nitrobenzoyl chloride in 0.5 ml of methylene chloride. The reaction mixture is stirred at room temperature for 1hour then quenched with 5 ml of saturated NaHCO$_3$. The methylene chloride is evaporated in vacuo and the residue is diluted with 5 ml of water and extracted with 20 ml of ethyl acetate. The organic layer is separated, washed with saturated NaHCO$_3$ and brine, dried with Na$_2$SO$_4$ and evaporated in vacuo to give 0.59 g of a yellow foam which is triturated with ether-hexanes to give 0.56 g of the desired product as off-white solid. MS(CI): 368(M+H)(Cl$^{35}$) 370(M+H)(Cl$^{37}$)

EXAMPLE 681

6,7-Dihydro-5-(4-amino-2-chlorobenzoyl)-5H-pyrrolo[1,2-a][1,5]benzodiazepine

To a solution of 0.50 g of 6,7-dihydro-5-(2-chloro-4-nitrobenzoyl)-5H-pyrrolo[1,2-a][1,5]benzodiazepine in 10 ml of ethyl alcohol and 2 ml of tetrahydrofuran is added 2.35 g of SnCl$_2$.2H$_2$O and the mixture stirred at 55° C. for 30 minutes. The solvents are evaporated in vacuo to a residue which is stirred with 20 ml of 1N NaOH and 40 ml of ethyl acetate for 15 minutes and filtered through diatomaceous earth. The filter pad is washed with 2×10 ml of ethyl acetate and the combined extracts washed with brine, dried (Na$_2$SO$_4$) and evaporated in vacuo to give 0.47 g of solid residue which is triturated with ether-hexane to give 0.43 g of light yellow crystalline solid. MS(CI): 338(M+H, Cl$^{35}$) 340(M+H, Cl$^{37}$)

EXAMPLE 682

N-[4-[(6,7-Dihydro-5H-pyrrolo[1,2-c][1,5]benzodiazepin-5-yl)carbonyl]-3-chlorophenyl]-3-fluoro-2-methylbenzamide To a mixture of 0.10 g of 6,7-dihydro-5-(4-amino-2-chlorobenzoyl)-5H-pyrrolo-[1,2-c][1,5]benzodiazepine and 0.06 g of triethylamine in 6 ml of dichloromethane is added 0.08 g of 3-fluoro-2-methylbenzoyl chloride in 0.5 ml of dichloromethane. The mixture is stirred for 2 hours at room temperature and then 2 ml of 1N NaOH added. The volatiles are evaporated under vacuum and the residue dissolved in 2 ml of tetrahydrofuran and 1 ml of methanol. The mixture is stirred for 2 hours and evaporated and the residue diluted with 2 ml of 1N NaOH and 5 ml of water. The mixture is extracted with ethyl acetate (15 ml) and the extract washed with brine and dried (Na$_2$SO$_4$). The solvent is removed and the residue triturated with diethyl ether-hexane to give 0.15 g of white solid: Mass Spectrum (CI)474(M+H, Cl$^{35}$); 476(M+H, Cl$^{37}$).

EXAMPLE 683

N-[4-[(6,7-Dihydro-5H-pyrrolo[1,2-a][1,5]benzodiazepin-5-yl)carbonyl]-3-chlorodichlorobenzamide To a mixture of 0.10 g of 6,7-dihydro-5-(4-amino-2-chlorobenzoyl)-5H-pyrrolo[1,2-c][1,5]benzodiazepine and 0.06 g of triethylamine in 6 ml of dichloromethane is added 0.10 g of 2,4-dichlorobenzoyl chloride in 0.5 ml of dichloromethane. The mixture is stirred at room temperature for 2 hours and 2 ml of 1N NaOH is added. The volatiles are removed under vacuum and to the residue is added 2 ml of tetrahydrofuran and 1 ml of methanol. The mixture is stirred at room temperature for 2 hours and the volatiles removed. To the residue is added 2 ml of 1N NaOH and 5 ml of H$_2$O. The mixture is extracted with ethyl acetate and the extract washed with brine and dried (Na$_2$SO$_4$). The solvent is removed and the solid triturated with diethyl ether-hexane to give 0.15 g of white solid, Mass Spectrum (CI): 510(M+H, Cl$^{35}$).

EXAMPLE 684

N-[4-(5H-Pyrrolo[2,1-c][1,4]benzodiazepin-10(11H)ylcarbonyl)phenyl]-2-(1H-[1,2,4]-triazol-1-yl)acetamide To a suspension of 0.20 g of 1,2,4-triazole sodium in 1 ml of 1,3-dimethyl-3,4,5,6-tetrahydro-2(1H)-pyrimidinone is added 0.10 g of 2-chloro-N-[4-(5H-pyrrolo[2,1-c][1,4]benzodiazepin-10(11H)-ylcarbonyl)phenyl]acetamide in 1 ml of 1,3-dimethyl-3,4,5,6-tetrahydro-2(1H)-pyrimidinone followed by stirring at room temperature for 3 hours. The reaction mixture is quenched with 15 ml of water and the resulting solid is collected, washed with water and hexanes to give 70 mg of the desired product as a tan solid. MS(CI): 413(M+H).

EXAMPLE 685

N-[4-(5H-Pyrrolo[2,1-c][1,4]benzodiazepin-10(11H)ylcarbonyl)phenyl]-2-(2-formyl-1-pyrrolo)acetamide To a suspension of 72 mg of sodium hydride (60% in oil) in 5 ml of tetrahydrofuran is added 0.14 g of pyrrole-2-carboxaldehyde. The mixture is stirred for 1 hour at room temperature and 94 mg of 1,3-dimethyl-3,4,5,6-tetrahydro-2(1H)-pyrimidinone and 0.19 g of 2-chloro-N-[4-(5H-pyrrolo[2,1-c][1,4]benzodiazepin-10(11H)-ylcarbonyl)phenyl]acetamide added. The mixture is stirred at room temperature, water added and the tetrahydrofuran evaporated in vacuo. The resulting suspension is filtered and the precipitate washed with water and hexanes. The collected solid is purified by column chromatography on silica gel by elution with 3:2 ethyl acetate-hexanes to give 50 mg of pink solid. MS(CI): 439(M+H).

EXAMPLE 686

N-[4-(3-Chloro-4H-pyrazolo[5,1-c][1,4]benzodiazepin-5-(10H)-ylcarbonyl)phenyl]-2-methyl-5-fluorobenzamide A mixture of 356 mg of N-[4H-pyrazolo[5,1-c][1,4]benzodiazepin-5(10H)-ylcarbonyl)-3-chlorophenyl]-5-fluoro-2-methylbenzamide and 122 mg of N-chlorosuccinimide in 5 ml of methylene chloride is refluxed on a steam bath for 3 hours. The reaction mixture is washed with saturated NaHCO$_3$, H$_2$O and brine, then dried over Na$_2$SO$_4$ and passed through a pad of hydrous magnesium silicate. The filtrate is evaporated in vacuo to give 190 mg of the desired product as a solid.

The following examples are prepared using the conditions of Example 465.

| Example No. | Compound |
|---|---|
| 687 | N-[4-(5H-pyrrolo[2,1-c][1,4]benzodiazepin-10(11H)-ylcarbonyl)phenyl]-2-bromobenzamide, white solid |
| 688 | N-[4-(5H-pyrrolo[2,1-c][1,4]benzodiazepin-10(11H)-ylcarbonyl)phenyl]-2-(acetoxy)benzamide, light yellow solid |
| 689 | N-[4-(5H-pyrrolo[2,1-c][1,4]benzodiazepin-10(11H)-ylcarbonyl)phenyl]-2-hydroxybenzamide, light yellow solid |
| 690 | N-[4-(5H-pyrrolo[2,1-c][1,4]benzodiazepin-10(11H)-ylcarbonyl)phenyl]-1-naphthylcarboxamide, white solid |
| 691 | N-[4-(5H-pyrrolo[2,1-c][1,4]benzodiazepin-10(11H)-ylcarbonyl)-3-methylphenyl]-2-methylbenzamide, amorphous solid |
| 692 | N-[4-(5H-pyrrolo[2,1-c][1,4]benzodiazepin-10(11H)-ylcarbonyl)phenyl]-2-chloro-4-fluorobenzamide, white foam |
| 693 | N-[4-(5H-pyrrolo[2,1-c][1,4]benzodiazepin-10(11H)-ylcarbonyl)phenyl]-2-(trifluoromethyl)-4-fluorobenzamide, white solid |
| 694 | N-[4-(5H-pyrrolo[2,1-c][1,4]benzodiaze- |

-continued

| Example No. | Compound |
|---|---|
|  | pin-10(11H)-ylcarbonyl)-3-methylphenyl]-5-fluoro-2-methylbenzamide, m.p. 180–182° C. |
| 695 | N-[4-(5H-pyrrolo[2,1-c][1,4]benzodiazepin-10(11H)-ylcarbonyl)-3-methoxyphenyl]-5-fluoro-2-methylbenzamide |
| 696 | N-[4-(5H-pyrrolo[2,1-c][1,4]benzodiazepin-10(11H)-ylcarbonyl)-3-chlorophenyl]-2-fluoro-4-(trifluorometyl)benzamide, m.p. 140–154° C. |
| 697 | N-[4-(5H-pyrrolo[2,1-c][1,4]benzodiazepin-10(11H)-ylcarbonyl)-3-chlorophenyl]-2-methylbenzeneacetamide, white glass |
| 698 | N-[4-(5H-pyrrolo[2,1-c][1,4]benzodiazepin-10(11H)-ylcarbonyl)-3-chlorophenyl]-2-fluoro-6-(trifluoromethyl)benzamide, white solid, m.p. 150–230° C. |
| 699 | N-[4-(5H-pyrrolo[2,1-c][1,4]benzodiazepin-10(11H)-ylcarbonyl)-3-chlorophenyl]-2-fluoro-3-(trifluoromethyl)benzamide, white glass |
| 700 | N-[4-(5H-pyrrolo[2,1-c][1,4]benzodiazepin-10(11H)-ylcarbonyl)-3-chlorophenyl]-2-chloro-5-(methylthio)benzamide, white crystals, m.p. 124–134° C. |
| 701 | N-[4-(5H-pyrrolo[2,1-c][1,4]benzodiazepin-10(11H)-ylcarbonyl)-3-chlorophenyl]-2,5-dimethylbenzamide, crystalline solid, m.p. 253–255° C. |
| 702 | N-[4-(5H-pyrrolo[2,1-c][1,4]benzodiazepin-10(11H)-ylcarbonyl)-3-chlorophenyl]-2-chloro,3,4-dimethoxybenzamide, yellow foam |
| 703 | N-[4-(5H-pyrrolo[2,1-c][1,4]benzodiazepin-10(11H)-ylcarbonyl)-6-chloro-3-methoxyphenyl]-2-methylbenzamide, cystals, m.p. 214–215° C. |
| 704 | N-[4-(5H-pyrrolo[2,1-c][1,4]benzodiazepin-10(11H)-ylcarbonyl)-2-methoxyphenyl]-2,5-dimethylbenzamide, crystals, m.p. 174–175° C. |
| 705 | N-[4-(5H-pyrrolo[2,1-c][1,4]benzodiazepin-10(11H)-ylcarbonyl)phenyl]-2-chloro-3,4-dimethoxybenzamide, white crystals, m.p. 242–244° C. |
| 706 | N-[4-(5H-pyrrolo[2,1-c][1,4]benzodiazepin-10(11H)-ylcarbonyl)phenyl-2,5-dimethylbenzamide, crystals, m.p. 158–160° C. |
| 707 | N-[4-(5H-pyrrolo[2,1-c][1,4]benzodiazepin-10(11H)-ylcarbonyl)-3-chlorophenyl]-2-(trifluoromethyl)-4-fluorobenzamide, white glass |

EXAMPLE 708

Methyl 4-[2-(2-chlorophenyl)-2-cyano-2-(4-morpholinyl)ethyl]benzoate

A 0.876 g sample of 60% sodium hydride in oil is washed with hexane followed by the addition of 60 ml of dry N,N-dimethylformamide. The reaction mixture is stirred for 1 hour under argon at room temperature after the addition of 4.73 g of α-(2-chlorophenyl)-4-morpholineacetonitrile. To the reaction mixture is added 4.58 g of methyl 4-(bromomethyl)benzoate and stirring continued for 3 hours. Several drops of acetic acid is added to ice water and the reaction quenched. The pH is 3–4 and saturated NaHCO₃ added to adjust the pH to 6–7. Upon cooling a solid forms which is filtered, washed with water and dried to give 5.92 g of yellow solid. Crystallization from methylene chloride-hexane gives 2.10 g of the desired product as a crystalline solid, m.p. 116°–118° C.

EXAMPLE 709

Methyl 4-[2-(2-chlorophenyl)-2-oxoethyl]benzoate

A mixture of 1.0 g of methyl [4-(2-chlorophenyl)-2-cyano-2-(4-morpholinyl)ethyl]benzoate and 14 ml of water is heated at reflux for 20 minutes then poured over crushed ice. After stirring for 15 minutes the resulting solid is collected, washed with water and air dried to give 0.63 g of tan solid, m.p. 40°–42° C.

EXAMPLE 710

4-[2-Chlorophenyl]-2-oxoethyl]benzoic acid

A mixture of 18.78 g of methyl 4-[2-(2-chlorophenyl)-2-oxoethyl]benzoate in 288.8 ml of CH₃OH, 72.2 ml of water and 5.2 g of NaOH is refluxed for 3 hours then acidified with 2N citric acid. The reaction mixture is evaporated in vacuo to remove the CH₃OH. The aqueous phase is extracted with CH₂Cl₂ and acidified with 1N HCl. The resulting solid is collected and dried under vacuum to give 17.27 g of the desired product, m.p. 168°–172° C.

EXAMPLE 711

3-Methoxy-4-nitrobenzoyl chloride

A stirred suspension of 1.0 g of 3-methoxy-4-nitrobenzoic acid and 1.40 ml of thionyl chloride is heated to reflux for 2 hours. The mixture is cooled to room temperature, 2 ml of iso-octane added and the mixture evaporated in vacuo to a solid residue. The residue is washed with iso-octane (2×2 ml), dried in vacuo to give 1.08 g of cream colored solid.

EXAMPLE 712

10,11-Dihydro-10-(4-nitro-3-methoxybenzoyl)-5H-pyrrolo[2,1-c][1,4]benzodiazepine To a solution of 0.55 g of 10,11-dihydro-5H-pyrrolo[2,1-c][1,4]benzodiazepine in 8 ml of methylene chloride is added 0.55 g of triethylamine followed by 0.97 g of 3-methoxy-4-nitrobenzoyl chloride. The reaction mixture is stirred at room temperature for 2 hours and then quenched with 10 ml of 1N NaOH. The methylene chloride layer is evaporated and the resulting suspension filtered. The precipitate is washed with 1N NaOH (2×5 ml), water (3×5 ml) and hexane (2×5 ml). The collected solid is dried in vacuo to give 1.13 g of off-white solid. MS(CI): 364(M+H).

EXAMPLE 713

10,11-Dihydro-10-(4-amino-3-methoxybenzoyl)-5H-pyrrolo[2,1-c][1,4]benzodiazepine A mixture of 0.91 g of 10,11-dihydro-10-(4-nitro-3-methoxybenzoyl)-5H-pyrrolo[2,1-c][1,4]benzodiazepine, 4.51 g of SnCl₂.2H₂O, 6 ml of ethyl alcohol, 6 ml of tetrahydrofuran and 16 ml of methylene chloride is stirred at 50° C. for 2 hours. The solvents are evaporated in vacuo and the residue dissolved in 80 ml of ethyl acetate. The solution is treated with 50 ml of 1N NaOH with stirring for 30 minutes. The resulting suspension is filtered through diatomaceous earth. The pad is washed with ethyl acetate (3×15 ml). The combined ethyl acetate solutions are washed with brine, dried (Na₂SO₄), filtered through hydrous magnesium silicate and evaporated in vacuo to 0.99 g of residue which is stirred with ether-hexanes to give 0.90 g of cream colored solid. MS(CI): 334(M+H).

EXAMPLE 714

10,11-Dihydro-10-[4-[(3-methylpropyloxycarbonyl)
amino]benzoyl]-5H-pyrrolo[2,1-c][1,4]
benzodiazepine To a stirred solution of 0.15 g of 10,11-dihydro-10-(4-aminobenzoyl)-5H-pyrrolo[2,1-c][1,4]benzodiazepine in 2 ml of methylene chloride is added 0.10 g of triethylamine followed by 0.10 g of isobutylchloroformate. The reaction mixture is stirred for 3 hours and then quenched with 1N NaOH. The organic layer is evaporated in vacuo to a residue which is stirred in 5 ml of tetrahydrofuran for 1 hour, then evaporated in vacuo to a residue. The residue is extracted with ethyl acetate-methylene chloride, washed with brine, dried ($Na_2SO_4$), filtered through hydrous magnesium silicate and evaporated in vacuo to give a residue which is stirred with ethyl acetate-methylene chloride to give 0.22 g of cream colored solid. MS(CI): 404(M+H).

EXAMPLE 715

10,11-Dihydro-10-[4-(pentanoyl)aminobenzoyl)]-
5H-pyrrolo[2,1-c][1,4]benzodiazepine To a stirred solution of 0.15 g of 10,11-dihydro-10-(4-aminobenzoyl)-5H-pyrrolo[2,1-c][1,4]benzodiazepine in 2 ml of methylene chloride is added 0.10 g of triethylamine followed by 0.09 g of valeryl chloride. The reaction mixture is stirred for 3 hours and then quenched with 4 ml of 1N NaOH. The methylene chloride is evaporated in vacuo and the residue dissolved in 5 ml of tetrahydrofuran for 1 hour and evaporated in vacuo to a residue. The residue is extracted with ethyl acetate-methylene chloride, washed with brine and the organic layer dried ($Na_2SO_4$), filtered through hydrous magnesium silicate, and evaporated in vacuo to give 0.23 g of a residue which is stirred with ether-hexanes to give 0.19 g of a white solid. MS(CI): 388(M+H).

EXAMPLE 716

10,11-Dihydro-10-[4-[(3-methylbutanoyl)amino]
benzoyl]-5H-pyrrolo[2,1-c][1,4]benzodiazepine To a stirred solution of 0.10 g of 10,11-dihydro-10-(4-amino-3-methoxybenzoyl)-5H-pyrrolo[2,1-c][1,4] benzodiazepine in 1 ml of methylene chloride is added 0.06 g of triethylamine followed by 0.05 g of iso-valeryl chloride. The reaction mixture is stirred for 3 hours and then quenched with 1N NaOH. The organic layer is evaporated in vacuo to a residue which is stirred in 5 ml of tetrahydrofuran for 1 hour, then evaporated in vacuo to a residue. The residue is extracted with ethyl acetate-methylene chloride, washed with brine, dried ($Na_2SO_4$), filtered through hydrous magnesium silicate and evaporated in vacuo to give 0.15 g of residue which is stirred with ether-hexane to give 0.13 g of light yellow solid. MS(CI): 418(M+H).

EXAMPLE 717

10,11-Dihydro-10-[3-methoxy-4-[(butylsulfonyl)
amino]benzoyl]-5H-pyrrolo[2,1-c][1,4]
benzodiazepine To a stirred solution of 0.10 g of 10,11-dihydro-10-(4-amino-3-methoxybenzoyl)-5H-pyrrolo[2,1-c][1,4] benzodiazepine in 2 ml of methylene chloride is added 60 mg of triethylamine followed by a solution of 56 mg of n-butylsulfonyl chloride in 0.5 ml of methylene chloride. After stirring at room temperature for 2 hours, the reaction mixture is evaporated in vacuo to a residue which is dissolved in methyl alcohol, stirred for 1hour and evaporated in vacuo to a residue which is treated with 2 ml of $NH_4Cl$ and extracted with 15 ml of ethyl acetate. The organic extract is washed with saturated $NaHCO_3$, brine, dried ($Na_2SO_4$), filtered through hydrous magnesium silicate and the filtrate evaporated to a residue. The residue is stirred with ether-hexanes to give 0.14 g of light yellow solid. MS(CI): 454(M+H).

UTILITY TESTING

Binding Assay to Rat Hepatic $V_1$ Receptors

Rat liver plasma membranes expressing the vasopressin $V_1$ receptor subtypes are isolated by sucrose density gradient according to the method described by Lesko et al., (1973). These membranes are quickly suspended in 50.0 mM Tris. HCl buffer, pH 7.4, containing 0.2% bovine serum albumin (BSA) and 0.1 mM phenylmethylsulfonylfluoride (PMSF) and kept frozen at –70° C. until used in subsequent binding experiments. For binding experiments, the following is added to the wells of a ninety-six well format microtiter plate: 100 µl of 100.0 mM Tris.HCl buffer containing 10.0 mM $MgCl_2$, 0.2% heat inactivated BSA and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [phenylalanyl-3,4,5, -$^3$H] vasopressin (S.A. 45.1 Ci/mmole) at 0.8 nM, and the reaction initiated by the addition of 80 µl of tissue membranes containing 20 µg of tissue protein. The plates are kept undisturbed on the bench top at room temperature for 120 min. to reach equilibrium. Non-specific samples are assayed in the presence of 0.1 µM of the unlabeled antagonist phenylalanylvasopressin, added in 20.0 µl volume.

For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH).

Binding Assay to Rat Kidney Medullary $V_2$ Receptors

Medullary tissues from rat kidneys are dissected out, cut into small pieces and soaked in a 0.154 mM sodium chloride solution containing 1.0 mM EDTA with many changes of the liquid phase, until the solution is clear of blood. The tissue is homogenized in a 0.25M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is centrifuged at 1500×g for 15 min. The nuclear pellet is discarded and the supernatant fluid recentrifuged at 40,000×g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al., J. Biol. Chem., 1953). The membrane suspension is stored at –70° C., in 50.0 mM Tris.HCl, containing 0.2% inactivated BSA and 0.1 mM PMSF in aliquots of 1.0 ml containing 10.0 mg protein per ml of suspension until use in subsequent binding experiments.

For binding experiments, the following is added in µl volume to wells of a 96 well format of a microtiter plate:

100.0 µl of 100.0 mM Tris.HCl buffer containing 0.2% heat inactivated BSA, 10.0 mM MgCl$_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H] Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min to reach equilibrium. Non-specific binding is assessed in the presence of 1.0 µM of unlabeled ligand, added in 20 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, OH). The results of this test on representative compounds of this invention are shown in Table XIII.

Radioligand Binding Experiments with Human Platelet Membranes (a) Platelet Membrane Preparation Frozen platelet rich plasma (PRP), (Platelet Source: Hudson Valley Blood Services, Westchester Medical Center, Valhalla, N.Y.) are thawed to room temperature. The tubes containing the PRP are centrifuged at 16,000×g for 10 min. at 4° C. and the supernatant fluid discarded. The platelets resuspended in an equal volume of 50.0 mM Tris. HCl, pH 7.5 containing 120 mM NaCl and 20.0 mM EDTA. The suspension is recentrifuged at 16,000×g for 10 min. This washing step is repeated one more time. The wash discarded and the lysed pellets homogenized in low ionic strength buffer of Tris.HCl, 1 5.0 mM, pH 7.5 containing 5.0 mM EDTA. The homogenate is centrifuged at 39,000×g for 10 min. The resulting pellet is resuspended in Tris.HCl buffer, 70.0 mM, pH 7.5 and recentrifuged at 39,000×g for 10 min. The final pellet is resuspended in 50.0 mM Tris.HCl buffer pH 7.4 containing 120 mM NaCl and 5.0 mM KCl to give 1.0–2.0 mg protein per ml of suspension.

(b)Binding to Vasopressin V$_1$ receptor subtype in Human Platelet Membranes

In wells of a 96 well format microtiter plate, add 100 µl of 50.0 mM Tris.HCl buffer containing 0.2% BSA and a mixture of protease inhibitors (aprotinin, leupeptin etc.). Then add 20 µl of [$^3$H]Ligand (Manning or Arg$^8$Vasopressin), to give final concentrations ranging from 0.01 to 10.0 nM. Initiate the binding by adding 80.0 µl of platelet suspension (approx. 100 µg protein). Mix all reagents by pipetting the mixture up and down a few times. Non specific binding is measured in the presence of 1.0 µM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel Harvester. Determine the radioactivity caught on the filter disks by the addition of liquid scintillant and counting in a liquid scintillator.

Binding to Membranes of Mouse Fibroblast Cell Line (LV-2) Transfected with the cDNA Expressing the Human V$_2$ Vasopressin Receptor (a) Membrane Preparation Flasks of 175 ml capacity, containing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300×g for 15 min. The Hank's based solution is aspirated off and the cells homogenized with a polytron at setting #6 for 10 sec in 10.0 mM Tris.HCl buffer, pH 7.4 containing 0.25M sucrose and 1.0 mM EDTA. The homogenate is centrifuged at 1500×g for 10 min to remove ghost membranes. The supernatant fluid is centrifuged at 100,000×g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

(b) Receptor Binding

For binding experiments, the following is added in µl volume to wells of a 96 well format of a microtiter plate: 100.0 µl of 100.0 mM Tris. HCl buffer containing 0.2% heat inactivated BSA, 10.0 mM MgCl$_2$ and a mixture of protease inhibitors: leupeptin, 1.0 mg%; aprotinin, 1.0 mg %; 1,10-phenanthroline, 2.0 mg %; trypsin inhibitor, 10.0 mg % and 0.1 mM PMSF., 20.0 µl of [$^3$H] Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min to reach equilibrium. Non specific binding is assessed in the presence of 1.0 µM of unlabeled ligand, added in 20 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, OH).

TABLE XIII

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (µM) | $V_2$ IC$_{50}$ (µM) |
|---|---|---|---|
| 1 | 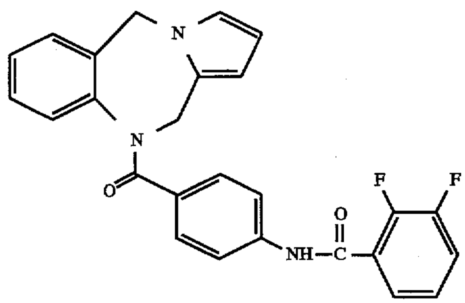 | 0.097 | 0.029 |
| 215 | 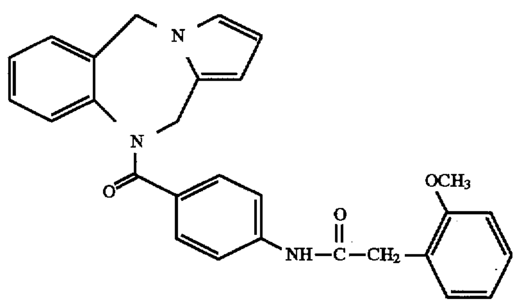 | 0.016 | 0.022 |
| 3 | 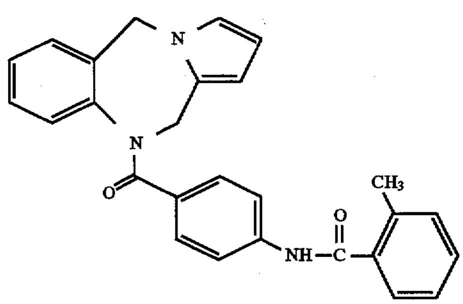 | 0.038 | 0.004 |
| 4 | 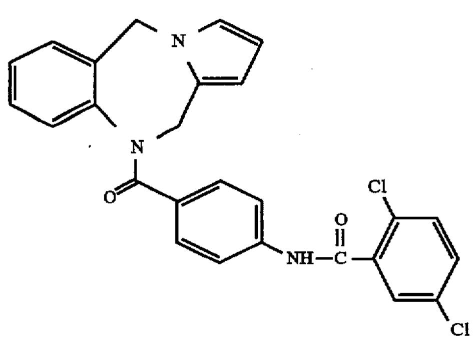 | 0.12 | 0.014 |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 5 | 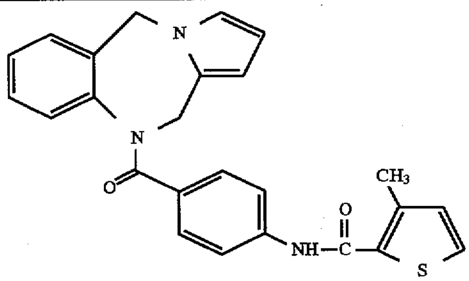 | 0.015 | 0.025 |
| 6 | 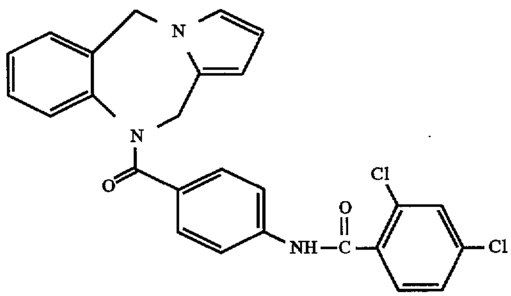 | 0.023 | 0.003 |
| 7 | 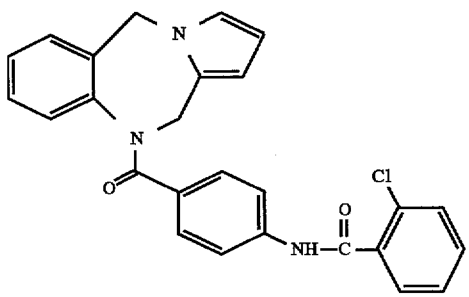 | 0.01 | 0.005 |
| 8 | 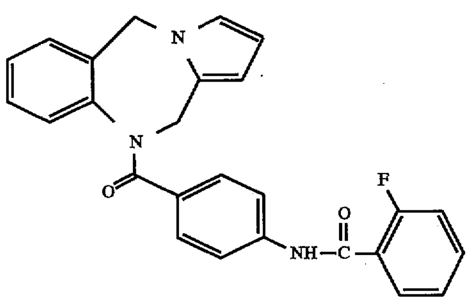 | 0.056 | 0.035 |
| 14 | 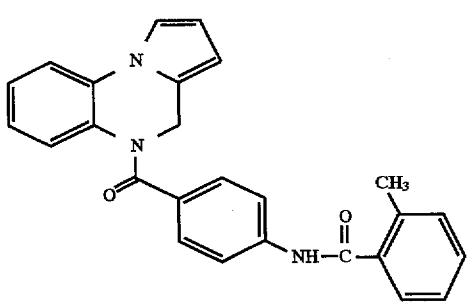 | 0.17 | 0.066 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 40 | 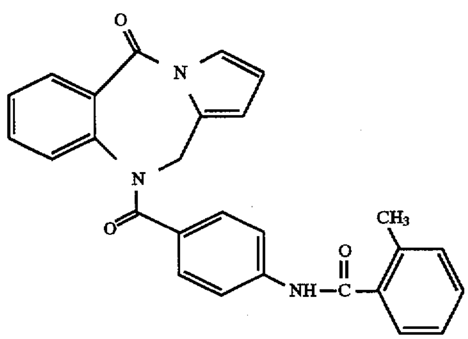 | 2.4 | 0.12 |
| 41 | 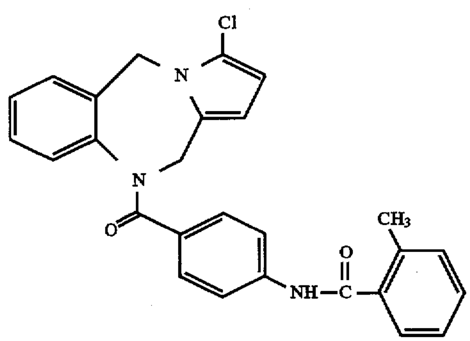 | 0.037 | 0.017 |
| 82 | 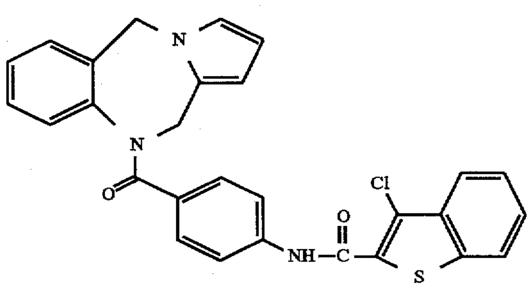 | (10 μM) 23% | (10 μM) 71% |
| 84 | 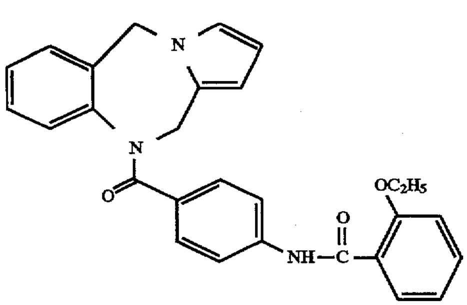 | 0.045 | 0.077 |

TABLE XIII-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | Structure | V₁ IC₅₀ (μM) | V₂ IC₅₀ (μM) |
|---|---|---|---|
| 85 | 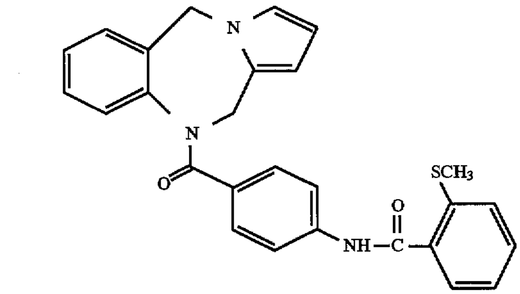 | 0.009 | 0.013 |
| 87 | 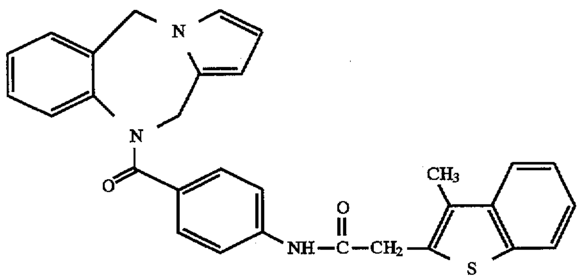 | (10 μM) 63% | (10 μM) 80% |
| 89 | 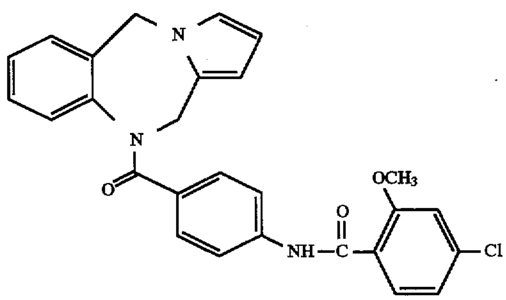 | 0.023 | 0.008 |
| 91 | 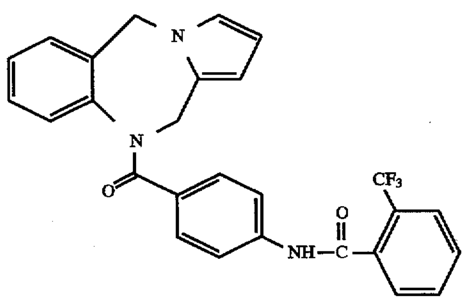 | 0.026 | 0.022 |
| 93 | 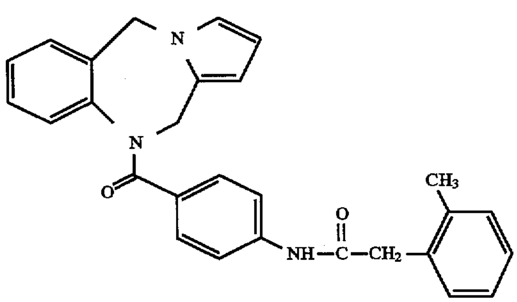 | 0.0009 | 0.0007 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---------|-----------|----------------------|----------------------|
| 96 | 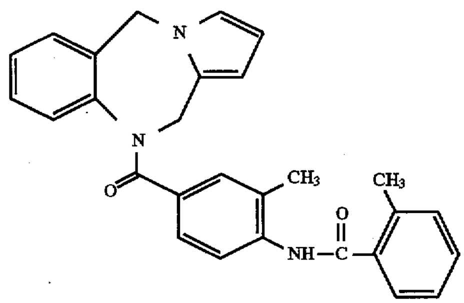 | 0.056 | 0.011 |
| 116 | 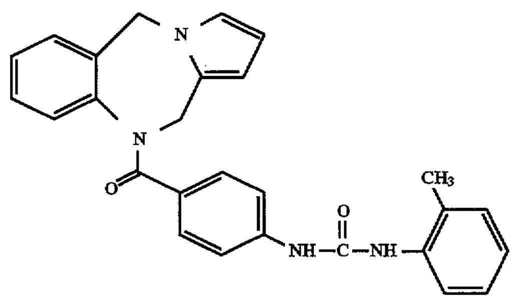 | 0.28 | 0.085 |
| 117 | 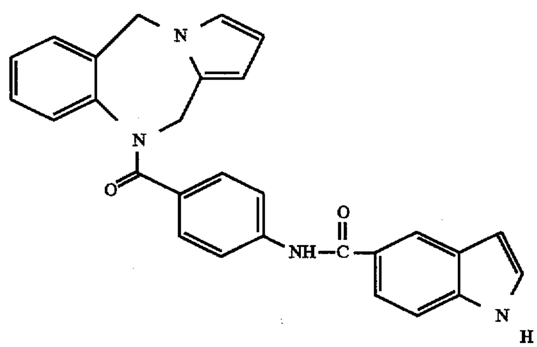 | 2.77 | 0.377 |
| 354 | 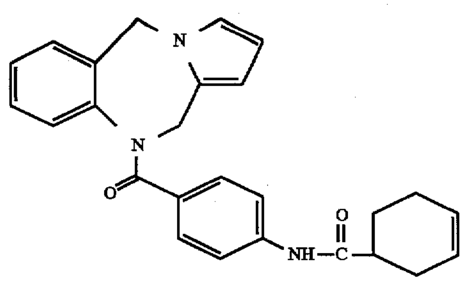 | 0.012 | 0.007 |

TABLE XIII-continued

Binding Assay to Rat Hepatic V₁ Receptors and Rat Kidney Medullary V₂ Receptors or
*Binding to V₁ Receptor Subtype in Human Platelet and **Binding to Membranes of Mouse Fibroblast
Cell Line (LV-2) Transfected with the cDNA Expressing the Human V₂ Receptor

| Ex. No. | Structure | $V_1$ IC$_{50}$ (μM) | $V_2$ IC$_{50}$ (μM) |
|---|---|---|---|
| 355 | 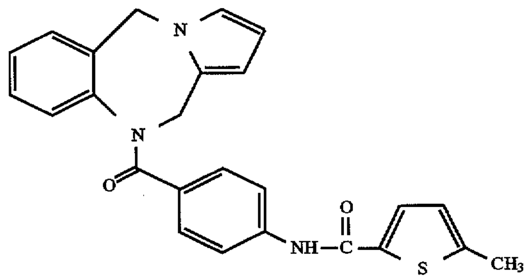 | 0.165 | 0.35 |
| 356 | 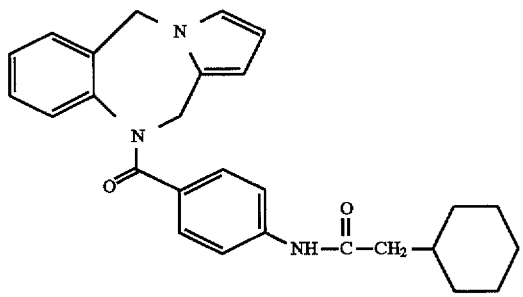 | 0.087 | 0.053 |
| 357 | 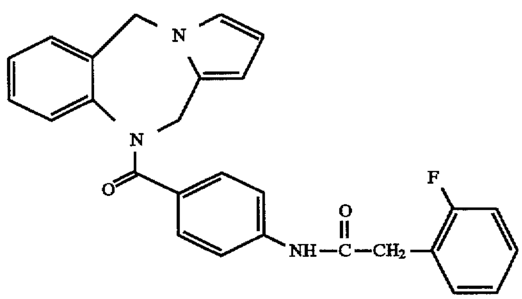 | 0.019 | 0.017 |
| 358 | 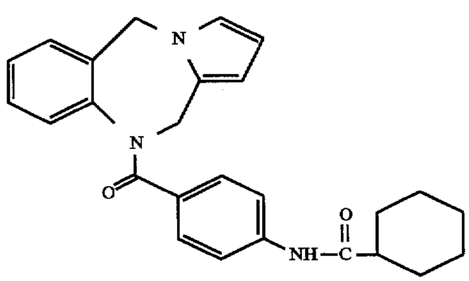 | 0.011 | 0.016 |
| 384 | 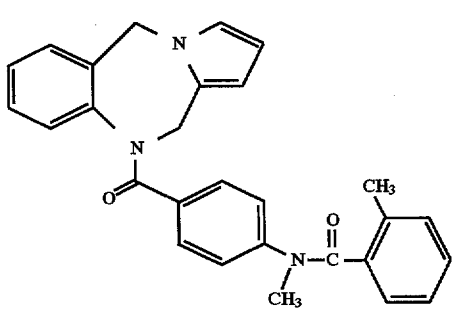 | 0.188 | 0.059 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 2 | 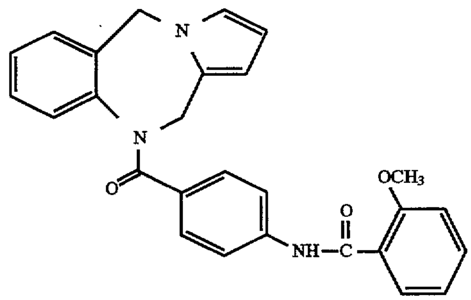 | 0.031 | 0.014 |
| 9 | 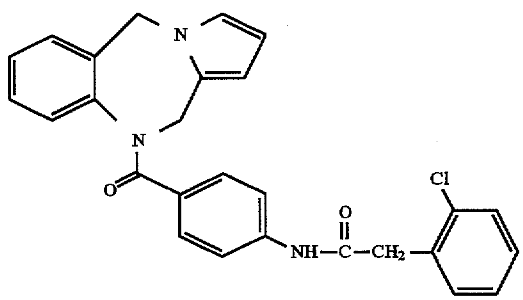 | 0.007 | 0.004 |
| 17 160 | | 1.2 | 0.11 |
| 21 | 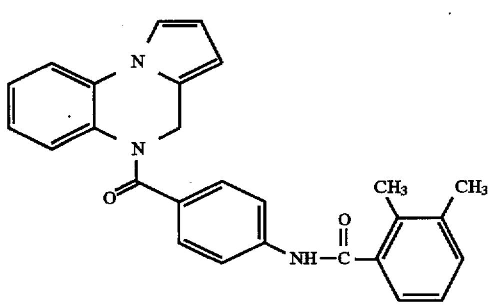 | 0.93 | 0.087 |

TABLE XIII-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ IC$_{50}$ (µM) | $V_2$ IC$_{50}$ (µM) |
|---|---|---|---|
| 36 179 | 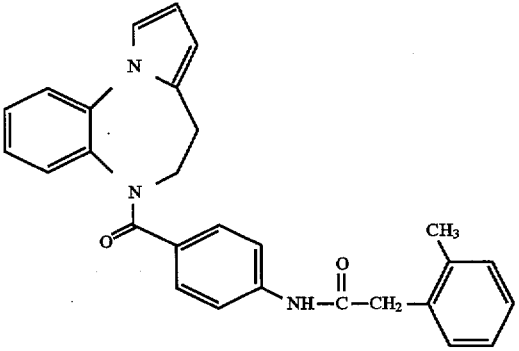 | 0.10 | 0.054 |
| 54 | 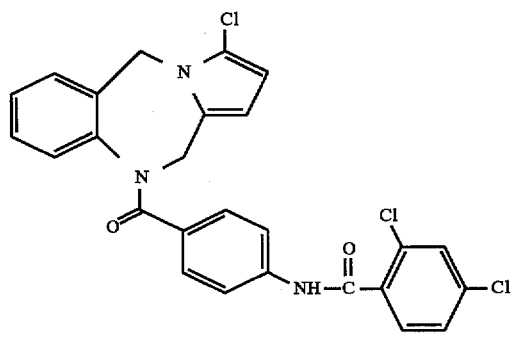 | 0.31* | 0.007** |
| 99 | 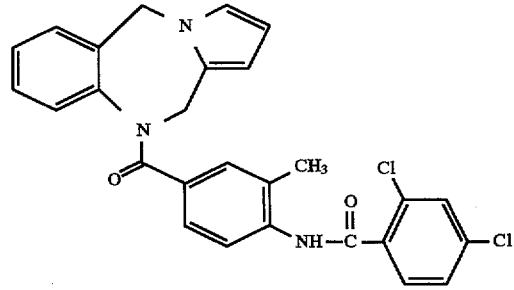 | 0.027 | 0.010 |
| 210 214 | 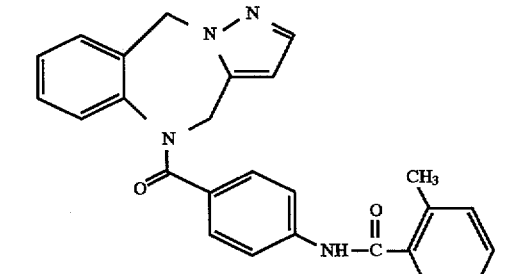 | 0.058 | 0.016 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (µM) | $V_2$ IC$_{50}$ (µM) |
|---|---|---|---|
| 217 | 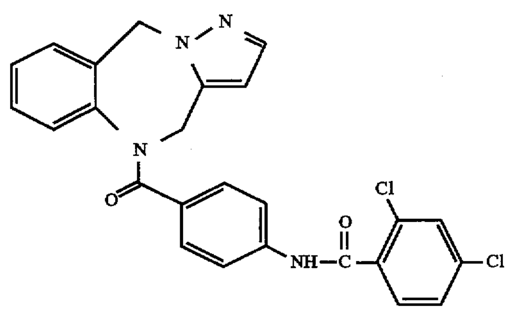 | 0.068<br>0.19* | 0.005<br>0.01** |
| 267<br>271 | 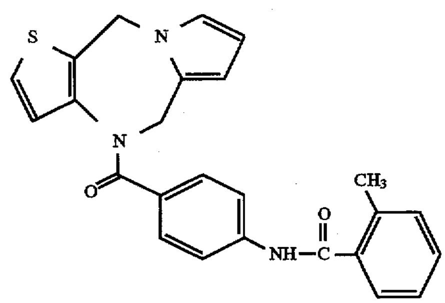 | 0.22 | 0.028 |
| 274 | 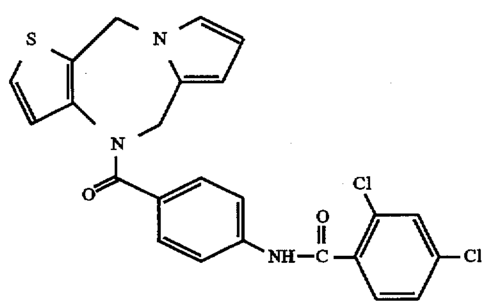 | 0.24* | 0.031** |
| 297<br>298 | 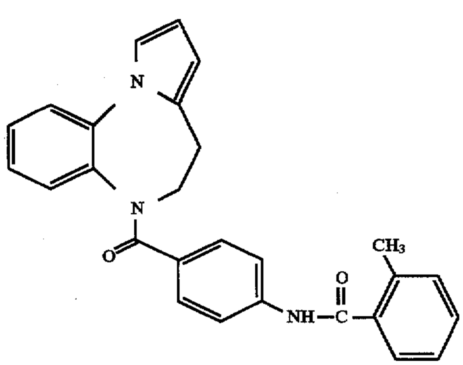 | 0.27 | 0.033 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (µM) | $V_2$ IC$_{50}$ (µM) |
|---|---|---|---|
| 465 | 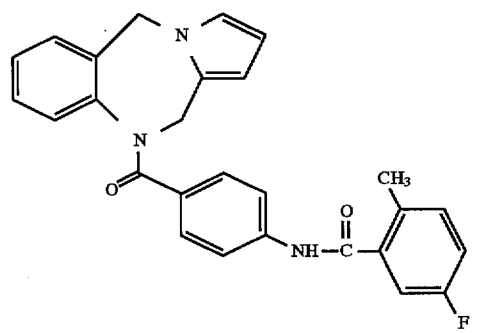 | 0.020* | 0.0015** |
| 466 | 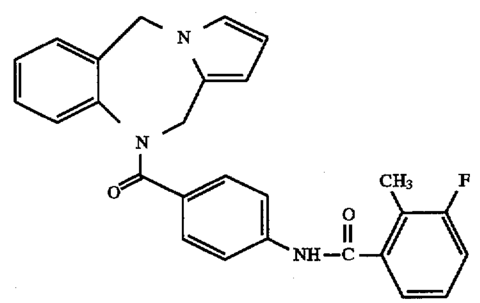 | 0.026 | 0.004 |
| 467 | 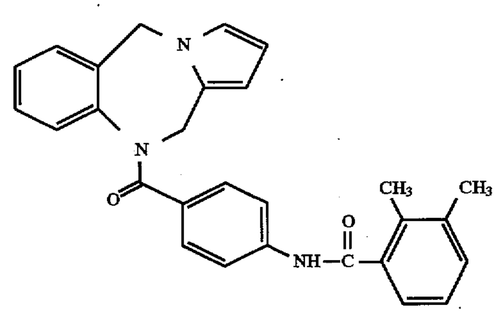 | 0.031 | 0.005 |
| 468 | 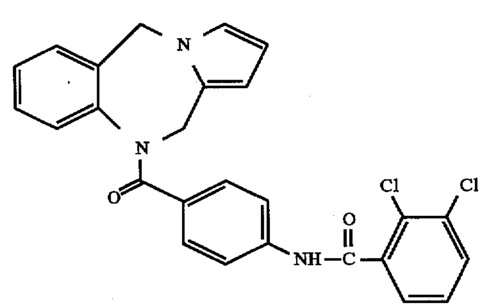 | 0.027 | 0.029 |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 469 | 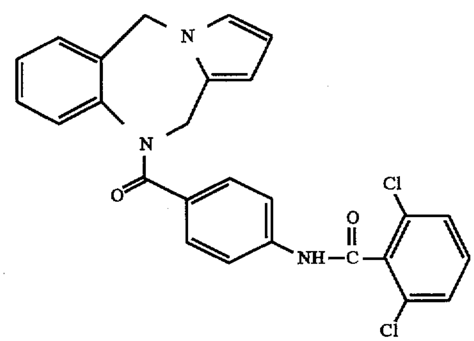 | 0.094 | 0.015 |
| 470 | 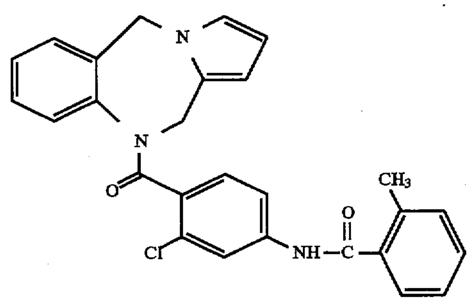 | 0.054 | 0.0045 |
| 471 | 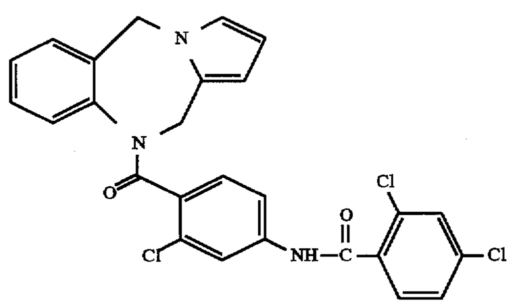 | 0.045 | 0.0083 |
| 472 | 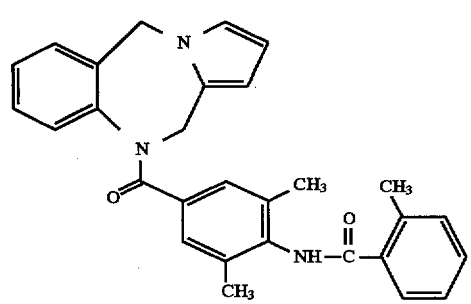 | 0.89 | (10 μM) 22% |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (μM) | $V_2$ IC$_{50}$ (μM) |
|---|---|---|---|
| 473 | 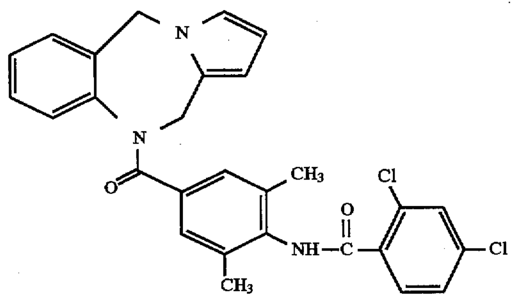 | (10 μM) 90% | (10 μM) 56% |
| 474 | 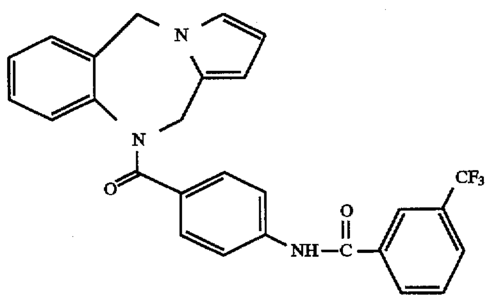 | 0.087 | 0.038 |
| 476 | 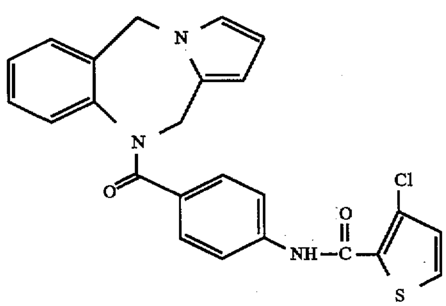 | 0.084 | 0.069 |
| 477 | 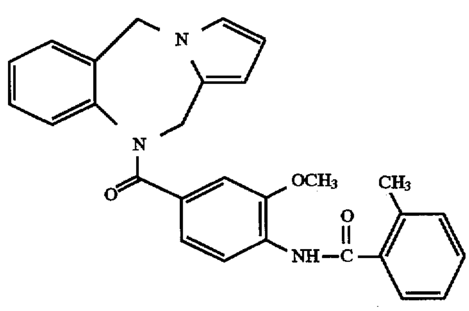 | 0.003* | 0.0032** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 478 | 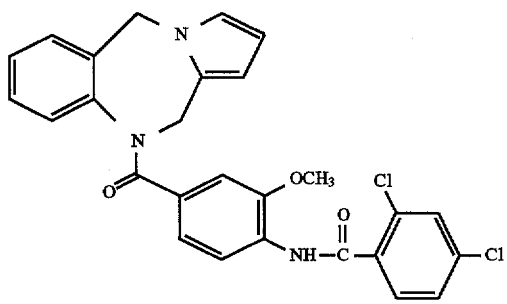 | 0.032* | 0.0019** |
| 479 | 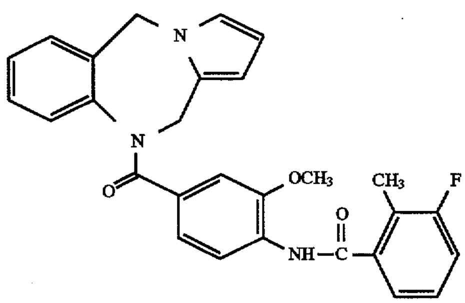 | 0.023* | 0.008 |
| 480 | 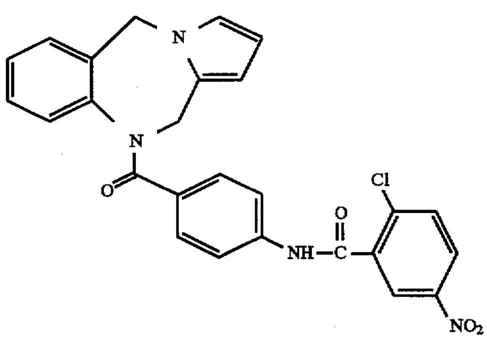 | 0.54* | 0.026** |
| 481 | 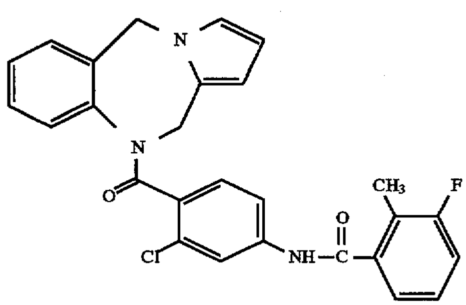 | 1.0 | 0.0034 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (μM) | $V_2$ IC$_{50}$ (μM) |
|---|---|---|---|
| 482 | 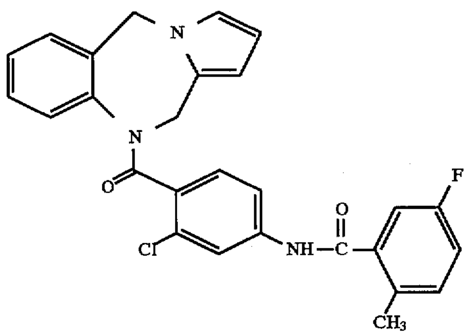 | 0.41 | 0.0023 |
| 484 | 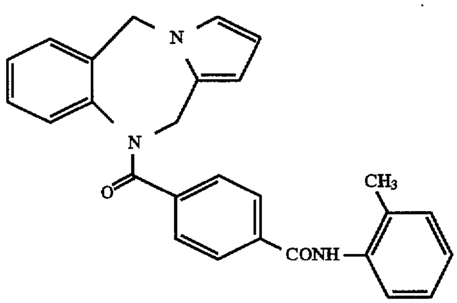 | 0.097 | 0.025 |
| 485 | 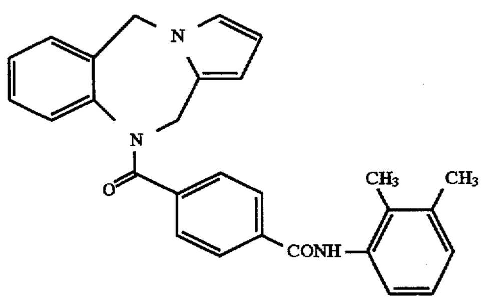 | 0.24 | 0.013 |
| 486 | 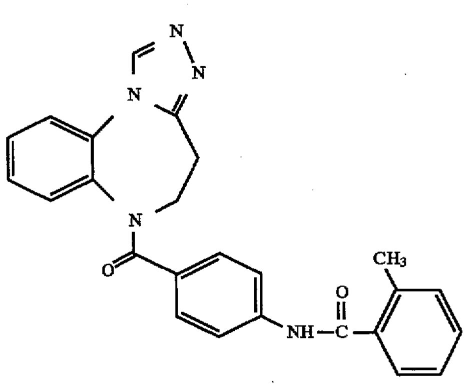 | (10 μM) 39% | (10 μM) 77% |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 488 | 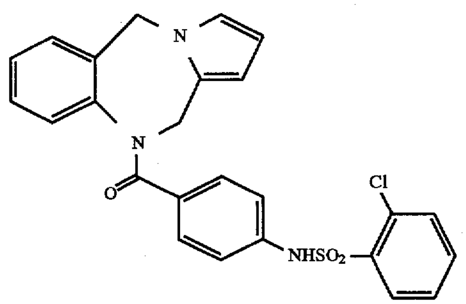 | (10 µM) 96% | (10 µM) 87% |
| 489 | 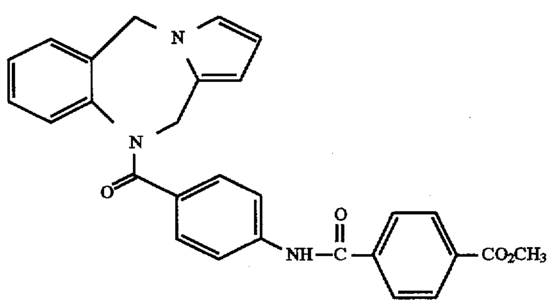 | (10 µM) 61% | (10 µM) 82% |
| 490 | 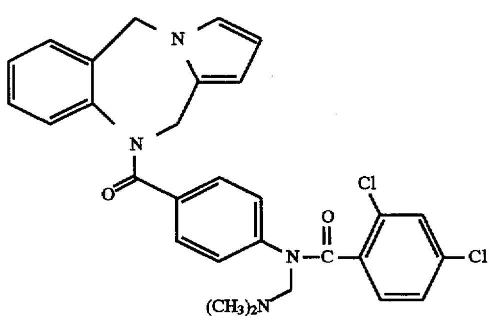 | 0.014 | 0.005 |
| 491 | 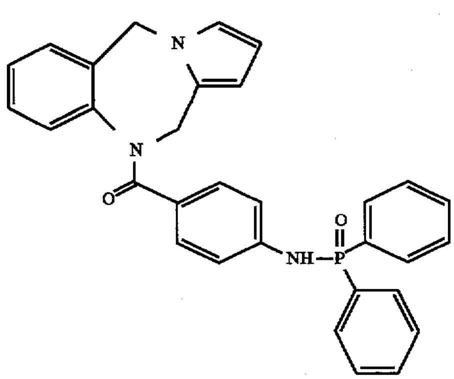 | (10 µM) 82% | (10 µM) 83% |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (µM) | $V_2$ IC$_{50}$ (µM) |
|---|---|---|---|
| 492 | 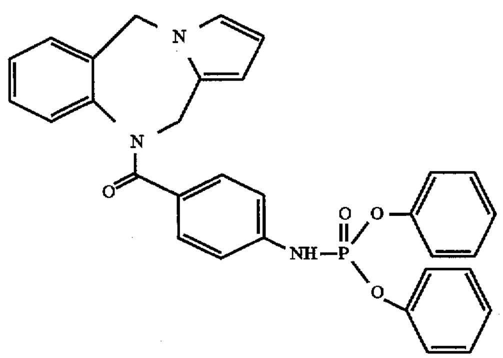 | 0.16 | 3.2 |
| 493 | 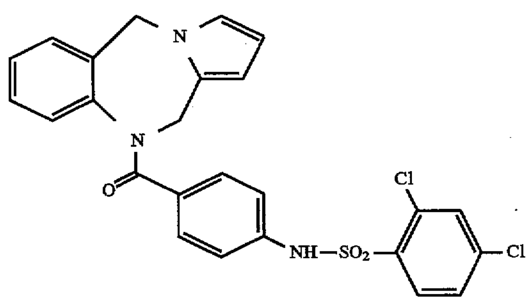 | 0.14 | (10 µM) 68% |
| 494 | 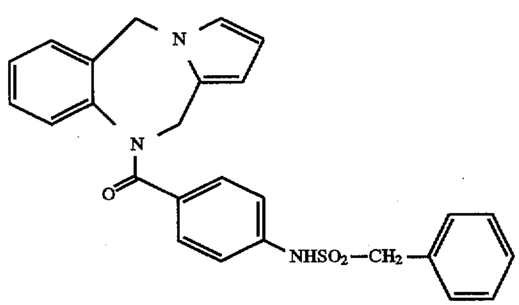 | 0.11 | 5.8 |
| 517 | 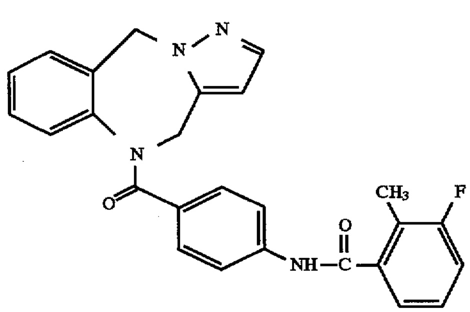 | 0.21 | 0.015 |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 518 | 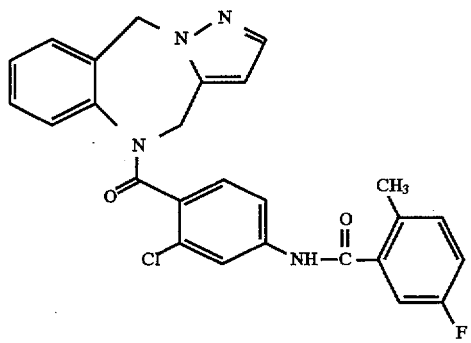 | 0.22* | 0.0017** |
| 519 | 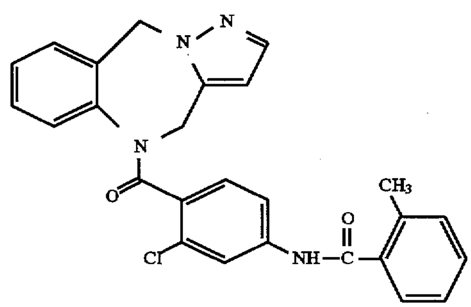 | 0.12* | 0.0032** |
| 520 | 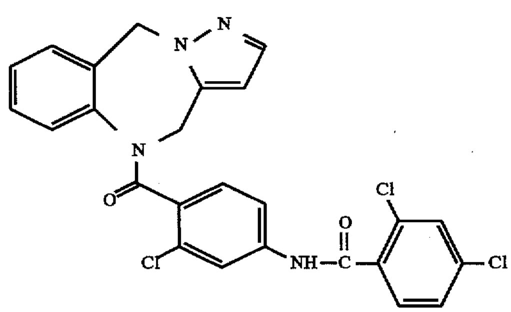 | 0.85* | 0.0044** |
| 523 | 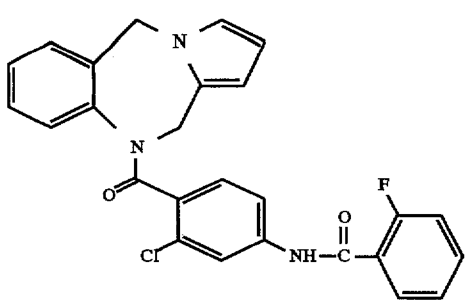 | 0.11* | 0.0028** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 524 | 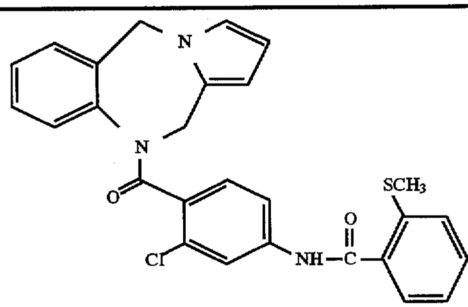 | 0.17* | 0.0012** |
| 525 | 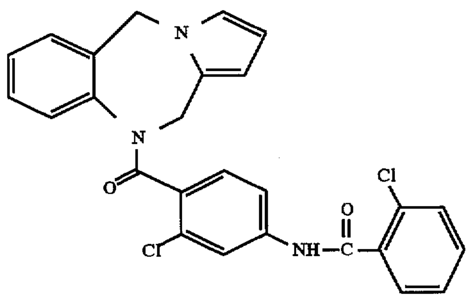 | 0.43* | 0.00042** |
| 526 | 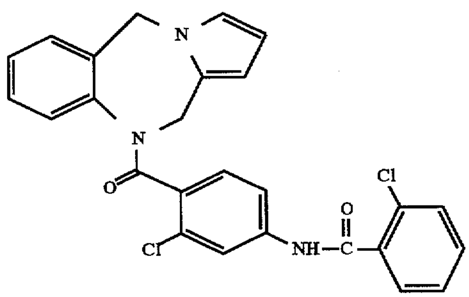 | 0.05* | 0.0033** |
| 527 | 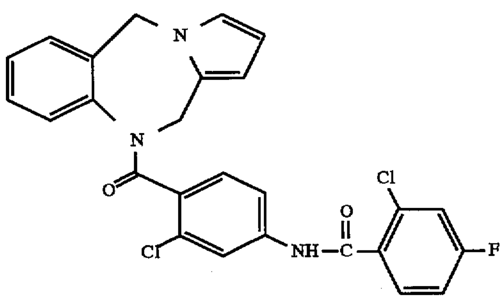 | 0.026* | 0.00067** |
| 528 | 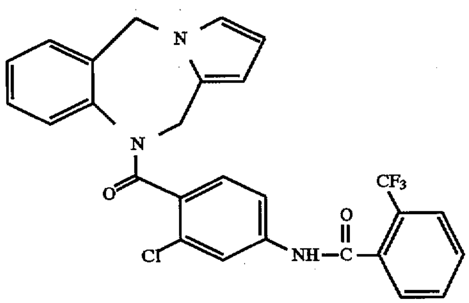 | 0.20* | 0.006** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 538 | 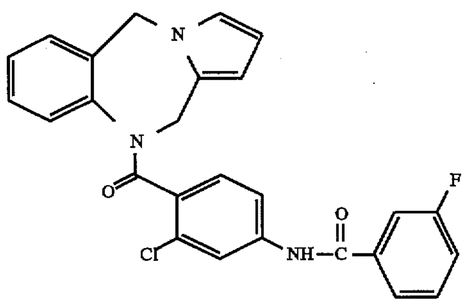 | 0.052* | 0.001** |
| 546 | 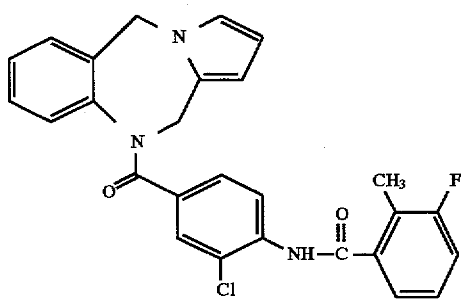 | 0.066* | 0.073** |
| 547 | 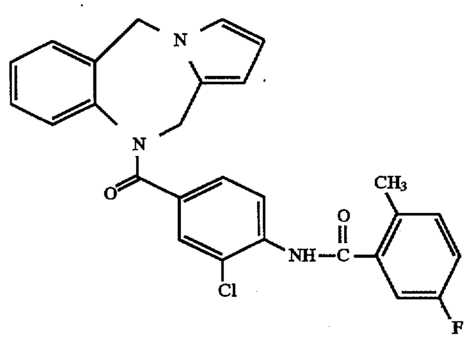 | 0.016* | 0.004** |
| 529 | 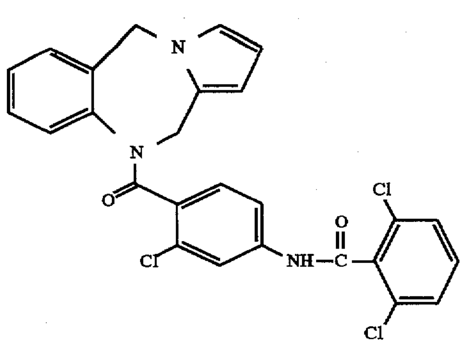 | 0.99* | 0.002** |

TABLE XIII-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ $IC_{50}$ (µM) | $V_2$ $IC_{50}$ (µM) |
|---|---|---|---|
| 530 | 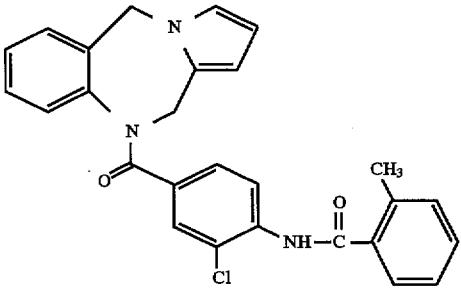 | 0.003* | 0.0037 |
| 580 | 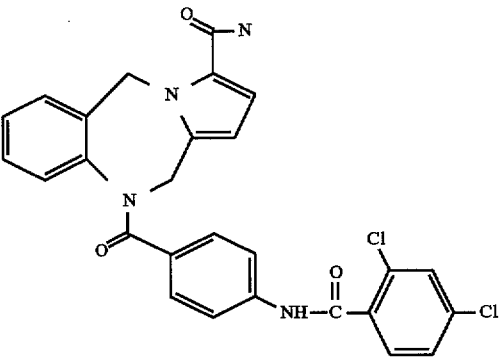 | 0.2 | 0.08 |
| 581 | 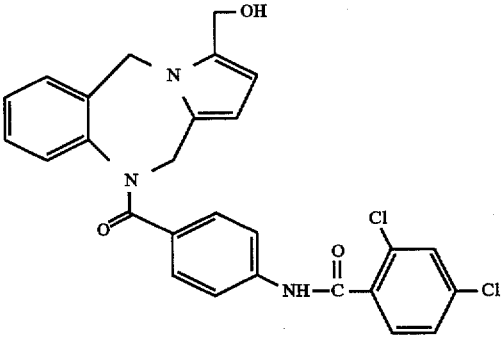 | 0.021 | 0.0053 |
| 582 | 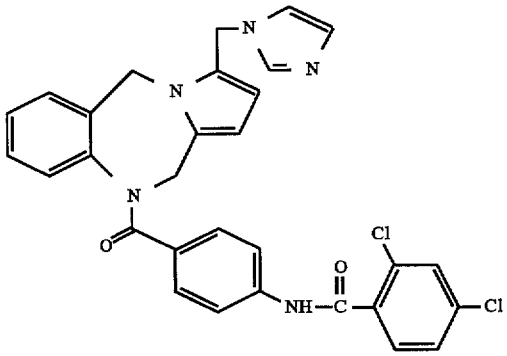 | 0.13 | 0.014 |

TABLE XIII-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | Structure | $V_1$ IC$_{50}$ (μM) | $V_2$ IC$_{50}$ (μM) |
|---|---|---|---|
| 583 | 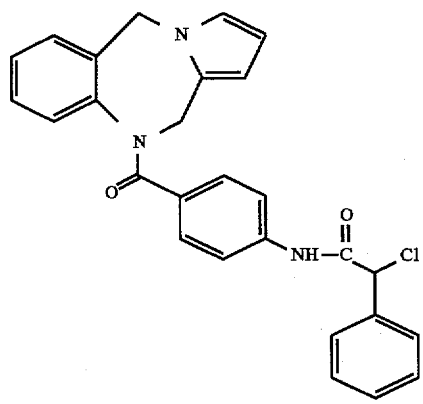 | 0.054 | 0.027 |
| 584 | 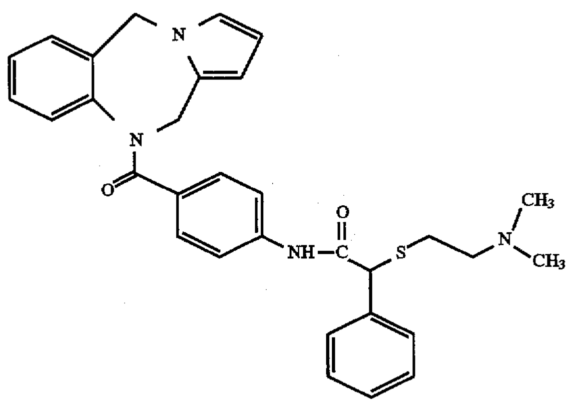 | 1.2 | 0.48 |
| 585 | 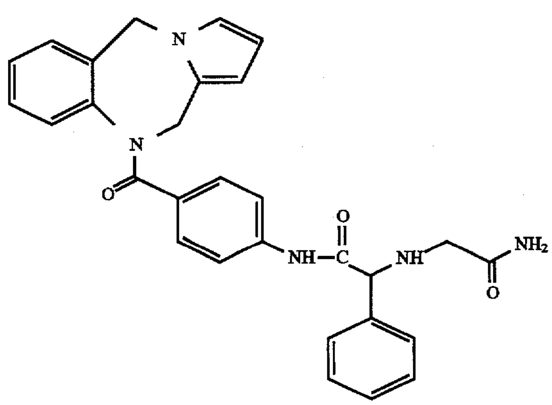 | 0.28 | 0.083 |

TABLE XIII-continued

Binding Assay to Rat Hepatic V₁ Receptors and Rat Kidney Medullary V₂ Receptors or
*Binding to V₁ Receptor Subtype in Human Platelet and **Binding to Membranes of Mouse Fibroblast
Cell Line (LV-2) Transfected with the cDNA Expressing the Human V₂ Receptor

| Ex. No. | Structure | $V_1$ $IC_{50}$ (μM) | $V_2$ $IC_{50}$ (μM) |
|---|---|---|---|
| 586 | 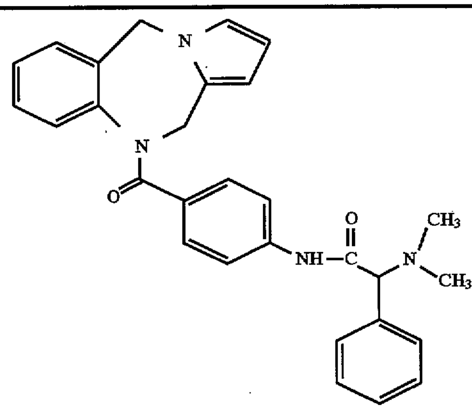 | 0.45 | 0.23 |
| 587 | 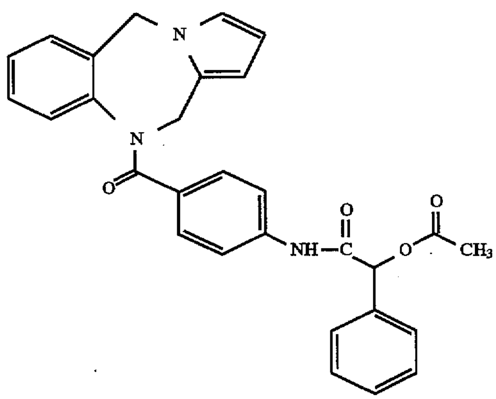 | 0.067 | 0.022 |
| 588 | 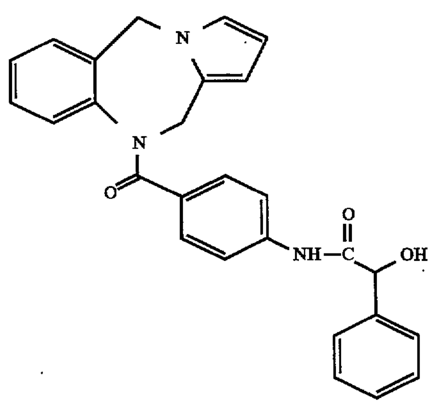 | 0.040 | 0.012 |
| 589 | 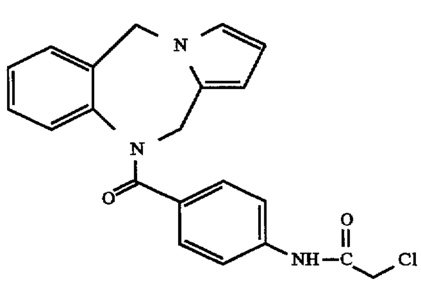 | (10 μM) 91% | (10 μM) 82% |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 590 | 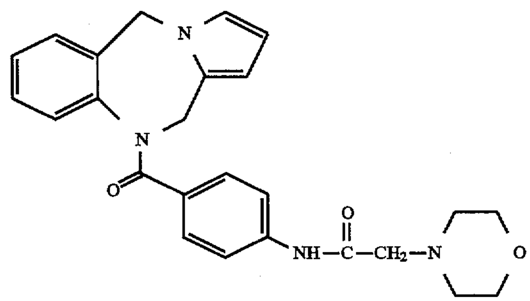 | (10 μM) 89% | (10 μM) 81% |
| 591 | 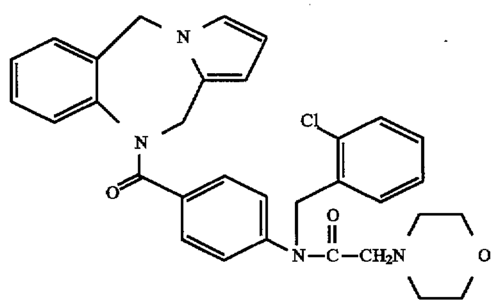 | (10 μM) 45% | (10 μM) 64% |
| 592 | 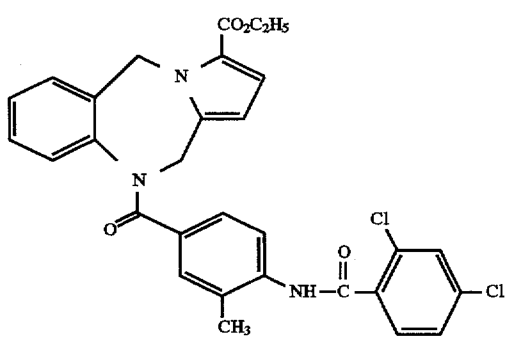 | 3.3 | 0.24 |
| 593 | 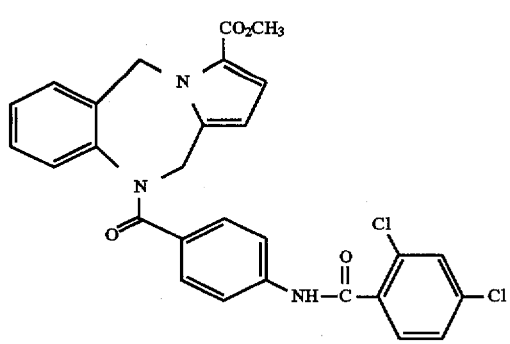 | 0.21 | 0.042 |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 594 | 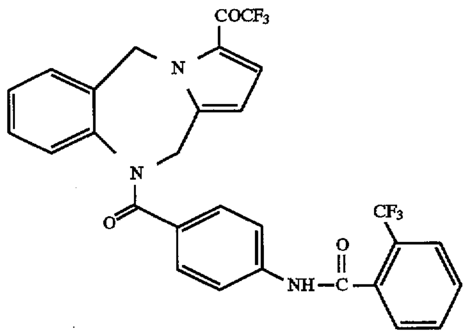 | (10 μM) 78% | (10 μM) 23% |
| 595 | 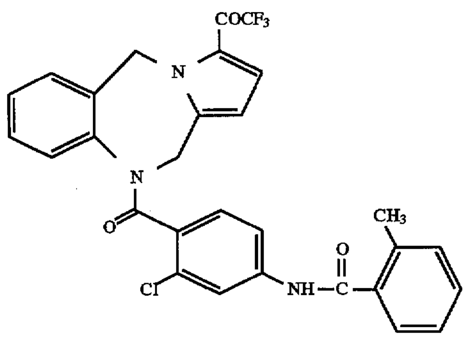 | (10 μM) 57% | (10 μM) 93% |
| 687 | 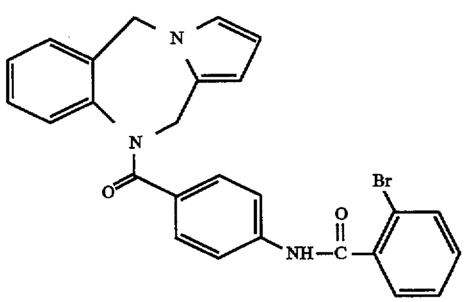 | 0.002* | 0.007** |
| 597 | 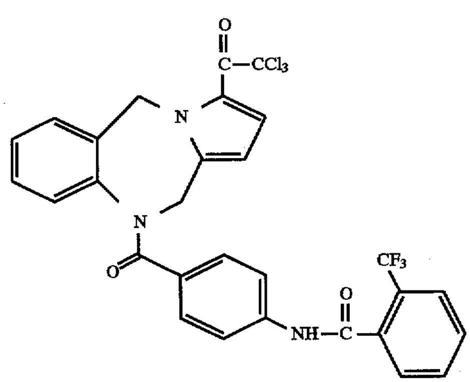 | (10 μM) 100% | (10 μM) 97% |

TABLE XIII-continued

Binding Assay to Rat Hepatic V₁ Receptors and Rat Kidney Medullary V₂ Receptors or
*Binding to V₁ Receptor Subtype in Human Platelet and **Binding to Membranes of Mouse Fibroblast
Cell Line (LV-2) Transfected with the cDNA Expressing the Human V₂ Receptor

| Ex. No. | Structure | V₁ IC₅₀ (μM) | V₂ IC₅₀ (μM) |
|---|---|---|---|
| 598 | 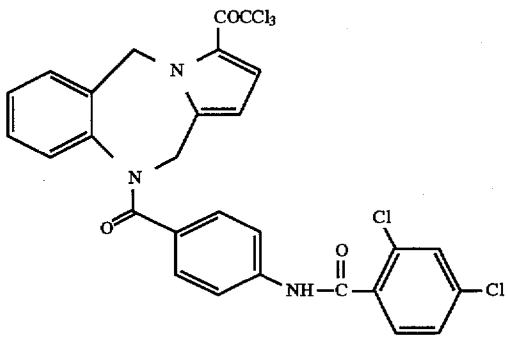 | (10 μM) 58% | (10 μM) 93% |
| 599 | 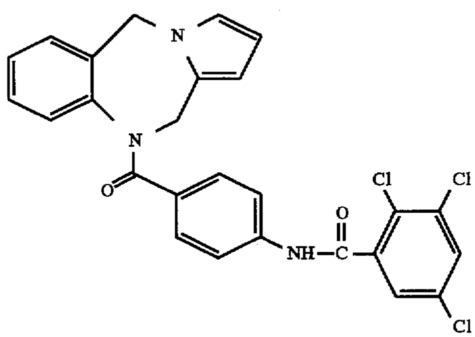 | 0.046 | 0.014 |
| 600 | 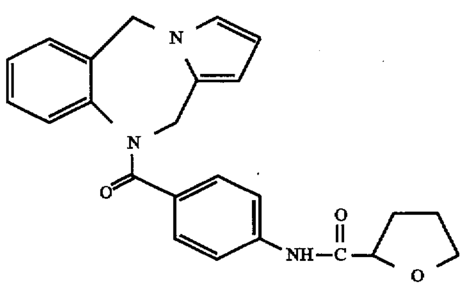 | 0.42 | 0.74 |
| 609 | 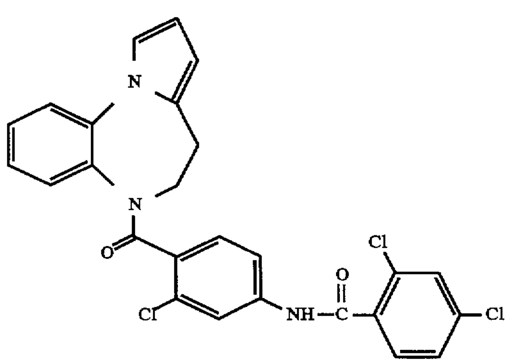 | 2.4* | 0.021** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 611 | 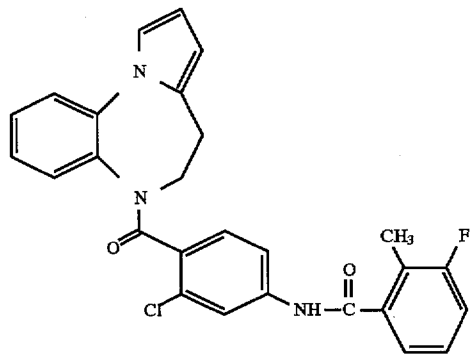 | 0.5* | 0.004** |
| 660 | 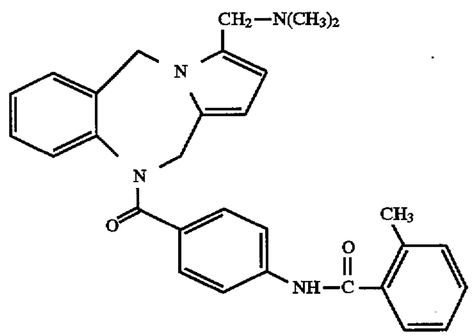 | 0.073 | 0.064 |
| 661 | 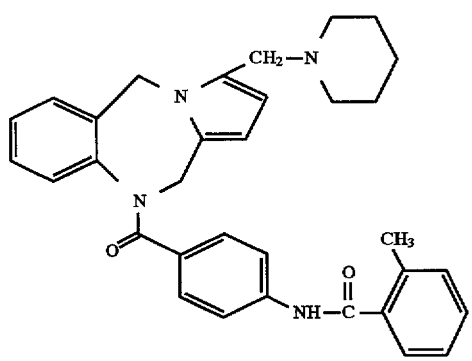 | 0.057 | 0.057 |
| 662 | 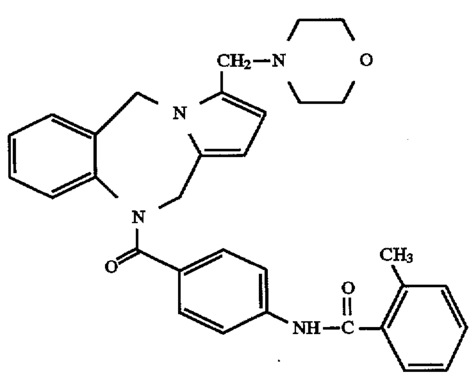 | 0.04 | 0.035 |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ IC$_{50}$ (μM) | $V_2$ IC$_{50}$ (μM) |
|---|---|---|---|
| 663 | 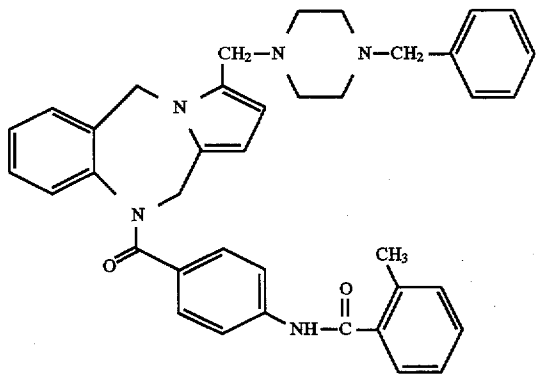 | 0.009 | 0.025 |
| 664 | 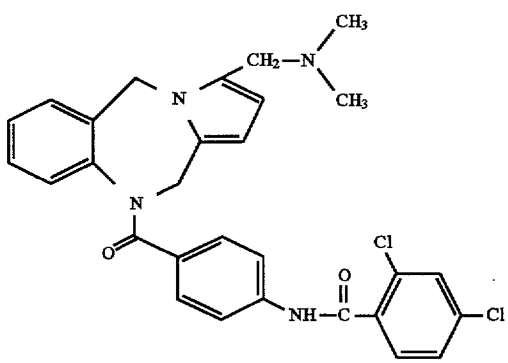 | 0.12 | 0.048 |
| 665 | 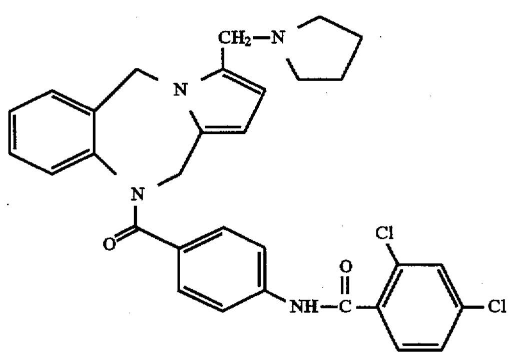 | 0.056 | 0.039 |
| 666 | 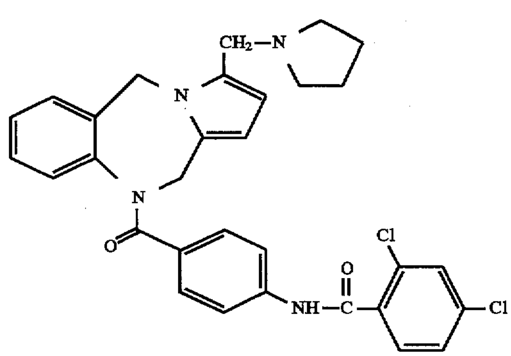 | 0.16 | 0.013 |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 667 | 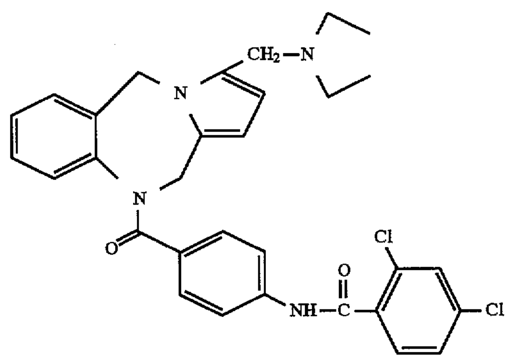 | 0.17 | 0.013 |
| 668 | 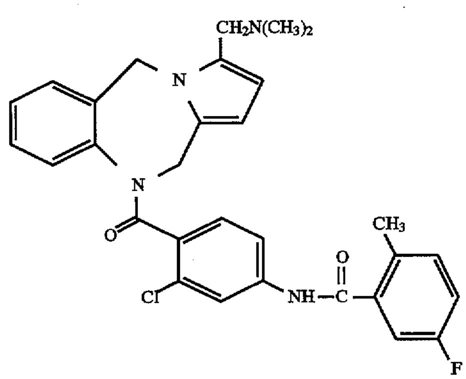 | 0.17* | 0.029** |
| 669 | 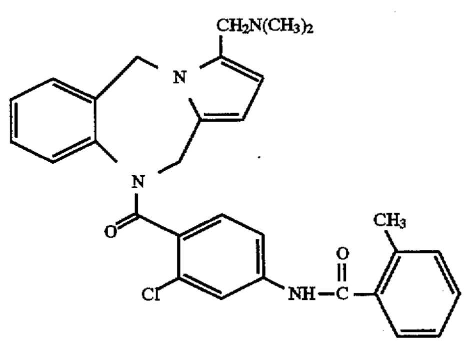 | 0.071* | 0.035** |
| 689 | 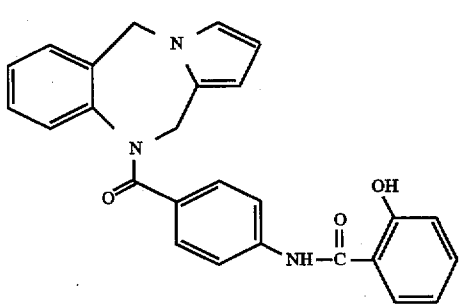 | 0.085* | 0.54** |

TABLE XIII-continued

Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 676 | 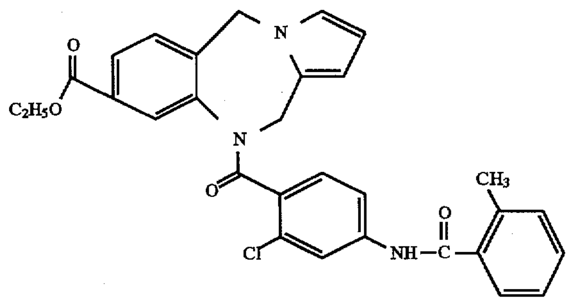 | (10 μM) 41% | (10 μM) 89% |
| 670 | 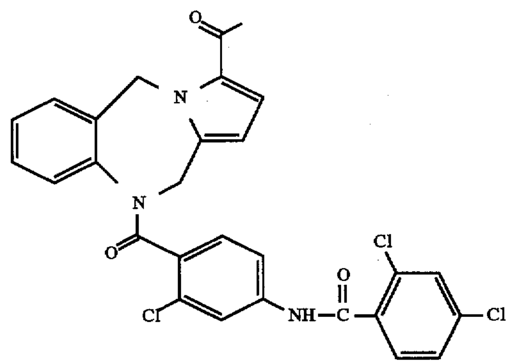 | 1.1 | 0.29 |
| 685 | 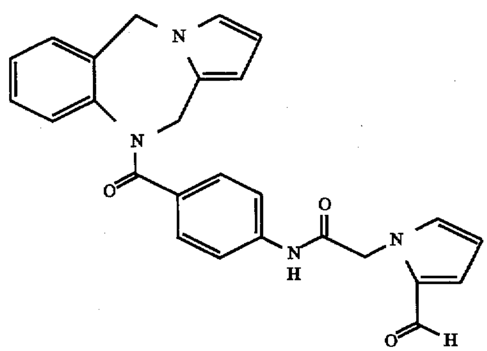 | 0.061* | 0.061** |
| 612 | 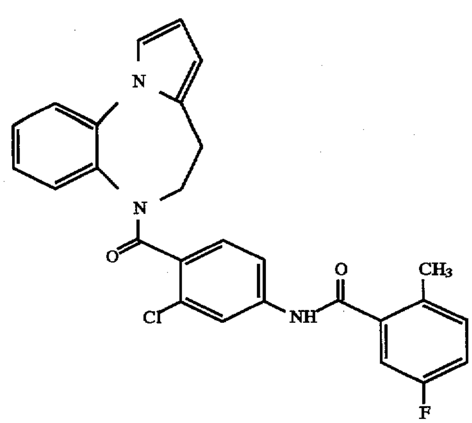 | 1.7* | 0.01** |

TABLE XIII-continued
Binding Assay to Rat Hepatic $V_1$ Receptors and Rat Kidney Medullary $V_2$ Receptors or
*Binding to $V_1$ Receptor Subtype in Human Platelet and **Binding to Membranes of Mouse Fibroblast
Cell Line (LV-2) Transfected with the cDNA Expressing the Human $V_2$ Receptor
| Ex. No. | Structure | $V_1$ $IC_{50}$ (µM) | $V_2$ $IC_{50}$ (µM) |
|---|---|---|---|
| 688 | 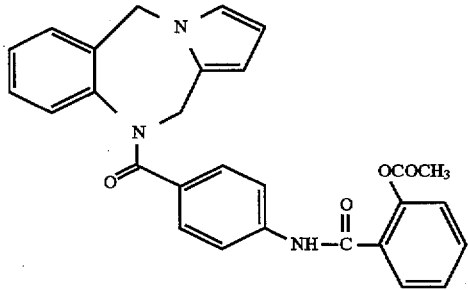 | 0.069* | 0.034** |
| 690 | 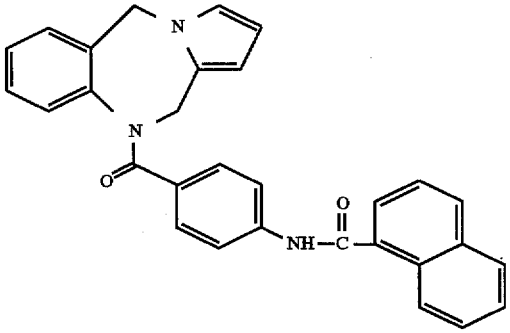 | 0.22* | 0.022** |
| 691 | 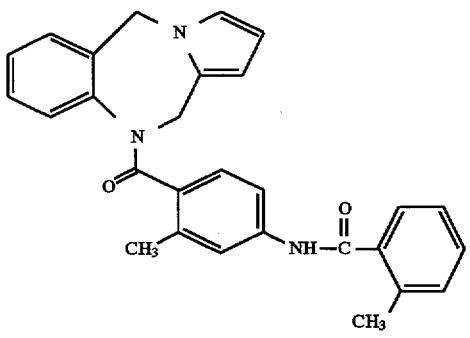 | 0.072* | 0.0029** |
| 692 | 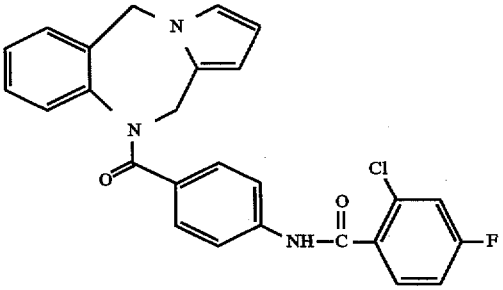 | 0.007* | 0.004** |

TABLE XIII-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ $IC_{50}$ (μM) | $V_2$ $IC_{50}$ (μM) |
|---|---|---|---|
| 693 | 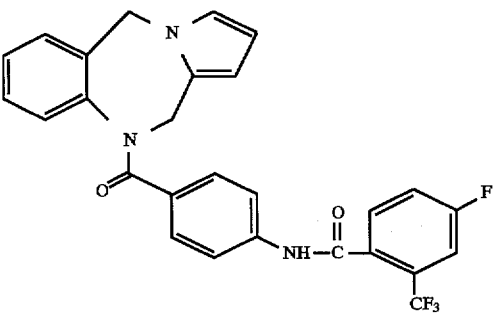 | 0.021* | 0.005** |
| 694 | 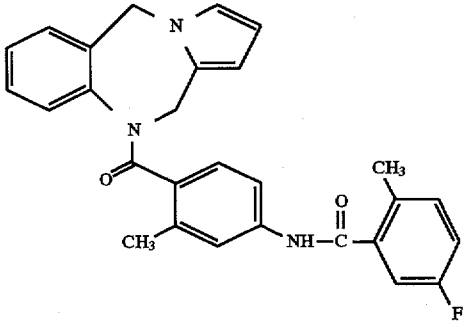 | 0.12 | 0.0017** |
| 695 | 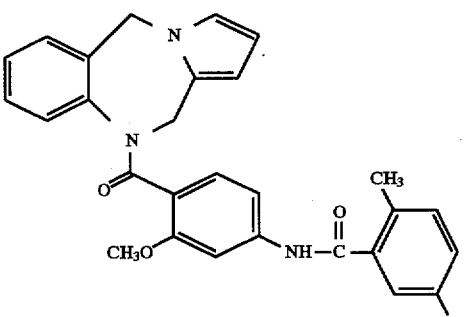 | 0.015* | 0.0018** |
| 696 | 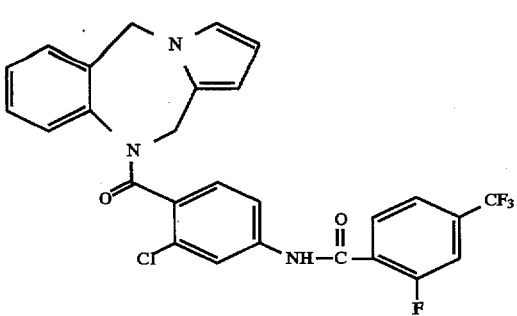 | 12.4* | 0.065** |

TABLE XIII-continued

Binding Assay to Rat Hepatic V₁ Receptors and Rat Kidney Medullary V₂ Receptors or
*Binding to V₁ Receptor Subtype in Human Platelet and **Binding to Membranes of Mouse Fibroblast
Cell Line (LV-2) Transfected with the cDNA Expressing the Human V₂ Receptor

| Ex. No. | Structure | $V_1$ $IC_{50}$ (μM) | $V_2$ $IC_{50}$ (μM) |
|---|---|---|---|
| 697 | 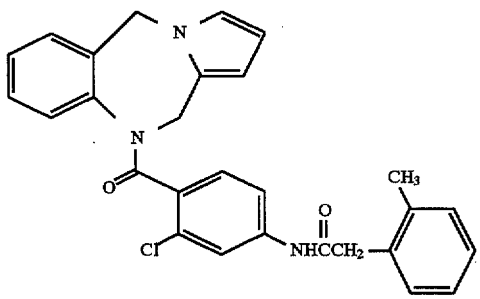 | 0.62* | 0.003** |
| 698 | 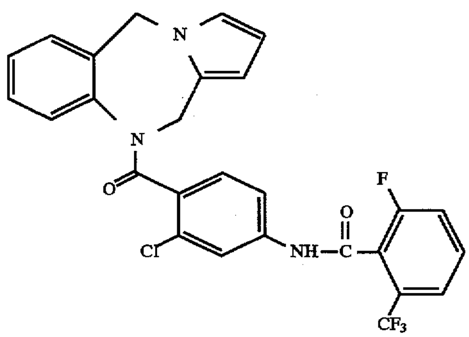 | 1.3* | 0.013** |
| 699 | 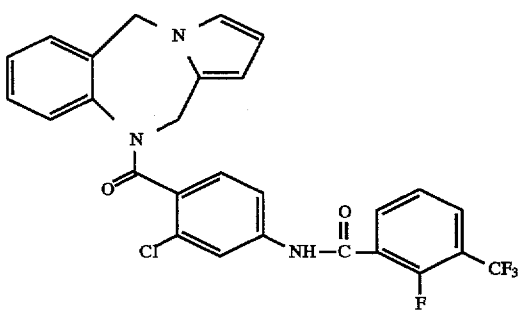 | (1 μM) 19% | (1 μM) 100% |
| 700 | 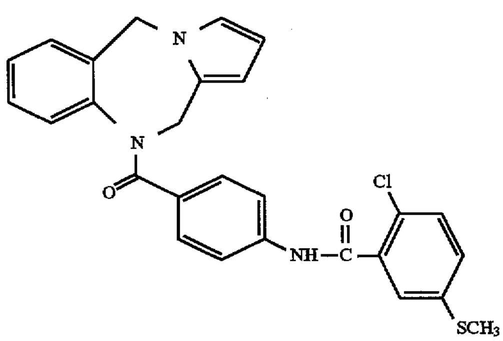 | (1 μM) 77%* | (10 μM) 100%** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (µM) | $V_2$ $IC_{50}$ (µM) |
|---|---|---|---|
| 701 | 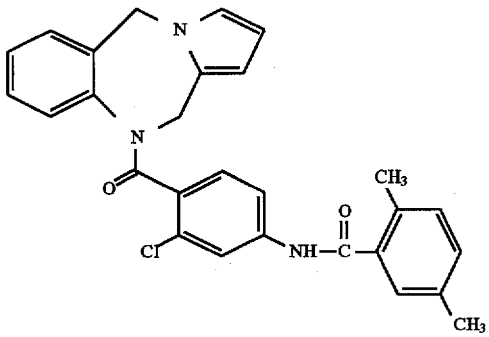 | 0.34* | (1 µM) 100% |
| 702 | 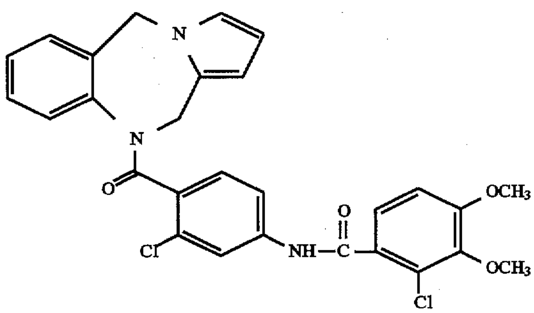 | (1 µM) 9%* | (1 µM) 85%** |
| 703 | 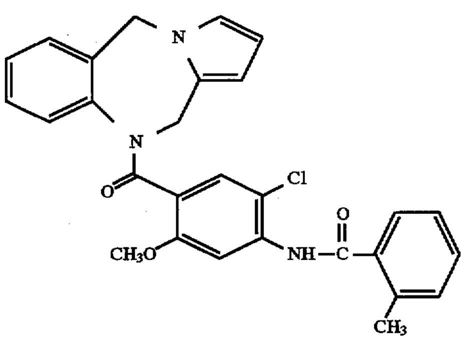 | (1 µM) 35%* | (1 µM) 87%** |
| 704 | 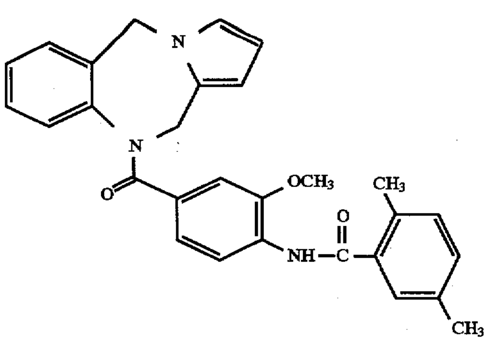 | (1 µM) 100%* | (1 µM) 92%** |

TABLE XIII-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 707 | 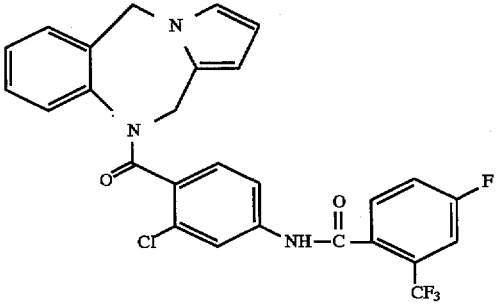 | 0.20* | 0.006** |
| 714 | 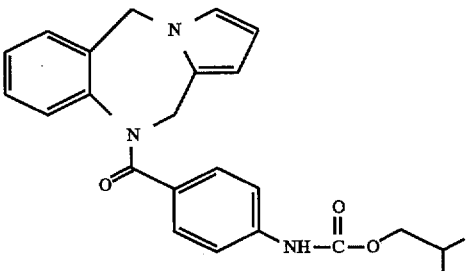 | 0.023* | 0.041** |
| 715 | 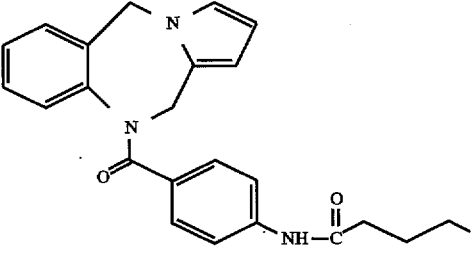 | 0.0078* | 0.073** |
| 716 | 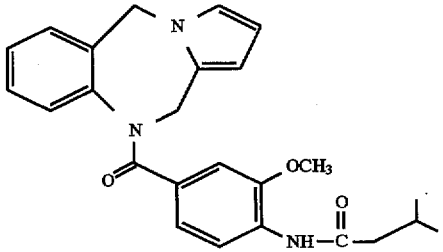 | 0.002* | 0.031** |

Vasopressin $V_2$ Antagonist Activity in Conscious Hydrated Rats

Conscious hydrated rats are treated with compounds under study from 0.1 to 100 mg/kg orally or vehicle. Two to four rats are used for each compound. One hour later, arginine vasopressin (AVP, antidiuretic hormore, ADH) dissolved in peanut oil is administered at 0.4 μg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measured and osmolality analyzed by use of a Fiske One-Ten osmometer (Fiske Assoc., Norwood, Mass., USA). Urinary sodium, potassium, and chloride are analyzed by use of ion-specific electrodes in a Beckman E3 (Electrolyte 3) Analyzer.

In the following results, decreased urine volume and decreased osmolality relative to AVP-control indicates activity. The results of this test on representative compounds of this invention are shown in Table XIV.

TABLE XIV

Vasopressin V₂ Antagonist Activity In Conscious Hydrated Rats

| Ex. No. | Dose (mg/kg) | N | Urine Volume (ml/4 hrs) | Osmolality (mOsm/kg) |
|---|---|---|---|---|
| * | | 78 | 1.3 ± 0.3 | 229 ± 6 |
| ** | | 6 | 12.1 ± 1 | 497 ± 53 |
| | | 4 | 12.4 ± 0.8 | 361 ± 30 |
| *** | | 76 | 2 ± 0.2 | 1226 ± 58 |
| 1 | 30 | 2 | 1.1 | 1504 |
| 215 | 30 | 2 | 0.7 | 1520 |
| 3 | 10 | 7 | 15.8 ± 1 | 567 ± 33 |
| | 3 | 8 | 9.6 ± 0.9 | 584 ± 56 |
| | 1 | 5 | 6.5 ± 1 | 515 ± 79 |
| 4 | 10 | 2 | 16.9 | 571 |
| | 3 | 4 | 9.5 ± 1.2 | 646 ± 115 |
| | 1 | 2 | 2 | 1129 |
| 5 | 30 | 2 | 7.7 | 955 |
| | 10 | 2 | 8.5 | 1079 |
| 6 | 30 | 5 | 17.9 ± 1.3 | 616 ± 87 |
| | 10 | 8 | 20.4 ± 1.1 | 346 ± 25 |
| | 3 | 4 | 15 ± 6 | 519 ± 30 |
| | 1 | 2 | 6 | 70 |
| 7 | 30 | 2 | 12.4 | 815 |
| | 10 | 2 | 9 | 780 |
| 8 | 30 | 2 | 9.1 | 1010 |
| | 10 | 2 | 3.4 | 1211 |
| 14 | 10 | 2 | 5.2 | 836 |
| | 3 | 2 | 4.5 | 1000 |
| 82 | 30 | 2 | 1.7 | 1808 |
| 84 | 30 | 2 | 6.5 | 425 |
| | 10 | 2 | 4.4 | 416 |
| 85 | 30 | 2 | 12.5 | 383 |
| | 10 | 2 | 2 | 1123 |
| 87 | 20 | 2 | 4.3 | 1300 |
| | 10 | 2 | 3 | 1488 |
| 89 | 30 | 2 | 3.3 | 1320 |
| 91 | 10 | 2 | 12.5 | 414 |
| | 3 | 2 | 2.3 | 1267 |
| 93 | 30 | 2 | 5.1 | 594 |
| 96 | 10 | 4 | 10.3 ± 1.3 | 647 ± 63 |
| | 3 | 2 | 4.4 | 716 |
| 116 | 30 | 2 | 8 | 1295 |
| | 10 | 2 | 5.5 | 1242 |
| 354 | 10 | 2 | 8.8 | 1010 |
| 356 | 10 | 2 | 5.8 | 1023 |
| 358 | 30 | 2 | 5.5 | 875 |
| 2 | 10 | 2 | 9.3 | 1015 |
| 9 | 10 | 2 | 5.8 | 702 |
| 99 | 30 | 2 | 15.2 | 334 |
| 467 | 10 | 2 | 18 | 365 |
| 466 | 10 | 2 | 14.1 | 522 |
| 17, 160 | 30 | 2 | 4.1 | 1374 |
| 489 | 10 | 2 | 6.1 | 1194 |
| 490 | 10 | 4 | 71.5 ± 1.6 | 487 ± 38 |
| 590 | 10 | 2 | 3 | 1355 |
| 581 | 10 | 4 | 4 ± 1.2 | 941 ± 219 |
| 469 | 10 | 2 | 11.3 | 548 |
| 599 | 10 | 2 | 18 | 407 |
| 470 | 10 | 3 | 17 | 387 |
| 484 | 10 | 2 | 8 | 785 |
| 485 | 10 | 2 | 4 | 961 |
| 471 | 10 | 4 | 14.1 ± 1.9 | 507 ± 38 |
| 479 | 10 | 2 | 6 | 1042 |
| 482 | 10 | 4 | 22 ± 0.9 | 372 ± 17 |
| 54 | 10 | 2 | 5 | 1275 |
| 274 | 10 | 2 | 3 | 1177 |
| 465 | 10 | 2 | 21.8 | 361 |
| 480 | 10 | 2 | 8.8 | 827 |
| 528 | 10 | 2 | 11.3 | 647 |
| 529 | 10 | 2 | 10.5 | 569 |
| 520 | 10 | 2 | 18.5 | 394 |
| 519 | 10 | 2 | 19.9 | 399 |
| 523 | 10 | 2 | 5 | 1218 |
| 524 | 10 | 2 | 10 | 528 |
| 525 | 10 | 2 | 13 | 557 |
| 526 | 10 | 2 | 17.8 | 455 |
| 527 | 10 | 2 | 19.5 | 430 |
| 530 | 10 | 2 | 6 | 914 |
| 518 | 10 | 2 | 17.5 | 363 |
| 668 | 10 | 2 | 20.7 | 378 |
| 609 | | | | |
| 611 | | | | |
| 472 | 10 | 2 | 4.3 | 1453 |
| 582 | 10 | 2 | 9.5 | 604 |
| 473 | 10 | 2 | 2.3 | 1493 |
| 474 | 10 | 2 | 11.5 | 619 |
| 594 | 10 | 4 | 4.9 ± 1.2 | 1172 ± 182 |
| 586 | 10 | 2 | 4.3 | 1196 |
| 584 | 10 | 2 | 2.5 | 1718 |
| 595 | 10 | 2 | 8.3 | 1474 |
| 588 | 10 | 2 | 9.5 | 687 |
| 287 | 10 | 2 | 9 | 868 |
| 210, 214 | 10 | 2 | 15.2 | 451 |
| 597 | 10 | 2 | 5.3 | 1250 |
| 517 | 10 | 2 | 14.7 | 411 |
| 217 | 10 | 2 | 14.3 | 466 |
| 585 | 10 | 2 | 3.3 | 1483 |
| 476 | 10 | 2 | 5 | 1233 |
| 593 | 10 | 2 | 11.8 | 577 |
| 596 | 10 | 2 | 2.8 | 1347 |
| 297 (298) | 10 | 2 | 7 | 796 |
| 477 | 10 | 2 | 5.3 | 701 |
| 478 | 10 | 2 | 3 | 1399 |
| 481 | 10 | 3 | 17.2 | 473 |
| 267, 271 | | | | |
| 592 | | | | |

*Water-load control
**Water-load Control + DMSO (10%) (20%)
***AVP-control

Vasopressin V₁ Antagonist Activity in Conscious Rats

Conscious rats are restrained in a supine position with elastic tape. The area at the base of the tail is locally anesthetized by subcutaneous infiltration with 2% procaine (0.2 ml). Using aseptic technique the ventral caudal tail artery is isolated and a cannula made of PE 10 and 20 (heat-fused) tubing is passed into the lower abdominal aorta. The cannula is secured, heparinized (1000 i.u./cc), sealed and the wound closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Statham P23Db pressure transducer and pulsatile blood pressure is recorded. Increase of systolic blood pressure responses to arginine vasopressin 0.01 and 0.2 international unit (I.U.) (350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 min. later. Percentage of antagonism by the compound is calculated using the pre-drug vasopressin vasopressor response as 100%.

The results of this test on representative compounds of this invention are shown in Table XV.

The results of this test on representative compounds of this invention in which the dose, the maximum % inhibition and the time in minutes, are shown in Table XVI.

TABLE XV

VASOPRESSIN (VAS) VASOPRESSOR RESPONSE

| | Dose (mg/kg) | VAS Dose i.u/kg I.V. | Min Post Dose | Control Before VAS | Response After VAS | Change | Average Change | % Inhibition |
|---|---|---|---|---|---|---|---|---|
| CONTROL | | 0.01 | 0 | 155 | 188 | 33 | 33.5 | |
| | | | | 156 | 190 | 34 | | |
| | | 0.02 | | 153 | 213 | 60 | 52.5 | |
| | | | | 165 | 210 | 45 | | |
| Ex. No. 1 | 10 i.v. | 0.01 | 30 | 161 | 165 | 4 | 4 | 88 |
| | | | | 170 | 174 | 4 | | |
| | | 0.02 | | 159 | 170 | 11 | 8 | 85 |
| | | | | 167 | 172 | 5 | | |
| | | 0.01 | 60 | 157 | 173 | 16 | 16.5 | 51 |
| | | | | 164 | 181 | 17 | | |
| | | 0.02 | | 157 | 182 | 25 | 20 | 62 |
| | | | | 178 | 193 | 15 | | |
| | | 0.01 | 90 | 151 | 176 | 25 | 21 | 37 |
| | | | | 159 | 176 | 17 | | |
| | | 0.02 | | 154 | 184 | 30 | 27 | 49 |
| | | | | 165 | 189 | 24 | | |
| | | 0.01 | 120 | 150 | 173 | 23 | 22.5 | 33 |
| | | | | 157 | 179 | 22 | | |
| | | 0.02 | | 150 | 191 | 41 | 37.5 | 29 |
| | | | | 162 | 196 | 34 | | |
| | | 0.01 | 180 | 148 | 177 | 29 | 29 | 13 |
| | | | | 155 | 184 | 29 | | |
| | | 0.02 | | 151 | 209 | 58 | 48 | 9 |
| | | | | 165 | 203 | 38 | | |
| | | 0.01 | 240 | 146 | 176 | 30 | 27 | 19 |
| | | | | 151 | 175 | 24 | | |
| | | 0.02 | | 151 | 200 | 49 | 39.5 | 25 |
| | | | | 162 | 192 | 30 | | |
| | | 0.01 | 300 | 146 | 176 | 30 | 32 | 4 |
| | | | | 151 | 185 | 34 | | |
| | | 0.02 | | 151 | 200 | 49 | 39.5 | 25 |
| | | | | 162 | 192 | 30 | | |
| SPONTANEOUSLY HYPERTENSIVE RATS n = 2 Body weight(s): 400,480 grams | | | | | | | | |
| CONTROL | | 0.01 | 0 | 131 | 168 | 37 | 31 | |
| | | | | 167 | 192 | 25 | | |
| | | 0.02 | | 131 | 190 | 59 | 50 | |
| | | | | 173 | 214 | 41 | | |
| Ex. No. 2 | 10 i.v. | 0.01 | 30 | 127 | 135 | 8 | 6.5 | 79 |
| | | | | 175 | 180 | 5 | | |
| | | 0.02 | | 135 | 144 | 9 | 8 | 84 |
| | | | | 178 | 185 | 7 | | |
| | | 0.01 | 60 | 137 | 144 | 7 | 8 | 74 |
| | | | | 172 | 181 | 9 | | |
| | | 0.02 | | 135 | 145 | 10 | 13 | 74 |
| | | | | 176 | 192 | 16 | | |
| | | 0.01 | 90 | 124 | 138 | 14 | 10.5 | 66 |
| | | | | 173 | 180 | 7 | | |
| | | 0.02 | | 132 | 147 | 15 | 15 | 70 |
| | | | | 173 | 188 | 15 | | |
| | | 0.01 | 120 | 135 | 143 | 8 | 9.5 | 69 |
| | | | | 167 | 178 | 11 | | |
| | | 0.02 | | 134 | 150 | 16 | 15 | 70 |
| | | | | 170 | 184 | 14 | | |
| | | 0.01 | 180 | 124 | 142 | 18 | 14 | 55 |
| | | | | 165 | 175 | 10 | | |
| | | 0.02 | | 129 | 150 | 21 | 22 | 56 |
| | | | | 162 | 185 | 23 | | |
| | | 0.01 | 240 | 125 | 144 | 19 | 16.5 | 47 |
| | | | | 164 | 178 | 14 | | |
| | | 0.02 | | 133 | 158 | 25 | 25 | 50 |
| | | | | 167 | 192 | 25 | | |
| | | 0.01 | 300 | 127 | 145 | 18 | 17.5 | 44 |
| | | | | 159 | 176 | 17 | | |
| | | 0.02 | | 134 | 170 | 36 | 31.5 | 37 |
| | | | | 163 | 190 | 27 | | |
| SPONTANEOUSLY HYPERTENSIVE RATS n = 2 Body weight(s): 430,480 grams | | | | | | | | |
| CONTROL | | 0.01 | 0 | 175 | 215 | 40 | 50 | |
| | | | | 175 | 235 | 60 | | |
| | | 0.02 | | 185 | 240 | 55 | 55 | |
| | | | | 200 | 255 | 55 | | |
| Ex. No. 3 | 3 i.v. | 0.01 | 30 | 180 | 190 | 10 | 15 | 70 |
| | | | | 175 | 195 | 20 | | |
| | | 0.02 | | 180 | 205 | 25 | 23.5 | 57 |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 185 | 207 | 22 | | |
| | | 0.01 | 60 | 185 | 190 | 5 | 12.5 | 75 |
| | | | | 180 | 200 | 20 | | |
| | | 0.02 | | 185 | 195 | 10 | 17.5 | 68 |
| | | | | 185 | 210 | 25 | | |
| | | 0.01 | 90 | 175 | 185 | 10 | 17.5 | 65 |
| | | | | 175 | 200 | 25 | | |
| | | 0.02 | | 185 | 195 | 10 | 15 | 73 |
| | | | | 185 | 205 | 20 | | |
| | | 0.01 | 120 | 170 | 185 | 15 | 20 | 60 |
| | | | | 175 | 200 | 25 | | |
| | | 0.02 | | 175 | 200 | 25 | 32.5 | 41 |
| | | | | 185 | 225 | 40 | | |
| | | 0.01 | 180 | 175 | 195 | 20 | 30 | 40 |
| | | | | 165 | 205 | 40 | | |
| | | 0.02 | | 180 | 235 | 55 | 55 | 0 |
| | | | | 185 | 240 | 55 | | |
| | | 0.01 | 240 | 165 | 195 | 30 | 40 | 20 |
| | | | | 160 | 210 | 50 | | |
| | | 0.02 | | 180 | 225 | 45 | 52.5 | 5 |
| | | | | 185 | 245 | 60 | | |
| SPONTANEOUSLY HYPERTENSIVE RATS n = 2 Body weight(s): 340,330 grams | | | | | | | | |
| CONTROL | | 0.01 | 0 | 170 | 215 | 45 | 53.5 | |
| | | | | 163 | 225 | 62 | | |
| | | 0.02 | | 185 | 225 | 40 | 52.5 | |
| | | | | 190 | 255 | 65 | | |
| Ex. No. 3 | 30 p.o. | 0.01 | 30 | 170 | 180 | 10 | 15 | 72 |
| | | | | 155 | 175 | 20 | | |
| | | 0.02 | | 175 | 190 | 15 | 20 | 62 |
| | | | | 160 | 185 | 25 | | |
| | | 0.01 | 60 | 165 | 190 | 25 | 22.5 | 57 |
| | | | | 150 | 170 | 20 | | |
| | | 0.02 | | 170 | 190 | 20 | 22.5 | 57 |
| | | | | 160 | 185 | 25 | | |
| | | 0.01 | 90 | 165 | 175 | 10 | 10 | 81 |
| | | | | 160 | 170 | 10 | | |
| | | 0.02 | | 165 | 185 | 20 | 20 | 62 |
| | | | | 160 | 180 | 20 | | |
| | | 0.01 | 120 | 160 | 175 | 15 | 10 | 81 |
| | | | | 165 | 170 | 5 | | |
| | | 0.02 | | 165 | 170 | 5 | 12.5 | 76 |
| | | | | 165 | 185 | 20 | 20 | 62 |
| | | 0.01 | 180 | 175 | 180 | 5 | 10 | 81 |
| | | | | 170 | 185 | 15 | | |
| | | 0.02 | | 170 | 185 | 15 | 17.5 | 67 |
| | | | | 165 | 185 | 20 | | |
| | | 0.01 | 240 | 170 | 175 | 5 | 5 | 91 |
| | | | | 160 | 165 | 5 | | |
| | | 0.02 | | 165 | 170 | 5 | 10 | 81 |
| | | | | 160 | 175 | 15 | | |
| SPONTANEOUSLY HYPERTENSIVE RATS n = 2 Body weight(s): 340,340 grams | | | | | | | | |
| CONTROL | | 0.01 | 0 | 155 | 215 | 60 | 57.5 | |
| | | | | 165 | 220 | 55 | | |
| | | 0.02 | | 190 | 230 | 40 | 50 | |
| | | | | 175 | 235 | 60 | | |
| Ex. No. 3 | 10 p.o. | 0.01 | 30 | 150 | 165 | 15 | 12.5 | 78 |
| | | | | 175 | 185 | 10 | | |
| | | 0.02 | | 155 | 175 | 20 | 17.5 | 65 |
| | | | | 175 | 190 | 15 | | |
| | | 0.01 | 60 | 150 | 160 | 10 | 17.5 | 70 |
| | | | | 155 | 180 | 25 | | |
| | | 0.02 | | 155 | 180 | 25 | 22.5 | 55 |
| | | | | 160 | 180 | 20 | | |
| | | 0.01 | 90 | 145 | 170 | 20 | 65 | 81 |
| | | | | 160 | 175 | 15 | | |
| | | 0.02 | | 155 | 205 | 50 | 40 | 20 |
| | | | | 155 | 185 | 30 | | |
| | | 0.01 | 120 | 150 | 165 | 15 | 15 | 74 |
| | | | | 160 | 175 | 15 | | |
| | | 0.02 | | 155 | 210 | 55 | 45 | 10 |
| | | | | 160 | 195 | 35 | | |
| | | 0.01 | 180 | 145 | 165 | 20 | 20 | 65 |
| | | | | 155 | 175 | 20 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.02 | | 150 | 190 | 40 | 35 | 30 |
| | | | | 165 | 195 | 30 | | |
| | | 0.01 | 240 | 145 | 165 | 20 | 22.5 | 61 |
| | | | | 160 | 185 | 25 | | |
| | | 0.02 | | 155 | 200 | 45 | 47.5 | 5 |
| | | | | 165 | 215 | 50 | | |
| SPONTANEOUSLY HYPERTENSIVE RATS n = 2 Body weight(s): 340,360 grams | | | | | | | | |
| CONTROL | | 0.01 | 0 | 167 | 209 | 42 | 35 | |
| | | | | 170 | 198 | 28 | | |
| | | 0.02 | | 170 | 232 | 62 | 54.5 | |
| | | | | 177 | 224 | 47 | | |
| Ex. No. 3 | 10 p.o. | 0.01 | 30 | 116 | 124 | 8 | 10 | 71 |
| | | | | 172 | 184 | 12 | | |
| | | 0.02 | | 113 | 128 | 15 | 18.5 | 66 |
| | | | | 168 | 190 | 22 | | |
| | | 0.01 | 60 | 115 | 122 | 7 | 10.5 | 70 |
| | | | | 170 | 184 | 14 | | |
| | | 0.02 | | 116 | 133 | 17 | 18.5 | 66 |
| | | | | 168 | 188 | 20 | | |
| | | 0.01 | 90 | 116 | 122 | 6 | 6.5 | 81 |
| | | | | 134 | 141 | 7 | | |
| | | 0.02 | | 160 | 185 | 25 | 24 | 56 |
| | | | | 167 | 190 | 23 | | |
| | | 0.01 | 120 | 162 | 172 | 10 | 14.5 | 59 |
| | | | | 165 | 184 | 19 | | |
| | | 0.02 | | 160 | 168 | 8 | 10.5 | 81 |
| | | | | 161 | 174 | 13 | | |
| | | 0.01 | 180 | 162 | 162 | 0 | 8 | 77 |
| | | | | 164 | 180 | 16 | | |
| | | 0.02 | | 156 | 165 | 9 | 13.5 | 75 |
| | | | | 163 | 181 | 18 | | |
| | | 0.01 | 240 | 162 | 168 | 6 | 8.5 | 76 |
| | | | | 170 | 181 | 11 | | |
| | | 0.02 | | 160 | 170 | 10 | 22.5 | 59 |
| | | | | 175 | 210 | 35 | | |
| SPONTANEOUSLY HYPERTENSIVE RATS n = 2 Body weight(s): 380,360 grams | | | | | | | | |
| CONTROL | | 0.01 | 0 | 147 | 182 | 35 | 40 | |
| | | | | 136 | 181 | 45 | | |
| | | 0.02 | | 150 | 213 | 63 | 54 | |
| | | | | 146 | 191 | 45 | | |
| Ex. No. 3 | 10 p.o. | 0.01 | 30 | 147 | 157 | 10 | 11 | 73 |
| | | | | 132 | 144 | 12 | | |
| | | 0.02 | | 148 | 162 | 14 | 16 | 70 |
| | | | | 134 | 152 | 18 | | |
| | | 0.01 | 60 | 143 | 155 | 12 | 11.5 | 71 |
| | | | | 136 | 147 | 11 | | |
| | | 0.02 | | 151 | 160 | 9 | 22.5 | 58 |
| | | | | 134 | 170 | 36 | | |
| | | 0.01 | 90 | 142 | 154 | 12 | 12 | 70 |
| | | | | 133 | 145 | 12 | | |
| | | 0.02 | | 145 | 162 | 17 | 17.5 | 68 |
| | | | | 130 | 148 | 18 | | |
| | | 0.01 | 120 | 139 | 154 | 15 | 12.5 | 69 |
| | | | | 133 | 143 | 10 | | |
| | | 0.02 | | 136 | 164 | 28 | 22.5 | 58 |
| | | | | 127 | 144 | 17 | | |
| | | 0.01 | 180 | 147 | 160 | 13 | 15.5 | 61 |
| | | | | 120 | 138 | 18 | | |
| | | 0.02 | | 144 | 168 | 24 | 25 | 54 |
| | | | | 122 | 148 | 26 | | |
| | | 0.01 | 240 | 145 | 163 | 18 | 19.5 | 51 |
| | | | | 122 | 143 | 21 | | |
| | | 0.02 | | 144 | 188 | 44 | 35.5 | 34 |
| | | | | 126 | 153 | 27 | | |
| | | 0.01 | 300 | 146 | 166 | 20 | 16.5 | 59 |
| | | | | 124 | 137 | 13 | | |
| | | 0.02 | | 153 | 180 | 27 | 24 | 56 |
| | | | | 134 | 155 | 21 | | |
| SPONTANEOUSLY HYPERTENSIVE RATS n = 2 Body weight(s): 500,390 grams | | | | | | | | |
| CONTROL | | 0.01 | 0 | 146 | 200 | 54 | 49 | |
| | | | | 139 | 183 | 44 | | |
| | | 0.02 | | 148 | 205 | 57 | 51.5 | |
| | | | | 146 | 192 | 46 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| Ex. No. 3 | 3 i.v. | 0.01 | 30 | 143 | 158 | 15 | 15 | 69 |
| | | | | 124 | 139 | 15 | | |
| | | 0.02 | | 145 | 166 | 21 | 22 | 57 |
| | | | | 160 | 183 | 23 | | |
| | | 0.01 | 60 | 143 | 161 | 18 | 21 | 57 |
| | | | | 131 | 155 | 24 | | |
| | | 0.02 | | 147 | 185 | 38 | 29 | 44 |
| | | | | 138 | 158 | 20 | | |
| | | 0.01 | 90 | 128 | 148 | 20 | 12 | 76 |
| | | | | 148 | 152 | 4 | | |
| | | 0.02 | | 154 | 188 | 34 | 28 | 46 |
| | | | | 133 | 155 | 22 | | |
| | | 0.01 | 120 | 137 | 155 | 18 | 20.5 | 58 |
| | | | | 148 | 171 | 23 | | |
| | | 0.02 | | 138 | 161 | 23 | 18.5 | 64 |
| | | | | 148 | 162 | 14 | | |
| | | 0.01 | 180 | 146 | 162 | 16 | 21 | 57 |
| | | | | 139 | 165 | 26 | | |
| | | 0.02 | | 148 | 179 | 31 | 28.5 | 45 |
| | | | | 146 | 172 | 26 | | |
| | | 0.01 | 240 | 142 | 166 | 24 | 32 | 35 |
| | | | | 132 | 172 | 40 | | |
| | | 0.02 | | 126 | 145 | 19 | 27.5 | 47 |
| | | | | 139 | 175 | 36 | | |
| | | 0.01 | 300 | 141 | 162 | 21 | 19 | 61 |
| | | | | 146 | 163 | 17 | | |
| | | 0.02 | | 146 | 179 | 33 | 30.5 | 41 |
| | | | | 145 | 173 | 28 | | |
| SPONTANEOUSLY HYPERTENSIVE RATS n = 2 Body weight(s): 510,510 grams | | | | | | | | |
| CONTROL | | 0.01 | 0 | 140 | 175 | 35 | 47.5 | |
| | | | | 142 | 202 | 60 | | |
| | | 0.02 | | 155 | 194 | 39 | 49.5 | |
| | | | | 154 | 214 | 60 | | |
| Ex. No. 4 | 10 p.o. | 0.01 | 30 | 133 | 173 | 40 | 44.5 | 6 |
| | | | | 139 | 188 | 49 | | |
| | | 0.02 | | 154 | 178 | 24 | 36 | 27 |
| | | | | 153 | 201 | 48 | | |
| | | 0.01 | 60 | 156 | 177 | 21 | 30.5 | 36 |
| | | | | 142 | 182 | 40 | | |
| | | 0.02 | | 156 | 182 | 26 | 44.5 | 10 |
| | | | | 145 | 208 | 63 | | |
| | | 0.01 | 90 | 153 | 180 | 27 | 38.5 | 19 |
| | | | | 141 | 191 | 50 | | |
| | | 0.02 | | 163 | 199 | 36 | 52 | −5 |
| | | | | 152 | 220 | 68 | | |
| | | 0.01 | 120 | 164 | 198 | 34 | 32.5 | 32 |
| | | | | 146 | 177 | 31 | | |
| | | 0.02 | | 161 | 194 | 33 | 50.5 | −2 |
| | | | | 146 | 214 | 68 | | |
| | | 0.01 | 180 | 149 | 183 | 34 | 35.5 | 25 |
| | | | | 141 | 178 | 37 | | |
| | | 0.02 | | 148 | 185 | 37 | 44 | 11 |
| | | | | 141 | 192 | 51 | | |
| | | 0.01 | 240 | 148 | 169 | 21 | 29 | 39 |
| | | | | 133 | 170 | 37 | | |
| | | 0.02 | | 158 | 184 | 26 | 26 | 47 |
| SPONTANEOUSLY HYPERTENSIVE RATS n = 2 Body weight(s): 460,510 grams | | | | | | | | |
| CONTROL | | 0.01 | 0 | 137 | 170 | 33 | 31.5 | |
| | | | | 139 | 169 | 30 | | |
| | | 0.02 | | 141 | 193 | 52 | 48 | |
| | | | | 122 | 166 | 44 | | |
| Ex. No. 5 | 10 i.v. | 0.01 | 30 | 141 | 146 | 5 | 5.5 | 83 |
| | | | | 120 | 126 | 6 | | |
| | | 0.02 | | 143 | 155 | 12 | 13.5 | 72 |
| | | | | 137 | 152 | 15 | | |
| | | 0.01 | 60 | 144 | 152 | 8 | 7.5 | 76 |
| | | | | 123 | 130 | 7 | | |
| | | 0.02 | | 144 | 155 | 11 | 10.5 | 78 |
| | | | | 124 | 134 | 10 | | |
| | | 0.01 | 90 | 148 | 155 | 7 | 9 | 71 |
| | | | | 141 | 152 | 11 | | |
| | | 0.02 | | 146 | 155 | 9 | 8 | 83 |
| | | | | 145 | 152 | 7 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.01 | 120 | 144 | 158 | 14 | 13 | 59 |
| | | | | 123 | 135 | 12 | | |
| | | 0.02 | | 148 | 164 | 16 | 15 | 69 |
| | | | | 126 | 140 | 14 | | |
| | | 0.01 | 180 | 143 | 156 | 13 | 12 | 62 |
| | | | | 124 | 135 | 11 | | |
| | | 0.02 | | 145 | 164 | 19 | 19 | 60 |
| | | | | 123 | 142 | 19 | | |
| | | 0.01 | 240 | 137 | 155 | 18 | 17 | 46 |
| | | | | 117 | 133 | 16 | | |
| | | 0.02 | | 135 | 160 | 25 | 23.5 | 51 |
| | | | | 118 | 140 | 22 | | |
| | | 0.01 | 300 | 130 | 161 | 31 | 30 | 5 |
| | | | | 112 | 141 | 29 | | |
| | | 0.02 | | 139 | 181 | 42 | 39.5 | 18 |
| | | | | 119 | 156 | 37 | | |
| SPONTANEOUSLY HYPERTENSIVE RATS n = 2 Body weight(s): 460,410 grams |||||||||
| CONTROL | | 0.01 | 0 | 143 | 189 | 46 | 36.5 | |
| | | | | 162 | 189 | 27 | | |
| | | 0.02 | | 151 | 195 | 44 | 42 | |
| | | | | 162 | 202 | 40 | | |
| Ex. No. 6 | 10 i.v. | 0.01 | 30 | 152 | 158 | 6 | 5.5 | 85 |
| | | | | 157 | 162 | 5 | | |
| | | 0.02 | | 144 | 165 | 21 | 16 | 62 |
| | | | | 147 | 158 | 11 | | |
| | | 0.01 | 60 | 150 | 163 | 13 | 7.5 | 79 |
| | | | | 177 | 179 | 2 | | |
| | | 0.02 | | 144 | 170 | 26 | 23 | 45 |
| | | | | 162 | 182 | 20 | | |
| | | 0.01 | 90 | 139 | 153 | 14 | 13.5 | 63 |
| | | | | 155 | 168 | 13 | | |
| | | 0.02 | | 145 | 168 | 23 | 27 | 36 |
| | | | | 154 | 185 | 31 | | |
| | | 0.01 | 120 | 143 | 160 | 17 | 15 | 59 |
| | | | | 154 | 167 | 13 | | |
| | | 0.02 | | 143 | 176 | 33 | 29.5 | 30 |
| | | | | 151 | 177 | 26 | | |
| | | 0.01 | 180 | 138 | 165 | 27 | 20.5 | 44 |
| | | | | 152 | 166 | 14 | | |
| | | 0.02 | | 148 | 189 | 41 | 35 | 17 |
| | | | | 157 | 186 | 29 | | |
| | | 0.01 | 240 | 143 | 175 | 32 | 24 | 34 |
| | | | | 163 | 179 | 16 | | |
| | | 0.02 | | 151 | 199 | 48 | 35.5 | 15 |
| | | | | 166 | 189 | 23 | | |
| | | 0.01 | 300 | 143 | 175 | 32 | 25.5 | 30 |
| | | | | 165 | 184 | 19 | | |
| | | 0.02 | | .152 | 193 | 41 | 36 | 14 |
| | | | | 173 | 204 | 31 | | |
| SPONTANEOUSLY HYPERTENSIVE RATS n = 2 Body weight(s): 480,520 grams |||||||||
| CONTROL | | 0.01 | 0 | 144 | 181 | 37 | 47 | |
| | | | | 134 | 191 | 57 | | |
| | | 0.02 | | 140 | 190 | 50 | 56 | |
| | | | | 150 | 212 | 62 | | |
| Ex. No. 7 | 10 i.v. | 0.01 | 30 | 141 | 151 | 10 | 6 | 87 |
| | | | | 152 | 154 | 2 | | |
| | | 0.02 | | 147 | 162 | 15 | 7.5 | 87 |
| | | | | 159 | 159 | 0 | | |
| | | 0.01 | 60 | 138 | 143 | 5 | 6 | 87 |
| | | | | 148 | 155 | 7 | | |
| | | 0.02 | | 136 | 145 | 9 | 8 | 86 |
| | | | | 148 | 155 | 7 | | |
| | | 0.01 | 90 | 134 | 147 | 13 | 8.5 | 82 |
| | | | | 142 | 146 | 4 | | |
| | | 0.02 | | 137 | 149 | 12 | 12.5 | 78 |
| | | | | 139 | 152 | 13 | | |
| | | 0.01 | 120 | 132 | 142 | 10 | 9.5 | 80 |
| | | | | 136 | 145 | 9 | | |
| | | 0.02 | | 134 | 150 | 16 | 13 | 77 |
| | | | | 141 | 151 | 10 | | |
| | | 0.01 | 180 | 136 | 151 | 15 | 17.5 | 63 |
| | | | | 138 | 158 | 20 | | |
| | | 0.02 | | 136 | 158 | 22 | 23 | 59 |

TABLE XV-continued

VASOPRESSIN (VAS) VASOPRESSOR RESPONSE

| Dose (mg/kg) | VAS Dose i.u./kg I.V. | Min Post Dose | Control Before VAS | Response After VAS | Change | Average Change | % Inhibition |
|---|---|---|---|---|---|---|---|
| | | | 134 | 158 | 24 | | |
| | 0.01 | 240 | 129 | 146 | 17 | 20.5 | 56 |
| | | | 132 | 156 | 24 | | |
| | 0.02 | | 131 | 157 | 26 | 30.5 | 46 |
| | | | 143 | 178 | 35 | | |
| | 0.01 | 300 | 128 | 146 | 18 | 20 | 57 |
| | | | 136 | 158 | 22 | | |
| | 0.02 | | 134 | 151 | 17 | 23 | 59 |
| | | | 145 | 174 | 29 | | |

SPONTANEOUSLY HYPERTENSIVE RATS n = 2 Body weight(s): 550,530 grams

| Dose (mg/kg) | VAS Dose i.u./kg I.V. | Min Post Dose | Control Before VAS | Response After VAS | Change | Average Change | % Inhibition |
|---|---|---|---|---|---|---|---|
| CONTROL | 0.01 | 0 | 142 | 191 | 49 | 37 | |
| | | | 145 | 170 | 25 | | |
| | 0.02 | | 152 | 213 | 61 | 51.5 | |
| | | | 147 | 189 | 42 | | |
| Ex. No. 8  10 i.v. | 0.01 | 30 | 156 | 178 | 22 | 14.5 | 61 |
| | | | 145 | 152 | 7 | | |
| | 0.02 | | 150 | 176 | 26 | 23.5 | 54 |
| | | | 139 | 160 | 21 | | |
| | 0.01 | 60 | 145 | 154 | 9 | 14.5 | 61 |
| | | | 150 | 170 | 20 | | |
| | 0.02 | | 145 | 162 | 17 | 21.5 | 58 |
| | | | 158 | 184 | 26 | | |
| | 0.01 | 90 | 146 | 154 | 8 | 10 | 73 |
| | | | 160 | 172 | 12 | | |
| | 0.02 | | 142 | 160 | 18 | 17.5 | 66 |
| | | | 161 | 178 | 17 | | |
| | 0.01 | 120 | 141 | 154 | 13 | 11.5 | 69 |
| | | | 156 | 166 | 10 | | |
| | 0.02 | | 139 | 154 | 15 | 15.5 | 70 |
| | | | 162 | 178 | 16 | | |
| | 0.01 | 180 | 139 | 156 | 17 | 14 | 62 |
| | | | 157 | 168 | 11 | | |
| | 0.02 | | 140 | 172 | 32 | 28 | 46 |
| | | | 158 | 182 | 24 | | |
| | 0.01 | 240 | 138 | 151 | 13 | 15 | 59* |
| | | | 148 | 165 | 17 | | |
| | 0.02 | | 143 | 178 | 35 | 29 | 44 |
| | | | 152 | 175 | 23 | | |
| | 0.01 | 300 | 143 | 161 | 18 | 18 | 51 |
| | | | 147 | 165 | 18 | | |
| | 0.02 | | 153 | 183 | 30 | 28 | 46 |
| | | | 157 | 183 | 26 | | |

SPONTANEOUSLY HYPERTENSIVE RATS n = 2 Body weight(s): 585,450 grams

| Dose (mg/kg) | VAS Dose i.u./kg I.V. | Min Post Dose | Control Before VAS | Response After VAS | Change | Average Change | % Inhibition |
|---|---|---|---|---|---|---|---|
| CONTROL | 0.01 | 0 | 167 | 183 | 16 | 22 | |
| | | | 162 | 190 | 28 | | |
| | 0.02 | | 163 | 193 | 30 | 50.5 | |
| | | | 154 | 225 | 71 | | |
| Ex. No. 41  10 i.v. | 0.01 | 30 | 153 | 164 | 11 | 12 | 45 |
| | | | 163 | 176 | 13 | | |
| | 0.02 | | 161 | 194 | 33 | 23.5 | 53 |
| | | | 155 | 169 | 14 | | |
| | 0.01 | 60 | 161 | 171 | 10 | 9 | 59 |
| | | | 159 | 167 | 8 | | |
| | 0.02 | | 156 | 172 | 16 | 18 | 64 |
| | | | 153 | 173 | 20 | | |
| | 0.01 | 90 | 154 | 169 | 15 | 14 | 36 |
| | | | 166 | 179 | 13 | | |
| | 0.02 | | 151 | 179 | 28 | 22.5 | 55 |
| | | | 153 | 170 | 17 | | |
| | 0.01 | 120 | 150 | 160 | 10 | 14 | 36 |
| | | | 151 | 169 | 18 | | |
| | 0.02 | | 149 | 163 | 14 | 16.5 | 67 |
| | | | 164 | 183 | 19 | | |
| | 0.01 | 180 | 153 | 167 | 14 | 13.5 | 39 |
| | | | 156 | 169 | 13 | | |
| | 0.02 | | 154 | 172 | 18 | 21 | 58 |
| | | | 155 | 179 | 24 | | |
| | 0.01 | 240 | 151 | 162 | 11 | 12.5 | 43 |
| | | | 151 | 165 | 14 | | |
| | 0.02 | | 156 | 179 | 23 | 23.5 | 53 |
| | | | 158 | 182 | 24 | | |
| | 0.01 | 300 | 145 | 160 | 15 | 15 | 32 |
| | | | 150 | 165 | 15 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.02 | | 150 | 180 | 30 | 27 | 47 |
| | | | | 155 | 179 | 24 | | |
| SPONTANEOUSLY HYPERTENSIVE RATS n = 2 Body weight(s): 400,400 grams | | | | | | | | |
| CONTROL | | 0.01 | 0 | 164 | 209 | 45 | 47.5 | |
| | | | | 160 | 210 | 50 | | |
| | | 0.02 | | 186 | 229 | 43 | 51.5 | |
| | | | | 156 | 216 | 60 | | |
| Ex. No. 82 | 10 i.v. | 0.01 | 30 | 156 | 195 | 39 | 36 | 24 |
| | | | | 152 | 185 | 33 | | |
| | | 0.02 | | 165 | 218 | 53 | 54 | −5 |
| | | | | 159 | 214 | 55 | | |
| Ex. No. 82 | 20 i.v. | 0.01 | 60 | 162 | 180 | 18 | 15.5 | 67 |
| | | | | 147 | 160 | 13 | | |
| | | 0.02 | | 161 | 199 | 38 | 37 | 28 |
| | | | | 151 | 187 | 36 | | |
| | | 0.01 | 90 | 158 | 181 | 23 | 23.5 | 51 |
| | | | | 144 | 168 | 24 | | |
| | | 0.02 | | 144 | 175 | 31 | 24 | 53 |
| | | | | 143 | 160 | 17 | | |
| | | 0.01 | 120 | 157 | 173 | 16 | 16.5 | 65 |
| | | | | 143 | 160 | 17 | | |
| | | 0.02 | | 161 | 200 | 39 | 38.5 | 25 |
| | | | | 152 | 190 | 38 | | |
| | | 0.01 | 180 | 149 | 171 | 22 | 18.5 | 61 |
| | | | | 139 | 154 | 15 | | |
| | | 0.02 | | 150 | 197 | 47 | 43.5 | 16 |
| | | | | 130 | 170 | 40 | | |
| | | 0.01 | 240 | 144 | 175 | 31 | 29 | 39 |
| | | | | 143 | 170 | 27 | | |
| | | 0.02 | | 150 | 198 | 48 | 42 | 18 |
| | | | | 146 | 182 | 36 | | |
| | | 0.01 | 300 | 152 | 185 | 33 | 32 | 33 |
| | | | | 136 | 167 | 31 | | |
| | | 0.02 | | 156 | 206 | 50 | 53 | −3 |
| | | | | 147 | 203 | 56 | | |
| SPONTANEOUSLY HYPERTENSIVE RATS n = 2 Body weight(s): 470,470 grams | | | | | | | | |
| CONTROL | | 0.01 | 0 | 147 | 191 | 44 | 46 | |
| | | | | 163 | 211 | 48 | | |
| | | 0.02 | | 154 | 212 | 58 | 61 | |
| | | | | 160 | 224 | 64 | | |
| Ex. No. 84 | 10 i.v. | 0.01 | 30 | 146 | 165 | 19 | 10.5 | 77 |
| | | | | 172 | 174 | 2 | | |
| | | 0.02 | | 152 | 168 | 16 | 14.5 | 76 |
| | | | | 159 | 172 | 13 | | |
| | | 0.01 | 60 | 152 | 167 | 15 | 16.5 | 64 |
| | | | | 154 | 172 | 18 | | |
| | | 0.02 | | 158 | 201 | 43 | 33.5 | 45 |
| | | | | 161 | 185 | 24 | | |
| | | 0.01 | 90 | 144 | 158 | 14 | 13 | 72 |
| | | | | 153 | 165 | 12 | | |
| | | 0.02 | | 152 | 173 | 21 | 26 | 57 |
| | | | | 156 | 187 | 31 | | |
| | | 0.01 | 120 | 150 | 166 | 16 | 19.5 | 58 |
| | | | | 143 | 166 | 23 | | |
| | | 0.02 | | 150 | 175 | 25 | 32.5 | 47 |
| | | | | 147 | 187 | 40 | | |
| | | 0.01 | 180 | 141 | 168 | 27 | 24.5 | 47 |
| | | | | 149 | 171 | 22 | | |
| | | 0.02 | | 148 | 170 | 22 | 31.5 | 48 |
| | | | | 148 | 189 | 41 | | |
| | | 0.01 | 240 | 131 | 154 | 23 | 26 | 43 |
| | | | | 143 | 172 | 29 | | |
| | | 0.02 | | 149 | 186 | 37 | 37 | 39 |
| | | | | 148 | 185 | 37 | | |
| | | 0.01 | 300 | 137 | 161 | 24 | 22.5 | 51 |
| | | | | 151 | 172 | 21 | | |
| | | 0.02 | | 148 | 193 | 45 | 43 | 30 |
| | | | | 150 | 191 | 41 | | |
| SPONTANEOUSLY HYPERTENSIVE RATS n = 2 Body weight(s): 600,490 grams | | | | | | | | |
| CONTROL | | 0.01 | 0 | 144 | 165 | 21 | 26.5 | |
| | | | | 127 | 159 | 32 | | |
| | | 0.02 | | 147 | 190 | 43 | 35.5 | |
| | | | | 137 | 165 | 28 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| Ex. No. 85 | 10 i.v. | 0.01 | 30 | 162 | 163 | 1 | 4.5 | 83 |
| | | | | 119 | 127 | 8 | | |
| | | 0.02 | | 156 | 166 | 10 | 9 | 75 |
| | | | | 130 | 138 | 8 | | |
| | | 0.01 | 60 | 156 | 162 | 6 | 7 | 74 |
| | | | | 124 | 132 | 8 | | |
| | | 0.02 | | 156 | 168 | 12 | 9.5 | 73 |
| | | | | 129 | 136 | 7 | | |
| | | 0.01 | 90 | 151 | 160 | 9 | 9.5 | 64 |
| | | | | 125 | 135 | 10 | | |
| | | 0.02 | | 143 | 150 | 7 | 7.5 | 79 |
| | | | | 124 | 132 | 8 | | |
| | | 0.01 | 120 | 145 | 152 | 7 | 9 | 66 |
| | | | | 123 | 134 | 11 | | |
| | | 0.02 | | 139 | 147 | 8 | 6.5 | 82 |
| | | | | 127 | 132 | 5 | | |
| | | 0.01 | 180 | 125 | 141 | 16 | 15.5 | 42 |
| | | | | 118 | 133 | 15 | | |
| | | 0.02 | | 129 | 147 | 18 | 19.5 | 45 |
| | | | | 106 | 127 | 21 | | |
| | | 0.01 | 240 | 129 | 144 | 15 | 12 | 55 |
| | | | | 107 | 116 | 9 | | |
| | | 0.02 | | 135 | 152 | 17 | 18 | 49 |
| | | | | 108 | 127 | 19 | | |
| | | 0.01 | 300 | 129 | 144 | 15 | 12 | 55 |
| | | | | 107 | 116 | 9 | | |
| | | 0.02 | | 135 | 152 | 17 | 18 | 49 |
| | | | | 108 | 127 | 19 | | |
| SPONTANEOUSLY HYPERTENSIVE RATS n = 2 Body weight(s): 540,530 grams | | | | | | | | |
| CONTROL | | 0.01 | 0 | 141 | 205 | 64 | 62.5 | |
| | | | | 138 | 199 | 61 | | |
| | | 0.02 | | 138 | 227 | 89 | 66.5 | |
| | | | | 143 | 187 | 44 | | |
| Ex. No. 87 | 10 i.v. | 0.01 | 30 | 136 | 210 | 74 | 50 | 20 |
| | | | | 145 | 171 | 26 | | |
| | | 0.02 | | 157 | 227 | 70 | 57 | 14 |
| | | | | 144 | 188 | 44 | | |
| Ex. No. 87 | 20 i.v. | 0.01 | 60 | 133 | 150 | 17 | 14.5 | 77 |
| | | | | 143 | 155 | 12 | | |
| | | 0.02 | | 150 | 191 | 41 | 32.5 | 51 |
| | | | | 143 | 167 | 24 | | |
| | | 0.01 | 90 | 140 | 163 | 23 | 24.5 | 61 |
| | | | | 141 | 167 | 26 | | |
| | | 0.02 | | 148 | 197 | 49 | 33.5 | 50 |
| | | | | 145 | 163 | 18 | | |
| | | 0.01 | 120 | 136 | 162 | 26 | 26 | 58 |
| | | | | 146 | 172 | 26 | | |
| | | 0.02 | | 152 | 196 | 44 | 35.5 | 47 |
| | | | | 150 | 177 | 27 | | |
| | | 0.01 | 180 | 130 | 163 | 33 | 26.5 | 58 |
| | | | | 139 | 159 | 20 | | |
| | | 0.02 | | 148 | 192 | 44 | 37.5 | 44 |
| | | | | 142 | 173 | 31 | | |
| | | 0.01 | 240 | 135 | 172 | 37 | 28.5 | 54 |
| | | | | 132 | 152 | 20 | | |
| | | 0.02 | | 136 | 191 | 55 | 41 | 38 |
| | | | | 133 | 160 | 27 | | |
| | | 0.01 | 300 | 140 | 177 | 37 | 30 | 52 |
| | | | | 128 | 151 | 23 | | |
| | | 0.02 | | 138 | 201 | 63 | 48.5 | 27 |
| | | | | 134 | 168 | 34 | | |
| SPONTANEOUSLY HYPERTENSIVE RATS n = 2 Body weight(s): 480,550 grams | | | | | | | | |
| CONTROL | | 0.01 | 0 | 149 | 178 | 29 | 40 | |
| | | | | 158 | 209 | 51 | | |
| | | 0.02 | | 150 | 213 | 63 | 62 | |
| | | | | 161 | 222 | 61 | | |
| Ex. No. 89 | 10 i.v. | 0.01 | 30 | 155 | 160 | 5 | 5 | 88 |
| | | | | 160 | 165 | 5 | | |
| | | 0.02 | | 160 | 170 | 10 | 5 | 92 |
| | | | | 160 | 160 | 0 | | |
| | | 0.01 | 60 | 160 | 170 | 10 | 7.5 | 81 |
| | | | | 160 | 165 | 5 | | |
| | | 0.02 | | 155 | 170 | 15 | 10 | 84 |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 175 | 180 | 5 | | |
| | | 0.01 | 90 | 150 | 155 | 5 | 7.5 | 81 |
| | | | | 160 | 170 | 10 | | |
| | | 0.02 | | 150 | 165 | 15 | 12.5 | 80 |
| | | | | 160 | 170 | 10 | | |
| | | 0.01 | 120 | 140 | 155 | 15 | 15 | 63 |
| | | | | 155 | 170 | 15 | | |
| | | 0.02 | | 140 | 170 | 30 | 27.5 | 56 |
| | | | | 155 | 180 | 25 | | |
| | | 0.01 | 180 | 135 | 160 | 25 | 25 | 38 |
| | | | | 155 | 180 | 25 | | |
| | | 0.02 | | 140 | 170 | 30 | 32.5 | 48 |
| | | | | 155 | 190 | 35 | | |
| | | 0.01 | 240 | 135 | 160 | 25 | 25 | 38 |
| | | | | 155 | 180 | 25 | | |
| | | 0.02 | | 140 | 170 | 30 | 35 | 44 |
| | | | | 150 | 190 | 40 | | |
| | | 0.01 | 300 | 130 | 155 | 25 | 27.5 | 31 |
| | | | | 150 | 180 | 30 | | |
| | | 0.02 | | 135 | 170 | 35 | 32.5 | 48 |
| | | | | 160 | 190 | 30 | | |
| SPONTANEOUSLY HYPERTENSIVE RATS n = 2 Body weight(s): 610,600 grams | | | | | | | | |
| CONTROL | | 0.01 | 0 | 144 | 190 | 46 | 48.5 | |
| | | | | 154 | 205 | 51 | | |
| | | 0.02 | | 150 | 220 | 70 | 62.5 | |
| | | | | 160 | 215 | 55 | | |
| Ex. No. 91 | 10 i.v. | 0.01 | 30 | 145 | 150 | 5 | 5 | 90 |
| | | | | 150 | 155 | 5 | | |
| | | 0.02 | | 150 | 160 | 10 | 7.5 | 88 |
| | | | | 150 | 155 | 5 | | |
| | | 0.01 | 60 | 157 | 160 | 3 | 6.5 | 87 |
| | | | | 155 | 165 | 10 | | |
| | | 0.02 | | 150 | 158 | 8 | 7 | 89 |
| | | | | 155 | 161 | 6 | | |
| | | 0.01 | 90 | 155 | 165 | 10 | 9 | 81 |
| | | | | 152 | 160 | 8 | | |
| | | 0.02 | | 150 | 165 | 15 | 12.5 | 80 |
| | | | | 150 | 160 | 10 | | |
| | | 0.01 | 120 | 150 | 170 | 20 | 13 | 73 |
| | | | | 140 | 146 | 6 | | |
| | | 0.02 | | 148 | 165 | 17 | 17.5 | 72 |
| | | | | 142 | 160 | 18 | | |
| | | 0.01 | 180 | 142 | 164 | 22 | 22 | 55 |
| | | | | 143 | 165 | 22 | | |
| | | 0.02 | | 149 | 167 | 18 | 29 | 54 |
| | | | | 145 | 185 | 40 | | |
| | | 0.01 | 240 | 146 | 165 | 19 | 20 | 59 |
| | | | | 129 | 150 | 21 | | |
| | | 0.02 | | 147 | 189 | 42 | 29.5 | 53 |
| | | | | 135 | 152 | 17 | | |
| | | 0.01 | 300 | 146 | 164 | 18 | 16.5 | 66 |
| | | | | 146 | 161 | 15 | | |
| | | 0.02 | | 144 | 167 | 23 | 32.5 | 48 |
| | | | | 147 | 189 | 42 | | |
| SPONTANEOUSLY HYPERTENSIVE RATS n = 2 Body weight(s): 560,630 grams | | | | | | | | |
| CONTROL | | 0.01 | 0 | 158 | 203 | 45 | 49.5 | |
| | | | | 154 | 208 | 54 | | |
| | | 0.02 | | 159 | 228 | 69 | 72 | |
| | | | | 160 | 235 | 75 | | |
| Ex. No. 93 | 10 i.v. | 0.01 | 30 | 160 | 162 | 2 | 2 | 96 |
| | | | | 139 | 141 | 2 | | |
| | | 0.02 | | 157 | 162 | 5 | 4.5 | 94 |
| | | | | 163 | 167 | 4 | | |
| | | 0.01 | 60 | 154 | 154 | 0 | 3 | 94 |
| | | | | 163 | 169 | 6 | | |
| | | 0.02 | | 161 | 166 | 5 | 5.5 | 92 |
| | | | | 164 | 170 | 6 | | |
| | | 0.01 | 90 | 150 | 155 | 5 | 5 | 90 |
| | | | | 163 | 168 | 5 | | |
| | | 0.02 | | 154 | 162 | 8 | 7 | 90 |
| | | | | 161 | 167 | 6 | | |
| | | 0.01 | 120 | 151 | 156 | 5 | 6 | 88 |
| | | | | 158 | 160 | 7 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.02 | | 155 | 160 | 5 | 7 | 90 |
| | | | | 160 | 169 | 9 | | |
| | | 0.01 | 180 | 151 | 161 | 10 | 13.5 | 73 |
| | | | | 151 | 168 | 17 | | |
| | | 0.02 | | 151 | 164 | 13 | 15.5 | 78 |
| | | | | 155 | 173 | 18 | | |
| | | 0.01 | 240 | 145 | 158 | 13 | 13 | 74 |
| | | | | 156 | 169 | 13 | | |
| | | 0.02 | | 148 | 166 | 18 | 17 | 76 |
| | | | | 158 | 174 | 16 | | |
| | | 0.01 | 300 | 146 | 158 | 12 | 12 | 76 |
| | | | | 156 | 168 | 12 | | |
| | | 0.02 | | 144 | 162 | 18 | 18.5 | 74 |
| | | | | 154 | 173 | 19 | | |
| SPONTANEOUSLY HYPERTENSIVE RATS n = 2 Body weight(s): 580,480 grams | | | | | | | | |
| CONTROL | | 0.01 | 0 | 155 | 202 | 47 | 45.5 | |
| | | | | 165 | 209 | 44 | | |
| | | 0.02 | | 160 | 225 | 65 | 61 | |
| | | | | 172 | 229 | 57 | | |
| Ex. No. 95 | 10 i.v. | 0.01 | 30 | 163 | 193 | 30 | 29.5 | 35 |
| | | | | 168 | 197 | 29 | | |
| | | 0.02 | | 170 | 225 | 55 | 56 | 8 |
| | | | | 170 | 227 | 57 | | |
| Ex. No. 95 | 20 i.v. | 0.01 | 60 | 154 | 171 | 17 | 15 | 67 |
| | | | | 156 | 169 | 13 | | |
| | | 0.02 | | 160 | 177 | 17 | 19.5 | 68 |
| | | | | 162 | 184 | 22 | | |
| | | 0.01 | 90 | 154 | 168 | 14 | 13.5 | 70 |
| | | | | 167 | 180 | 13 | | |
| | | 0.02 | | 158 | 177 | 19 | 24 | 61 |
| | | | | 164 | 193 | 29 | | |
| | | 0.01 | 120 | 147 | 167 | 20 | 24 | 47 |
| | | | | 161 | 189 | 28 | | |
| | | 0.02 | | 153 | 174 | 21 | 28.5 | 53 |
| | | | | 161 | 197 | 36 | | |
| | | 0.01 | 180 | 146 | 168 | 22 | 23.5 | 48 |
| | | | | 156 | 181 | 25 | | |
| | | 0.02 | | 154 | 189 | 35 | 34 | 44 |
| | | | | 161 | 194 | 33 | | |
| | | 0.01 | 240 | 151 | 168 | 17 | 21.5 | 53 |
| | | | | 154 | 180 | 26 | | |
| | | 0.02 | | 153 | 189 | 36 | 34 | 44 |
| | | | | 165 | 197 | 32 | | |
| | | 0.01 | 300 | 142 | 165 | 23 | 24.5 | 46 |
| | | | | 151 | 177 | 26 | | |
| | | 0.02 | | 148 | 193 | 45 | 37.5 | 39 |
| | | | | 163 | 193 | 30 | | |
| SPONTANEOUSLY HYPERTENSIVE RATS n = 2 Body weight(s): 470,470 grams | | | | | | | | |
| CONTROL | | 0.01 | 0 | 134 | 163 | 29 | 32.5 | |
| | | | | 144 | 180 | 36 | | |
| | | 0.02 | | 137 | 193 | 56 | 57.5 | |
| | | | | 153 | 212 | 59 | | |
| Ex. No. 96 | 10 i.v. | 0.01 | 30 | 144 | 157 | 13 | 11.5 | 65 |
| | | | | 143 | 153 | 10 | | |
| | | 0.02 | | 139 | 150 | 11 | 19.5 | 66 |
| | | | | 148 | 176 | 28 | | |
| | | 0.01 | 60 | 141 | 149 | 8 | 7 | 78 |
| | | | | 149 | 155 | 6 | | |
| | | 0.02 | | 140 | 155 | 15 | 12.5 | 78 |
| | | | | 148 | 158 | 10 | | |
| | | 0.01 | 90 | 133 | 148 | 15 | 13.5 | 58 |
| | | | | 148 | 160 | 12 | | |
| | | 0.02 | | 136 | 151 | 15 | 16 | 72 |
| | | | | 146 | 163 | 17 | | |
| | | 0.01 | 120 | 134 | 148 | 14 | 13.5 | 58 |
| | | | | 146 | 159 | 13 | | |
| | | 0.02 | | 137 | 151 | 14 | 17.5 | 70 |
| | | | | 148 | 169 | 21 | | |
| | | 0.01 | 180 | 136 | 153 | 17 | 15.5 | 52 |
| | | | | 140 | 154 | 14 | | |
| | | 0.02 | | 139 | 153 | 14 | 16 | 72 |
| | | | | 136 | 154 | 18 | | |
| | | 0.01 | 240 | 133 | 152 | 19 | 18.5 | 43 |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 138 | 156 | 18 | | |
| | | 0.02 | | 136 | 173 | 37 | 39.5 | 31 |
| | | | | 145 | 187 | 42 | | |
| | | 0.01 | 300 | 138 | 154 | 16 | 15.5 | 52 |
| | | | | 137 | 152 | 15 | | |
| | | | | 147 | 184 | 37 | 42 | 27 |
| | | | | 138 | 185 | 47 | | |
| SPONTANEOUSLY HYPERTENSIVE RATS n = 2 Body weight(s): 500,440 grams | | | | | | | | |
| CONTROL | | 0.01 | 0 | 158 | 181 | 23 | 29 | |
| | | | | 148 | 183 | 35 | | |
| | | 0.02 | | 161 | 198 | 37 | 48 | |
| | | | | 151 | 210 | 59 | | |
| Ex. No. 116 | 10 i.v. | 0.01 | 30 | 160 | 181 | 21 | 22.5 | 22 |
| | | | | 162 | 186 | 24 | | |
| | | 0.02 | | 160 | 191 | 31 | 36.5 | 24 |
| | | | | 156 | 198 | 42 | | |
| | | 0.01 | 60 | 158 | 180 | 22 | 18 | 38 |
| | | | | 156 | 170 | 14 | | |
| | | 0.02 | | 160 | 197 | 37 | 33.5 | 30 |
| | | | | 160 | 190 | 30 | | |
| | | 0.01 | 90 | 159 | 182 | 23 | 19 | 34 |
| | | | | 157 | 172 | 15 | | |
| | | 0.02 | | 163 | 201 | 38 | 32 | 33 |
| | | | | 162 | 188 | 26 | | |
| | | 0.01 | 120 | 157 | 175 | 18 | 19.5 | 33 |
| | | | | 158 | 179 | 21 | | |
| | | 0.02 | | 154 | 203 | 49 | 40 | 17 |
| | | | | 167 | 198 | 31 | | |
| | | 0.01 | 180 | 153 | 170 | 17 | 18 | 38 |
| | | | | 157 | 176 | 19 | | |
| | | 0.02 | | 155 | 201 | 46 | 40 | 17 |
| | | | | 176 | 210 | 34 | | |
| | | 0.01 | 240 | 153 | 169 | 16 | 16 | 45 |
| | | | | 156 | 172 | 16 | | |
| | | 0.02 | | 152 | 188 | 36 | 38.5 | 20 |
| | | | | 156 | 197 | 41 | | |
| | | 0.01 | 300 | 153 | 176 | 23 | 22 | 24 |
| | | | | 127 | 148 | 21 | | |
| | | 0.02 | | 154 | 205 | 51 | 41.5 | 14 |
| | | | | 163 | 195 | 32 | | |
| SPONTANEOUSLY HYPERTENSIVE RATS n = 2 Body weight(s): 460,570 grams | | | | | | | | |
| CONTROL | | 0.01 | 0 | 146 | 184 | 38 | 36.5 | |
| | | | | 156 | 191 | 35 | | |
| | | 0.01 | | 146 | 210 | 64 | 56.5 | |
| | | | | 160 | 209 | 49 | | |
| Ex. No. 117 | 10 i.v. | 0.01 | 30 | 154 | 195 | 41 | 36 | 1 |
| | | | | 162 | 193 | 31 | | |
| | | 0.02 | | 154 | 220 | 66 | 63 | −12 |
| | | | | 162 | 222 | 60 | | |
| | 20 i.v. | 0.01 | 60 | 154 | 182 | 28 | 36 | 1 |
| | | | | 164 | 208 | 44 | | |
| | | 0.02 | | 157 | 197 | 40 | 40 | 29 |
| | | | | 173 | 213 | 40 | | |
| | | 0.01 | 90 | 158 | 174 | 16 | 22.5 | 38 |
| | | | | 162 | 191 | 29 | | |
| | | 0.02 | | 160 | 208 | 48 | 46 | 19 |
| | | | | 165 | 209 | 44 | | |
| | | 0.01 | 120 | 151 | 171 | 20 | 23 | 37 |
| | | | | 154 | 180 | 26 | | |
| | | 0.02 | | 150 | 183 | 33 | 38 | 33' |
| | | | | 158 | 201 | 43 | | |
| | | 0.01 | 180 | 141 | 168 | 27 | 26.5 | 27 |
| | | | | 150 | 176 | 26 | | |
| | | 0.02 | | 143 | 185 | 42 | 46 | 19 |
| | | | | 151 | 201 | 50 | | |
| | | 0.01 | 240 | 139 | 168 | 29 | 25 | 32 |
| | | | | 146 | 167 | 21 | | |
| | | 0.02 | | 143 | 175 | 32 | 40.5 | 28 |
| | | | | 146 | 195 | 49 | | |
| | | 0.01 | 300 | 137 | 164 | 27 | 26 | 29 |
| | | | | 149 | 174 | 25 | | |
| | | | | 144 | 183 | 39 | 42.5 | 25 |
| | | | | 149 | 195 | 46 | | |

TABLE XV-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| SPONTANEOUSLY HYPERTENSIVE RATS n = 2 Body weight(s): 570,460 grams | | | | | | | | |
| CONTROL | | 0.01 | 0 | 135 | 171 | 36 | 34.5 | |
| | | | | 121 | 154 | 33 | | |
| | | 0.02 | | 138 | 184 | 46 | 47.5 | |
| | | | | 156 | 205 | 49 | | |
| Ex. No. 157 | 10 i.v. | 0.01 | 30 | 136 | 175 | 39 | 26 | 25 |
| | | | | 152 | 165 | 13 | | |
| | | 0.02 | | 148 | 199 | 51 | 38 | 20 |
| | | | | 153 | 178 | 25 | | |
| | | 0.01 | 60 | 150 | 179 | 29 | 26.5 | 23 |
| | | | | 135 | 159 | 24 | | |
| | | 0.02 | | 160 | 191 | 31 | 31.5 | 34 |
| | | | | 153 | 185 | 32 | | |
| | | 0.01 | 90 | 145 | 167 | 22 | 21 | 39 |
| | | | | 161 | 181 | 20 | | |
| | | 0.02 | | 148 | 185 | 37 | 40 | 16 |
| | | | | 152 | 195 | 43 | | |
| | | 0.01 | 120 | 136 | 161 | 25 | 26.5 | 23 |
| | | | | 138 | 166 | 20 | | |
| | | 0.02 | | 140 | 183 | 43 | 39.5 | 17 |
| | | | | 150 | 186 | 36 | | |
| | | 0.01 | 180 | 131 | 164 | 33 | 32.5 | 6 |
| | | | | 132 | 164 | 32 | | |
| | | 0.02 | | 137 | 185 | 48 | 52 | −9 |
| | | | | 140 | 196 | 56 | | |
| | | 0.01 | 240 | 140 | 167 | 27 | 28.5 | 17 |
| | | | | 155 | 185 | 30 | | |
| | | 0.02 | | 138 | 167 | 29 | 35.5 | 25 |
| | | | | 143 | 185 | 42 | | |
| | | 0.01 | 300 | 138 | 162 | 24 | 25.5 | 26 |
| | | | | 141 | 168 | 27 | | |
| | | 0.02 | | 146 | 176 | 30 | 40 | 16 |
| | | | | 156 | 206 | 50 | | |
| SPONTANEOUSLY HYPERTENSIVE RATS n = 2 Body weight(s): 400,470 grams | | | | | | | | |
| CONTROL | | 0.01 | 0 | 146 | 191 | 45 | 41 | |
| | | | | 161 | 198 | 37 | | |
| | | 0.02 | | 157 | 207 | 50 | 50 | |
| | | | | 163 | 213 | 50 | | |
| Ex. No. 357 | 10 i.v. | 0.01 | 30 | 144 | 159 | 15 | 16.5 | 60 |
| | | | | 167 | 185 | 18 | | |
| | | 0.02 | | 145 | 169 | 24 | 16 | 68 |
| | | | | 164 | 172 | 8 | | |
| | | 0.01 | 60 | 156 | 160 | 4 | 4.5 | 89 |
| | | | | 164 | 169 | 5 | | |
| | | 0.02 | | 145 | 159 | 14 | 10.5 | 79 |
| | | | | 164 | 171 | 7 | | |
| | | 0.01 | 90 | 142 | 153 | 11 | 8 | 80 |
| | | | | 167 | 172 | 5 | | |
| | | 0.02 | | 143 | 154 | 11 | 10.5 | 79 |
| | | | | 168 | 178 | 10 | | |
| | | 0.01 | 120 | 140 | 151 | 11 | 8 | 80 |
| | | | | 165 | 170 | 5 | | |
| | | 0.02 | | 136 | 139 | 3 | 6 | 88 |
| | | | | 165 | 174 | 9 | | |
| | | 0.01 | 180 | 147 | 154 | 7 | 9.5 | 77 |
| | | | | 162 | 174 | 12 | | |
| | | 0.02 | | 142 | 154 | 12 | 11 | 78 |
| | | | | 162 | 172 | 10 | | |
| | | 0.01 | 240 | 145 | 169 | 14 | 14 | 66 |
| | | | | 159 | 173 | 14 | | |
| | | | | 157 | 175 | 17 | 14.5 | 71 |
| | | | | 160 | 172 | 12 | | |
| | | 0.01 | 300 | 148 | 164 | 16 | 16 | 61 |
| | | | | 151 | 167 | 16 | | |
| | | 0.02 | | 148 | 169 | 21 | 16 | 68 |
| | | | | 158 | 169 | 11 | | |
| SPONTANEOUSLY HYPERTENSIVE RATS n = 2 Body weight(s): 500,460 grams | | | | | | | | |
| CONTROL | | 0.01 | 0 | 139 | 190 | 51 | 36.5 | |
| | | | | 159 | 181 | 22 | | |
| | | 0.02 | | 155 | 212 | 57 | 39.5 | |
| | | | | 166 | 188 | 22 | | |
| Ex. No. 358 | 10 i.v. | 0.01 | 30 | 147 | 163 | 16 | 12 | 67 |
| | | | | 161 | 169 | 8 | | |

TABLE XV-continued

VASOPRESSIN (VAS) VASOPRESSOR RESPONSE

| Dose (mg/kg) | VAS Dose i.u./kg I.V. | Min Post Dose | Control Before VAS | Response After VAS | Change | Average Change | % Inhibition |
|---|---|---|---|---|---|---|---|
| | 0.02 | | 149 | 169 | 20 | 24 | 39 |
| | | | 162 | 190 | 28 | | |
| | 0.01 | 60 | 145 | 153 | 8 | 13 | 64 |
| | | | 153 | 171 | 18 | | |
| | 0.02 | | 142 | 155 | 13 | 10 | 75 |
| | | | 160 | 167 | 7 | | |
| | 0.01 | 90 | 142 | 157 | 25 | 17.5 | 52 |
| | | | 156 | 166 | 10 | | |
| | 0.02 | | 148 | 161 | 13 | 11 | 72 |
| | | | 161 | 170 | 9 | | |
| | 0.01 | 120 | 144 | 153 | 9 | 8 | 78 |
| | | | 159 | 166 | 7 | | |
| | 0.02 | | 139 | 155 | 16 | 14 | 65 |
| | | | 155 | 167 | 12 | | |
| | 0.01 | 180 | 134 | 158 | 24 | 17.5 | 52 |
| | | | 147 | 158 | 11 | | |
| | 0.02 | | 146 | 162 | 16 | 14.5 | 63 |
| | | | 154 | 167 | 13 | | |
| | 0.01 | 240 | 139 | 153 | 14 | 12 | 67 |
| | | | 143 | 153 | 10 | | |
| | 0.02 | | 144 | 162 | 18 | 15.5 | 61 |
| | | | 145 | 158 | 13 | | |
| | 0.01 | 300 | 137 | 163 | 26 | 19 | 48 |
| | | | 137 | 149 | 12 | | |
| | 0.02 | | 140 | 158 | 18 | 16 | 59 |
| | | | 141 | 155 | 14 | | |
| SPONTANEOUSLY HYPERTENSIVE RATS n = 2 Body weight(s): 520,515 grams | | | | | | | |
| CONTROL | 0.01 | 0 | 141 | 165 | 24 | 23.5 | |
| | | | 145 | 168 | 23 | | |
| | 0.02 | | 145 | 182 | 37 | 37 | |
| | | | 153 | 190 | 37 | | |
| Ex. No. 384  10 i.v. | 0.01 | 30 | 145 | 157 | 12 | 9 | 62 |
| | | | 156 | 162 | 6 | | |
| | 0.02 | | 150 | 168 | 18 | 14.5 | 61 |
| | | | 158 | 169 | 11 | | |
| | 0.01 | 60 | 151 | 160 | 9 | 9 | 62 |
| | | | 158 | 167 | 9 | | |
| | 0.02 | | 152 | 162 | 10 | 10.5 | 72 |
| | | | 160 | 171 | 11 | | |
| | 0.01 | 90 | 154 | 170 | 16 | 12 | 49 |
| | | | 160 | 168 | 8 | | |
| | 0.02 | | 157 | 177 | 20 | 15.5 | 58 |
| | | | 162 | 173 | 11 | | |
| | 0.01 | 120 | 149 | 159 | 10 | 10.5 | 55 |
| | | | 131 | 142 | 11 | | |
| | 0.02 | | 150 | 162 | 12 | 11.5 | 69 |
| | | | 164 | 175 | 11 | | |
| | 0.01 | 180 | 150 | 162 | 12 | 11 | 53 |
| | | | 158 | 168 | 10 | | |
| | 0.02 | | 156 | 167 | 11 | 13.5 | 64 |
| | | | 160 | 176 | 16 | | |
| | 0.01 | 240 | 145 | 156 | 11 | 11 | 53 |
| | | | 155 | 166 | 11 | | |
| | 0.02 | | 145 | 161 | 16 | 15 | 59 |
| | | | 160 | 174 | 14 | | |
| | 0.01 | 300 | 148 | 162 | 14 | 12 | 49 |
| | | | 152 | 162 | 10 | | |
| | 0.02 | | 151 | 168 | 17 | 17 | 54 |
| | | | 158 | 175 | 17 | | |
| SPONTANEOUSLY HYPERTENSIVE RATS n = 2 Body weight(s): 455,500 grams | | | | | | | |
| CONTROL | 0.01 | 0 | 96 | 135 | 39 | 36 | |
| | | | 151 | 184 | 33 | | |
| | 0.02 | | 131 | 154 | 23 | 36 | |
| | | | 158 | 207 | 49 | | |
| Ex. No. 407  10 i.v. | 0.01 | 30 | 120 | 131 | 11 | 9.5 | 74 |
| | | | 150 | 158 | 8 | | |
| | 0.02 | | 132 | 142 | 10 | 13 | 64 |
| | | | 153 | 169 | 16 | | |
| | 0.01 | 60 | 112 | 139 | 27 | 25.5 | 29 |
| | | | 150 | 174 | 24 | | |
| | 0.02 | | 128 | 131 | 3 | 10 | 72 |
| | | | 154 | 174 | 24 | | |
| | 0.01 | 90 | 90 | 114 | 24 | 19 | 47 |

TABLE XV-continued

VASOPRESSIN (VAS) VASOPRESSOR RESPONSE

| Dose (mg/kg) | VAS Dose i.u./kg I.V. | Min Post Dose | Control Before VAS | Response After VAS | Change | Average Change | % Inhibition |
|---|---|---|---|---|---|---|---|
| | | | 152 | 166 | 14 | | |
| | 0.02 | | 87 | 122 | 35 | 26.5 | 26 |
| | | | 154 | 172 | 18 | | |
| | 0.01 | 120 | 120 | 127 | 7 | 8.5 | 76 |
| | | | 145 | 155 | 10 | | |
| | 0.02 | | 113 | 127 | 14 | 17 | 53 |
| | | | 147 | 167 | 20 | | |
| | 0.01 | 180 | 112 | 124 | 12 | 11.5 | 68 |
| | | | 141 | 152 | 11 | | |
| | 0.02 | | 109 | 129 | 20 | 20 | 44 |
| | | | 139 | 159 | 20 | | |
| | 0.01 | 240 | 114 | 130 | 16 | 18 | 50 |
| | | | 131 | 151 | 20 | | |
| | 0.02 | | 120 | 136 | 16 | 21.5 | 40 |
| | | | 142 | 169 | 27 | | |
| | 0.01 | 300 | 115 | 130 | 15 | 20 | 44 |
| | | | 130 | 155 | 25 | | |
| | 0.02 | | 116 | 137 | 21 | 22.5 | 38 |
| | | | 136 | 160 | 24 | | |

SPONTANEOUSLY HYPERTENSIVE RATS n = 2 Body weight(s): 470,550 grams

TABLE XVI

VASOPRESSIN (VAS) VASOPRESSOR RESPONSE

| Ex. No. | Dose mg/kg | Max. % Inhibition | Time (min) |
|---|---|---|---|
| 2 | 30 i.v. | 74 | 120 |
| 9 | 10 i.v. | 95 | 60 |
| 17 | 30 i.v. | 50 | 60 |
| 36 | 30 i.v. | 71 | 60 |
| 99 | 10 i.v. | 76 | 120 |
| 210 | 10 i.v. | 78 | 90 |
| 217 | 30 i.v. | 57 | 90 |
| 271 | 10 i.v. | 56 | 60 |
| 274 | 10 i.v. | 59 | 300 |
| 465 | 10 i.v. | 85 | 90 |
| 466 | 30 i.v. | 94 | 94 |
| 467 | 10 i.v. | 65 | 120 |
| 468 | 10 i.v. | 68 | 30 |
| 469 | 10 i.v. | 69 | 30 |
| 470 | 10 i.v. | 87 | 180 |
| | 30 p.o. | 69 | 180 |
| 471 | 30 i.v. | 85 | 90 |
| 472 | 30 i.v. | 36 | 90 |
| 474 | 30 i.v. | 80 | 60 |
| 476 | 10 i.v. | 78 | 30 |
| | 30 p.o. | 19 | 180 |
| 477 | 10 i.v. | 88 | 180 |
| | 30 p.o. | 82 | 30 |
| 478 | 10 i.v. | 76 | 120 |
| 479 | 10 i.v. | 83 | 60 |
| | 30 p.o. | 69 | 90 |
| 480 | 10 i.v. | 29 | 300 |
| 481 | 30 p.o. | 58 | 80 |
| 482 | 10 i.v. | 40 | 60 |
| 484 | 10 i.v. | 79 | 300 |
| | 30 p.o. | 22 | 180 |
| 485 | 30 i.v. | 64 | 60 |
| 488 | 30 i.v. | 43 | 60 |
| 489 | 30 i.v. | 39 | 120 |
| 490 | 10 i.v. | 74 | 90 |
| | 10 p.o. | 65 | 120 |
| 517 | 10 i.v. | 81 | 90 |
| 525 | 30 i.v. | 70 | 60 |
| 527 | 30 i.v. | 85 | 180 |
| 528 | 30 i.v. | 66 | 300 |
| 530 | 30 i.v. | 89 | 120 |
| 581 | 10 i.v. | 94 | 30 |
| | 30 p.o. | 79 | 30 |
| 582 | 10 i.v. | 75 | 180 |
| 585 | 10 i.v. | 56 | 30 |
| 587 | 10 i.v. | 75 | 60 |
| 588 | 10 i.v. | 65 | 90 |
| | 30 p.o. | 80 | 120 |
| 590 | 30 i.v. | 89 | 120 |
| 592 | 30 i.v. | 37 | 90 |
| 593 | 30 i.v. | 67 | 60 |
| 594 | 30 i.v. | 36 | 180 |
| 595 | 30 i.v. | 44 | 90 |
| 599 | 30 i.v. | 86 | 90 |
| 600 | 30 i.v. | 78 | 60 |

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000×g for 10 min. The clear supernatant is removed and recentrifuged at 165,000×g for 30 min. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM MgCl$_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 min., at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites (IC$_{50}$) are calculated by a computer assisted LUNDON-2 program (LUNDON SOFTWARE INC., Ohio, USA).

The results of this assay on representative examples are shown in Table XVII.

TABLE XVII

| | Oxytocin | | |
|---|---|---|---|
| Ex. No. | Dose (μM) | % Inhibition at 10 μM | IC$_{50}$ |
| 3 | 10 | 90 | 0.36 |
| 4 | 10 | 98 | 0.66 |
| 6 | 10 | 92 | 0.35 |
| 7 | 10 | 97 | 0.13 |
| 17 | 10 | 31 | |
| 36 | 10 | 67 | 2.45 |
| 54 | 10 | 94 | 0.16 |
| 85 | 10 | 98 | 0.46 |
| 93 | 10 | 87 | 0.06 |
| 96 | 10 | 94 | 1.2 |
| 160 | 10 | 31 | |
| 164 | 10 | 67 | 2.45 |
| 210 | 10 | 64 | 4 |
| 214 | 10 | 64 | 4 |
| 215 | 10 | 74 | 0.57 |
| 217 | 10 | 87 | 1.2 |
| 274 | 10 | 95 | 1 |
| 297 | 10 | 76 | 4 |
| 298 | 10 | 76 | 4 |
| 416 | 10 | 44.6 | 7.4 |
| 417 | 10 | 21 | |
| 418 | 10 | 39 | |
| 419 | 10 | 28 | |
| 420 | 10 | 16 | |
| 429 | 10 | 11 | |
| 430 | 10 | 16 | |
| 431 | 10 | 18 | |
| 432 | 10 | 19 | |
| 433 | 10 | 12 | |
| 435 | 10 | 10 | |
| 436 | 10 | 32 | |
| 441 | 1 | 22 | |
| 443 | 10 | 70 | |
| 444 | 10 | 21 | |
| 448 | 10 | 11 | |
| 449 | 10 | 14 | |
| 450 | 10 | 22 | |
| 451 | 10 | 43 | |
| 452 | 10 | 36 | |
| 455 | 10 | 75 | 2.9 |
| 460 | 10 | 77 | 3.1 |
| 461 | 10 | 44.6 | 7.4 |
| 462 | 10 | 14 | |
| 463 | 10 | 55 | 8.5 |
| 464 | 10 | 71 | 2.4 |
| 465 | 10 | 93 | 0.033 |
| 468 | 10 | 96 | 0.26 |
| 469 | 10 | 96 | 0.265 |
| 470 | 2.5 | 92 | 0.22 |
| 471 | 10 | 99 | 0.35 |
| 472 | 10 | 0 | |
| 473 | 10 | 20 | |
| 474 | 10 | 18 | |
| 476 | 10 | 94 | 0.82 |

TABLE XVII-continued

| | Oxytocin | | |
|---|---|---|---|
| Ex. No. | Dose (μM) | % Inhibition at 10 μM | IC$_{50}$ |
| 477 | 1.25 | 97 | 0.029 |
| 478 | 1.25 | 97 | 0.04 |
| 479 | 10 | 76 | 0.15 |
| 480 | 10 | 98 | 0.15 |
| 481 | 10 | 88 | 0.24 |
| 482 | 10 | 97 | 0.126 |
| 485 | 10 | 86 | 2.2 |
| 486 | 10 | 18 | |
| 489 | 10 | 44 | |
| 490 | 10 | 99 | 0.3 |
| 491 | 10 | 46 | |
| 517 | 10 | 91 | 0.32 |
| 519 | 10 | 97 | 0.48 |
| 520 | 10 | 79 | 2.2 |
| 524 | 10 | 84 | 1.8 |
| 525 | 10 | 98 | 0.28 |
| 526 | 10 | 97 | 0.47 |
| 527 | 10 | 92 | 0.45 |
| 528 | 10 | 90 | 1.17 |
| 529 | 10 | 92 | 0.45 |
| 530 | 10 | 99 | 0.31 |
| 538 | 10 | 90 | 0.9 |
| 546 | 10 | 91 | 0.99 |
| 547 | 5 | 97 | 0.26 |
| 580 | 10 | 79 | 2.96 |
| 581 | 10 | 99 | 0.2 |
| 582 | 10 | 96 | 0.675 |
| 583 | 10 | 61 | 4 |
| 584 | 10 | 26 | |
| 585 | 10 | 70 | 4.7 |
| 586 | 10 | 61 | 4.7 |
| 587 | 10 | 56 | 8 |
| 588 | 10 | 90 | 2 |
| 589 | 10 | 79 | 2.9 |
| 590 | 10 | 12 | |
| 591 | 10 | 29 | |
| 592 | 10 | 41 | |
| 593 | 10 | 82 | 1.1 |
| 594 | 10 | 19 | |
| 595 | 10 | 49 | |
| 596 | 10 | 86 | 4 |
| 597 | 10 | 42 | |
| 598 | 10 | 2 | |
| 599 | 10 | 92 | 0.35 |
| 609 | 10 | 66 | 2.7 |
| 664 | 10 | 95 | 1.4 |
| 665 | 10 | 97 | 1 |
| 666 | 10 | 83 | 2.1 |
| 667 | 10 | 89 | 1.6 |
| 676 | 10 | 32 | |

The compounds of the present invention can be used in the form of salts derived from pharmaceutically or physiologically acceptable acids or bases. These salts include but are not limited to the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo. When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol(e.g., glycerol, propylene glycol and liquid polyethylene glycol), suitable mixtures thereof, and vegetable oils.

We claim:

1. A compound selected from Formula I:

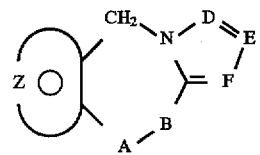

Formula I wherein;

A—B is $$-(CH_2)-\underset{R_3}{N}- \quad \text{or} \quad -\underset{R_3}{N}-(CH_2)-$$

the moiety

represents a fused thiophene or fused substituted thiophene optionally substituted by one or two substituents selected from ($C_1$–$C_3$) lower alkyl, halogen, or ($C_1$–$C_3$) lower alkoxy;

the moiety:

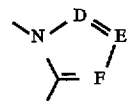

is a five-membered aromatic (unsaturated) fused nitrogen-containing heterocyclic ring wherein D is carbon or nitrogen, E, and F are carbon and wherein the carbon atoms may be optionally substituted by a substituent selected from halogen, ($C_1$–$C_3$) lower alkyl, hydroxy, $COCCl_3$, $COCF_3$,

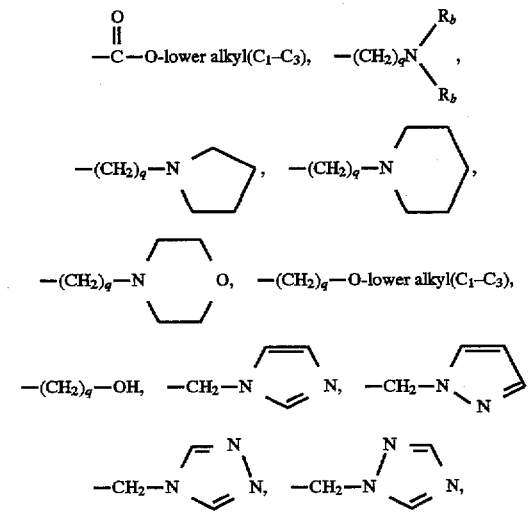

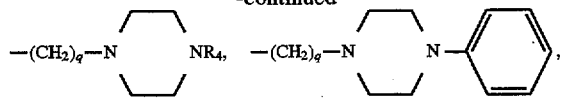

—CHO, amino, ($C_1$–$C_3$) lower alkoxy, ($C_1$–$C_3$) lower alkylamino, CONH ($C_1$–$C_3$) lower alkyl, or-CON[lower alkyl ($C_1$–$C_3$)]$_2$, $R_b$ is independently selected from H, —CH$_3$, or —C$_2$H$_5$;

q is 1 or 2;

$R_3$ is the moiety

—CAr wherein Ar is a moiety selected from the group

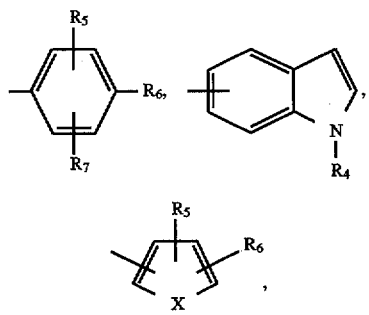

and X is selected from O, S, NH, —NCH$_3$, or —N—COCH$_3$;

$R_4$ is selected from H, lower alkyl ($C_1$–$C_3$), —CO-lower alkyl ($C_1$–$C_3$), SO$_2$ lower alkyl ($C_1$–$C_3$), or the moieties of the formulae:

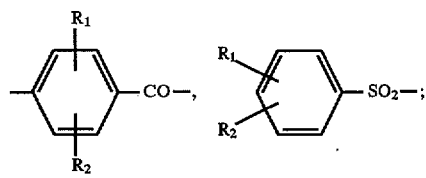

$R_1$ and $R_2$ are, independently, H, ($C_1$–$C_3$) lower alkyl, ($C_1$–$C_3$) lower alkoxy, or halogen;

$R_5$ is H, ($C_1$–$C_3$) lower alkyl, ($C_1$–$C_3$) lower alkoxy or halogen;

$R_6$=is selected from:

(a) moieties of the formula:

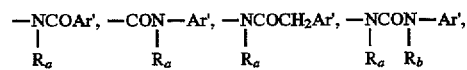

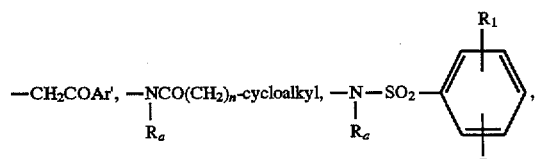

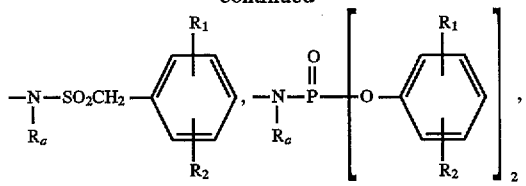

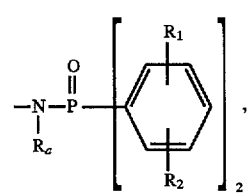

—NH—C(=O)—O-lower alkyl($C_1$–$C_8$) straight or branched,

—NH—C(=O)-lower alkyl($C_1$–$C_8$) straight or branched,

—NHSO$_2$-lower alkyl($C_1$–$C_8$) straight or branched,

—NH—C(=O)—O-lower alkenyl($C_1$–$C_8$) straight or branched,

—NH—C(=O)-lower alkenyl($C_1$–$C_8$) straight or branched,

—NHSO$_2$-lower alkenyl($C_1$–$C_8$) straight or branched, wherein cycloalkyl is defined as $C_3$ to $C_6$ cycloalkyl, cyclohexenyl or cyclopentenyl;

n is 0–2;

$R_a$ is independently selected from H, —CH$_3$, —C$_2$H$_5$,

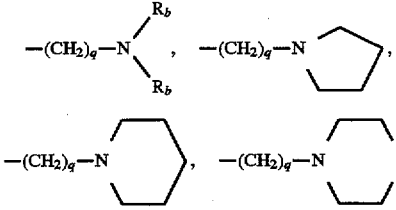

—(CH$_2$)$_q$Olower alkyl ($C_1$–$C_3$), or —CH$_2$CH$_2$OH;

$R_b$ is as hereinbefore defined;

q is 1 or 2;

(b) a moiety of the formula:

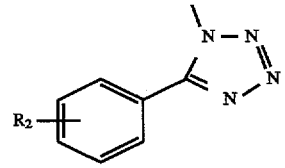

where $R_2$ is as hereinbefore defined;

(c) a moiety of the formula:

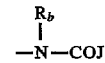
—N—COJ wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —$CH_2$—K wherein K is halogen, ($C_1$–$C_3$) lower alkoxy, tetrahydrofuran, tetrahydrothiophene or the heterocyclic ring moiety:

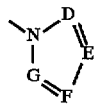

wherein D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$) lower alkoxy, or —$CO_2$-lower alkyl ($C_1$–$C_3$); and $R_a$ and $R_b$ are as hereinbefore defined;

(d) a moiety selected from those of the formulae:

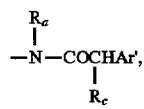

wherein $R_c$ is selected from halogen, ($C_1$–$C_3$)lower alkyl, —O-lower alkyl ($C_1$–$C_3$), OH

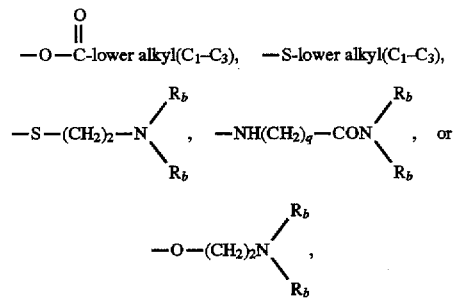

q is 1 or 2;

$R_a$ and $R_b$ are as hereinbefore defined;

wherein Ar' is selected from the group:

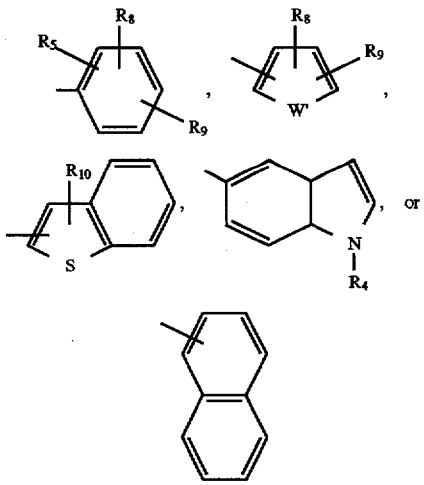

wherein

W' is selected from O, S, NH, N-lower alkyl ($C_1$–$C_3$), —NHCO-lower alkyl ($C_1$–$C_3$), or $NSO_2$-lower alkyl ($C_1$–$C_3$);

$R_7$ is selected from H, lower alkyl ($C_1$–$C_3$), halogen, —O-lower alkyl ($C_1$–$C_3$), or $CF_3$;

$R_8$ and $R_9$ are independently selected from hydrogen, lower alkyl ($C_1$–$C_3$), S-lower alkyl ($C_1$–$C_3$), halogen, —N—lower alkyl ($C_1$–$C_3$), —$OCF_3$, —CN, —OH, —S—$CF_3$, —$NO_2$, $NH_2$, or —O-lower alkyl ($C_1$–$C_3$);

$R_{10}$ is H, halogen, or lower alkyl-($C_1$–$C_3$);

and the pharmaceutically acceptable salts, esters and pro-drug forms thereof.

2. A compound according to claim 1 wherein $R_3$ is the moiety:

and Ar is the moiety

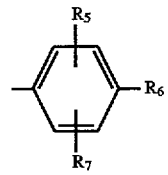

wherein $R_5$, $R_6$, and $R_7$ are as defined in claim 1 or a pharmaceutically acceptable salt, ester or pro-drug form thereof.

3. A compound according to claim 1 wherein $R_3$ is the moiety:

and Ar is the moiety

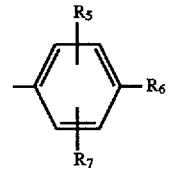

wherein $R_5$, $R_6$, and $R_7$ are as defined in claim 1 and Ar' is selected from the moieties

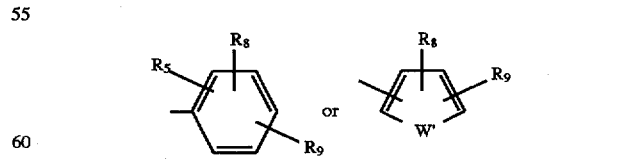

wherein $R_5$, $R_8$, $R_9$ and W' are as defined in claim 1, or a pharmaceutically acceptable salt, ester or pro-drug form thereof.

4. A compound according to claim 1 wherein $R_3$ is the moiety:

$$-\overset{O}{\underset{\|}{C}}Ar$$

and Ar is the moiety

[structure: benzene ring with R$_5$, R$_6$, R$_7$ substituents]

wherein R$_5$ and R$_7$ are as defined in claim 1 and R$_6$ is selected from:

(a) moieties of the formula:

$$-\underset{R_a}{\underset{|}{N}}COAr', \quad -CO\underset{R_a}{\underset{|}{N}}-Ar', \quad -\underset{R_a}{\underset{|}{N}}COCH_2Ar', \quad -\underset{R_a}{\underset{|}{N}}CO\underset{R_b}{\underset{|}{N}}-Ar',$$

$$-CH_2COAr', \quad -\underset{R_a}{\underset{|}{N}}CO(CH_2)_n\text{-cycloalkyl}, \quad -\underset{R_a}{\underset{|}{N}}-SO_2-[\text{aryl with } R_1, R_2],$$

$$-\underset{R_a}{\underset{|}{N}}-SO_2CH_2-[\text{aryl with } R_1, R_2], \quad -\underset{R_a}{\underset{|}{N}}-\overset{O}{\underset{\|}{P}}(-O-[\text{aryl with } R_1, R_2])_2,$$

$$-\underset{R_a}{\underset{|}{N}}-\overset{O}{\underset{\|}{P}}(-[\text{aryl with } R_1, R_2])_2,$$

$-NH-\overset{O}{\underset{\|}{C}}-$O-lower alkyl(C$_1$-C$_8$) straight or branched, $-NH-\overset{O}{\underset{\|}{C}}-$lower alkyl(C$_1$-C$_8$) straight or branched, $-NHSO_2$-lower alkyl(C$_1$-C$_8$) straight or branched, $-NH-\overset{O}{\underset{\|}{C}}-$O-lower alkenyl(C$_1$-C$_8$) straight or branched, $-NH-\overset{O}{\underset{\|}{C}}-$lower alkenyl(C$_1$-C$_8$) straight or branched, $-NHSO_2$-lower alkenyl(C$_1$-C$_8$) straight or branched, wherein cycloalkyl is defined as C$_3$ to C$_6$ cycloalkyl, cyclohexenyl or cyclopentenyl;

n is 0–2;

R$_a$ is independently selected from H, —CH$_3$, —C$_2$H$_5$, $$-(CH_2)_q-N\begin{matrix}R_b\\R_b\end{matrix}, \quad -(CH_2)_q-N\text{(pyrrolidinyl)},$$

$$-(CH_2)_q-N\text{(piperidinyl)}, \quad -(CH_2)_q-N\text{(morpholinyl)O},$$

q is 1 or 2;

R$_b$ is selected from H, —CH$_3$, or C$_2$H$_5$; or (b) a moiety of the formula:

$$-\underset{R_b}{\underset{|}{N}}-COJ$$

wherein J is R$_a$, lower alkyl (C$_1$–C$_8$) branched or unbranched, lower alkenyl (C$_2$–C$_8$) branched or unbranched, —O-lower alkyl (C$_1$–C$_8$) branched or unbranched, —O-lower alkenyl (C$_2$–C$_8$) branched or unbranched, tetrahydrofuran, tetrahydrothiophene, or —CH$_2$—K wherein K is halogen, (C$_1$–C$_3$) lower alkoxy, tetrahydrofuran, tetrahydrothiophene or the heterocyclic ring moiety:

[5-membered ring with N, D, E, F, G]

wherein D, E, F and G are selected from carbon or nitrogen and wherein the carbon atoms may be optionally substituted with halogen, (C$_1$–C$_3$)lower alkyl, hydroxy, —CO-lower alkyl (C$_1$–C$_3$), CHO, (C$_1$–C$_3$)lower alkoxy, or —CO$_2$-lower alkyl (C$_1$–C$_3$); and R$_a$ and R$_b$ are as hereinbefore defined; or (c) a moiety selected from those of the formulae:

$$-\underset{R_c}{\underset{|}{N}}-COCHAr',$$

wherein R$_c$ is selected from halogen, (C$_1$–C$_3$) lower alkyl, —O-lower alkyl (C$_1$–C$_3$), OH, $$-O-\overset{O}{\underset{\|}{C}}-\text{lower alkyl}(C_1-C_3), \quad -S\text{-lower alkyl}(C_1-C_3),$$

$$-S-(CH_2)_2-N\begin{matrix}R_b\\R_b\end{matrix}, \quad -NH(CH_2)_q-CON\begin{matrix}R_b\\R_b\end{matrix}, \quad \text{or}$$

$$-O-(CH_2)_2N\begin{matrix}R_b\\R_b\end{matrix},$$

q is 1 or 2; and R$_a$ and R$_b$ are as hereinbefore defined;

wherein Ar' is selected from the group:

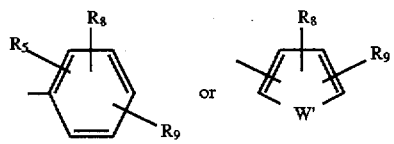

wherein $R_8$, $R_9$ and W' are as defined in claim 1, or a pharmaceutically acceptable salt, ester or pro-drug form thereof.

5. A compound selected from Formula I:

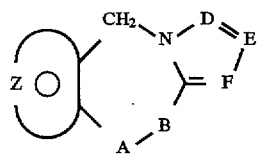

Formula I wherein;

A—B is

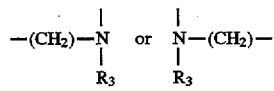

the moiety

represents a fused thiophene or fused substituted thiophene optionally substituted by one or two substituents selected from ($C_1$–$C_3$) lower alkyl, halogen, or ($C_1$–$C_3$) lower alkoxy;

the moiety:

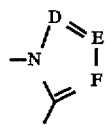

is a five-membered aromatic (unsaturated) fused nitrogen-containing heterocyclic ring wherein D, E, and F are carbon and wherein the carbon atoms may be optionally substituted by a substituent selected from halogen, ($C_1$–$C_3$) lower alkyl, hydroxy, $COCCl_3$, $COCF_3$,

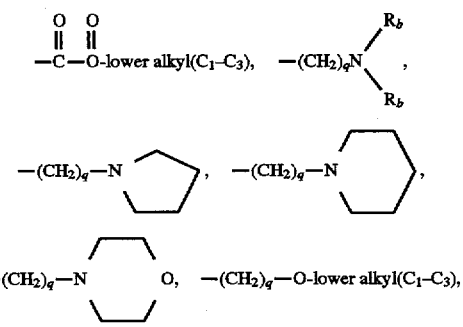

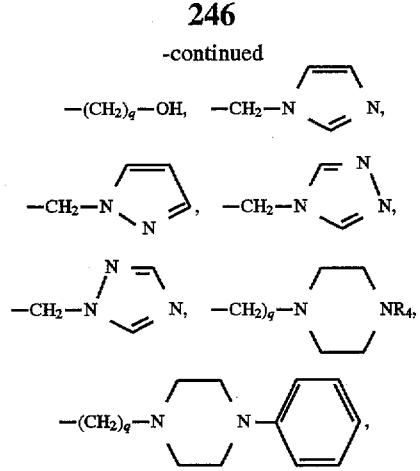

—CHO, amino, ($C_1$–$C_3$) lower alkoxy, ($C_1$–$C_3$) lower alkylamino, CONH ($C_1$–$C_3$) lower alkyl, or 13 CON[lower alkyl ($C_1$–$C_3$)]$_2$, $R_b$ is independently selected from H, —$CH_3$, or —$C_2H_5$;

q is 1 or 2;

$R_3$ is the moiety

—CAr wherein Ar is a moiety selected from the group

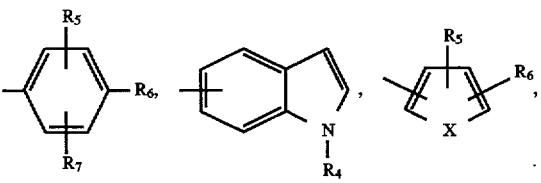

and X is selected from O, S, NH, —$NCH_3$, or —N—$COCH_3$;

$R_4$ is selected from H, lower alkyl ($C_1$–$C_3$), —CO-lower alkyl ($C_1$–$C_3$), $SO_2$ lower alkyl ($C_1$–$C_3$), or the moieties of the formulae:

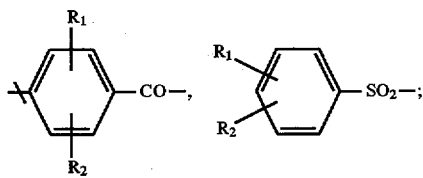

$R_1$ and $R_2$ are, independently, H, ($C_1$–$C_3$) lower alkyl, ($C_1$–$C_3$) lower alkoxy, or halogen;

$R_5$ is H, ($C_1$–$C_3$) lower alkyl, ($C_1$–$C_3$) lower alkoxy or halogen;

$R_6$ is selected from:
(a) moieties of the formula:

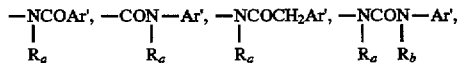

-continued

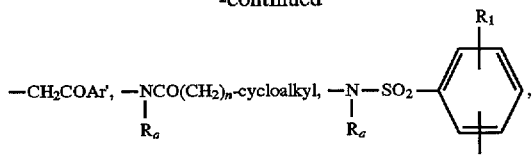

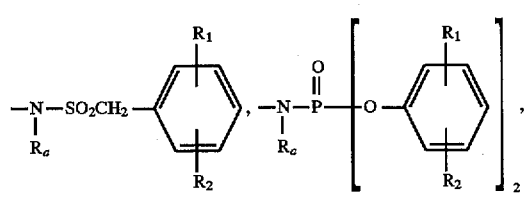

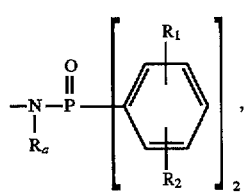

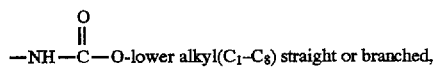

—NH—C(=O)—O-lower alkyl(C$_1$-C$_8$) straight or branched,

—NH—C(=O)-lower alkyl(C$_1$-C$_8$) straight or branched,

—NHSO$_2$-lower alkyl(C$_1$-C$_8$) straight or branched,

—NH—C(=O)—O-lower alkenyl(C$_1$-C$_8$) straight or branched,

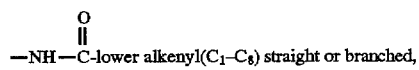

—NH—C(=O)-lower alkenyl(C$_1$-C$_8$) straight or branched,

—NHSO$_2$-lower alkenyl(C$_1$-C$_8$) straight or branched, wherein cycloalkyl is defined as C$_3$ to C$_6$ cycloalkyl, cyclohexenyl or cyclopentenyl;

n is 0-2;

Ra is independently selected from H, —CH$_3$, —C$_2$H$_5$,

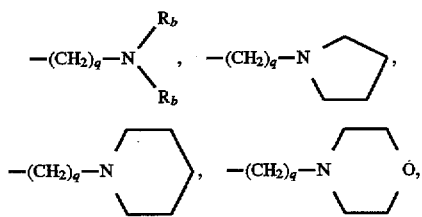

—(CH$_2$)$_q$Olower alkyl (C$_1$C$_3$), or —CH$_2$CH$_2$OH;

R$_b$ is as hereinbefore defined;

q is 1 or 2;

(b) a moiety of the formula:

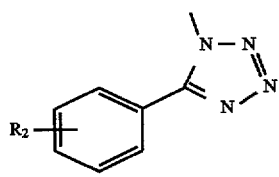

where R$_2$ is as hereinbefore defined;

(c) a moiety of the formula:

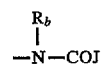

wherein J is R$_a$, lower alkyl (C$_1$-C$_8$) branched or unbranched, lower alkenyl (C$_2$-C$_8$) branched or unbranched, —O-lower alkyl (C$_1$-C$_8$) branched or unbranched, —O-lower alkenyl (C$_2$-C$_8$) branched or unbranched, tetrahydrofuran, tetrahydrothiophene, or —CH$_2$—K wherein K is halogen, (C$_1$-C$_3$) lower alkoxy, tetrahydrofuran, tetrahydrothiophene or the heterocyclic ring moiety:

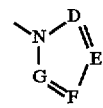

wherein D, E, F and G are selected from carbon or nitrogen and wherein the carbon atoms may be optionally substituted with halogen, (C$_1$-C$_3$)lower alkyl, hydroxy, —CO-lower alkyl (C$_1$-C$_3$), CHO, (C$_1$-C$_3$)lower alkoxy, or 13 CO$_2$-lower alkyl (C$_1$-C$_3$); and R$_a$ and R$_b$ are as hereinbefore defined;

(d) a moiety selected from those of the formulae:

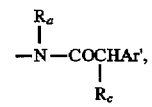

wherein R$_c$ is selected from halogen, (C$_1$-C$_3$) lower alkyl, —O-lower alkyl (C$_1$-C$_3$), OH

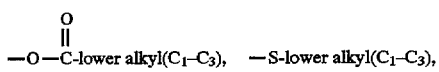

—O—C(=O)-lower alkyl(C$_1$-C$_3$), —S-lower alkyl(C$_1$-C$_3$),

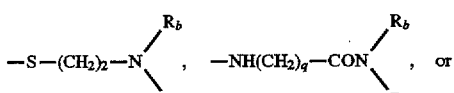

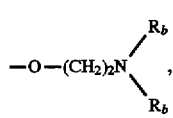

q is 1 or 2;

Ra and R$_b$ are as hereinbefore defined;

wherein Ar' is selected from the group:

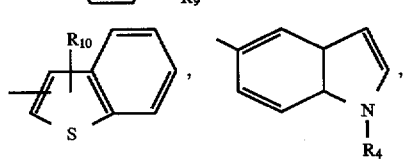

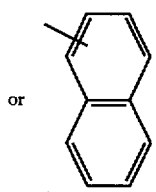

or wherein

W' is selected from O, S, NH, N-lower alkyl (C₁-C₃), —NHCO-lower alkyl (C₁-C₃), or NSO₂-lower alkyl (C₁-C₃);

R₇ is selected from H, lower alkyl (C₁-C₃), halogen, —O-lower alkyl (C₁-C₃), or CF₃;

R₈ and R₉ are independently selected from hydrogen, lower alkyl (C₁-C₃), S-lower alkyl (C₁-C₃), halogen, —N—lower alkyl (C₁-C₃), —OCF₃, —CN, —OH, —S—CF₃, —NO₂, NH₂, or —O-lower alkyl (C₁-C₃);

R₁₀ is H, halogen, or lower alkyl-(C₁-C₃); and the pharmaceutically acceptable salts, esters and pro-drug forms thereof.

6. A compound according to claim 5 wherein R₃ is the moiety:

and Ar is the moiety

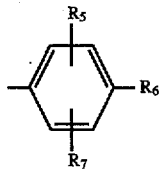

wherein R₅, R₆, and R₇ are as defined in claim 1 or a pharmaceutically acceptable salt, ester or pro-drug form thereof.

7. A compound according to claim 5 wherein R₃ is the moiety:

and Ar is the moiety

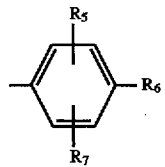

wherein R₅, R₆, and R₇ are as defined in claim 1 and Ar' is selected from the moieties

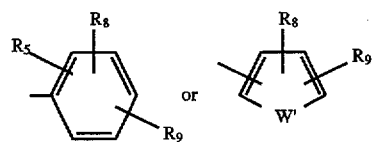

wherein R₅, R₈, R₉ and W' are as defined in claim 1, or a pharmaceutically acceptable salt, ester or pro-drug form thereof.

8. A compound according to claim 5 wherein R₃ is the moiety:

and Ar is the moiety

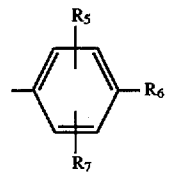

wherein R₅ and R₇ are as defined in claim 1 and R₆ is selected from:

(a) moieties of the formula:

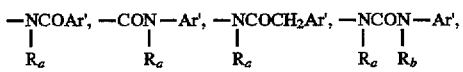

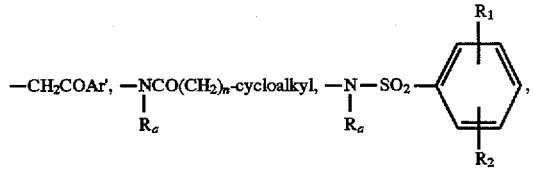

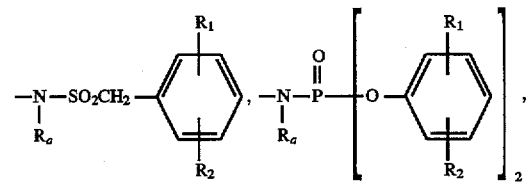

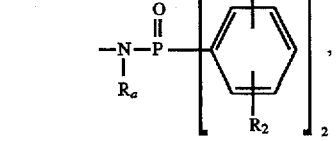

—NH—C(=O)—O-lower alkyl(C₁-C₈) straight or branched,

—NH—C(=O)-lower alkyl(C₁-C₈) straight or branched,

—NHSO₂-lower alkyl(C₁-C₈) straight or branched,

—NH—C(=O)—O-lower alkenyl(C₁-C₈) straight or branched,

-continued

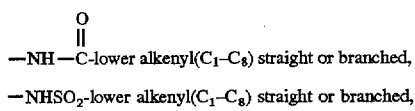
—NH—C-lower alkenyl($C_1$-$C_8$) straight or branched,

—NHSO$_2$-lower alkenyl($C_1$-$C_8$) straight or branched, wherein cycloalkyl is defined as $C_3$ to $C_6$ cycloalkyl, cyclohexenyl or cyclopentenyl;

n is 0-2;

$R_a$ is independently selected from H, —CH$_3$, —C$_2$H$_5$,

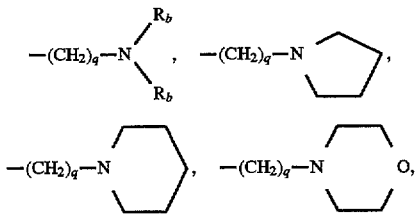

—(CH$_2$)$_q$—O-lower alkyl ($C_1$$C_3$), or —CH$_2$CH$_2$OH;
q is 1 or 2;

$R_b$ is selected from H, —CH$_3$, or C$_2$H$_5$; or (b) a moiety of the formula:

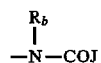

wherein J is $R_a$, lower alkyl ($C_1$-$C_8$) branched or unbranched, lower alkenyl ($C_2$-$C_8$) branched or unbranched, —O-lower alkyl ($C_1$-$C_8$) branched or unbranched, —O-lower alkenyl ($C_2$-$C_8$) branched or unbranched, tetrahydrofuran, tetrahydrothiophene, or —CH$_2$—K wherein K is halogen, ($C_1$-$C_3$) lower alkoxy, tetrahydrofuran, tetrahydrothiophene or the heterocyclic ring moiety:

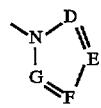

wherein D, E, F and G are selected from carbon or nitrogen and wherein the carbon atoms may be optionally substituted with halogen, ($C_1$-$C_3$) lower alkyl, hydroxy, —CO-lower alkyl ($C_1$-$C_3$), CHO, ($C_1$-$C_3$)lower alkoxy, or —CO$_2$-lower alkyl ($C_1$-$C_3$); and $R_a$ and $R_b$ are as hereinbefore defined; or (c) a moiety selected from those of the formulae:

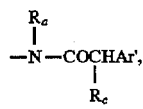

wherein $R_c$ is selected from halogen, ($C_1$-$C_3$) lower alkyl, —O-lower alkyl ($C_1$-$C_3$), OH,

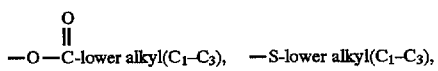

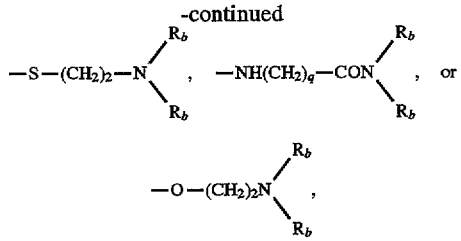

q is 1 or 2; and $R_a$ and $R_b$ are as hereinbefore defined;
wherein Ar' is selected from the group:

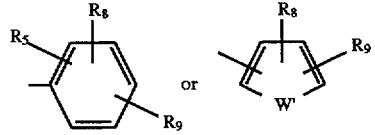

wherein $R_8$, $R_9$ and W' are as defined in claim 1, or a pharmaceutically acceptable salt, ester or pro-drug form thereof.

9. A compound selected from Formula I:

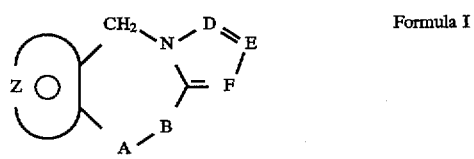

Formula I wherein;

A—B is

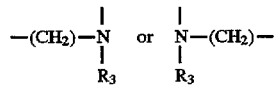

the moiety

represents a fused thiophene or fused substituted thiophene optionally substituted by one or two substituents selected from ($C_1$-$C_3$) lower alkyl, halogen, or ($C_1$-$C_3$) lower alkoxy;

the moiety:

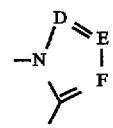

is a five-membered aromatic (unsaturated) fused nitrogen-containing heterocyclic ring wherein D is nitrogen and E, and F are carbon and wherein the carbon atoms may be optionally substituted by a substituent selected from halogen, ($C_1$-$C_3$) lower alkyl, hydroxy, COCCl$_3$, COCF$_3$,

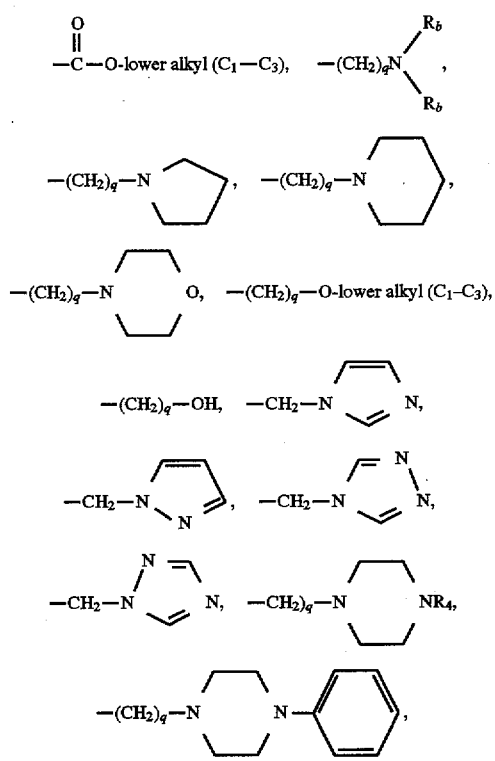

—CHO, amino, (C$_1$-C$_3$) lower alkoxy, (C$_1$-C$_3$) lower alkylamino, CONH (C$_1$-C$_3$) lower alkyl, or —CON [lower alkyl (C$_1$-C$_3$)]$_2$, R$_b$ is independently selected from H, —CH$_3$, or —C$_2$H$_5$; q is 1 or 2;

R$_3$ is the moiety

wherein Ar is a moiety selected from the group

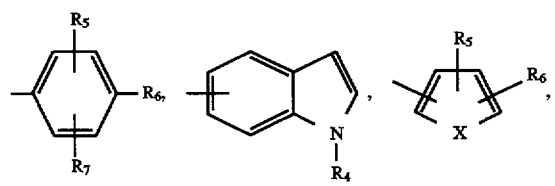

and X is selected from O, S, NH, —NCH$_3$, or —N—COCH$_3$;

R$_4$ is selected from H, lower alkyl (C$_1$-C$_3$), —CO-lower alkyl (C$_1$-C$_3$), SO$_2$ lower alkyl (C$_1$-C$_3$), or the moieties of the formulae:

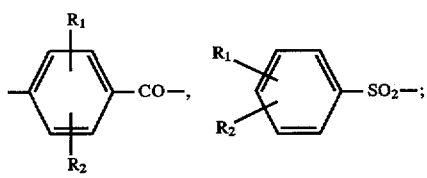

R$_1$ and R$_2$ are, independently, H, (C$_1$-C$_3$) lower alkyl, (C$_1$-C$_3$) lower alkoxy, or halogen;

R$_5$ is H, (C$_1$-C$_3$) lower alkyl, (C$_1$-C$_3$) lower alkoxy or halogen;

R$_6$=is selected from:

(a) moieties of the formula:

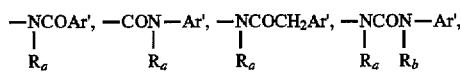

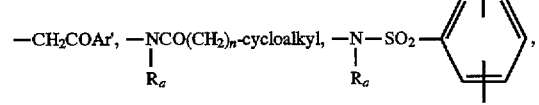

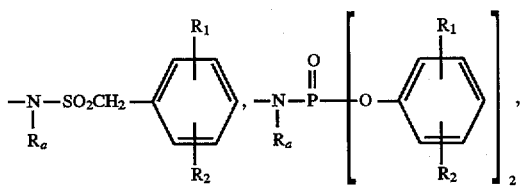

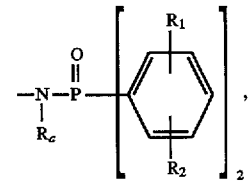

$$-NH-\overset{O}{\underset{\|}{C}}-O\text{-lower alkyl}(C_1-C_8) \text{ straight or branched,}$$

$$-NH-\overset{O}{\underset{\|}{C}}\text{-lower alkyl}(C_1-C_8) \text{ straight or branched,}$$

—NHSO$_2$-lower alkyl(C$_1$-C$_8$) straight or branched, $$-NH-\overset{O}{\underset{\|}{C}}-O\text{-lower alkenyl}(C_1-C_8) \text{ straight or branched,}$$

$$-NH-\overset{O}{\underset{\|}{C}}\text{-lower alkenyl}(C_1-C_8) \text{ straight or branched,}$$

—NHSO$_2$-lower alkenyl(C$_1$-C$_8$) straight or branched, wherein cycloalkyl is defined as C$_3$ to C$_6$ cycloalkyl, cyclohexenyl or cyclopentenyl;

n is 0-2;

R$_a$ is independently selected from H, —CH$_3$, —C$_2$H$_5$,

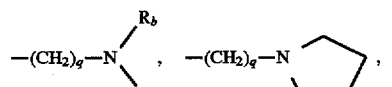

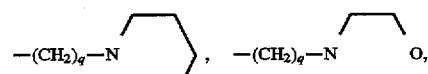

—(CH$_2$)$_q$Olower alkyl (C$_1$C$_3$), or —CH$_2$CH$_2$OH;

R$_b$ is as hereinbefore defined;

q is 1 or 2;

(b) a moiety of the formula:

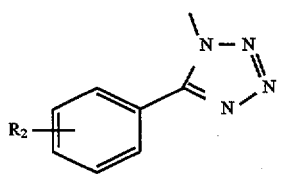

where $R_2$ is as hereinbefore defined;

(c) a moiety of the formula:

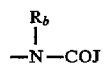

wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —$CH_2$—K wherein K is halogen, ($C_1$–$C_3$) lower alkoxy, tetrahydrofuran, tetrahydrothiophene or the heterocyclic ring moiety:

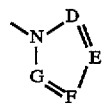

wherein D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$) lower alkoxy, or —$CO_2$-lower alkyl ($C_1$–$C_3$); and $R_a$ and $R_b$ are as hereinbefore defined;

(d) a moiety selected from those of the formulae:

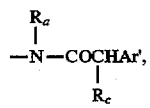

wherein $R_c$ is selected from halogen, ($C_1$–$C_3$) lower alkyl, —O-lower alkyl ($C_1$–$C_3$), OH

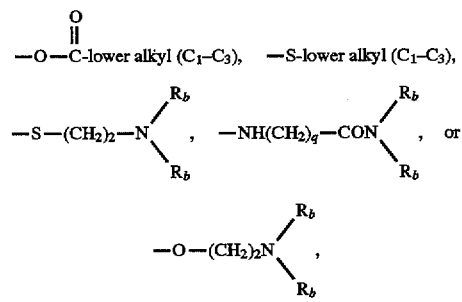

q is 1 or 2;

$R_a$ and $R_b$ are as hereinbefore defined;

wherein Ar' is selected from the group:

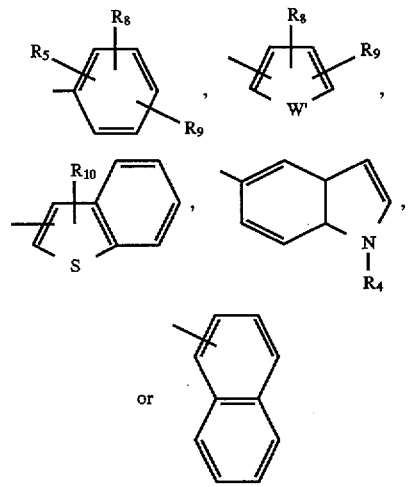

wherein

W' is selected from O, S, NH, N-lower alkyl ($C_1$–$C_3$), —NHCO-lower alkyl ($C_1$–$C_3$), or $NSO_2$-lower alkyl ($C_1$–$C_3$);

$R_7$ is selected from H, lower alkyl ($C_1$–$C_3$), halogen, —O-lower alkyl ($C_1$–$C_3$), or $CF_3$;

$R_8$ and $R_9$ are independently selected from hydrogen, lower alkyl ($C_1$–$C_3$), S-lower alkyl ($C_1$–$C_3$), halogen, —N—lower alkyl ($C_1$–$C_3$), —$OCF_3$, —CN, —OH, —S—$CF_3$, —$NO_2$, $NH_2$, or —O-lower alkyl ($C_1$–$C_3$);

$R_{10}$ is H, halogen, or lower alkyl-($C_1$–$C_3$); and the pharmaceutically acceptable salts, esters and pro-drug forms thereof.

10. A compound according to claim 9 wherein $R_3$ is the moiety:

and Ar is the moiety

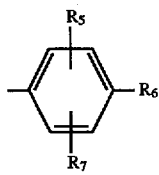

wherein $R_5$, $R_6$, and $R_7$ are as defined in claim 1 or a pharmaceutically acceptable salt, ester or pro-drug form thereof.

11. A compound according to claim 9 wherein $R_3$ is the moiety:

and Ar is the moiety

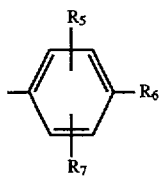

wherein $R_5$, $R_6$, and $R_7$ are as defined in claim 1 and Ar' is selected from the moieties

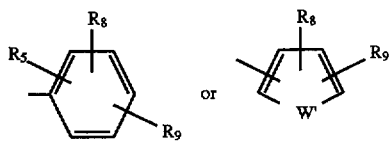

wherein $R_5$, $R_8$, $R_9$ and W' are as defined in claim 1, or a pharmaceutically acceptable salt, ester or pro-drug form thereof.

12. A compound according to claim 9 wherein $R_3$ is the moiety:

and Ar is the moiety

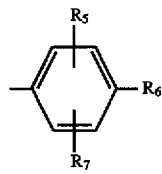

wherein $R_5$ and $R_7$ are as defined in claim 1 and $R_6$ is selected from:

(a) moieties of the formula:

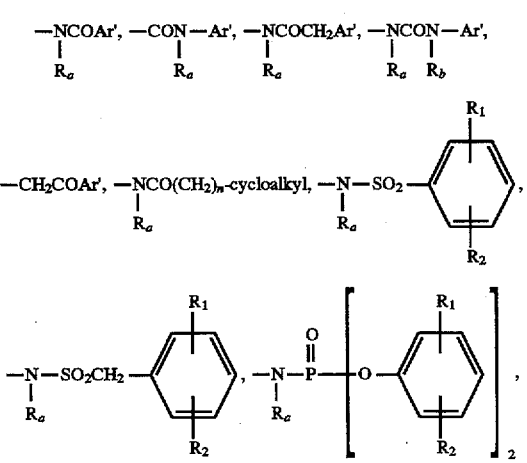

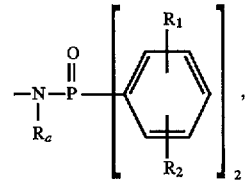

—NH—C(=O)—O-lower alkyl($C_1$–$C_8$) straight or branched,

—NH—C(=O)-lower alkyl($C_1$–$C_8$) straight or branched,

—NHSO$_2$-lower alkyl($C_1$–$C_8$) straight or branched,

—NH—C(=O)—O-lower alkenyl($C_1$–$C_8$) straight or branched,

—NH—C(=O)-lower alkenyl($C_1$–$C_8$) straight or branched,

—NHSO$_2$-lower alkenyl($C_1$–$C_8$) straight or branched, wherein cycloalkyl is defined as $C_3$ to $C_6$ cycloalkyl, cyclohexenyl or cyclopentenyl;

n is 0–2;

$R_a$ is independently selected from H, —CH$_3$, —C$_2$H$_5$,

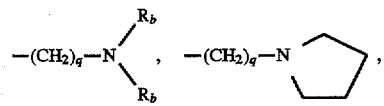

—(CH$_2$)$_q$—O-lower alkyl ($C_1$$C_3$), or —CH$_2$CH$_2$OH;

q is 1 or 2;

$R_b$ is selected from H, —CH$_3$, or C$_2$H$_5$; or (b) a moiety of the formula:

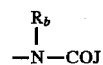

wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —CH$_2$—K wherein K is halogen, ($C_1$–$C_3$) lower alkoxy, tetrahydrofuran, tetrahydrothiophene or the heterocyclic ring moiety:

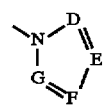

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$)lower alkoxy, or 13 CO$_2$-lower alkyl (C$_1$-C$_3$); and R$_a$ and R$_b$ are as hereinbefore defined; or (c) a moiety selected from those of the formulae:

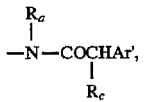

wherein R$_c$ is selected from halogen, (C$_1$-C$_3$) lower alkyl, —O-lower alkyl (C$_1$-C$_3$), OH,

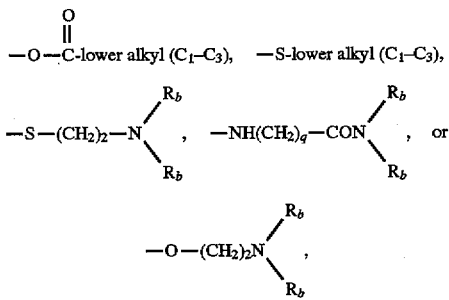

q is 1 or 2; and R$_a$ and R$_b$ are as hereinbefore defined; wherein Ar' is selected from the group:

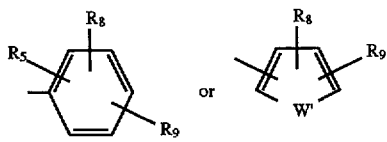

wherein R$_8$, R$_9$ and W' are as defined in claim 1, or a pharmaceutically acceptable salt, ester or pro-drug form thereof.

13. The compound according to claim 1 N-[4-(5H-pyrrolo[1,2-a]thieno [3,2-e][1,4]diazepin-4(10H)ylcarbonyl)phenyl]-2,4-dichlorobenzamide.

14. The compound according to claim 1 N-[4-(5H-pyrrolo[1,2-a]thieno[3,2-e][1,4]diazepin-4 (10H)ylcarbonyl)-3-chlorophenyl]-5-fluoro-2-methylbenzamide.

15. The compound according to claim 1 N-[4-(5H-pyrrolo[1,2-a]thieno[3,2-e][1,4]diazepin-4(10H)ylcarbonyl)-3-chlorophenyl]-3-fluoro-2-methylbenzamide.

16. The compound according to claim 1 N-[4-(5H-pyrrolo[1,2-a]thieno[3,2-e][1,4]diazepin-4(10H)ylcarbonyl)-3-chlorophenyl]-2-chloro-4-fluorobenzamide.

17. The compound according to claim 1 N-[4-(5H-pyrrolo[1,2-a]thieno[3,2-e][1,4]diazepin-4(10H)ylcarbonyl)-3-chlorophenyl]-2-chloro-5-fluorobenzamide.

18. The compound according to claim 1 N-[4-(5H-pyrrolo[1,2-a]thieno[3,2-e][1,4]diazepin-4(10H)ylcarbonyl)-3-chlorophenyl]-2-methylbenzamide.

19. The compound according to claim 1 N-[4-(5H-pyrrolo[1,2-a]thieno[3,2-e][1,4]diazepin-4(10H)ylcarbonyl)-3-chlorophenyl]-2,4-dichlorobenzamide.

20. The compound according to claim 1 N-[4-(5H-pyrrolo[1,2-a]thieno[3,2-e][1,4]diazepin-4(10H)ylcarbonyl)-3-chlorophenyl]-2-chlorobenzamide.

21. The compound according to claim 1 N-[4-[[8-[(dimethylamino)methyl]-5H-pyrrolo[1,2-a]thieno[3,2-e][1,4]diazepin-4(10H)-yl]carbonyl]-3-chlorophenyl]-2-methylbenzamide.

22. The compound according to claim 1 N-[4-[[8-[(dimethylamino)methyl]-5H-pyrrolo[1,2-a]thieno[3,2-e][1,4]diazepin-4(10H)-yl]carbonyl]-3-chlorophenyl]-5-fluoro-2-methylbenzamide.

23. The compound according to claim 1 N-[4-[[8-](dimethylamino)methyl]-5H-pyrrolo[1,2-a]thieno[3,2-e][1,4]diazepin-4(10H)-yl]carbonyl]-3-chlorophenyl]-3-fluoro-2-methylbenzamide.

24. The compound according to claim 1 N-[4-[[8-[(dimethylamino)methyl]-5H-pyrrolo[1,2-a]thieno[3,2-e]1,4]diazepin-4(10H)-yl]carbonyl]-3-chlorophenyl]-2,4-dichlorobenzamide.

25. The compound according to claim 1 N-[4-[[8-[(dimethylamino)methyl]-5H-pyrrolo[1,2-a]thieno[3,2-e]1,4]diazepin-4(10H)-yl]carbonyl]-3-chlorophenyl]-2-chlorobenzamide.

26. The compound according to claim 1 N-[4-[[8-[(dimethylamino)methyl]-5H-pyrrolo[1,2-a]thieno[3,2-e]1,4]diazepin-4(10H)-yl]carbonyl]-3-chlorophenyl]-2-chloro-4-fluorobenzamide.

27. The compound according to claim 1 N-[4-[[8-[(dimethylamino)methyl]-5H-pyrrolo[1,2-a]thieno[3,2-e]1,4]diazepin-4(10H)-yl]carbonyl]-3-chlorophenyl]-2-chloro-5-fluorobenzamide.

28. The compound according to claim 1 N-[4-(5H-pyrrolo[1,2-a]thieno[3,2-e][1,4]diazepin-4(10H)ylcarbonyl)phenyl]-5-fluoro-2-methylbenzamide.

29. The compound according to claim 1 N-[4-(5H-pyrrolo[1,2-a]thieno[3,2-e][1,4]diazepin-4(10H)ylcarbonyl)-3-methylphenyl]-5-fluoro-2-methylbenzamide.

30. The compound according to claim 1 N-[4-(5H-pyrrolo[1,2-a]thieno[3,2-e][1,4]diazepin-4(10H)-ylcarbonyl)-3-methylphenyl]-3-fluoro-2-methylbenzamide.

31. The compound according to claim 1 N-[4-(5H-pyrrolo[1,2-a]thieno[3,2-e][1,4]diazepin-4(10H)ylcarbonyl)-3-methylphenyl]-2-chloro-4-fluorobenzamide.

32. The compound according to claim 1 N-[4-(5H-pyrrolo[1,2-a]thieno[3,2-e][1,4]diazepin-4(10H)ylcarbonyl)-3-methylphenyl]-2-chloro-5-fluorobenzamide.

33. The compound according to claim 1 N-[4-(5H-pyrrolo[1,2-a]thieno[3,2-e][1,4]diazepin-4(10H)ylcarbonyl)-3-methylphenyl]-2-methylbenzamide.

34. The compound according to claim 1 N-[4-(5H-pyrrolo[1,2-a]thieno[3,2-e][1,4]diazepin-4(10H)ylcarbonyl)-3-methylphenyl]-2,4-dichlorobenzamide.

35. The compound according to claim 1 N-[4-(5H-pyrrolo[1,2-a]thieno[3,2-e][1,4]diazepin-4(10H)ylcarbonyl)-3-methylphenyl]-2-chlorobenzamide.

36. The compound according to claim 1 N-[4-[[8[(dimethylamino)methyl]-5H-pyrrolo[1,2-a]thieno[3,2-e][1,4]diazepin-4(10H)-yl]carbonyl]-3-methylphenyl]-2-methylbenzamide.

37. The compound according to claim 1 N-[4-[[8-[(dimethylamino)methyl]-5H-pyrrolo[1,2-a]thieno[3,2-e][1,4]diazepin-4(10H)-yl]carbonyl]-3-methylphenyl]-5-fluoro-2-methylbenzamide.

38. The compound according to claim 1 N-[4-[[8-[(dimethylamino)methyl]-5H-pyrrolo[1,2-a]thieno[3,2-e][1,4]diazepin-4(10H)-yl]carbonyl]-3-methylphenyl]-3-fluoro-2-methylbenzamide.

39. The compound according to claim 1 N-[4-[[8-[(dimethylamino)methyl]-5H-pyrrolo[1,2-a]thieno[3,2-e][1,4]diazepin-4(10H)-yl]carbonyl]-3-methylphenyl]-2,4-dichlorobenzamide.

40. The compound according to claim 1 N-[4-[[8-[(dimethylamino)methyl]-5H-pyrrolo[1,2-a]thieno[3,2-e][1,4]diazepin-4(10H)-yl]carbonyl]-3-methylphenyl]-2-chlorobenzamide.

41. The compound according to claim 1 N-[4-[[8-[(dimethylamino)methyl]-5H-pyrrolo[1,2-a]thieno[3,2-e][1, 4]diazepin-4(10H)-yl]carbonyl]-3-methylphenyl]-2-chloro-4-fluorobenzamide.

42. The compound according to claim 1 N-[4-[[8-[(dimethylamino)methyl]-5H-pyrrolo[1,2-a]thieno[3,2-e][1,4]diazepin-4(10H)-yl]carbonyl]-3-methylphenyl]-2-chloro-5-fluorobenzamide.

43. The compound according to claim 1 N-[4-(5H-pyrazolo[1,5-a]thieno[3,2-e][1,4]diazepin-4(10H)ylcarbonyl)phenyl]-2-methylbenzamide.

44. The compound according to claim 1 N-[4-(5H-pyrazolo[1,5-a]thieno[3,2-e][1,4]diazepin-4(10H)ylcarbonyl)-3-chlorophenyl]-2-methylbenzamide.

45. The compound according to claim 1 N-[4-(5H-pyrazolo[1,5-a]thieno[3,2-e][1,4]diazepin-4(10H)ylcarbonyl)-3-chlorophenyl]-2-methyl-5-fluorobenzamide.

46. The compound according to claim 1 N-[4-(5H-pyrazolo[1,5-a]thieno[3,2-e][1,4]diazepzn-4(10H)ylcarbonyl)-3-chlorophenyl]-2-methyl-3-fluorobenzamide.

47. The compound according to claim 1 N-[4-(5H-pyrazolo[1,5-a]thieno[3,2-e][1,4]diazepzn-4(10H)ylcarbonyl)-3-chlorophenyl]-2-methyl-5-chlorobenzamide.

48. The compound according to claim 1 N-[4-(5H-pyrazolo[1,5-a]thieno[3,2-e][1,4]diazepin-4(10H)ylcarbonyl)-3-chlorophenyl]-2,5-dimethylbenzamide.

49. The compound according to claim 1 N-[4-(5H-pyrazolo[1,5-a]thieno[3,2-e][1,4]diazepin-4(10H)ylcarbonyl)phenyl]-2-chloro-5-fluorobenzamide.

50. The compound according to claim 1 N-[4-(5H-pyrazolo[1,5-a]thieno[3,2-e][1,4]diazepin-4(10H)ylcarbonyl)-3-chlorophenyl]-2-(trifluoromethyl)-benzamide.

51. The compound according to claim 1 N-[4-(5H-pyrazolo[1,5-a]thieno[3,2-e][1,4]diazepin-4(10H)ylcarbonyl)-3-methylphenyl]-2-methyl-5-fluorobenzamide.

52. The compound according to claim 1 N-[4-(5H-pyrazolo[1,5-a]thieno[3,2-e][1,4]diazepin-4(10H)ylcarbonyl)-3-methylphenyl]-2-methyl-3-fluorobenzamide.

53. The compound according to claim 1 N-[4-(5H-pyrazolo[1,5-a]thieno[3,2-e][1,4]diazepin-4(10H)ylcarbonyl)-3-methylphenyl]-2-chloro-5-fluorobenzamide.

54. The compound according to claim 1 N-[4-(5H-pyrazolo[1,5-a]thieno[3,2-e][1,4]diazepin-4(10H)ylcarbonyl)-3,6-dimethylphenyl]-2-methyl-5-fluorobenzamide.

55. The compound according to claim 1 N-[4-(5H-pyrazolo[1,5-a]thieno[3,2-e][1,4]diazepin-4(10H)ylcarbonyl)phenyl]-2,5-dimethylbenzamide.

56. The compound according to claim 1 N-[4-(5H-pyrazolo[1,5-a]thieno[3,2-e][1,4]diazepin-4(10H)-ylcarbonyl)-3-chlorophenyl]-2,3-dimethylbenzamide.

57. The compound according to claim 1 N-[4-(5H-pyrazolo[1,5-a]thieno[3,2-e][1,4]diazepin-4(10H)ylcarbonyl)-3-chlorophenyl]-3-methylthiophene-2-carboxamide.

58. The compound according to claim 1 N-[4-(5H-pyrazolo[1,5-a]thieno[3,2-e][1,4]diazepin-4(10H)ylcarbonyl)-3-chlorophenyl]-2-methylthiophene-3-carboxamide.

59. The compound according to claim 1 N-[4-(5H-pyrazolo[1,5-a]thieno[3,2-e][1,4]diazepin-4(10H)ylcarbonyl)-3-chlorophenyl]-2-(trifluoromethyl)-benzamide.

60. The compound according to claim 1 N-[4-(5H-pyrazolo[1,5-a]thieno[3,2-e][1,4]diazepin-4(10H)ylcarbonyl)phenyl]-2-chloro-6-fluorobenzamide.

61. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carrier.

62. The pharmaceutical composition of claim 61 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

63. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

64. The method of claim 63 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

* * * * *